US008600932B2

(12) United States Patent
Poling et al.

(10) Patent No.: US 8,600,932 B2
(45) Date of Patent: Dec. 3, 2013

(54) TELEMATIC ASSET MICROFLUIDIC ANALYSIS

(75) Inventors: David Glen Poling, Boulder, CO (US); Daniel John Wallace, Boulder, CO (US)

(73) Assignee: Trimble Navigation Limited, Sunnyvale, CA (US)

( * ) Notice: Subject to any disclaimer, the term of this patent is extended or adjusted under 35 U.S.C. 154(b) by 185 days.

(21) Appl. No.: 13/108,903

(22) Filed: May 16, 2011

(65) Prior Publication Data

US 2011/0282631 A1    Nov. 17, 2011

Related U.S. Application Data

(63) Continuation-in-part of application No. 11/801,093, filed on May 7, 2007.

(51) Int. Cl.
    *G06F 17/30*  (2006.01)
(52) U.S. Cl.
    USPC .......................................... 707/609; 137/551
(58) Field of Classification Search
    USPC ............. 707/609; 702/23; 137/899, 551–559
    See application file for complete search history.

(56) References Cited

U.S. PATENT DOCUMENTS

| | | | |
|---|---|---|---|
| 5,400,246 A | 3/1995 | Wilson et al. | |
| 5,635,907 A | 6/1997 | Bernard et al. | |
| 5,754,137 A | 5/1998 | Durrstein | |
| 5,991,690 A | 11/1999 | Murphy | |
| 6,064,942 A | 5/2000 | Johnson et al. | |
| 6,204,772 B1 | 3/2001 | DeMay et al. | |
| 6,225,901 B1 | 5/2001 | Kail, IV | |
| 6,236,924 B1 | 5/2001 | Motz et al. | |
| 6,272,537 B1 | 8/2001 | Kekic et al. | |
| 6,496,206 B1 | 12/2002 | Mernyk et al. | |
| 6,564,127 B1 | 5/2003 | Bauerle et al. | |
| 6,732,162 B1 | 5/2004 | Wood et al. | |
| 6,788,199 B2 | 9/2004 | Crabtree et al. | |
| 6,853,894 B1 | 2/2005 | Kolls | |
| 6,879,910 B2 | 4/2005 | Shike | |
| 6,885,288 B2 | 4/2005 | Pincus | |
| 6,995,667 B2 | 2/2006 | He et al. | |
| 7,283,975 B2 | 10/2007 | Broughton | |
| 7,313,604 B2 | 12/2007 | Wood et al. | |
| 7,457,762 B2 | 11/2008 | Wetzer et al. | |
| 7,646,336 B2 | 1/2010 | Tan et al. | |
| 7,689,329 B2 | 3/2010 | Avery et al. | |
| 7,720,703 B1 | 5/2010 | Broughton | |

(Continued)

FOREIGN PATENT DOCUMENTS

| | | |
|---|---|---|
| EP | 0660660 B1 | 7/1995 |
| EP | 0660660 B2 | 7/1995 |

(Continued)

OTHER PUBLICATIONS

Bagley, Katherine "High-School Inventors", *Popular Science*, vol. 279 #3, (Sep. 2011),2 pages.

*Primary Examiner* — Thu-Nguyet Le

(57) ABSTRACT

A fluid analyzing system wherein an electronic control module is coupled with an asset and a telematics device. The electronic control module initiates the acquisition of a sample of an asset's fluid and analyzes the sample in response to an analysis trigger. An asset management system located remotely from the asset and telematics device receives the results of the fluid analysis wirelessly via the telematics device.

22 Claims, 69 Drawing Sheets

(56) References Cited

U.S. PATENT DOCUMENTS

| | | |
|---|---|---|
| 2001/0039489 A1 | 11/2001 | Ford et al. |
| 2003/0120509 A1 | 6/2003 | Bruch et al. |
| 2003/0158640 A1 | 8/2003 | Pillar et al. |
| 2003/0193406 A1 | 10/2003 | Kinugawa |
| 2003/0210143 A1 | 11/2003 | Haddad |
| 2004/0024510 A1 | 2/2004 | Finley et al. |
| 2004/0054600 A1 | 3/2004 | Shike et al. |
| 2004/0148083 A1 | 7/2004 | Arakawa et al. |
| 2004/0177032 A1 | 9/2004 | Bradley et al. |
| 2004/0217864 A1 | 11/2004 | Nowak et al. |
| 2005/0040944 A1 | 2/2005 | Contestabile |
| 2005/0065678 A1 | 3/2005 | Smith et al. |
| 2005/0149261 A9 | 7/2005 | Lee et al. |
| 2005/0151655 A1 | 7/2005 | Hamrick et al. |
| 2005/0156715 A1 | 7/2005 | Zou et al. |
| 2005/0173004 A1* | 8/2005 | Apostolides .................. 137/512 |
| 2005/0246094 A1 | 11/2005 | Moscatiello |
| 2005/0253703 A1 | 11/2005 | He |
| 2006/0053075 A1 | 3/2006 | Roth et al. |
| 2006/0220815 A1 | 10/2006 | Thomas |
| 2007/0050137 A1 | 3/2007 | Woon et al. |
| 2008/0068177 A1 | 3/2008 | Copeland |
| 2008/0086508 A1 | 4/2008 | Ballew |
| 2008/0086509 A1 | 4/2008 | Wallace |

FOREIGN PATENT DOCUMENTS

| | | |
|---|---|---|
| EP | 0989525 | 3/2000 |
| EP | 1178458 | 2/2002 |
| EP | 1191157 A1 | 3/2002 |
| EP | 1273721 A1 | 1/2003 |
| WO | WO-99/23783 | 5/1999 |

\* cited by examiner

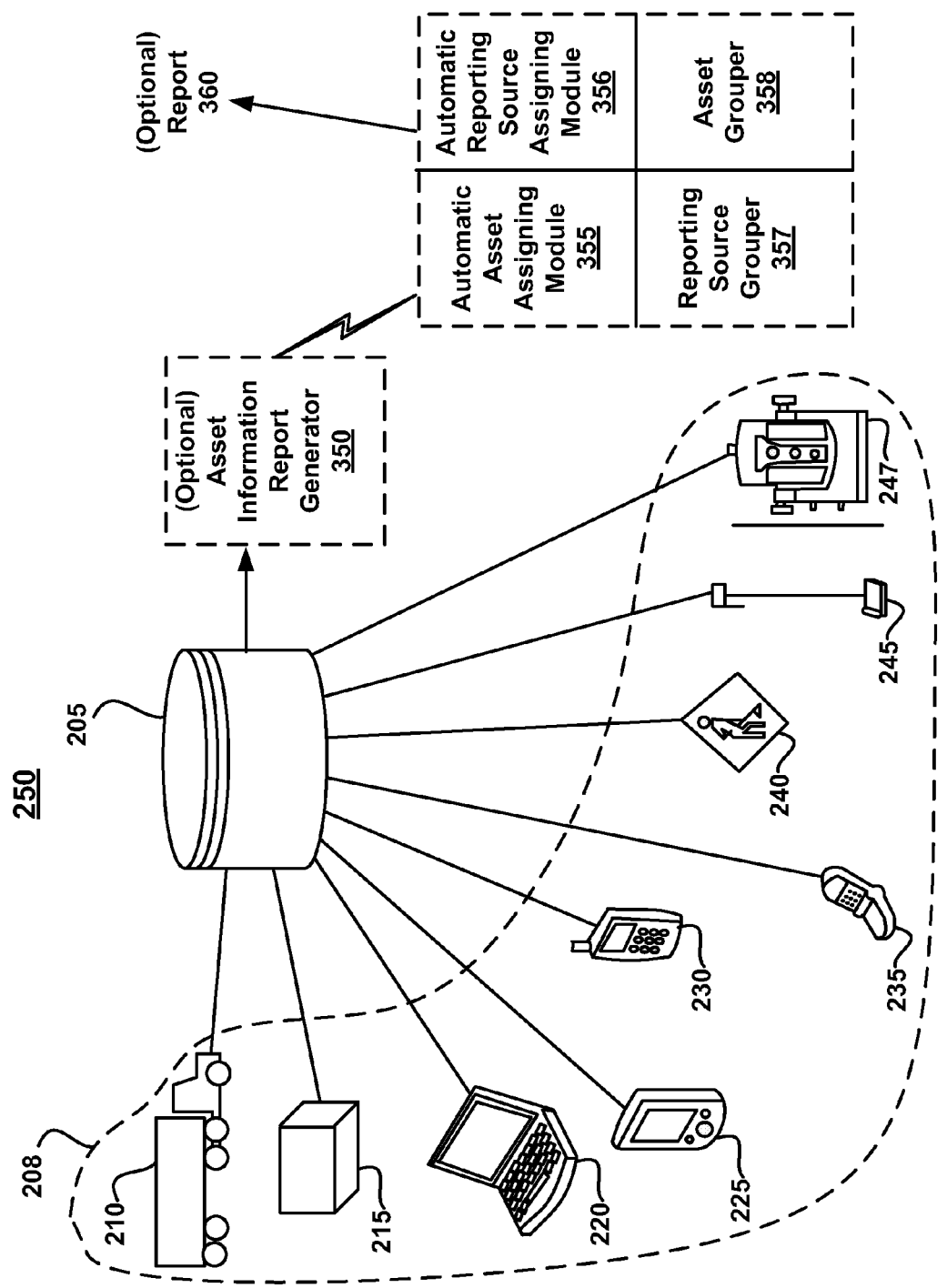

1100

1110

WEEKLY TRUCK USAGE REPORT

| | TYPE 601 | DAY 1104 | DATE 1106 | HOURS OPERATED 1108 |
|---|---|---|---|---|
| ASSET 540B | TRUCK | MON | AUG, 14 | 8 |
| ASSET 540B | TRUCK | TUES | AUG, 15 | 7.9 |
| ASSET 540B | TRUCK | WED | AUG, 16 | 8 |
| ASSET 540B | TRUCK | THUR | AUG, 17 | 8.1 |
| ASSET 540B | TRUCK | FRI | AUG, 18 | 5.7 |

ASSET LOCATION REPORT — 3205

| ASSET 3202 | TIME 3203 | LOCATION 3204 |
|---|---|---|
| GENERATOR 3173 | 14 AUG 2006 – 11:04am | LAT 37.1637 LON -95.3221 |
| GENERATOR 3173 | 14 AUG 2006 – 5:04pm | LAT 37.1637 LON -95.3221 |
| GENERATOR 3173 | 19 AUG 2006 – 8:19am | LAT 37.1637 LON -95.3221 |
| GENERATOR 3173 | 22 AUG 2006 – 4:15pm | LAT 37.1637 LON -95.3221 |
| GENERATOR 3173 | 29 AUG 2006 – 7:37pm | LAT 38.9886 LON -95.3029 |

ACCESSES A DATABASE POPULATED WITH INFORMATION ABOUT AN ASSET RECEIVED FROM A FIRST REPORTING SOURCE, INFORMATION ABOUT THE ASSET RECEIVED FROM A SECOND REPORTING SOURCE, AND INSPECTION INFORMATION ABOUT THE ASSET RECEIVED FROM A FIRST ENABLED DEVICE.
3702

UPDATES A CLIENT INFORMATION SYSTEM WITH DATA FROM THE DATABASE.
3704

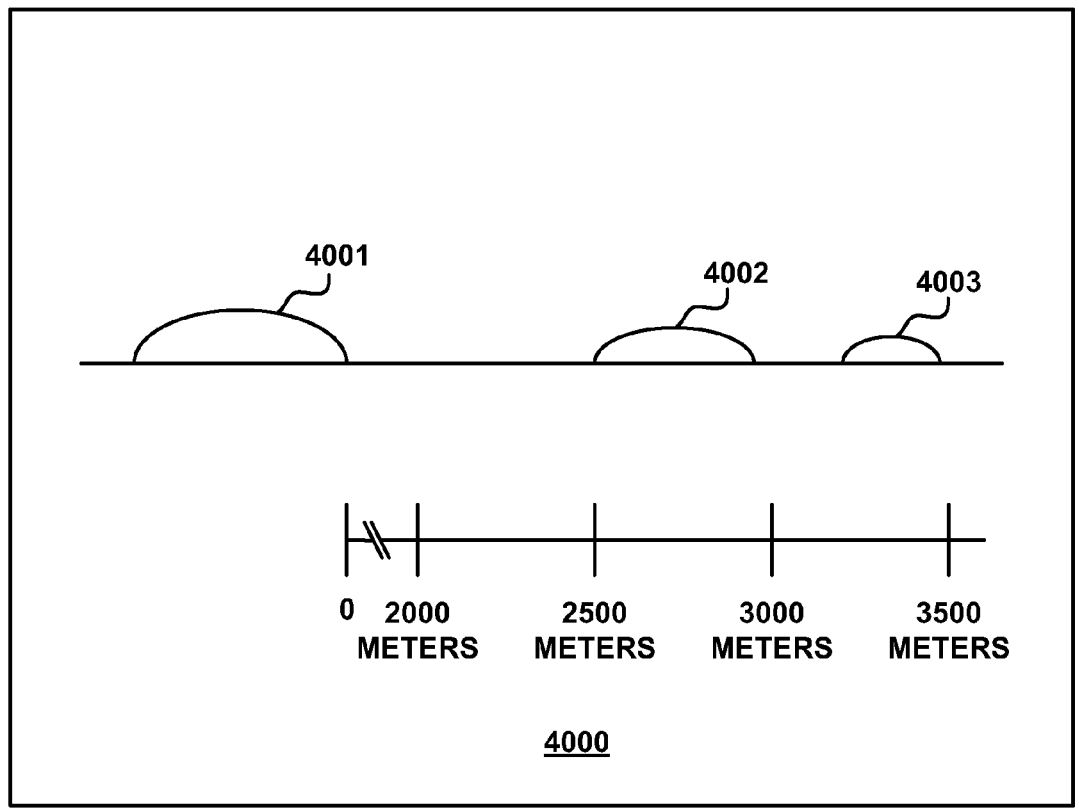
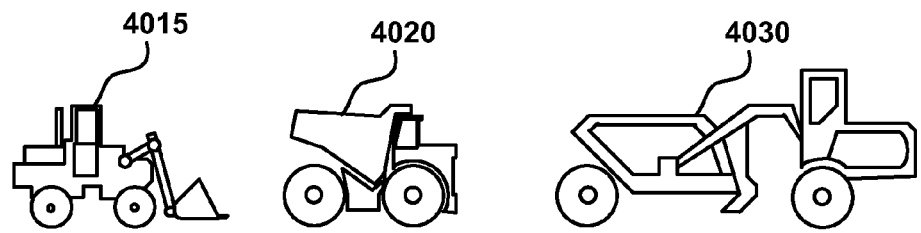
FIG. 40

4300

WEEKLY TRUCK USAGE REPORT — 4310

| TYPE 601 | DAY 4304 | DATE 4306 | HOURS OPERATED 4308 |
|---|---|---|---|
| ASSET 540B | TRUCK | MON | AUG, 14 | 8 |
| ASSET 540B | TRUCK | TUES | AUG, 15 | 7.9 |
| ASSET 540B | TRUCK | WED | AUG, 16 | 8 |
| ASSET 540B | TRUCK | THUR | AUG, 17 | 8.1 |
| ASSET 540B | TRUCK | FRI | AUG, 18 | 5.7 |

GENERATES AN ASSET INFORMATION REPORT FROM A DATABASE, WHEREIN THE ASSET INFORMATION REPORT COMPRISES AT LEAST A PORTION OF REAL-TIME INFORMATION ABOUT THE ASSET WHEN THE REAL-TIME INFORMATION ABOUT THE ASSET IS AVAILABLE.
4402

AUGMENTS THE ASSET INFORMATION REPORT BY EXTRAPOLATING AT LEAST A PORTION OF HISTORICAL ASSET INFORMATION STORED AT THE DATABASE WHEN AT LEAST A PORTION OF THE REAL-TIME INFORMATION IS NOT AVAILABLE.
4404

```
┌─────────────────────────────────────────┐
│ RECEIVING AT LEAST ONE ASSET CHARACTERISTIC │
│       FROM A REPORTING SOURCE.              │
│                 4720                        │
└─────────────────────────────────────────┘
                    │
                    ▼
┌─────────────────────────────────────────┐
│  AUTOMATICALLY ASSOCIATING THE ASSET    │
│   CHARACTERISTIC WITH A GRAPHICAL       │
│   REPRESENTATION OF THE ASSET BASED     │
│       ON THE ASSET CHARACTERISTIC.      │
│                 4730                    │
└─────────────────────────────────────────┘
                    │
                    ▼
┌─────────────────────────────────────────┐
│  PROVIDING THE GRAPHICAL REPRESENTATION OF │
│  THE ASSET ON A GRAPHICAL USER INTERFACE.  │
│                 4740                       │
└─────────────────────────────────────────┘
```

```
┌─────────────────────────────────────┐
│ UTILIZING A REPORTING DEVICE        │
│ ASSOCIATED WITH AN ASSET TO ACQUIRE │
│ AT LEAST ONE ASSET CHARACTERISTIC.  │
│ 4820                                │
└─────────────────────────────────────┘
                 │
                 ▼
┌─────────────────────────────────────┐
│ PROVIDING THE ASSET CHARACTERISTIC  │
│ TO AN ASSET MANAGER.                │
│ 4830                                │
└─────────────────────────────────────┘
                 │
                 ▼
┌─────────────────────────────────────┐
│ AUTOMATICALLY DETERMINING AN ASSET  │
│ CLASSIFICATION OF THE ASSET BASED   │
│ ON THE ASSET CHARACTERISTIC.        │
│ 4840                                │
└─────────────────────────────────────┘
```

```
┌─────────────────────────────────────────┐
│ DETERMINING WHETHER A REPORTING DEVICE IS │
│    IN A SLEEP MODE OR AN ACTIVE MODE.    │
│                  5002                    │
└─────────────────────────────────────────┘
                    ↓
┌─────────────────────────────────────────┐
│ IN RESPONSE TO DETERMINING THE REPORTING │
│  DEVICE IS IN THE SLEEP MODE, MAINTAINING│
│              THE SLEEP MODE.             │
│                  5004                    │
└─────────────────────────────────────────┘
                    ↓
┌─────────────────────────────────────────┐
│ IN RESPONSE TO DETERMINING A STATE CHANGE│
│    ASSOCIATED WITH THE REPORTING DEVICE, │
│  POWERING UP THE REPORTING DEVICE TO THE │
│                ACTIVE MODE.              │
│                  5006                    │
└─────────────────────────────────────────┘
                    ↓
┌─────────────────────────────────────────┐
│     REPORTING THE STATE CHANGE TO AN     │
│              ASSET MANAGER.              │
│                  5008                    │
└─────────────────────────────────────────┘
```

```
DETECTING AN ASSET MOVING FROM A FIRST POSITION
TO A SECOND POSITION.
5102
           │
           ▼
PROVIDED A REPORTING DEVICE ASSOCIATED WITH
THE ASSET IS IN A SLEEP MODE, THE METHOD
FURTHER COMPRISING POWERING UP THE REPORTING
DEVICE TO AN ACTIVE MODE AND REPORTING THE
MOVING TO AN ASSET MANAGER.
5104
           │
           ▼
PROVIDED THE REPORTING DEVICE IS IN THE ACTIVE
MODE, THE METHOD FURTHER COMPRISING
REPORTING THE MOVING TO THE ASSET MANAGER.
5106
           │
           ▼
POWERING DOWN THE REPORTING DEVICE TO THE
SLEEP MODE IN RESPONSE TO THE REPORTING THE
MOVING TO THE ASSET MANAGER.
5108
```

FIG. 51

5400
> PROJECT RELATED USER SELECTABLE OPTIONS
> 5410
>
>  SCHEDULE 5422
>
>  COST 5424
>
>  WORKFORCE 5426
>
>  EQUIPMENT 5428
FIG. 54A

5450
```
SELECTABLE OPTIONS LEVEL II
           5460
```
 EQUIPMENT 5428
 ASSET 5465
 LOCATION 5470
 STATUS 5475
FIG. 54B

5500

| COMPANY OVERVIEW 5510 ||||
|---|---|---|---|
| PROJECT 5420A || PROJECT 5420B ||
| SCHEDULE 5422A | OK | SCHEDULE 5422B | OK |
| COST 5424A | UNDER 2% | COST 5424B | UNDER 2% |
| WORKFORCE 5426A | 90.0% | WORKFORCE 5426B | 90.0% |
| EQUIPMENT 5428A | 85.0% | EQUIPMENT 5428B | 85.0% |

| EQUIPMENT 5428A | | |
|---|---|---|
| ASSET 5465 | LOCATION 5470 | STATUS 5475 |
| GRADER 5465A | B4 5470A | FLAT TIRE 5475A |
| DOZER 5465B | C1 5470B | OPERATIONAL 5475B |
| N 5465C | N1 5470C | DUE FOR MAINT. 5475C |

```
ACCESSING A DATABASE COMPRISING INFORMATION
FROM A FIRST REPORTING SOURCE ABOUT AN ASSET
AND INFORMATION FROM A SECOND REPORTING
SOURCE ABOUT THE ASSET.
5602
```
↓
```
UTILIZING A PRE-DEFINED USER SELECTABLE CRITERIA
TO SELECT PORTIONS OF THE INFORMATION FROM THE
FIRST REPORTING SOURCE AND THE INFORMATION
FROM THE SECOND REPORTING SOURCE.
5604
```
↓
```
TAILORING THE ASSET INFORMATION REPORT,
WHEREIN THE PRE-DEFINED PORTIONS OF THE
INFORMATION ABOUT THE ASSET ARE UTILIZED
FOR TAILORING THE ASSET INFORMATION REPORT.
5606
```
↓
```
CONFIGURING A LAYOUT OF THE ASSET
INFORMATION REPORT BASED ON A GRAPHICAL
USER INTERFACE (GUI).
5608
```

FIG. 56

6000
ACQUIRES A SAMPLE OF AN ASSET FLUID IN RESPONSE TO OCCURRENCE OF AN ANALYSIS TRIGGER
6010
MICROFLUIDIC ANALYZER COUPLED WITH ASSET ANALYZES SAMPLE IN RESPONSE TO AN ANALYSIS TRIGGER
6020
PROVIDES RESULTS OF ANALYSIS TO TELEMATIC DEVICE
6030
FIG. 60A

6000 Continued

ADDS A TEST AGENT TO MICROFLUIDIC ANALYZER FOR USE IN ANALYSIS OF SAMPLE FLUID
6040

TELEMATIC ASSET MICROFLUIDIC ANALYSIS

CROSS REFERENCE TO RELATED APPLICATIONS

Continuation-in-Part

This application claims priority and is a continuation-in-part to the co-pending patent application Ser. No. 11/801,093, entitled "SYSTEM AND METHOD FOR ASSET MANAGEMENT," by Daniel Wallace, with filing date May 7, 2007, and assigned to the assignee of the present application, the disclosure of which is hereby incorporated herein by reference.

CROSS REFERENCE TO RELATED APPLICATIONS

This Application is related to U.S. patent application Ser. No. 11/801,060, entitled "System and Method for Providing Asset Management Information to a Customer," assigned to the assignee of the present application, filed May 7, 2007.

This Application is related to U.S. patent application Ser. No. 11/801,041, entitled "Method for Providing Status Information Pertaining to an Asset," assigned to the assignee of the present application, filed May 7, 2007.

This Application is related to U.S. patent application Ser. No. 11/801,061, entitled "Enabling Notifications Pertaining to an Asset," assigned to the assignee of the present application, filed May 7, 2007.

This Application is related to U.S. patent application Ser. No. 11/801,091, entitled "Receiving Information Pertaining to a Construction Project," assigned to the assignee of the present application, filed May 7, 2007.

This Application is related to U.S. patent application Ser. No. 11/801,101, entitled "Limiting Access to Asset Management Information," assigned to the assignee of the present application, filed May 7, 2007.

This Application is related to U.S. patent application Ser. No. 11/801,014, entitled "Externally Augmented Asset Management," assigned to the assignee of the present application, filed May 7, 2007.

This Application is related to U.S. patent application Ser. No. 11/801,090, entitled "Impromptu Asset Tracking," assigned to the assignee of the present application, filed May 7, 2007.

This Application is related to U.S. patent application Ser. No. 11/801,017, entitled "Integrated Asset Management," assigned to the assignee of the present application, filed May 7, 2007.

This Application is related to U.S. patent application Ser. No. 11/801,019, entitled "Utilizing Historical Data in an Asset Management Environment," assigned to the assignee of the present application, filed May 7, 2007.

This Application is related to U.S. patent application Ser. No. 11/801,077, entitled "Method for Automatic Asset Classification," assigned to the assignee of the present application, filed May 7, 2007.

This Application is related to U.S. patent application Ser. No. 11/801,089, entitled "Method for Controlling Power Usage of a Reporting Device," assigned to the assignee of the present application, filed May 7, 2007.

This Application is related to U.S. patent application Ser. No. 11/801,116, entitled "Method for Delivering Tailored Asset Information to a Device," assigned to the assignee of the present application, filed May 7, 2007.

This Application is related to U.S. patent application Ser. No. 11/801,092, entitled "Method for Enhancing Revenue Generation for a Manufactured Asset," assigned to the assignee of the present application, filed May 7, 2007.

This Application is related to U.S. patent application Ser. No. 11/901,088, entitled "Detecting Construction Equipment Process Failure," assigned to the assignee of the present application, filed May 7, 2007, and issued into U.S. Pat. No. 7,898,403 on Mar. 1, 2011.

This Application is related to U.S. patent application Ser. No. 11/901,554, entitled "Unreported Event Status Change Determination and Alerting," assigned to the assignee of the present application, filed Sep. 17, 2007.

BACKGROUND

Presently, a cutting edge operational workplace does not always keep track with advancements in technology in every field. For example, it is not uncommon to find a shop that rents or sells the latest device managing its business using methods such as pen and paper or computing systems that are three-to-five generations behind present computing technology. One of the main adages for relying on an antiquated management system is "if it ain't broke don't fix it."

However, as modern technology advances, many establishments are realizing the advantages of certain products and are phasing them into the antiquated systems. For example, a rental company may rent an asset with an initial rental contract typed up on an early generation personal computer in a DOS program. Moreover, when the rental is returned, the same rental company may check the vehicle back into the system using a pencil and paper check-in method. That is, there may be a lot walker that walks around the returned asset and visually inspects the asset for maintenance issues, any damage, engine hours, total miles, etc.

Each of these metrics may be used by the lot walker to establish whether the asset needs any maintenance, or other attention, before being returned to the rental fleet. The resulting response is then written on a piece of paper, and affixed to the returned asset. In some cases, the asset may need more than one type of attention resulting in an asset with a plurality of papers affixed to the asset. The asset will then be re-assigned accordingly and may return to the rental lot at some later date. Moreover, as the asset is taken through the different return-to-rental status process(es), the piece(s) of paper may need to be updated, added to, or otherwise manipulated.

At the same time, the rental asset may also be affixed with a global navigation satellite system (GNSS) receiver. For example, to reduce the cost of insurance, aid in theft recovery, or the like, the rental company may have affixed the GNSS, or the asset may have arrived with the GNSS affixed. In some cases, the GNSS may be used by the user operating the asset to find directions from one location to another, or the GNSS may be used to find the position of the asset. For example, the GNSS may be used by law enforcement to recover a stolen piece of asset; the GNSS may be used by emergency personnel to find the location of the asset to provide aid or assistance; or the like.

Although the management methods described herein have used rental companies as an example, the problems associated with asset management are not limited to rental companies. An operational company may have the same asset management protocols and problems. For example, the company may have an asset that is checked out to the field by the means of an operator grabbing the asset and going. In the same way, the asset may be returned to the lot and the operator simply returns the keys to the storage location. Thus, after the asset has left, the only way of knowing what the asset is doing for the day, if it is at the right location, or even if it is used for the right job includes contacting the operator during the workday or asking the operator at the end of the day.

As margins in the asset operating business, such as construction, and the like, are reduced, it is becoming more important to properly manage the assets. For this reason, most asset operating businesses require their employees to have a phone on their person. That way, when the asset is in the field, the operator can be contacted and advised about where to operate the asset and what job should be performed.

However, this method of command and control is deleteriously unreliable. For example, the operator may not know their location, or may be wrong about their location. Additionally, the operator may misstate the job being performed, or spend more time on break than actually operating the asset. Each of these errors and omissions will further affect the already tight margins faced by the asset operating business.

Further, many assets (e.g., including vehicles and other construction equipment machines as described herein) have fluids which are vital to their continued and proper operation. These fluids are often analyzed to determine, among other things, whether they retain the properties required for proper asset operation and to determine wear characteristics of the asset based upon the chemical/metallurgical content of the analyzed fluid. For example, fluid analysis is often performed during routine preventative maintenance to provide information on lubricant and machine condition. By tracking analysis results over the life of a machine, trends can be established and/or monitored in ways which can help eliminate or predict the need for repairs.

Typically, after taking a fluid sample from an asset, a technician will need to mail, or otherwise physically deliver that fluid sample to a remote lab. Lab-on-a-chip ("LOC") devices do exist which can expedite this process by integrating one or more of several laboratory functions on a single chip. A microfluidic analyzer can be an example of an LOC. Microfluidic analyzers are common in the biotech field because they allow technicians to analyze bodily fluids without sending results to a remote lab. LOC devices and microfluidic analysis techniques can also be utilized by a trained on-location technician in order to analyze a sample of the fluid of an asset in-situ, without resorting to sending the asset fluid sample to a remote laboratory for analysis.

Frequently, end-users of assets are not skilled in fluid analysis or even in the protocols for sampling of fluids. Among other scenarios, this can be problematic, for example, if an asset is in use at a remote, difficult to access work site and/or when an asset is rented out or used for long periods of time in a situation where there is no one trained, capable, or even cognizant of performing the analyses and/or sampling of fluids.

DISCLOSURE OF THE INVENTION

A system and method for asset management is disclosed. The method receives information from a first reporting source about an asset. In addition, information from a second reporting source about an asset is also received. A database is then populated with the information from the first reporting source and the information from the second reporting source such that information from the first reporting source and information from the second reporting source can be collected from the database

BRIEF DESCRIPTION OF THE DRAWINGS

The accompanying drawings, which are incorporated in and form a part of this application, illustrate embodiments of the present invention, and together with the description, serve to explain the principles of the invention. Unless noted, the drawings referred to in this description should be understood as not being drawn to scale.

FIG. 2B is a network diagram of an exemplary method for asset management including an asset information report generator and its modules in accordance with one embodiment of the present invention.

FIG. 11 is a block diagram of an exemplary printable format of a custom asset information report generated by an asset management system in accordance with one embodiment of the present invention.

FIG. 32 is a block diagram of an exemplary printable format of an asset information report generated by an asset management system in accordance with one embodiment of the present invention.

FIG. 40 shows exemplary construction equipment assets in conjunction with an elevation view of mounds of material on a job site.

FIG. 43 is a block diagram of an exemplary printable format of a custom asset information report generated by an asset management system in accordance with one embodiment of the present invention.

FIG. 44 is a flowchart of an exemplary method for utilizing historical data in an asset management environment in accordance with one embodiment of the present invention.

FIG. 47 is a flow diagram of an exemplary method for automatically associating an asset with a graphical representation in accordance with one embodiment of the present invention.

FIG. 48 is a flow diagram of an exemplary method for automatically classifying an asset in accordance with one embodiment of the present invention.

FIG. 50 is a flow diagram of an exemplary method for managing power and reporting a state change of a reporting device in accordance with one embodiment of the present invention.

FIG. 51 is a flow diagram of an exemplary method for managing power of a reporting device in response to detecting movement of an asset in accordance with embodiments of the present invention.

FIG. 54A is a block diagram of an exemplary listing of top level user selectable items for defining a GUI dashboard in accordance with one embodiment of the present invention.

FIG. 54B is a block diagram of an exemplary listing of sub level user selectable items for defining a GUI dashboard in accordance with one embodiment of the present invention.

FIG. 55A is a block diagram of an exemplary top level user-defined GUI dashboard in accordance with one embodiment of the present invention.

FIG. 55B is a block diagram of an exemplary second level user-defined GUI dashboard in accordance with one embodiment of the present invention.

FIG. 56 is a flowchart of an exemplary method for delivering tailored asset information to a device in accordance with one embodiment of the present invention.

FIGS. 60A-60D illustrate a flow diagram of an example method of analyzing fluids, in accordance with various embodiments.

BEST MODE FOR CARRYING OUT THE INVENTION

Reference will now be made in detail to various embodiments of the invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following description of the present invention, numerous specific details are set forth in order to provide a thorough understanding of the present invention. In other instances, well-known methods, procedures, objects, and circuits have not been described in detail as not to unnecessarily obscure aspects of the present invention.

Exemplary Computer System

Figure 1:
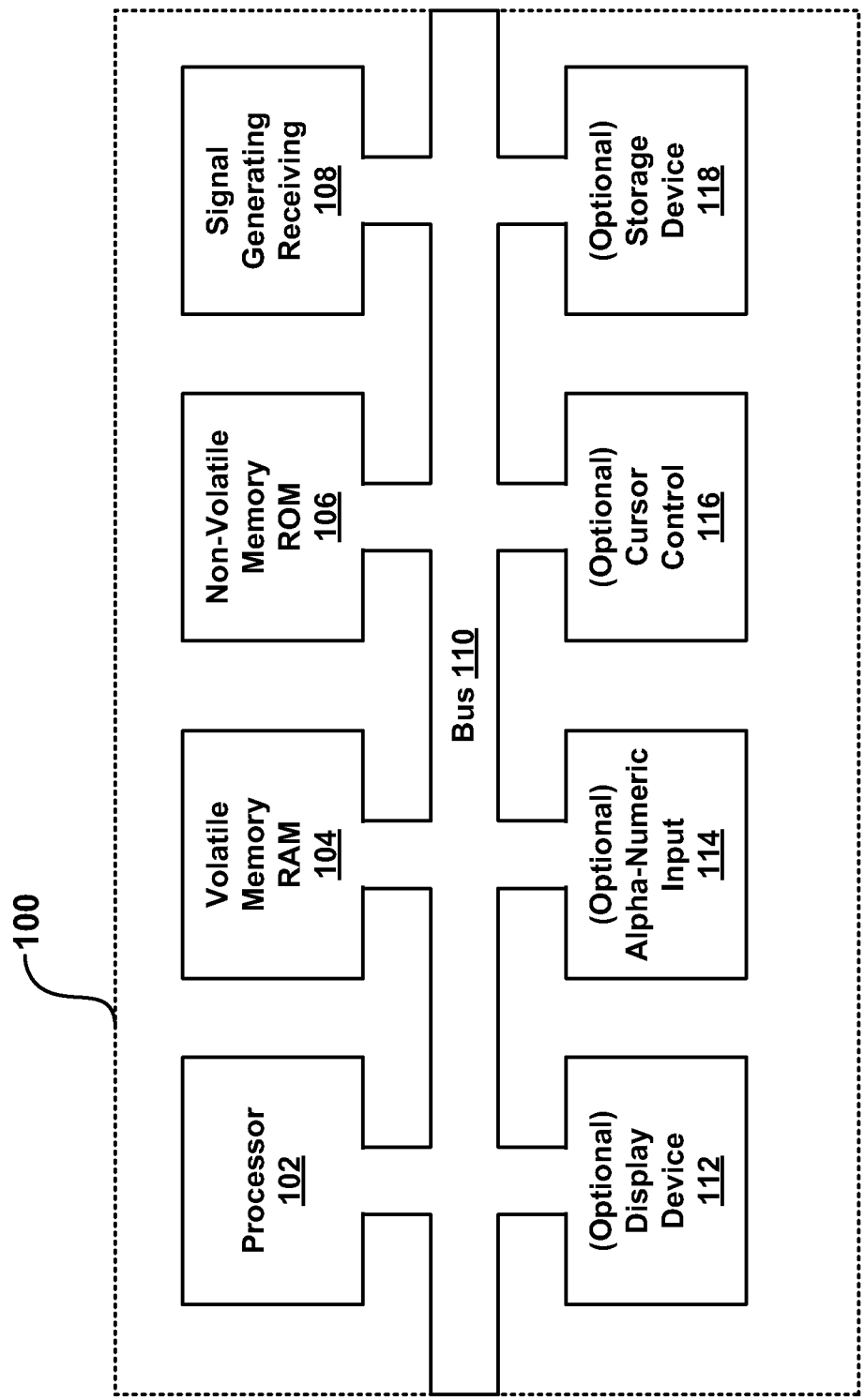
FIG. 1 is a block diagram of an exemplary computer system used in accordance with one embodiment of the present invention.

With reference now to FIG. 1, a block diagram of an embodiment of an exemplary computer system 100 used in accordance with the present invention. It should be appreciated that computing system 100 is not strictly limited to be a computer system. As such, computing system 100 of the present embodiment may be well suited to be any type of computing device (e.g., server computer, portable computing device, desktop computer, mobile phone, pager, personal digital assistant, etc.). Within the present discussions of the present invention, certain processes and steps are discussed that are realized, in one embodiment, as a series of instructions (e.g., software program) that reside within computer readable memory units and executed by a processor(s) of computing system 100. When executed, the instructions cause computer system 100 to perform specific actions and exhibit specific behavior that may be described in detail herein.

Computer system 100 of FIG. 1 comprises an address/data bus 110 for communicating information, one or more central processors 102 coupled with bus 110 for processing information and instructions. Central processor unit(s) 102 may be a microprocessor or any other type of processor. The computer system 100 also includes data storage features such as a computer usable volatile memory unit 104 (e.g., random access memory, static RAM, dynamic RAM, etc.) coupled with bus 110 for storing information and instructions for central processor(s) 102, a computer usable non-volatile memory unit 106 (e.g., read only memory, programmable ROM, flash memory, EPROM, EEPROM, etc.) coupled with bus 110 for storing static information and instructions for processor(s) 102. Computer system 100 also includes one or more signal generating and receiving devices 108 coupled with bus 110 for enabling computer system 100 to interface with other electronic devices and computer systems. The communication interface(s) 108 of the present embodiment may include wired and/or wireless communication technology.

Optionally, computer system 100 may include an alphanumeric input device 114 including alphanumeric and function keys coupled to the bus 110 for communicating information and command selections to the central processor(s) 102. The computer system 100 can include an optional cursor control or cursor directing device 116 coupled to the bus 110 for communicating user input information and command selections to the central processor(s) 102. The cursor-directing device 116 may be implemented using a number of well-known devices such as a mouse, a track-ball, a track-pad, an optical tracking device, and a touch screen, among others. Alternatively, it may be appreciated that a cursor may be directed and/or activated via input from the alphanumeric input device 114 using special keys and key sequence commands. The present embodiment is also well suited to directing a cursor by other means such as, for example, voice commands.

The computing system 100 of FIG. 1 may also include one or more optional computer usable data storage devices 118 such as a magnetic or optical disk and disk drive (e.g., hard drive or floppy diskette) coupled with bus 110 for storing information and instructions. An optional display device 112 may be coupled to bus 110 of computing system 100 for displaying video and/or graphics. It should be appreciated that optional display device 112 may be a cathode ray tube (CRT), flat panel liquid crystal display (LCD), field emission display (FED), plasma display or any other display device suitable for displaying video and/or graphic images and alphanumeric characters recognizable to a user.

Construction Services Industry

The construction services industry is an industry made up of both horizontal and vertical participants. In general, horizontal participants are those involved in actual activities of some sort at a job site, while vertical participants typically play a role as a direct enabler to the horizontal participants. In some instances, a single person or an entity can be considered a horizontal participant, a vertical participant, or both, depending upon the nature of the activity being performed. Various embodiments of the present invention, as detailed below, are directed toward the participants in the construction services industry.

Examples of horizontal participants include, but are not limited to: machine suppliers (e.g., Caterpillar® dealer, John Deere dealer, and etc.), construction contractors (both general contractors and sub-contractors), construction materials suppliers (e.g., suppliers of materials such as gravel, steel, concrete, wood, drywall, asphalt, and etc.), construction equipment rental companies, construction equipment maintenance companies, surveying firms (when working on a job site), geologists (when working on a job site), civil engineering firms, construction project management firms, and the like.

Examples of vertical participants include, but are not limited to: Construction insurance companies (e.g., companies providing insurance for construction equipment, job completion, accidents, and the like), safety inspection companies, construction project management software providers, fuel suppliers, construction materials suppliers, machine suppliers, geologists, surveyors, civil engineering firms, construction project management firms, construction equipment rental companies, construction equipment maintenance companies, contractors, and the like.

Section I

Asset Management

Overview

Embodiments described herein provide a method and system for asset management. In general, embodiments described herein utilize a plurality of disparate sources for monitoring an asset. Each disparate source provides an asset report which is populated in a database. The database is organized to combine the plurality of asset reports resulting in an organized single source of asset information. The resulting database will provide a vast plethora of asset management data with a depth significantly greater than a single information source can provide.

Moreover, by utilizing a plurality of disparate sources to provide information, the asset manager's asset awareness is significantly increased while the opportunity for asset loss due to asset source reporter failure is significantly decreased. In other words, single asset source reporter failure will not result in complete loss of asset management capabilities for the asset manager.

Furthermore, due to the asset management capabilities described herein a significant business management tool is realized. That is, because the asset management system is useful at all levels of asset management, the asset management system provides significant value added features at the manufacture level, the rental/lease level, and the owner level. Moreover, the value added features may very likely be "sell themselves" features.

For instance, the present example will focus on the exemplary construction of a supermarket. Although the following example is provided in the context of the construction field, the asset management system described herein is well suited to assets other than construction. The use of construction assets provides a well-rounded example and is utilized herein merely for purposes of brevity and clarity.

In the construction business, there are pluralities of assets required to complete a project such as building a supermarket. First, the site must be surveyed and marked; this requires survey equipment. Next, the site must be cleared and leveled; this requires graters, levelers, dozers, saws, debris transportation vehicles, etc. After clearing and leveling the site, the construction can begin; this requires diggers, pavers, concrete trucks, supply vehicles, cranes, tools, etc. Even with this exemplary construction site, the number and cost of all the assets required is significant.

Due to the significant cost and specialization of much of the construction equipment used in the supermarket construction site, the construction company may own some assets, rent some assets and lease some assets, depending on the company and the cost/usefulness of the asset in question. For example, an asset that is rarely used may be cheaper to rent or lease than to buy, while an asset often used may be cheaper to buy than to rent or lease.

The present asset management system is beneficial across the entire range of own, lease, rent and manufacture. For example, as described in detail herein, the asset management system allows a user to track an asset including its location and operation. Thus, a maintenance schedule may be provided by the asset management system. In addition, excessive wear and tear or unscheduled maintenance needs will also be recognized by the asset management system.

Therefore, because the asset location is also tracked by the asset management system, when maintenance is needed, or will be needed, the maintenance needs will be known and the location of the asset may also be known. Thus, the maintenance can be performed on the machine at the site. This results in a significant reduction in asset downtime, parts ordering hold-ups, surprise excesses in work performed by a machine and the like.

For example, if a dozer is operating at peak operation for an unexpectedly extended time period, such as disaster relief, the asset management system will be aware of the scheduled maintenance requirements and update its future maintenance forecast based on the present increase in operation time. Thus, the dozer can be serviced, in the field if necessary, when scheduled maintenance is due instead of passing the scheduled maintenance intervals, on purpose or accident, as presently occurs.

Moreover, due to the maintenance and other information tracked by the asset management system described herein, the manufacturer can begin to offer a scheduled/unscheduled maintenance program along with its sales or leases. For example, the manufacturer may sell the dozer to a construction outfit. Then, the manufacturer would utilize the asset management system to track the asset. When the scheduled maintenance is due, the manufacturer could call the buyer to schedule the maintenance or could visit the asset in the field and perform the scheduled maintenance during the dozer's downtime.

For example, the asset management system may note that the dozer's operating schedule is 6 am to 8 pm, 7 days a week. Thus, the manufacturer could visit the dozer on site during the hours of 9 pm to 5 am to perform the scheduled maintenance without hindering the dozer's operation. In so doing, the manufacturer would realize the additional income of service contracts while the buyer would realize the additional benefit of reduced downtime for the asset.

However, service contracts are not limited to the manufacturer. A rental company could utilize the same method described above to provide the same service to a renter. In addition, the rental company could track the asset's operation and location to ensure no rental contract rules were broken and that the asset is not being operated in a detrimental fashion. For example, the rental company could track any stresses placed on the asset, the speeds at which the asset was operated, any unscheduled maintenance issues occurring with the asset about which the renter may be ignoring or be unaware, and the like. Thus, the asset management system provides asset security to the rental company in addition to the income of service contracts while the renter would realize the additional benefit of reduced operational downtime for the rented asset and possibly reduced emergency repairs.

In a similar manner, the owner of the asset could also utilize the above stated advantages to ensure proper equipment treatment, monitor operators using the equipment, manage the asset for scheduled/unscheduled maintenance and the like.

Moreover, the manufacturer/rental agency/owner could also use the asset management system to track the location of the asset to reduce the opportunity of misuse and speed the recovery of theft or loss. For example, an area, such as a geo-fence, described in detail herein, could be established as a location within which the asset should remain. When the asset leaves the established area, the asset management system could provide an alert regarding the event. The user would then be able to view the location of the asset and inform the proper party of the incident. For example, in the matter of theft, the police could be contacted, while in the matter of an operator inadvertently leaving a site, the operator could be contacted to quickly resolve the matter and reduce any collateral damage that may have occurred.

Because of the significant advantages such as cost saving, asset downtime reduction and the like, the asset management system has the opportunity to propagate its own distribution. For example, initially the manufacturer may utilize the asset management system. As such, the purchaser would soon realize that scheduled maintenance is performed during regular asset downtime, and unscheduled maintenance is occurring before the asset is completely destroyed or the problem is significantly noticeable. Specifically, the purchaser would be interested in how the manufacturer knows when the scheduled maintenance is due or that a problem is occurring. Once the purchaser realized the gains in operation time, and the reductions in missed maintenance costs and the like, the purchaser would want to have the same insight for their own assets.

This same business method applies to the renter model wherein a renter notes the capabilities of the rental agency. The method even expands to the peer-to-peer model in which one asset manufacturer/renter/owner notes that another asset manufacturer/renter/owner has created new maintenance revenue, reduced asset downtime, increased asset lifespan due to regular maintenance, and the like.

Asset Management Network

Figure 2A:
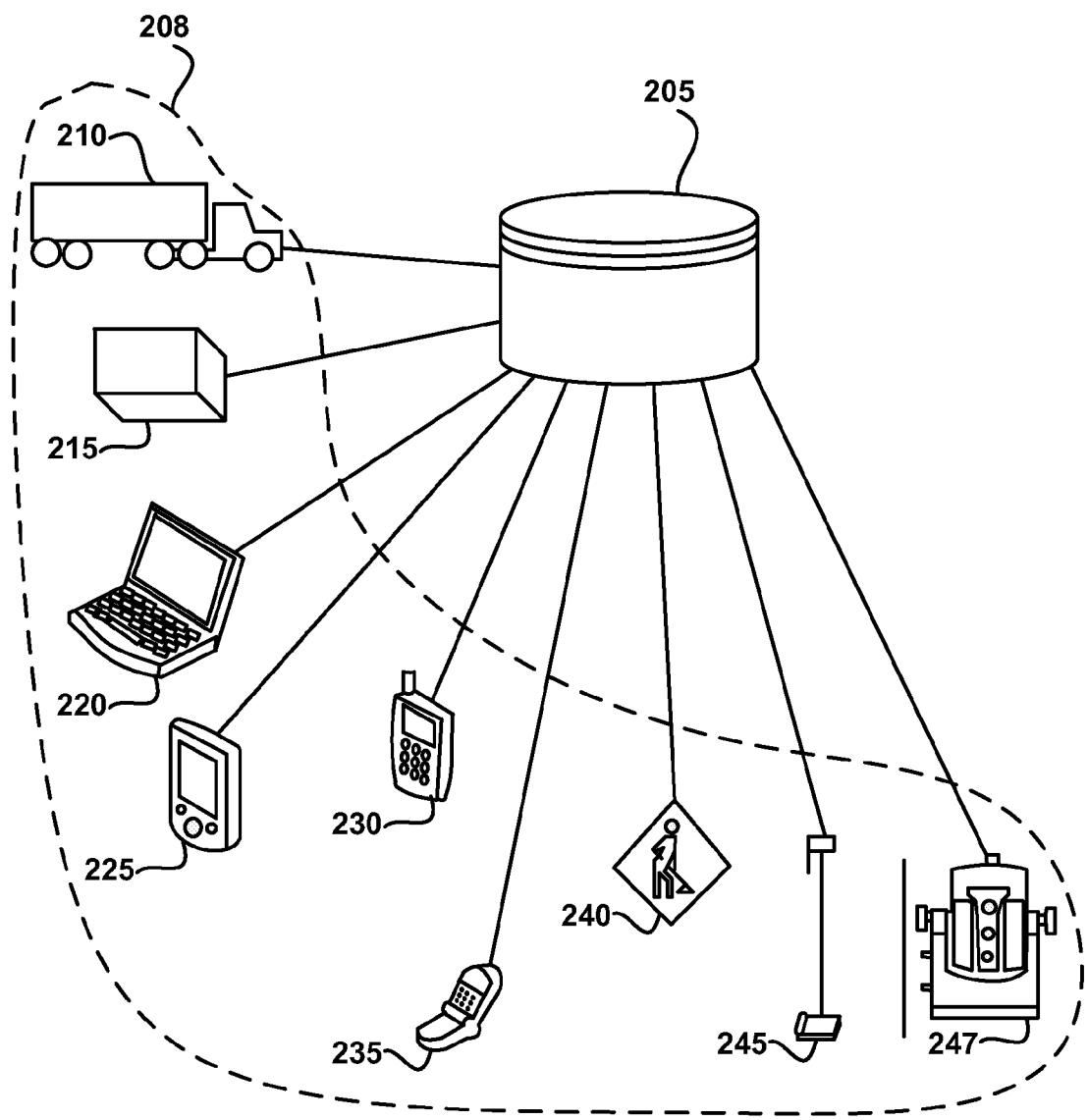
FIG. 2A is a network diagram of an exemplary method for asset management in accordance with one embodiment of the present invention.

With reference now to FIG. 2A, a network diagram of an exemplary method for asset management is shown in accordance with one embodiment of the present invention. Asset management network 200 includes a database 205, and a plurality of reporting sources 208.

Database 205 receives information from at least two reporting sources 208 and the data within database 205 is organized such that information regarding an asset can be ascertained. For example, the data within database 205 may be organized such that information regarding a particular asset, or a plurality of assets, can be ascertained or accessed.

In one embodiment, database 205 is a single database on a single computing system such as computing system 100. In another embodiment, database 205 may actually consist of a plurality of databases on a single computing system or on a plurality of computing systems. Moreover, the plurality of databases may be in the same location or spread throughout a plurality of locations. Additionally, the plurality of databases may be wired or wirelessly coupled together to form a network of databases upon which the asset information may be stored. In one embodiment, the asset may be machinery, a vehicle, an electrical or mechanical device, an inanimate object or any other traceable item.

Plurality of reporting sources 208 include devices such as, but not limited to, permanently mounted device 210, asset mountable/detachable device 215, portable computing device 220, personal digital assistant 225, smart phone 230, mobile phone 235, human intelligence (HumInt) 240, global navigation satellite system (GNSS) survey rover 245 and machine control system 247. Although, a plurality of reporting sources 208 is shown, the list is exemplary. It is appreciated that the reporting source 208 may include any number of reporting sources and reporting source methods including audio, video, text, Braille, code, passwords and the like. For example, reporting sources 208 can include electronic devices, GNSS enabled devices, machine controls, video enabled devices (e.g., camera enabled handheld devices (such as a mobile phone with camera/video, PDA with camera/video, watch with camera/video, etc.), video cameras, webcams, and the like), human sources, the asset being monitored, other assets, and the like. In one embodiment, any or all of the reporting sources 208 are capable of providing asset information including, but not limited to, location information, operation information and status information.

In one embodiment, asset mountable/detachable device 215 may be a TrimTrac™ device, a CrossCheck® device (both provided by Trimble Navigation Limited), a radio frequency identifier (RFID), a global navigation satellite system (GNSS) receiver, a video device providing a video feed, and the like. Moreover, each reporting source 208 may include capabilities such as position fixing, photography, text messaging, voice messaging, data messaging, radio frequency identification tag reading and the like. Furthermore, in one embodiment, any or all of the reporting sources 208 may be capable of asset operation monitoring. For example, any or all of the reporting sources 208 may be capable of being connected to the asset to monitor aspects of the asset including, but not limited to, a J-bus, a CAN-bus, a processor coupled with the asset, a diagnostic evaluator, an engine microprocessor, a mileage indicator, a speedometer, a tachometer, an oil pressure indicator, a wheel pressure indicator, a hydraulic indicator, an engine time monitor, an ignition switched power source, and the like.

With reference now to FIG. 2B, a network diagram of an exemplary method for asset management is shown in accordance with another embodiment of the present invention. In one embodiment, asset management network 250 includes a database 205, and a plurality of reporting sources 208 which are similar in form and function to that of FIG. 2A and are not described again in detail for purposes of brevity and clarity. However, asset management network 250 also includes the optional asset information report generator 350 and optional asset information report 360. Further details of the description and operation of optional asset information report generator 350 and optional asset information report 360 are provided in the discussion of FIG. 3.

Asset management network 250 also includes an automatic asset assigning module 355, an automatic reporting source assigning module 356, a reporting source grouper 357 and an asset grouper 358. In general, these components are optional and are used to provide further organization to the asset information report 360. For example, a preference may be selected to group a plurality of assets based on location, etc. such as described in more detail herein.

Basically, automatic asset assigning module 355 is configured to assign an asset to a section in the asset information report 360. Automatic reporting source assigning module 356 is configured to assign first reporting source 208A, second reporting source 208B and any or all other reporting sources 208 to a section in asset information report 360. Reporting source grouper 357 is configured to group first reporting source 208A, second reporting source 208B and any or all other reporting sources 208 into at least one source group based on location. Asset grouper 358 is configured to group at least one asset into at least one group.

Asset Management System

Figure 3:
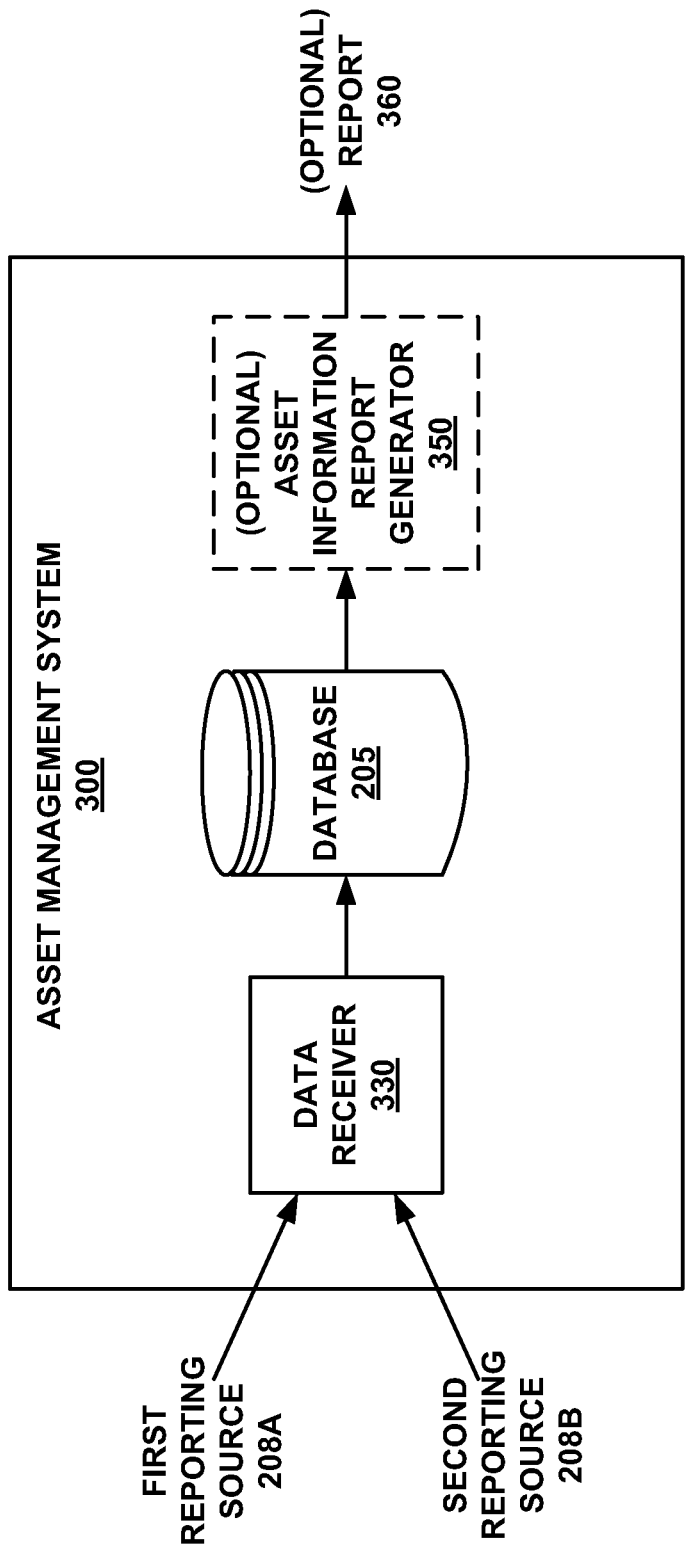
FIG. 3 is a block diagram of an exemplary asset management system in accordance with one embodiment of the present invention.

Referring now to FIG. 3, a block diagram of an exemplary asset management system 300 is shown in accordance with one embodiment of the present invention. In one embodiment, asset management system 300 receives input from a first reporting source 208A and a second reporting source 208B.

In general, the first reporting source 208A and the second disparate reporting source 208B are selected from the group of reporting sources 208 of FIG. 2A. Furthermore, the first reporting source 208A and second reporting source 208B may be similar or different reporting sources. Moreover, there may be more than two different reporting sources providing information to asset management system 300. For example, there may be three, four, seven, fifteen, or any number of different reporting sources providing information to asset management system 300. The use of two different reporting sources herein is shown merely for purposes of brevity and clarity. In one embodiment, the reporting sources input to asset management system 300 consists of information about an asset such as, but not limited to, operation, location, status, and the like.

In one embodiment, asset management system 300 includes a data receiver 330 and a database 205. In general, data receiver 330 is a wired or wireless connection that provides a connection between the asset management system 300 and the outside reporting sources such as first reporting source 208A and second reporting source 208B. In one embodiment, the connection is a network connection such as a local area network (LAN) connection, a wide area network (WAN) connection, a virtual private network (VPN), a cellular network, or the like. In another embodiment, the data receiver 330 will receive the information from the reporting sources via a direct connection. For example, the first reporting source 208A may be communicatively coupled (either wired such as via a universal serial bus (USB), firewire, or other data port, or wirelessly such as Bluetooth or the like) with the data receiver 330 and the information may be received directly to data receiver 330.

Data receiver 330 then (wired or wirelessly, via cell, WiFi, etc.) passes the received asset information to the database 205 wherein the information regarding the asset is stored. As stated herein, database 205 may be a single database on a single computing system or may actually consist of a plurality of databases on a single computing system or on a plurality of computing systems. Moreover, the plurality of databases may be in the same location or spread throughout a plurality of locations. Additionally, the plurality of databases may be wired or wirelessly coupled together to form a network of databases upon which the asset information may be stored.

In one embodiment, asset management system 300 may also include an optional report generator 350 which may provide an optional asset information report 360. In general, optional report generator 350 is one of a myriad of possible methods for organizing and presenting the information stored in database 205. For example, a user may query the asset management system 300 regarding one or more assets. The asset management system 300 may simply provide the results of the query to the optional report generator 350. Optional report generator 350 then generates optional asset information report 360 which would include the answers to the user's query. The optional asset information report 360 may be presented in a plurality of ways depending on user preference, system requirements and the like. For example, the optional asset information report 360 may be provided in a visual format, such as a piece of paper, or a graphic user interface (GUI) displayed on a cellphone, a PDA or laptop or desktop computer system. In another embodiment the optional asset information report 360 may be provided in an audible format, or in Braille, or the like.

Asset Management Operation

Figure 4:
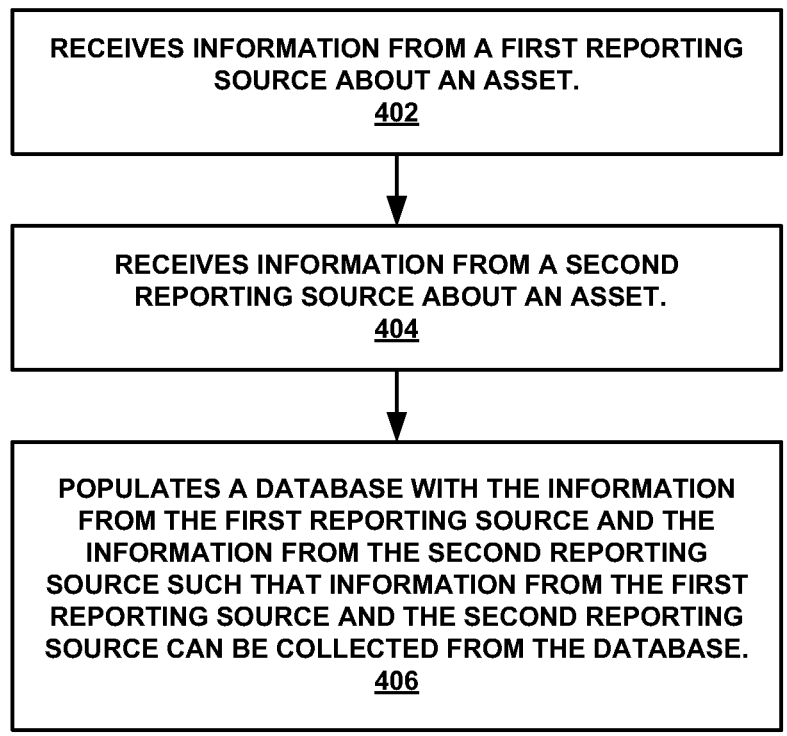
FIG. 4 is a flowchart of an exemplary method for asset management in accordance with one embodiment of the present invention.

With reference now to FIG. 4, a flowchart of an exemplary method for asset management is shown in accordance with one embodiment of the present invention.

With reference now to 402 of FIG. 4 and to FIG. 3, one embodiment receives information from a first reporting source 208A about an asset. As described in detail herein, in one embodiment the information is received to database 205 via data receiver 330. The information may be received wired or wirelessly as well as by direct connection of reporting source and data receiver 330 or over a network.

In one embodiment, the data receiver 330 receives asset location data from first reporting source 208A. In general, asset location data refers to geographic location information. For example, if the asset is a vehicle, the location data may include, but is not limited to, whether the vehicle is at a site, on a road, in the correct area of a site, etc. In general, the asset location data may be received from sources such as, but not limited to, a TrimTrac™ device, a CrossCheck® device (both provided by Trimble Navigation Limited), a mobile phone, a video device, a personal digital assistant, a portable computing device, a radio frequency identifier, a global navigation satellite system (GNSS) and human intelligence (HumInt).

In another embodiment, data receiver 330 receives asset operation data from first reporting source 208A. In general, asset operation data refers to actual asset operations. For example, if the asset is a vehicle, then the operation data may include speed of asset, mileage, hours, time since oil change or other scheduled maintenance, any squawks, what vehicle is actually doing or has previously done, and the like. Moreover, asset operation data may include actual or previous operation of the vehicle. In general, the asset operation data could be generated from operation monitoring devices including, but not limited to, a J-bus, a CAN-bus, an asset processor, a diagnostic evaluator, an engine microprocessor, a mileage indicator, a speedometer, a tachometer, an oil pressure indicator, a wheel pressure indicator, a hydraulic indicator, an engine time monitor, an ignition switched power source, and the like.

Referring now to 404 of FIG. 4 and to FIG. 3, one embodiment receives information from a second reporting source 208B about an asset. As described in detail herein, in one embodiment, the information is received to database 205 via data receiver 330. The information may be received wired or wirelessly as well as by direct connection of reporting source and data receiver 330 or over a network.

In one embodiment, the data receiver 330 receives asset location data from second reporting source 208B. In general, asset location data refers to geographic location information. For example, if the asset is a vehicle, the location data may include, but is not limited to, whether the vehicle is at a site, on a road, in the correct area of a site, etc. In general, the asset location data may be received from sources such as, but not limited to, a TrimTrac™ device, a CrossCheck® device (both provided by Trimble Navigation Limited), a mobile phone, a video device, a personal digital assistant, a portable computing device, a radio frequency identifier (RFID), a global navigation satellite system (GNSS) receiver and human intelligence (HumInt).

In another embodiment, data receiver 330 receives asset operation data from second reporting source 208B. In general, asset operation data refers to actual asset operations. For example, if the asset is a vehicle, then the operation data may include speed of asset, mileage, hours, time since oil change or other scheduled maintenance, any squawks, what vehicle is actually doing or has previously done, and the like. Moreover, asset operation data may include actual or previous operation of the vehicle. In general, the asset operation data could be generated from operation monitoring devices including, but not limited to, a J-bus, an asset processor, a diagnostic evaluator, an engine microprocessor, a mileage indicator, a speedometer, a tachometer, an oil pressure indicator, a wheel pressure indicator, a hydraulic indicator, an engine time monitor, an ignition switched power source, and the like.

Moreover, as described herein, although two reporting sources 208 are shown, the present invention is well suited to receiving information from more than two reporting sources 208 (as shown in FIG. 2A). For example, in one embodiment, the data receiver 330 may receive asset information from a multiplicity of sources such as any or all of sources 210-240.

With reference now to 406 of FIG. 4 and to FIG. 3, one embodiment populates database 205 with information from first reporting source 208A and second reporting source 208B such that information regarding the asset can be ascertained from database 205. In one embodiment, the database 205 provides real-time location and/or operation monitoring capabilities for the asset. In another embodiment, the database 205 provides near real-time location and operation monitoring capabilities for asset.

That is, any or all of the reporting sources 208 providing information about the asset may be configured to provide information constantly, regularly scheduled information updates, or provide information updates only when requested by a user. For example, the reporting source may be a PDA 225 incorporating a global navigation satellite system (GNSS) receiver with positioning capabilities based on signals from Galileo, GPS, Glonass, WAAS-wide area augmentation service, Egnos and the like. The GNSS PDA 225 may provide constant location information updates to the database. This may be important if the asset is regularly changing location or tracking its movement is important. For example, the asset could include items such as, but not limited to, tracking a concrete truck or the load of concrete in the truck, an armored vehicle, a vehicle performing a lot of movement or the like. In the same manner, any of the information about the asset can be constantly updated, the use of location information herein is merely provided as one example for purposes of brevity and clarity.

However, if the actions of the asset do not require constant updates, then the information may not be constantly provided to the database 205. Using the location example again, if the asset is sitting in the same area, e.g., it is broken, unused, awaiting maintenance, or the like, the location information may only be provided on a scheduled update period. For example, in the morning the location of the asset may be checked and then again in the evening, or only once a day, or only once a week, etc. Additionally, the asset information may be modified based on the asset's status. That is, if the asset is unused, the asset information may be updated only periodically. However, when the asset becomes operational, the information may be updated on a more regular basis, or even constantly.

In addition, in one embodiment, the asset information is presented in the form of an asset information report 360 generated from the data in the database 205. In one embodiment, the data presented in asset information report 360 is a combination of all the information received about an asset from every reporting source 208. However, in another embodiment, the data presented in asset information report 360 is a combination of only portions of the information received about an asset from any or all of reporting sources 208.

For example, database 205 may have redundant information regarding the asset from a plurality of reporting sources 208. That is, more than one reporting source 208 may be providing asset location information. In one embodiment, all the information regarding the asset, including the redundant information, in the database may be used by report generator 350 when generating asset information report 360. However, in another embodiment, report generator 350 may remove the redundant information before generating asset information report 360 to reduce bandwidth, increase report clarity, or the like. In yet another embodiment, the redundant information may be removed at the database level to manage the size of database 205.

Moreover, in one embodiment asset information report 360 may be represented on a GUI, on paper, may be audibly provided, may be digitally provided to another database or application software, or may be provided in another user selected format. For example, the asset information report may be provided in an other than visual format for a user during times, such as, when the asset information report is being provided over a communications network, or for a visually impaired user, or for a user who cannot refer to a visual asset information report for operational/safety reasons, or the like.

Asset Information Report

Figure 5:
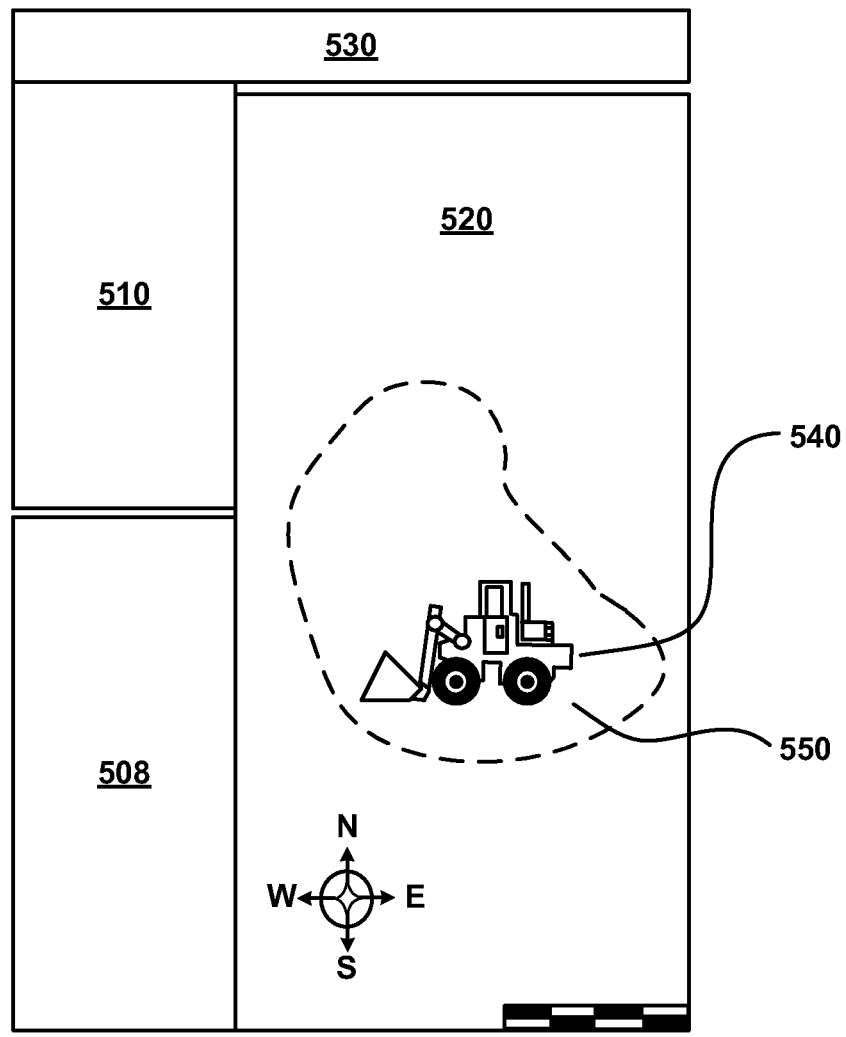
FIG. 5 is a block diagram of an exemplary GUI display of an asset information report generated by the asset management system in accordance with one embodiment of the present invention.

With reference now to FIG. 5, an exemplary GUI version of asset information report 360 is shown in accordance with one embodiment of the present invention. In one embodiment, asset information report 360 includes an asset 540, an asset column 510, an information source column 508, a map section 520 and a user toolbar section 530. In general, the user toolbar section 530 provides a means for user interaction with asset information report 360.

In one embodiment, the asset 540 is automatically assigned to the asset column 510 in the database 205 which may be further viewed in asset information report 360. Moreover, one embodiment automatically assigns first reporting source 208A and second reporting source 208B to information source column 508 of asset information report 360. In yet another embodiment, an icon for first reporting source 208A and second reporting source 208B is automatically provided on asset information report 360. For example, the icon is based on at least one characteristic of first reporting source 208A and second reporting source 208B.

Asset information report 360 also provides a grouping capability for grouping first reporting source 208A and second reporting source 208B into at least one group on asset information report 360. In one embodiment, the grouping of the sources providing asset location information is organized according to grouping methods such as, but not limited to, location of first reporting source 208A and second reporting source 208B, e.g., the same work site, same geo-fence location, etc; type of first reporting source 208A and second reporting source 208B, e.g., GNSS, 225, laptop 220, etc; assigned area of first reporting source 208A and second reporting source 208B, e.g., the same work site, same geo-fence location, etc; user assigned to first reporting source 208A and second reporting source 208B, company providing first reporting source 208A and second reporting source 208B, company utilizing first reporting source 208A and second reporting source 208B, and the like.

In another embodiment, asset information report 360 provides a grouping capability for grouping a plurality of assets into at least one group on asset information report 360. In one embodiment, the grouping of the plurality of assets is selected from the grouping methods such as, but not limited to, the location of the asset, the type of asset, the assigned area of the asset, the user assigned to the asset, the company providing the asset, and the company utilizing the asset.

In addition, when asset information report 360 is provided on a GUI, a map image 520 may also be automatically provided. In one embodiment, the map image 520 is a satellite image. In another embodiment, the map image 520 is selected from image types such as, but not limited to, a topographic image, a road map image, a hybrid image, a site design, computer aided design (CAD) file, geographic information system (GIS) map, and the like. Furthermore, in one embodiment, a user modifiable geo-fence 550 may be positioned on a portion of map image 520. In general, a geofence 550 is a user selectable boundary which may be drawn or placed on map image 520.

For example, if a user is focused on an area of interest, the user can selectively mark the area of interest on map image 520 by drawing a boundary around the area. Then, the report generator 350 will update asset information report 360 to show the boundary line and recognize the coordinates of the boundary line as a geofence 550. The geo-fence 550 can then be used as a virtual fence, per se. That is, if an asset 540 is in a geo-fence 550, the asset 540 information can be configured such that an alert or message of some type will be generated when the asset 540 leaves the area defined by geo-fence 550.

In addition, in one embodiment, an icon (or other recognition type such as name, capacity, etc.) for the asset 540 may be automatically provided on asset information report 360. Wherein the icon is based on at least one asset 540 characteristic received by at least one of first reporting source 208A and second reporting source 208B. For example, the asset is a 5-ton truck and reporting source 208A is reporting information received from diagnostic systems such as the J-bus or the like. Part of the asset information report may include a vehicle identification (VIN) number or other identifying characteristics about the asset. When the information is retrieved from database 205 by report generator 350 and provided on asset information report 360, the information will be automatically turned into an identifier for the asset. In one embodiment, the information is directly translated into an identifier, such as if the diagnostic system defined itself as a system for a 5-ton truck. However, in another embodiment, the report generator 350 may recognize the VIN number (or other identifier) and access another database, e.g., the Internet, and search the VIN number to identify the type of asset. Then, the report generator 350 may either output the identity description in asset information report 360 or may further access an icon database (such as a local database, the Internet, or the like) and match the description of the asset with an icon. For example, a description "5-ton truck" may result in a 5-ton truck icon or simply a large truck icon. That is, the description and icon may be exact matches or the icon may be only a close approximation. Moreover, the asset identity description may be included with the asset icon or may not, depending on user preference.

As stated herein, in one embodiment asset information report 360 may not include information on every asset stored on database 205 or even every piece of information regarding a particular asset stored on database 205. For example, a user may have different levels of access to database 205 and may therefore receive an asset information report 360 that is limited in scope based on the user's level of access. Although a user may have database limitations within any of the formats of asset information report 360, the limitations of a specific user access is further described in conjunction with FIG. 6.

Figure 6:
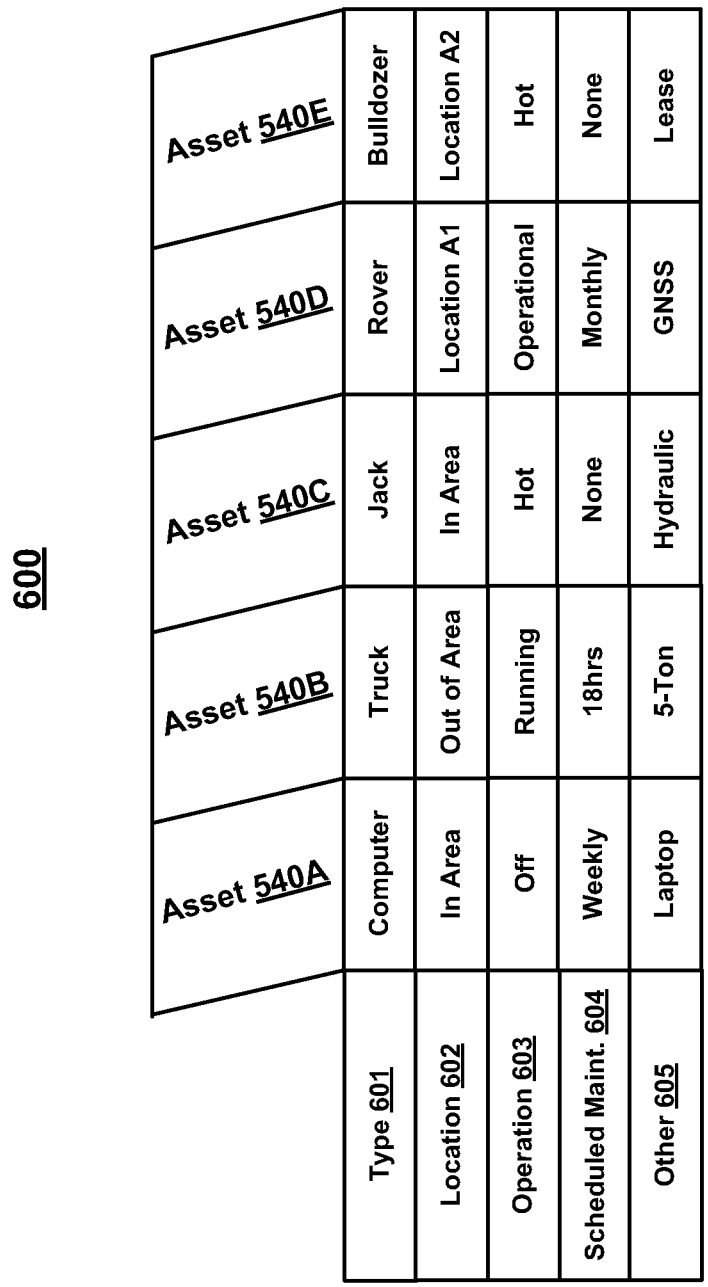
FIG. 6 is a block diagram of an exemplary printable format of an asset information report generated by the asset management system in accordance with one embodiment of the present invention.

With reference now to FIG. 6, a block diagram of an exemplary printable format 600 of an asset information report 360 generated by the asset management system 300 is shown in accordance with one embodiment of the present invention. In one embodiment, asset information report 600 includes asset type 601, location 602, operation 603, scheduled maintenance 604 and other 605. In asset information report 600, three assets are shown. However, the number of assets shown and the asset information provided is merely exemplary. That is, the configuration of asset information report 600 is one of a plurality of possible report configurations and is provided herein merely for purposes of brevity and clarity.

Moreover, as stated herein, asset information report 600 may include repetitious data from a plurality of information sources 208 or asset information report 600 may be pared down to include information related to only a selection of information sources 208, only provide non-redundant information, or the like.

In general, asset information report 600 is used herein to illustrate access and configuration issues which may be utilized by the asset management system 300. For example, in one embodiment, the complete database 205 of asset information includes five assets (e.g., asset 540A-540E) and five types of information (asset type 601, location 602, operation 603, scheduled maintenance 604 and other 605). Thus, a complete asset information report including all of the data within database 205 would look similar to asset information report 600. However, it is quite possible for an asset information report 600 to include less than all the asset information within database 205.

Therefore, if every asset in database 205 was under the control of a single user, then the user's asset information report 600 may include every asset as well as any or all of the user selected information about the asset. However, if every asset in database 205 is not under the control of a single user, then each user's asset information report may include only portions of asset information report 600 shown.

For example, a rental company may have five assets (540A-540E) in the database and may utilize asset information report 600 to keep track of the assets location 602, operation 603, scheduled maintenance 604 and other 605. However, when the asset is rented, the rental company may reduce their own access to database 205 and allow the renter limited access to database 205. For example, the rental company rents asset 540B. Then, for matters of privacy, the rental company may limit their access to the location 602 of the asset. In other words, the rental company may establish a geo-fence that reduces the location 602 information to within an area or outside of an area. At the same time, the rental company may continue to monitor the assets operation 603 and scheduled maintenance 604.

Additionally, the renter may receive limited access to the rental companies database 205 and therefore receive an asset information report 600 that includes any or all of the information related to the specific asset rented (e.g., 540B). For example, the renter may be able to access location 602 and operation 603 information but may not be able to view scheduled maintenance information 604. In another embodiment, the renter may be able to access only portions of information such as whether the machine is running, but not the speed at which it is traveling.

By utilizing the method of asset information report 600 partitioning, limiting, and access management described herein. The present invention allows information about an asset to be provided to as few or as many users as desired. In addition, the present invention also provides any or all of the users with varying levels of information access based on user preference or other information management schemes.

Thus, embodiments of the present invention provide an automated asset management system and method. Embodiments further provide automated asset management system and method which includes asset location information. Embodiments further provide automated asset management system and method which includes asset operation information. Embodiments further provide an asset management system and method which is user configurable and which may be displayed in a plurality of formats and configurations based on user and system manager preferences. For example, the displayed results may be provided at user selectable refresh rates, at system selected refresh rates, based on billing methods, or the like.

Section II

Enhancing Asset Management

Enhanced Asset Management System

An enhanced asset information system is one which further increases the efficiency, ease, or methods with which asset information may be utilized. This can comprise additions or modifications to asset information system 300 which allow asset information reports to be customized and/or formatted for or coupled to customer applications which exist apart from the asset information system.

Figure 7:
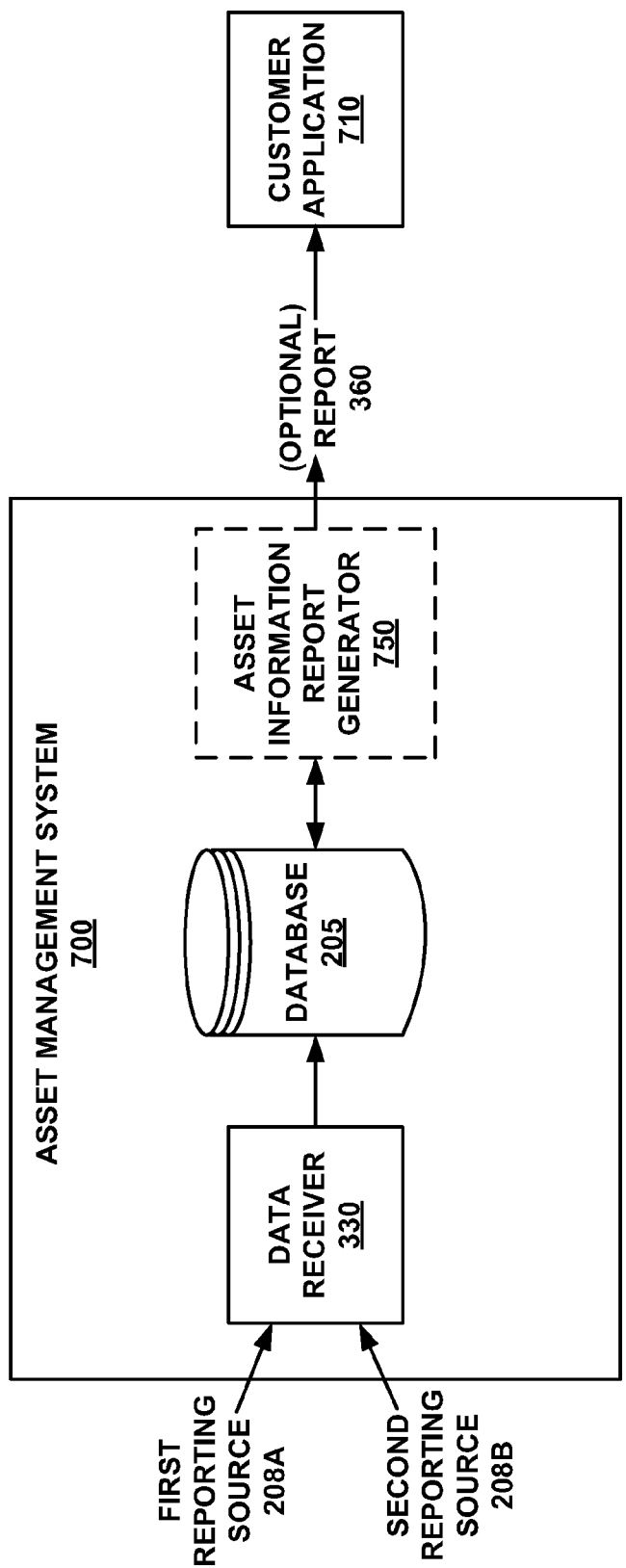
FIG. 7 is a block diagram of an exemplary asset management system communicatively coupled with a customer application in accordance with one embodiment of the present invention.

Providing Asset Management Information to a Customer Application With reference now to FIG. 7, an exemplary enhanced asset management system 700 is shown communicatively coupled with a customer application 710 in accordance with one embodiment of the present invention. Asset management system 700 is comprised of data receiver 330, database 205, and asset information report generator 750.

In general, data receiver 330 is configured for receiving information about an asset from multiple reporting sources (such as sources 208A and 208B). Data receiver 330 reports this asset information to database 205, which is then populated with a first portion of information about an asset from a first reporting source 208A, a second portion of information about an asset from a second reporting source 208B, and so on for other reporting sources 208 which report information about an asset. Moreover, database 205 may similarly receive and maintain information for a plurality of assets. The specific functions and operation of data receiver 330 and database 205 have been previously described, and for purposes of brevity and clarity will not be re-described herein except as necessary to identify any differences or previously undescribed features.

Asset information report generator 750 operates in the same fashion and possesses the same qualities as optional asset information report generator 350, which has been previously described. Thus, like asset information report generator 350, asset information report generator 750 is configured to communicatively couple with database 205 for generating an asset information report 360 from asset information data provided from database 205. As previously described an asset information report 360 comprises data, such as operational data or location data for at least one asset. However, as represented in the embodiment of asset management system 700, asset information report generator 750 is additionally configured to be optionally communicatively coupled with a customer application 710 (or multiple customer applications (710a, 710b . . . 710n)) for providing an asset information report 360 from database 205 to the customer application. Thus, in addition to the previously described techniques for providing asset information via reports 360, the embodiment of asset management system 700 is configured for providing one or more asset information reports 360 to one or more customer applications 710.

A customer application 710 as discussed herein is a software application used for reporting, managing, viewing, processing, or manipulating asset information. For example, a customer application is a software application such as, but not limited to, a spreadsheet application, a word processing application, a database application, an accounting application, a project management application, a payroll application, a billing application, a rental asset management application, an inventory application, a database file, a computer server, and the like. Often, customers have one or more internal processes on customer applications 710 which may benefit from the use of asset management information that is maintained in database 205. Previous descriptions of asset management report 360 described asset management information provided in formats such as a printed report or in a graphical user interface by asset information report generator 350. In addition to such report formats, asset information report generator 750 is also configured to provide an asset information report 360 from database 205 to customer application 710, in an electronic format compatible with the use by customer application 710.

Figure 8:
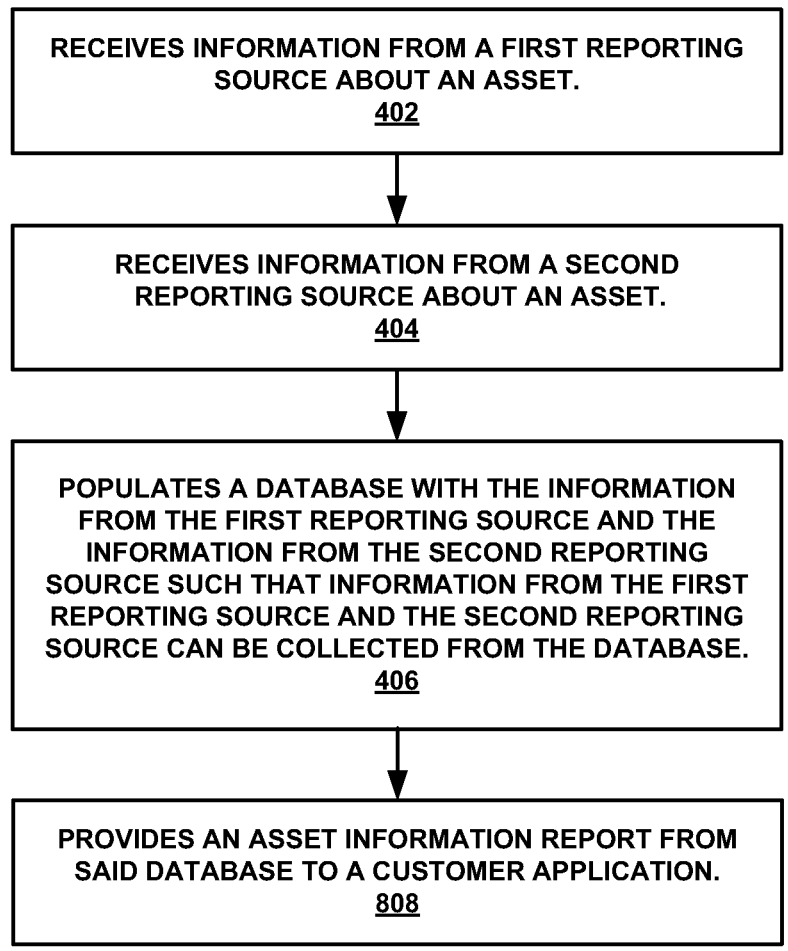
FIG. 8 is an expanded block diagram of an asset information report generator utilized in conjunction with an exemplary asset management system in accordance with one embodiment of the present invention.

FIG. 8 is a flowchart 800 of an exemplary method for providing asset management information to a customer application 710 in accordance with one embodiment of the present invention. In FIG. 8, elements 402, 404, and 406 have been previously described, and in the interests of brevity and clarity will not be redescribed herein. Instead reference is made to previous descriptions of these flowchart elements.

With reference now to element 808 of FIG. 8 and to FIG. 7, one embodiment provides an asset information report 360 from database 205 to a customer application 710. In such situations where a customer utilizing asset management system 700 desires to use asset management information in their own customer application 710, communicatively coupling asset management information from database 205 to a customer application 710 provides beneficial efficiency gains in many instances. For example, communicatively coupling an asset information report 360 directly or indirectly into a customer application 710 offers a significant time savings and labor reduction over printing or viewing a report 360 and then manually reentering information from the report into the customer application 710. This can reduce or eliminate process bottlenecks that are often associated with manually inputting data into a customer application. Reducing or eliminating such data entry bottlenecks provides useful access to the asset information within a customer application 710 in real time or near real time, without the hours or even days of delay to access of asset information that present methods of data entry may impose.

Consider an example of an equipment rental company which utilizes a database to track maintenance requirements for construction equipment assets and other rental assets rented by the company. For purposes of this example, the rental company's maintenance database can be considered a customer application 710. Printed asset information report 600, shown in FIG. 6, displays data fields (type information 601, location information 602, operation information 603, scheduled maintenance information 604, and other information 605) for rented assets of a computer 504A, a truck 540B, and a jack 540C. In this example, all of this asset information is used in the rental company's maintenance database. Rather than printing this report and then manually re-keying information from the report into the maintenance database, asset information report generator 750 allows the information to be coupled either directly or indirectly into the customer application with minimal effort on the part of an operator of asset management system 700.

For example, in one embodiment, a user of the asset information report generator 750 selects a database file type (or another file type, depending on the customer application 710) as the output format of an asset information report 360. In one embodiment, asset information report generator 750 sends a query for the desired asset information to database 205. In one embodiment, this query indicates the customer application 710 that the data will be formatted for is a particular type of maintenance database (or some other type of customer application 710), or else indicates the proper electronic file type, such as a database file, in which the asset information report 360 will be delivered to the customer application 710. In one embodiment, database 205 responds to the query by supplying an asset information report 360, which is formatted in an electronic file type, such as a database file which is readable and usable by customer application 710 (a maintenance database in this example). Asset information report generator 750 then stores this asset information report 360 as an electronic file or forwards it on to customer application 710, depending upon a user selection.

In another embodiment, asset information report generator 750 sends a query to database 205 for asset information. In one embodiment, such as in the case of a custom report, this query is generated from a custom report module (described below) accessed by information report generator 750. Asset information report generator 750 then formats the asset information received from database 205 into an asset information report 360 in an electronic file type readable by customer application 710 (which in this example is a maintenance database). In one embodiment asset information report generator 750 references instructions in a custom report module to format the asset information report 360 into a proper electronic file format for customer application 710. In one embodiment, after the asset information report 360 is properly formatted, such as into a database file, it is forwarded to customer application 710. In another embodiment, asset information generator 750 instead stores the formatted asset information report 360 as an electronic file.

Storing the asset information report 360 allows the user to select a means for transferring the electronic file to the customer application 710, such as by: transferring the file onto a portable media (disk, flash drive, etc.) and manually copying the file to a computer system or network that customer application 710 is running on or from; emailing the file to an account accessible from the computer system or network that customer application 710 is located on; manually or automatically accessing the stored file via a wired or wireless coupling between asset management system 700 and customer application 710, such as, Bluetooth, an intranet, a local area network, a wide area network, the Internet, a radio network, a cellular phone network, or other similar wired or wireless information means for transferring information.

Although, flowchart 800 describes a method for reporting on a single asset, it is appreciated that in some embodiments database 205 receives information for a plurality of assets. In such embodiments, providing an asset information report 360 from database 205, can comprise receiving an asset information query about a grouping of the plurality of assets. Many such groupings are possible, such as, for example, groupings based upon: a period of time of operation of an asset (such as a day, date, time of day, range of time, and etc.); location of operation of an asset (such as inside a particular geo-fence); type of an asset (truck, bulldozer, computer, and etc.), area assigned to an asset (such as a geo-fenced area around a construction site); user assigned to an asset (such as a particular worker); and company assigned to an asset (such as an entity that rents, owns, or operates the asset). As previously described, asset information report generator 750 then stores or forwards asset information received in response to such a query. In some embodiments, as previously described, asset information report generator 750 performs formatting, if necessary, to format the asset information report 360 into a correct electronic file type for a customer application 710 that is designated as a recipient of the asset information 360.

Thus, an asset information report 360 in an electronic format that is useable by a customer application 710 can be directly or indirectly coupled into the customer application 710. Compared to manually entering information from the asset information report into the customer application 710, this saves time, improves operating efficiency of a company, and reduces data errors.

Customized Asset Information Report

In some instances, a standard asset information report 360 that is generated with asset information report generator 750 may contain more or less information than is needed for a particular customer application 710. Likewise, a standard asset information report 360 generated by asset information report generator 750 may arrange asset information in a manner that is not preferred by a customer or is incompatible or inconsistent with an arrangement of asset information utilized within a customer application 710. Moreover, in some instances, asset information report generator 750 may be unequipped for providing an asset information report 360 in a desired electronic file format that is compatible with a particular customer application 710. In such instances it may be desirable to have a customized asset information report 360. In one embodiment, a capability for generating customized asset information reports 360 is provided by configuring asset report generator 750 to recognize and utilize one or more plug-in type custom report generator modules.

Figure 9:
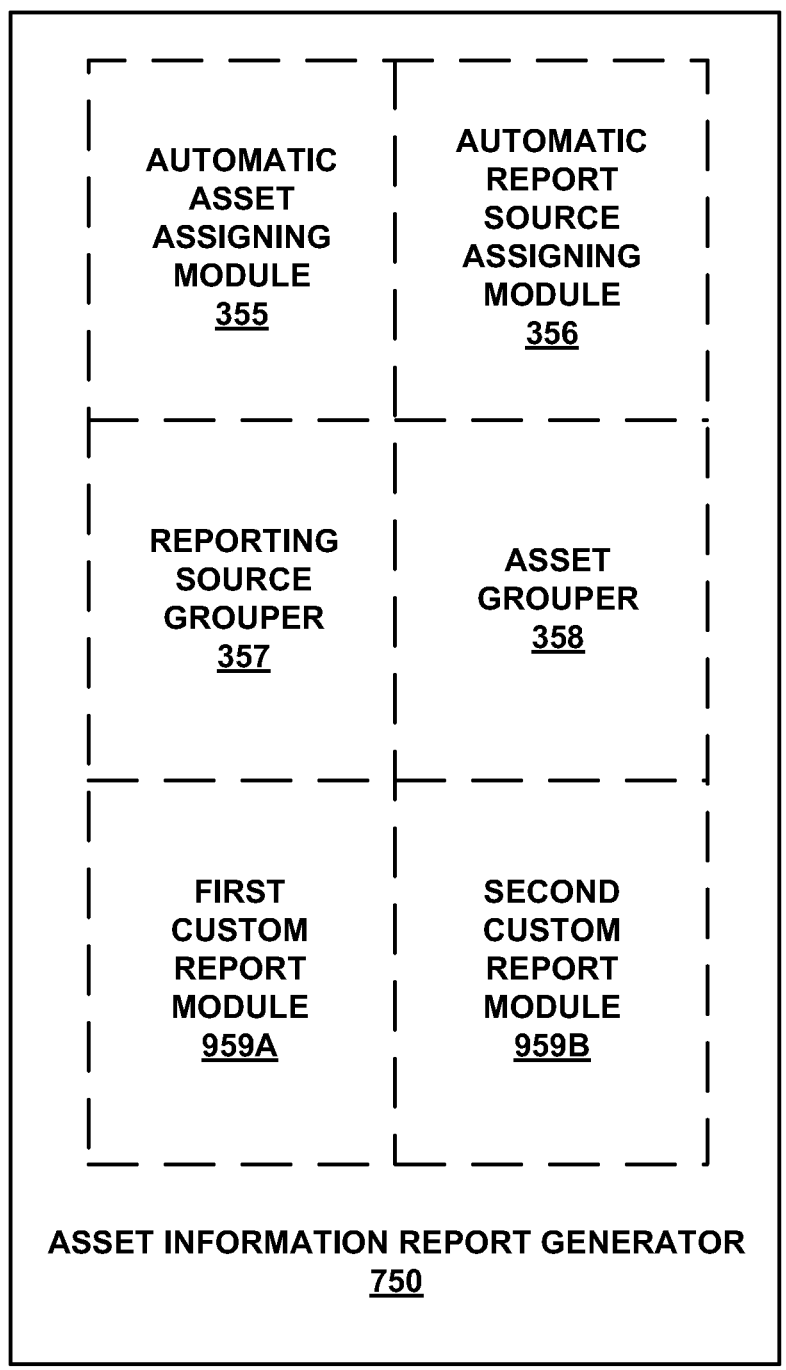
FIG. 9 is a flowchart of an exemplary method for providing asset management information to a customer application in accordance with one embodiment of the present invention.

With reference now to FIG. 9, an expanded block diagram of an asset information generator 750 which is utilized in conjunction with exemplary asset management system 700 is shown in accordance with one embodiment of the present invention. As shown in FIG. 8, asset information report generator 750 is comprised of an automatic asset assigning module 355, an automatic reporting source assigning module 356, a reporting source grouper 357, and an asset grouper 358, all of which have been previously described. The embodiment of asset information report generator 750 shown in FIG. 9 also comprises a first custom report module 959A and a second custom report module 959B. It will be appreciated that fewer or more custom report modules may be included in other embodiments of asset information report generator 750, depending on the number of customized asset information reports that a user desires to generate.

Figure 10:
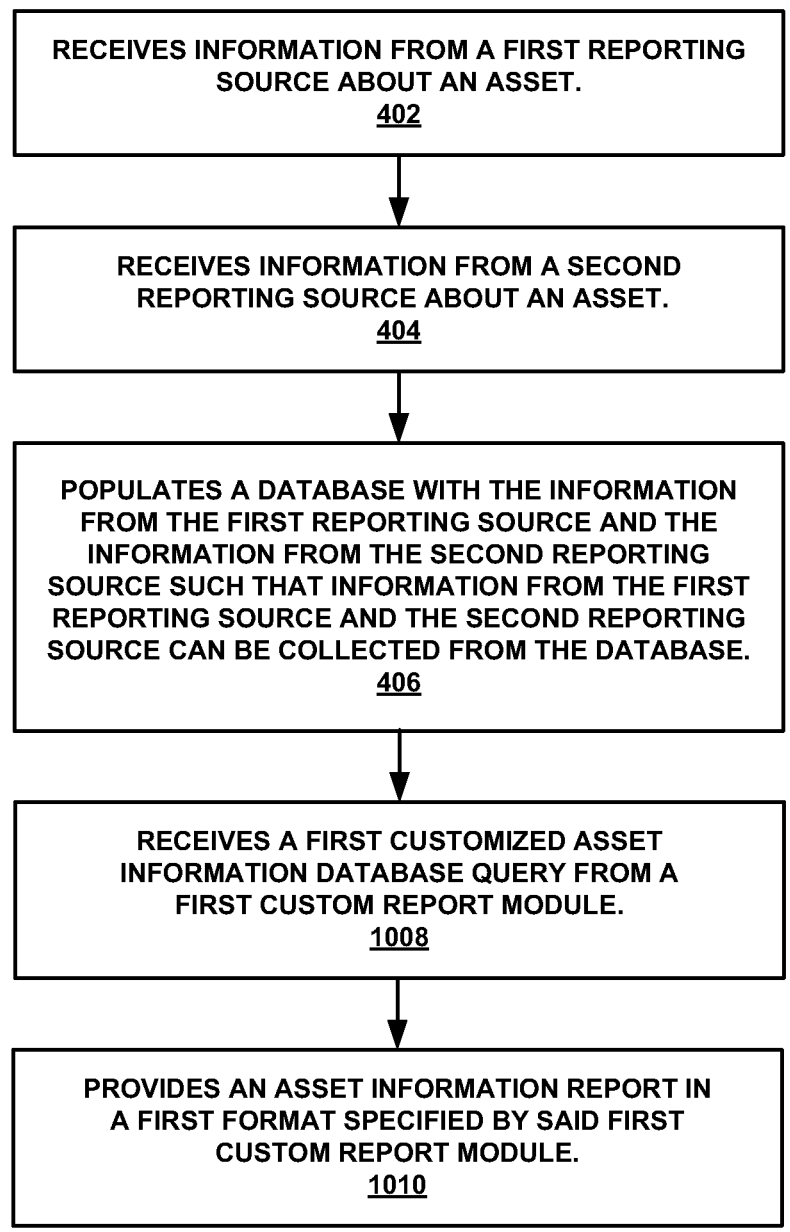
FIG. 10 is a flowchart of an exemplary method for providing customized asset management in accordance with one embodiment of the present invention.

FIG. 10 is a flowchart 1000 of an exemplary method for providing customized asset management information in accordance with one embodiment of the present invention. In FIG. 10, elements 402, 404, and 406 have been previously described, and in the interests of brevity and clarity will not be re-described herein. Instead reference is made to previous descriptions of these flowchart elements.

With reference now to 1008 of FIG. 10 and to FIGS. 7 and 9, one embodiment receives a first customized asset information database query from a first custom report module 959A. For example, in one embodiment, first custom report module 959A issues a customized asset information query, via asset information report generator 750, to database 205 to query information for a customized asset information report 360. In one embodiment, this is a customized query for particular information about a particular asset or a particular grouping of assets. In one embodiment, the query is a standard or customized query for asset, the response to which will be formatted in a customized manner according to instructions provided by first custom report module 959A.

With reference now to 1010 of FIG. 10 and to FIGS. 7 and 9, one embodiment provides an asset information report 360 in a first format specified by the first custom report module 959A. In one embodiment, first custom report module 959A formats information received from database 205 in response to query. For example, the information may be formatted into a customized asset information report 360 arrangement and then output into an electronic file, a printed report, a graphic user interface. Such a report can also be saved, output, or provided to a customer application 710.

In one embodiment, providing an asset information report 360 comprises providing an asset information report 360 in a customized electronic file type format that is useable by a customer application 710. This is especially useful when generation of an asset information report 360 for a particular customer application 710 is not otherwise supported by asset information generator 750. For example the electronic file type may be a file type used by a customer application 710 such as, but not limited to: a spreadsheet application, a word processing application, a database application, an accounting application, a project management application, a payroll application, a billing application, a rental asset management application, an inventory application, and the like.

In one embodiment, providing an asset information report 360 comprises providing an asset information report 360 where the asset information is displayed in a customized configuration, such as a customized visual configuration. This can include a visual presentation of icons overlaid on a map, a special arrangement of rows and columns of data, or some other customized visual arrangement of asset information that is specified by a custom report module, such as custom report module 959A. In one embodiment, providing an asset information report comprises providing the asset information report with particular set of asset information that that is specified by first custom report module 959A. This is useful, for instance, when a standard asset information report 360 available from asset information report generator 750 contains too much information or not enough information for a customer.

With reference now to FIG. 11, a diagram of an exemplary printable format 1100 of a custom asset information report 360 generated by asset management system 700 is shown in accordance with one embodiment of the present invention. As shown in FIG. 11, an asset information report with a customized title 1110 "WEEKLY TRUCK USAGE REPORT" has been generated by custom report module 959A. The report has been formatted with information from a customized query of asset information regarding asset 540B, a truck. Information is arranged in a customized configuration of rows and columns, where each row represents asset 540B and each column represents particular asset information pertaining to asset 540B. Column 601 represents asset type. Column 1104 represents a day of a work week. Column 1106 represents a calendar date associated with the particular day of the work week. Finally, column 1108 represents the total hours that asset 540B was utilized during a particular day and date.

This customized printable format 1100 is used, for instance, by a payroll department to determine if the hours an asset has actually been operated correspond to automated time clock entries for an operator of the asset. In this example, the employee is a truck operator who wears an RFID name badge which triggers a time clock entry while the employee's name badge is in the cab of truck 540B. If the employee (or more specifically his name badge) was shown by time clock entries to be in the cab of truck 540B for eight hours each workday (Monday through Friday), it is easy to determine that there may be a discrepancy between the employee's clocked time and the hours (5.7) that asset 540B was operated on Friday, August 18th. An investigation may show that the employee may sat idle for just over two hours, left his name badge in a non-operated vehicle, or else truck 540B may not have been operated as efficiently as possible during the work day. Furthermore, in one embodiment, if eight hours of operating time are the standard amount of expected operating time, block 1120 can be automatically flagged or highlighted to indicate a large variance from the expected operating time of asset 540B.

A custom report module such as custom report module 959A, may be implemented in numerous ways. For example, in one embodiment, custom report module 959A comprises a file accessed by asset information report generator 750. In one embodiment, this file may contain a set of pre-constructed database queries for issuing to database 205. These queries can be issued manually by a user or automatically, such as upon startup or at pre-determined time intervals. In one embodiment where asset information report generator 750 is implemented in a Windows® type operating environment, each custom report module is implemented as a dynamic linked library (DLL) file that is stored in a directory which is automatically accessed by asset information report generator 750. For ease of programming, in one embodiment, asset information report generator 750 is implemented using a .NET programming language. This allows a custom report module to also be written in a .NET compatible language, which will facilitate streamlined interoperation with the functionality, user interfaces provided, and other modules of asset information report generator 750. In such an embodiment, a custom report module written in a .NET programming language may also be stored in a directory accessible by asset information report generator 750, for example as a DLL file.

If additional customized asset information reports 360 are desired, additional custom report modules (959B . . . 959n) are added to asset information generator 750 to facilitate generation of the desired reports. For example, in FIG. 9 asset information report generator 750 is shown configured with a second custom report module 959B. In one embodiment, second custom report module 959B automatically issues a second customized asset information query to database 205, for the purpose of generating a second customized asset information report 360. A second asset information report is then provided by asset information report generator 750 in a second format specified by second custom report module 959B. Additional custom report modules (959B . . . 959n) are implemented in and operate in a manner consistent with the described implementation and operation of custom report module 959A.

By building in the capability to recognize and utilize custom report modules, such as custom report module 959A, numerous parties are allowed to implement plug-in type custom report modules for asset information report generator 750. For example, in one embodiment, the original manufacturer of asset management system 700 can create a custom report module 959A for use by one or more customers. This is useful for upgrades or for tailoring asset management system 750 to the needs of a particular customer. Likewise, a technically savvy customer may create their own custom report module 959A. Additionally, the manufacturer, the customer, or both have the flexibility to engage an independent contractor to create a custom report module 959A to fill a particular need.

Thus, embodiments of the present invention provide enhanced asset management systems and methods. Embodiments further provide automated methods to customize asset information reports both visually and electronically. Embodiments also provide for automated methods to provide asset information reports for customer software applications that run independently from the enhanced management system. Additionally, methods and systems are provided for saving an electronic file formatted for use in a customer application or for manually or automatically providing such a formatted file to a customer application.

Section III

Providing Status Information Pertaining to an Asset

Overview

Referring to FIG. 3, information about assets from more than one reporting source 208A and 208B can be received by an asset management system 300 and stored in a database 205. The asset management system 300, according to one embodiment, can be provided by a rental company. Construction company employees, according to one embodiment, can use a client computer to request and display information stored in the database 205. For example, they can use a client computer to display visual representations including schematic diagrams or pictorial images of a construction site and the assets that are being used in the construction site.

According to one embodiment, the asset information can include status information about an asset that is received from at least one reporting source 208A or 208B. Examples of status information include alerts and warnings. According to one embodiment, status information pertaining to an asset can be provided to a client, for example, for the purpose of displaying a visual representation of the asset's status information.

Asset Management System

Figure 12:
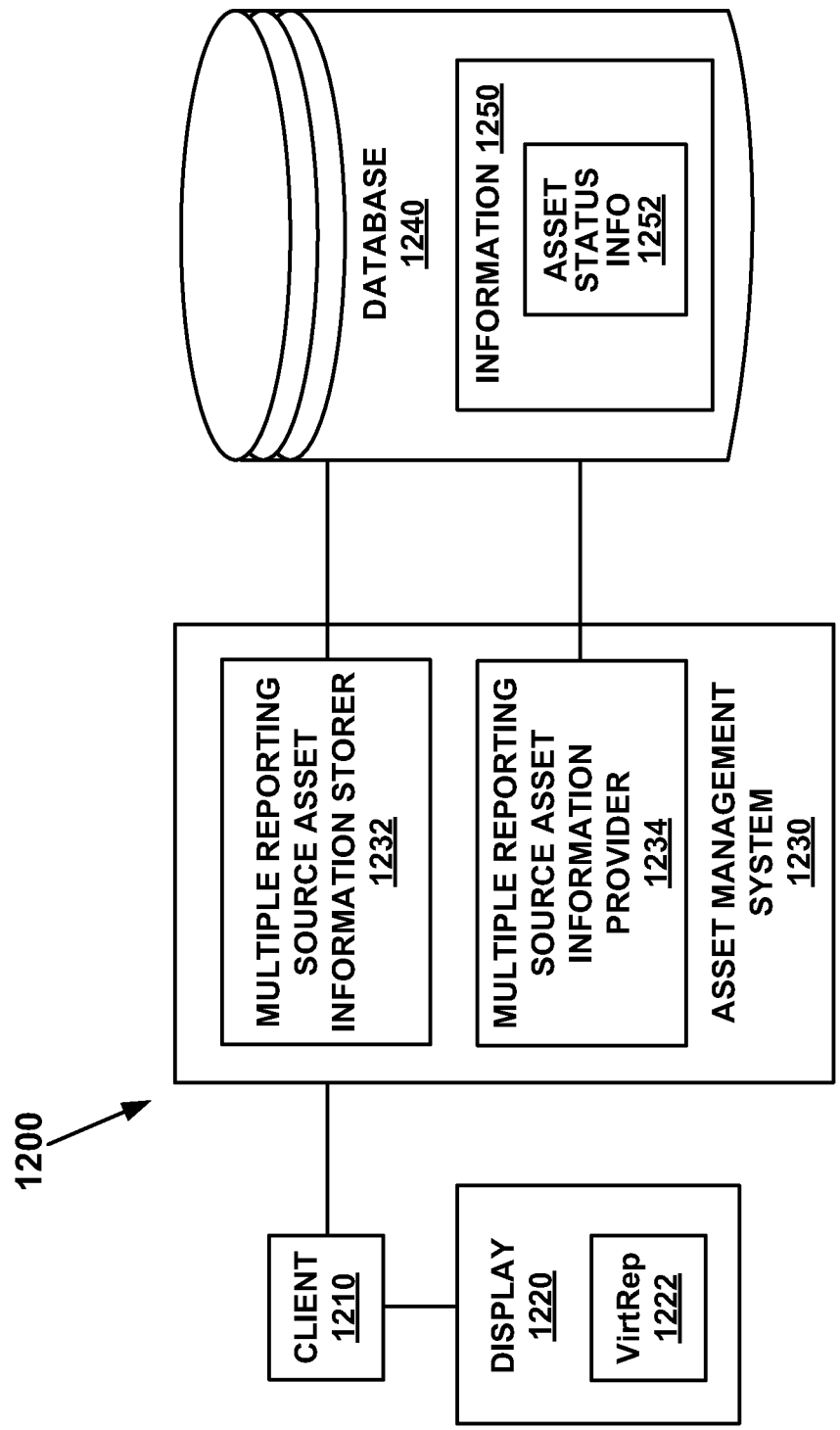
FIG. 12 depicts an asset management system that communicates with a client, according to one embodiment of the present invention.

FIG. 12 depicts an asset management system that communicates with a client, according to one embodiment. The blocks that represent features in FIG. 12 can be arranged differently than as illustrated, and can implement additional or fewer features than what are described herein. Further, the features represented by the blocks in FIG. 12 can be combined in various ways. The system 1200 can be implemented using software, hardware, firmware, or a combination thereof.

FIG. 12 depicts a client 1210, a display 1220, an asset management system 1230 and a database 1240. The asset management system 1230 includes a multiple reporting source asset information storer 1232 and a multiple reporting source asset information provider 1234. The database 1240 includes information 1250 about assets and asset status information 1252.

The asset management system 1230 can receive information about an asset from more than one reporting source 208. The information about the asset, according to one embodiment, is stored in a database 1240 resulting in stored information 1250. The information 1250 about the assets includes status information about the asset 1252, according to one embodiment. According to one embodiment, status information 1252 pertaining to an asset can be provided to a client 1210, for example, for the purpose of displaying a visual representation (VirtRep) 1222 of the asset's status information 1252.

Assets

Examples of assets include but are not limited to graders, levelers, dozers, saws, debris transportation vehicles, diggers, pavers, concrete trucks, supply trucks, cranes, tools, service trucks, compressors and so on. Although many of the descriptions of embodiments provided herein refer to construction assets, various embodiments are well suited to other types of assets. Refer to Section 1, among other places, for more information on assets.

Reporting Sources

Referring to FIG. 2A, examples of reporting sources 208 include, but are not limited to, permanently mounted devices 210, asset mountable/detachable device 215, portable computing device 220, personal digital assistant (PDA) 225, smart phone 230, mobile phone 235 and human intelligence 240. Refer to the discussion of reporting sources 208 in Section I for more information on reporting sources.

Information about an Asset

According to one embodiment, information from a first reporting source about an asset is received and information from a second reporting source about the asset is also received. The information received from the two reporting sources can be stored in a database 1240 resulting in stored information 1250. Refer to the description of step 406 (FIG. 4) for more information on populating a database.

According to one embodiment, the information 1250 is asset location data. Examples of asset location data include, but are not limited to, whether a vehicle is at a site, on a road, or in the correct area of a site. According to another embodiment, the information 1250 is asset operation data. Examples of asset operation data include, but are not limited to, speed an asset is traveling, time since the last oil change or other scheduled maintenance was performed on the asset, any indications of potential malfunction of the asset, and the activity the vehicle is currently engaging in or has previously engaged in. Squeaks may be an indication of potential malfunction of the asset.

The information 1250 can be used to determine how much an asset has been used, where the asset is located, whether it is being used appropriately, whether it has left a designated area as demarcated, for example, by a geo-fence, when the asset needs maintenance, which service truck would be best for performing the maintenance, and so on. Refer to the description of steps 402 and 404 (FIG. 4) of Section I for more information on "information about an asset."

Status Information

According to one embodiment, the asset information 1250 can include status information 1252 about an asset that is received from at least one reporting source 208A or 208B. Examples of status information 1252 include alerts and warnings.

According to one embodiment, status information 1252 pertaining to an asset can be provided to a client 1210, for example, for the purpose of displaying a visual representation 1222 of the asset's status information 1252. An asset management system 1230 can provide the status information 1252 to the client 1210 in the form of notifications. A client 1210 can request the status information 1250 from the asset management system 1230, for example, by periodically polling the asset management system 1230 in real-time.

Examples of status information 1252 are alerts and warnings, such as an asset may be moved outside of a geo-fence, an asset may need maintenance or be close to needing maintenance, an asset may be being used inappropriately, or an asset may be in a dangerous situation. Another example of status information pertains to productivity such as a warning that a grader only graded 1000 feet when it should have graded 2000 feet. Yet another example of status information pertains to whether an asset was used outside of its design or tolerance. These are just a few examples of status information. Embodiments of the present invention can be used for many different types of status information that an owner or user of assets may want to know.

According to one embodiment, the asset status information 1252 can be cleared, for example, after someone has seen a visual representation of the status information 1222. For example, a person using the client 1210 can clear the status information 1252 for a particular asset out of the database 1240 after they have seen the visual representation 1222 of that asset's status information.

Visual Representations of Status Information

The client 1210's display 1220 can be used for displaying a visual representation of a construction site and visual representations of the assets that are being used on that construction site. The visual representation of the construction site may be a map of the construction site. The visual representations of assets may be icons. The visual representations of assets can be positioned to indicate their respective locations in the construction site map. The visual representations of the assets may look similar to the assets that they represent. For example a visual representation of a service truck may look like a service truck.

A visual representation of status information, according to one embodiment, is at least a part of a visual representation of an asset. For example, a visual representation of an asset can include a visual representation of that asset's status information.

According to one embodiment, the visual representation of an asset may change colors in order to display status information 1252 about that asset. For example, the visual representation may be red to indicate a critical condition, yellow to indicate a warning, and green to display status information that is neither critical nor a warning. According to one embodiment, the color of the entire visual representation may be changed or a part of the visual representation may be changed.

According to another embodiment, status information 1252 about an asset may be displayed by outlining a visual representation of an asset with a color. According to one embodiment, the outline which indicates the status information is considered to be a part of the visual representation of an asset. According to yet another embodiment, status information 1252 is displayed by fading a visual representation 1222 in and out (also known as "blinking"). The rate at which the visual representation 1222 "blinks" can also be used to convey status information 1252. For example, the visual representation 1222 may blink faster for higher priority status information. According to yet another embodiment, different methods can be combined to display a visual representation 1222 of status information 1252. For example, an icon may turn red and blink rapidly to indicate a critical situation. According to another embodiment, status information 1252 is displayed when the client 1210 detects that a user has caused a cursor to be positioned in close proximity to hover over the visual representation of an asset.

Figure 13:
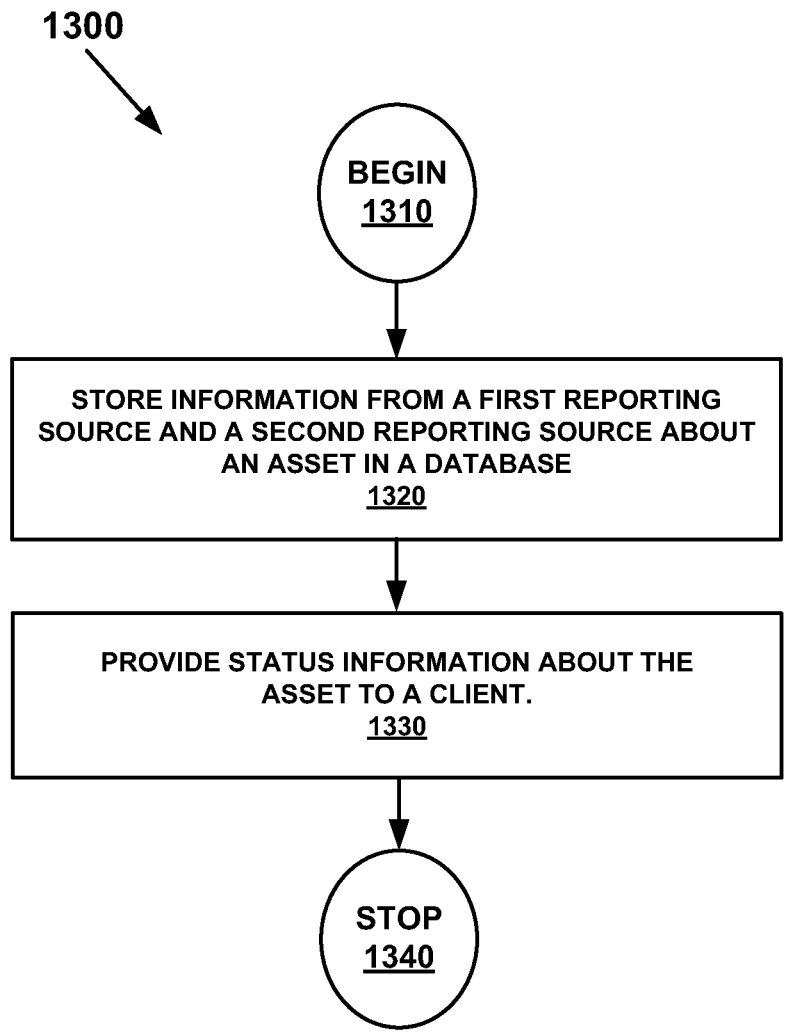
FIG. 13 is a flowchart of a method for limiting access to asset management information, according to one embodiment.

Operational Example of a Method for Providing Status Information Pertaining to an Asset FIG. 13 is a flowchart of a method for limiting access to asset management information, according to one embodiment. Although specific steps are disclosed in flowchart 1300, such steps are exemplary. That is, embodiments of the present invention are well suited to performing various other steps or variations of the steps recited in flowchart 1300. It is appreciated that the steps in flowchart 1300 may be performed in an order different than presented, and that not all of the steps in flowchart 1300 may be performed.

All of, or a portion of, the embodiments described by flowchart 1300 can be implemented using computer-readable and computer-executable instructions which reside, for example, in computer-usable media of a computer system or like device. As described above, certain processes and steps of the present invention are realized, in one embodiment, as a series of instructions (e.g., software program) that reside within computer readable memory of a computer system and are executed by the of the computer system. When executed, the instructions cause the computer system to implement the functionality of the present invention as described below.

In step 1310, the method begins.

In step 1320, information from a first reporting source and a second reporting source about an asset is stored in a database. For example, information from a first and a second reporting source 208 can be received for assets as depicted in FIGS. 8 and 10. Assume for the sake of illustration that the first reporting source is an asset mountable/detachable device 215. The device 215 may be mounted on the assets. The device 215 can be used to collect information about an asset as the asset, for example, moves around. Assume for the sake of illustration that the second reporting source is a personal digital assistant 225 (PDA). An employee of a construction company or a dealer may walk around and enter information pertaining to the assets into the PDA 225. Therefore, according to one embodiment, information about an asset can be received from more than one reporting source 208. Refer to the subheading "information" of Section III and the discussion of step 404 for more information on receiving information about the asset from a first and a second reporting source.

A multiple reporting source asset information storer 1232 (FIG. 12) can store the received information resulting in stored information 1250. Refer to the description of step 406 (FIG. 4) of Section I for more information on storing information in a database (also known as populating a database.)

Assume for the sake of illustration that the asset is a bulldozer. The device 215 can periodically send location information about the bulldozer to the asset management system 1230 (FIG. 12). The asset management system 1230 can compare the location of the bulldozer to a geo-fence. Assume for the sake of illustration that the bulldozer is taken outside of a geo-fence. By comparing the location of the bulldozer to the geo-fence, the asset management system 1230 can determine that the bulldozer has been taken outside of the geo-fence. According to one embodiment, the asset status information 1252 for the bulldozer will reflect that the bulldozer has been taken outside of the geo-fence.

In step 1330, the status information about the asset is provided to a client. The status information can be used to display a visual representation of the status information on the client. For example, the client 1210 can poll the asset management system 1230 to obtain asset status information 1252. The client 1210 can receive the status information 1252 indicating that the bulldozer has been taken outside of the geofence. The client 1210 can display a visual representation 1222 of the status information 1252. For example, an icon of the bulldozer may turn red or start to blink rapidly. Refer to the "Visual Representation of Status Information" subheading of Section III for more information.

In step 1340, the method ends.

Section IV

Enabling Notifications Pertaining to an Asset

Overview

Figure 21:
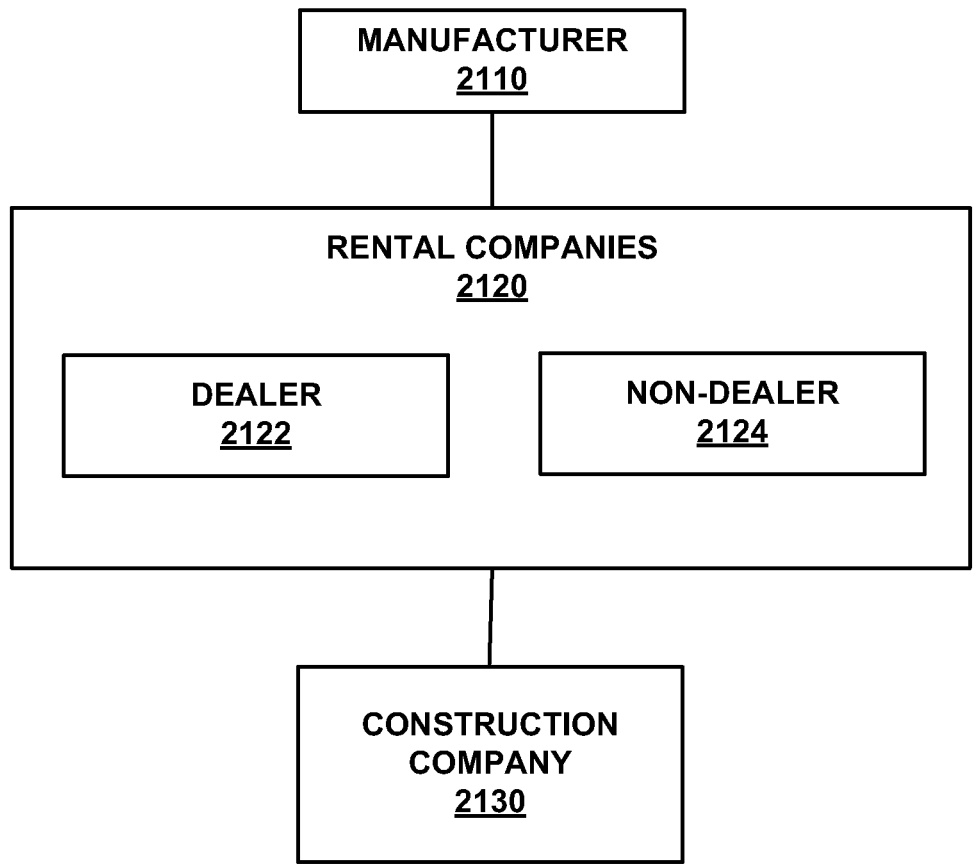
FIG. 21 is a block diagram that depicts a relationship between manufacturers of construction assets, rental companies that rent construction assets, and construction companies, according to one embodiment.

Referring to FIG. 21, Construction companies 2130 typically own a core set of assets that they use to perform work on a construction site. If the construction company 2130 needs more assets than they own, they may rent the additional assets from a rental company 2120. The rental company may be a dealer 2122 or a non-dealer 2125. A rental company 2120 may also own assets that they do not rent out. For example, the rental company may own service vehicles that they use to maintain other assets that have been rented out.

Referring to FIG. 3, information about assets from more than one reporting source 208A and 208B can be received by an asset management system 300 and stored in a database 205. According to one embodiment, the received information is used to enable providing notifications pertaining to assets to construction companies and/or rental companies.

Asset Management System

Figure 14:
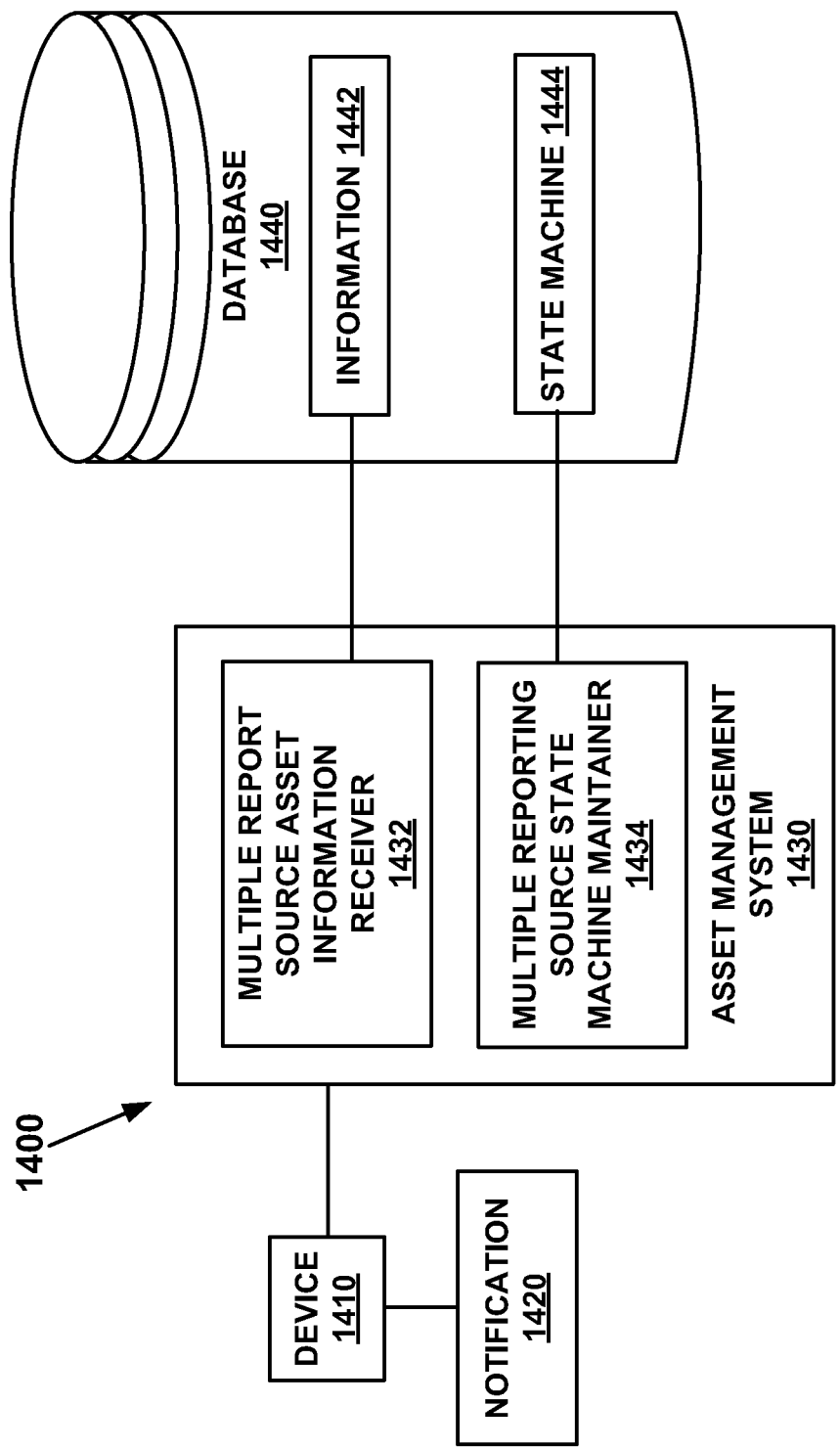
FIG. 14 depicts an asset management system for enabling notifications pertaining to an asset, according to one embodiment.

FIG. 14 depicts an asset management system for enabling notifications pertaining to an asset, according to one embodiment. The blocks that represent features in FIG. 14 can be arranged differently than as illustrated, and can implement additional or fewer features than what are described herein. Further, the features represented by the blocks in FIG. 14 can be combined in various ways. The system 1400 can be implemented using software, hardware, firmware, or a combination thereof.

System 1400 depicts a device 1410, a notification 1420, an asset management system 1430, and a database 1440. The asset management system 1430 includes a multiple report source information receiver 1432 and a multiple report source state machine maintainer 1434. The database 1440 includes information 1442 about assets and state machines 1444 that pertain to assets.

The asset management system 1430 can receive information about an asset from more than one reporting source 208. The information that multiple report source information receiver 1432 receives from the multiple reporting sources 208 can be stored in a database 1440 resulting in stored information 1442. The multiple report source information receiver 1432, according to one embodiment, communicates the received information to the multiple report source state machine maintainer 1434, which uses the received information to maintain state machines 1444 that pertain to assets. The state machines 1444, according to one embodiment, enable providing notifications 1420 that pertain to assets.

Figure 15:
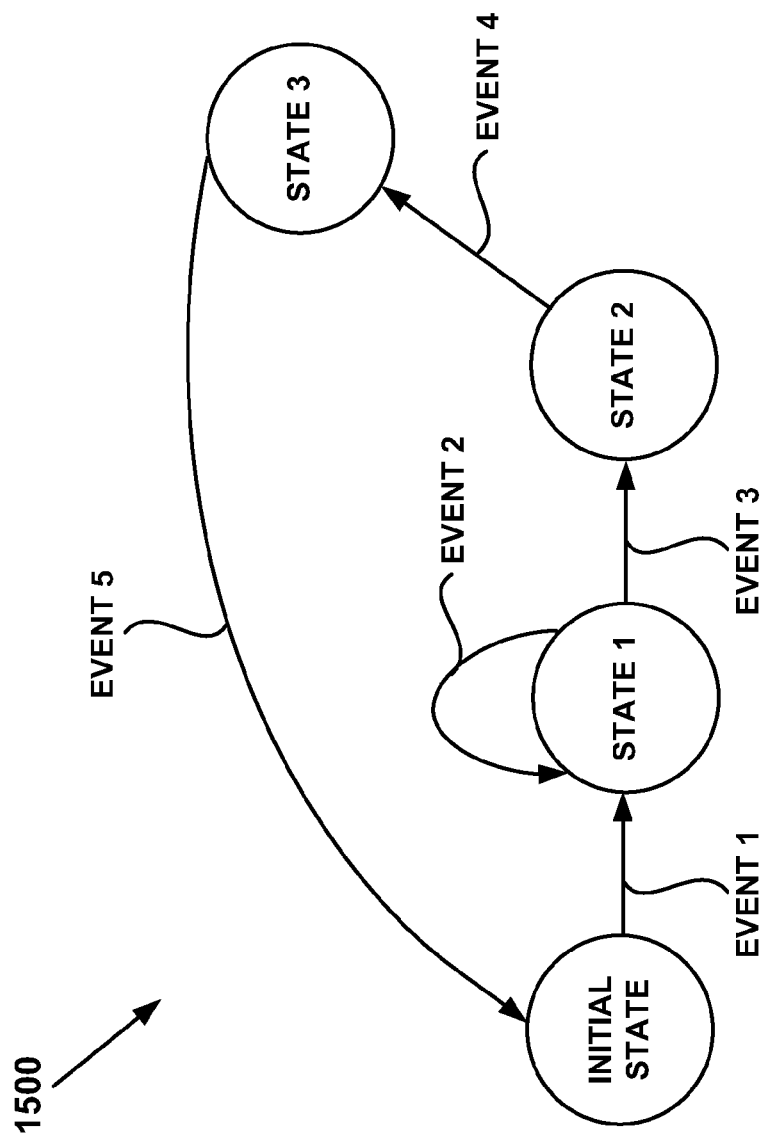
FIG. 15 is a diagram of an example of a state machine associated with an asset, according to one embodiment.

FIG. 15 is a diagram of an example of a state machine 1500 associated with an asset, according to one embodiment. State machine 1500 (FIG. 15) is an example of a state machine 1444 (FIG. 14). Referring to FIG. 15, an initial state can be associated with an asset. As events occur, the state associated with the asset can change. For example, when event 1 occurs, the state machine 1500 for the asset transitions from the initial state to state 1. When event 3 occurs the state machine 1500 transitions from state 1 to state 2 and so on with event 4, state 3, and event 5. However, some events do not result in a transition between states. For example, event 2 results in the state remaining the same.

Certain events can result in a notification being communicated to a device. Refer to the subheading entitled "Configuring" of Section IV, among other places, for more information on events resulting in a notification being communicated to a device.

According to one embodiment, state machines and/or notifications can be saved in the database. In the event of a system failure, the stored state machines and/or notifications can be used as a part of restarting and potential post-processing.

Assets

Examples of assets include but are not limited to, graders, levelers, dozers, saws, debris transportation vehicles, diggers, pavers, concrete trucks, supply trucks, cranes, tools, service trucks, compressors and so on. Although many of the descriptions of embodiments provided herein refer to construction assets, various embodiments are well suited to other types of assets. Refer to Section I, among other places, for more information on assets.

Reporting Sources

Referring to FIG. 2A, examples of reporting sources 208 include, but are not limited to, permanently mounted devices 210, asset mountable/detachable device 215, portable computing device 220, personal digital assistant (PDA) 225, smart phone 230, mobile phone 235 and human intelligence 240. Refer to the discussion of reporting sources 208 in Section I for more information on reporting sources.

Information about an Asset

According to one embodiment, information from a first reporting source about an asset is received and information from a second reporting source about the asset is also received. The information received from the two reporting sources can be stored in a database 1440 resulting in stored information 1442. Refer to the description of step 406 (FIG. 4) for more information on populating a database.

According to one embodiment, the information 1442 is asset location data. Examples of asset location data include, but are not limited to, whether a vehicle is at a site, on a road, or in the correct area of a site. According to another embodiment, the information 1442 is asset operation data. Examples of asset operation data include, but are not limited to, speed an asset is traveling, time since the last oil change or other scheduled maintenance was performed on the asset, any indications of potential malfunction of the asset, and the activity the vehicle is currently engaging in or has previously engaged in. Squeaks may be an indication of potential malfunction of the asset.

The information 1442 can be used to determine how much an asset has been used, where the asset is located, whether it is being used appropriately, whether it has left a designated area as demarcated, for example, by a geo-fence, when the asset needs maintenance, which service truck would be best for performing the maintenance, and so on. Refer to the description of steps 402 and 404 (FIG. 4) of Section I for more information on "information about an asset." The information about an asset can indicate what events are occurring with respect to an asset.

States and Events

As depicted in FIG. 15, a state machine 1500 includes states and events. The events are used to determine how to transition from state to state, according to one embodiment. Examples of states include that an asset is within a site (WithinSite), the asset is outside of a site (OutsideSite), The asset is on (IgnitionOn), the asset is moving (Moving), the asset's door is open (DoorOpen), and the asset needs to be maintained (MaintenancePending). Examples of events include, that an asset has entered a site (EnterSite), an asset has left a site (LeaveSite), an asset has been turned on (IgnitionOn), an asset has been turned off (IgnitionOff), an asset has started to move (StartedMoving), an asset has stopped moving (StoppedMoving), the door has been opened (DoorOpen), the door has been closed (DoorClosed), maintenance is due (MaintenanceDue), and the maintenance has been completed (MaintenanceDone).

According to one embodiment, information pertaining to dispatching, monitoring assets, scheduling assets, cargo carried by an asset, among other things, can be used to determine events and/or states.

According to one embodiment, time can be used as a part of defining an event. The time may be specified in terms of a period of time. Examples of using time to define events includes "Enter Site 'Lincoln Office' between 9 am and 5 pm" and "No IgnitionOn occurs between 9 am and 9:15 am." As can be seen, a state can reflect time information that is used as a part of defining an event that causes transition to that state.

According to one embodiment, the number of times a state or event occurs or is entered can be used. Examples are "more than 1 SpeedingEvent in a shift" or "no PositionUpdate events in the last 30 minutes."

Other examples of states and events are "NotWithinSite 'Lincoln Office' at 5 pm," "WithinSite 'PickUpPoint' at anytime between 10 am and 10:30 am," "IgnitionIsOn at 5 pm," or "Event IgnitionIsOn did not occur anytime between 9 am and 9:15 am."

According to one embodiment, states and/or events can also be combined. For example, "MaintenanceIsPending when EnterSite 'Lincoln Office' between 9 am and 5 pm." Another example of combining states and/or events is "DoorIsOpen when StartedMoving occurred."

Information describing an event can come from one or more reporting sources and databases that are external to an asset, according to one embodiment. For example, a compressor may have been taken out of the yard however the asset management system 300 indicates that the compressor is not ready to be used so an alert is generated. In another example, the state of the asset may indicate that the asset is located on a site for a particular job, that the asset is within 20 hours of maintenance, and a weather service predicts that a storm will reach the job's site tomorrow. However, for monetary reasons it would be best to perform the maintenance tomorrow even though a storm is predicted.

According to one embodiment, states and/or events can be combined by implementing a state machine within a state. For example a state of Moving may include a state machine that specifies, among other things, events DoorOpen which transitions to a DoorOpen state. In another example, the Moving state may also include an event of LeaveSite which transitions to an OutsideSite state.

According to one embodiment, a state machine can be implemented using lists. For example, a state machine 1444 for a bulldozer may have a list of what events pertain to bulldozers and which events cause a transition between particular states. According to another embodiment, a state machine 1444 can be implemented using an object oriented design pattern called "State." For more information refer to "Design Patterns: Elements of Reusable Object-Oriented Software," By Gamma et al. ISBN 0201-63361-2, the contents of which are incorporated herein.

Notifications

According to one embodiment, logic associated with a state may specify that a notification 1420 will be communicated to a device 1410. For example, the state MaintenancePending may specify that a notification 1420 indicating maintenance is pending be transmitted to a device 1410. According to one embodiment, there are different types of notifications 1420. There are alert notifications, warning notifications, and informational notifications, among other things. An alert notification may pertain to an asset moving outside of a geo-fence, an asset speeding, an asset nearing a cliff, or an asset running out of oil. A warning notification may pertain to maintenance being due within a certain amount of time, for example. Informational notifications may pertain to an asset being at a particular location or the asset being moved.

Notifications 1420 may be communicated to a device 1410, for example, in the form of an email, a fax, or paging a device 1410. These are just a few examples of how notifications 1420 may be communicated to a device 1410. The notifications 1420 can include timing information. For example, a notification 1420 can indicate how long a state pertained to an asset, when the state was entered, when the state was exited, how many times an event occurred, or how many times a state was entered or exited. In a specific example, a notification 1420 may indicate that an asset has moved from location a to b during the time x and y. In another example, a notification 1420 may indicate that the ignition was on for an asset from 9 am until 5 pm on Jul. 16, 2006.

According to one embodiment, notifications 1420 are not necessarily communicated to a device 1410 immediately upon detection. For example, an informational notification may not be sent immediately to a device 1410. It may be saved in a database 1440 for a period of time. The asset management system 1430 can periodically review the saved notifications and determine whether to transmit them to the appropriate device.

According to one embodiment, notifications 1420 are communicated for example when the wrong type of attachment is attached to an asset. For example, a notification can be communicated when a large bucket is attached to a rather small machine that could potentially cause damage to the machine.

Configuring

A user of a device 1410 can specify what assets, states or events that they are interested in receiving notifications 1420 for. They can also specify what form the notification 1420 will take, such as an email or page a device 1410. According to one embodiment, a state machine 1444 for a particular asset can be configured by specifying which states, events, among other things, pertain to that asset. For example, the IgnitionOn state may pertain to a bulldozer but not pertain to a bucket that attaches to a bulldozer. Therefore, the state machine 1444 for a bulldozer may include an IgnitionOn state while a state machine 1444 for a bucket may not include an IgnitionOn state.

According to one embodiment, a user can interact with their device 1410 to configure which states and events for a particular asset they are interested in receiving notifications for. The device 1410 can transmit the configuration to the asset management system 1430. The asset management system 1430 can use the configuration to create a state machine 1444. The state machine 1444 can be used to determine what notifications 1420 to send, when to send notifications 1420, and what the notifications 1420 will contain, among other things.

Figure 16:
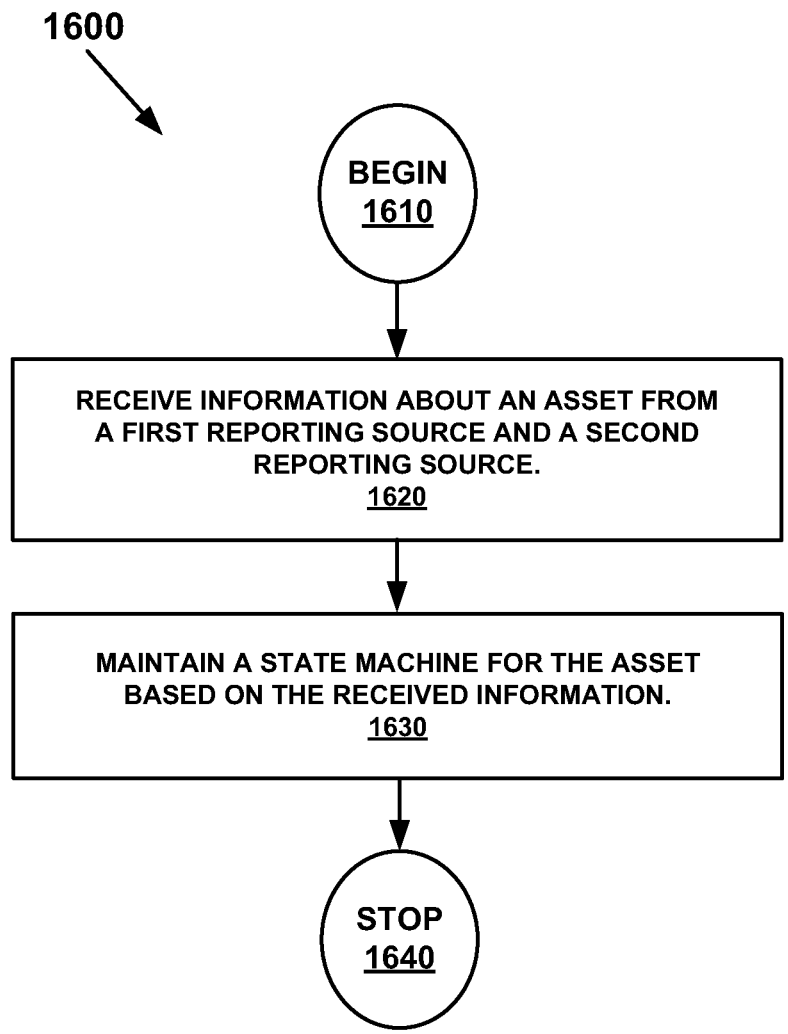
FIG. 16 is a flowchart of a method for enabling notifications pertaining to an asset, according to one embodiment.

Operational Example of a Method for Enabling Notifications Pertaining to an Asset FIG. 16 is a flowchart of a method for enabling notifications pertaining to an asset, according to one embodiment. Although specific steps are disclosed in flowchart 1600, such steps are exemplary. That is, embodiments of the present invention are well suited to performing various other steps or variations of the steps recited in flowchart 1600. It is appreciated that the steps in flowchart 1600 may be performed in an order different than presented, and that not all of the steps in flowchart 1600 may be performed.

All of, or a portion of, the embodiments described by flowchart 1600 can be implemented using computer-readable and computer-executable instructions which reside, for example, in computer-usable media of a computer system or like device. As described above, certain processes and steps of the present invention are realized, in one embodiment, as a series of instructions (e.g., software program) that reside within computer readable memory of a computer system and are executed by the of the computer system. When executed, the instructions cause the computer system to implement the functionality of the present invention as described below.

In step 1610, the method begins.

In step 1620, receiving information about an asset from a first reporting source and a second reporting source. The received information about an asset can indicate what events are occurring with respect to an asset. Information from a first and a second reporting source 208 can be received for assets as depicted in FIGS. 8 and 10. Assume for the sake of illustration that the first reporting source is an asset mountable/detachable device 215. The device 215 may be mounted on the assets. The device 215 can be used to collect information about an asset as the asset, for example, moves around. Further, the device 215 may be connected to a Jbus associated with the asset and therefore may be able to detect whether the asset is turned on or not, among other things.

Assume for the sake of illustration that the second reporting source is a personal digital assistant 225 (PDA). An employee of a construction company or a dealer may walk around and enter information pertaining to the assets into the PDA 225. Therefore, according to one embodiment, the multiple report source information receiver 1432 can receive the information about an asset from more than one reporting source 208. Refer to the subheading "information" of Section III and the discussion of step 404 for more information on receiving information about the asset from a first and a second reporting source.

Further, the received information can be stored in the database 1440 resulting in stored information 1442 (FIG. 14). Refer to the description of step 406 (FIG. 4) of Section I for more information on receiving and storing information in a database. Storing information in a database is also known as populating a database.

According to one embodiment, vehicle tracking and communication used by a fleet management system can be used as a part of communicating information about an asset. For more information about vehicle tracking and communication used by a fleet management system refer to U.S. Pat. No. 6,611,755 B1 by Coffee et al., filed on Dec. 19, 1999 and entitled "VEHICLE TRACKING, COMMUNICATION AND FLEET MANAGEMENT SYSTEM", assigned to Trimble Navigation Ltd., of Sunnyvale Calif. (US). According to one embodiment, a PROTRAK system or a Galileo system (each of PROTRAK and Galileo, either alone or with various suffixes attached, is a trademark of Fleet Management Services, Inc. of Chandler, Ariz.) can be used as a part of communicating information about an asset.

In step 1630, maintaining a state machine for the asset based on the received information. When an event occurs, the state machine 1444 is used to determine if a transition is to be made from one state to another state. For example, assume that an asset is sitting in a construction site. It is off and the door is closed. An operator wants to get into the asset and start using it. In this illustration, before the operator gets into the asset, the state WithinSite applies. The event of the operator opening the door causes the DoorOpen state to be entered. At this point of this illustration, the state machine for this asset reflects the states WithinSite and DoorOpen. The operator closes the door so the state DoorOpen no longer applies to the asset. When the events IgnitionOn and StartedMoving occur, the state machine will transition to the Moving state. At this point in the illustration, the states WithinSite and Moving apply to the asset.

In step 1640, the method ends.

Section V

Receiving Information Pertaining to a Construction Project

Overview

According to one embodiment, a construction company receives information about assets, such as bulldozers, backhoes, buckets, compressors, as a part of managing a construction project. For example, construction company employees may want to know where a particular asset is, what the asset is doing, and so on. The employees can use this information to determine whether an asset should be moved to a different location or used on a different activity, among other things.

As described in Section I, among other places, information about assets from more than one reporting source 208A and 208B can be received by an asset management system 300 and stored in a database 205. Different types of assets are used for different types of construction activities and cost different amounts. Since assets have different capabilities, a construction project uses different types of assets for different activities, which is an example of construction project objectives. Different types of reporting sources also have different capabilities and cost different amounts. According to one embodiment, different types of reporting sources are associated with different assets based on the capabilities of the assets and the objectives of the construction project. The capabilities of an asset shall be considered a part of the asset's "characteristics," according to one embodiment.

Assets

Examples of assets include but are not limited to graders, levelers, dozers, saws, debris transportation vehicles, diggers, pavers, concrete trucks, supply trucks, cranes, tools, service trucks, compressors and so on. Although many of the descriptions of embodiments provided herein refer to construction assets, various embodiments are well suited to other types of assets. Refer to Section 1, among other places, for more information on assets.

Asset Characteristics and Construction Project Objectives

Examples of asset characteristics include the cost of the asset, the mobility of the asset, the amount of information that is communicated about an asset, the ability of the asset to provide power to a reporting source, the size of the asset, the accuracy of location information that can be provided for the asset, and the timeliness of providing information about the asset, among other things. Examples of construction project objectives include how the asset will be used for a construction project, the amount of information that an asset management system would want to receive in order to manage an asset, the timeliness that an asset management system would want the asset information in order to manage the asset, the accuracy of the location of the asset that the asset management system would want in order to manage the asset, among other things. Another example of a construction project objective pertains to the relative cost of a reporting source in comparison to the relative cost of an asset. For example, the more expensive that an asset is the more justification there is to associate a relatively expensive reporting source with that asset. The more power and the more capabilities, for example, that a reporting source has the more expensive that reporting source will be. The CrossCheck® is relatively more expensive than the RFID tag type reporting source. The cost of the TrimTrac™ and the Mountable Reporting Source (MRS) 1800 are in between. A construction project may involve one or more construction sites.

Reporting Sources

Referring to FIG. 2A, examples of reporting sources 208 include, but are not limited to, permanently mounted devices 210, asset mountable/detachable device 215, portable computing device 220, personal digital assistant (PDA) 225, smart phone 230, mobile phone 235 and human intelligence 240. Refer to the discussion of reporting sources 208 in Section I for more information on reporting sources. Examples of asset mountable/detachable devices 215 are CrossCheck®, TrimTrac™, mountable reporting source (FIG. 18), and an RFID tag type reporting source.

For more information about TrimTrac™ refer to U.S. patent application Ser. No. 10/952,607 by Nichols et al, filed on Sep. 28, 2004 and entitled "Method and System For Controlling A Valuable Movable Item", assigned to the assignee of the present invention and refer to U.S. patent application Ser. No. 11/076,923 by Workman et al, filed on Mar. 31, 2005 and entitled "A portable Motion-Activated Position Reporting Device", assigned to the assignee of the present invention. Refer to Section VIII for more information on RFID tag type reporting sources.

Different types of reporting sources have different capabilities. For example, a CrossCheck® typically has a constant supply of power and is capable of communicating relatively large amounts of asset information frequently over relatively large distances. An RFID tag type reporting source does not have a supply of power and is capable of communicating a relatively small amount of asset information, such as an identifier, over a relatively short distance. Typically, the more capabilities that a reporting source has the more expensive it is. Therefore, it does not make good business sense to associate expensive reporting sources with relatively inexpensive assets. According to one embodiment, this concern is addressed, among other things, by associating different types of reporting sources with different assets based on the characteristics of the assets and objectives of the construction project.

Information about an Asset

According to one embodiment, information from a first reporting source about an asset is received and information from a second reporting source about the asset is also received. The information received from the two reporting sources can be stored in a database resulting in stored information. Refer to the description of step 406 (FIG. 4) for more information on populating a database.

According to one embodiment, the information is asset location data. Examples of asset location data include, but are not limited to, whether a vehicle is at a site, on a road, or in the correct area of a site. According to another embodiment, the information is asset operation data. Examples of asset operation data include, but are not limited to, speed an asset is traveling, time since the last oil change or other scheduled maintenance was performed on the asset, any indications of potential malfunction of the asset, and the activity the vehicle is currently engaging in, has previously engaged in, or will engage in. Squeaks may be an indication of potential malfunction of the asset.

The information can be used to determine how much an asset has been used, where the asset is located, whether it is being used appropriately, whether it has left a designated area as demarcated, for example, by a geo-fence, when the asset needs maintenance, which service truck would be best for performing the maintenance, and so on. Refer to the description of steps 402 and 404 (FIG. 4) of Section I for more information on "information about an asset." The information about an asset can indicate what events are occurring with respect to an asset.

Associating Reporting Sources with Assets

Figure 17:
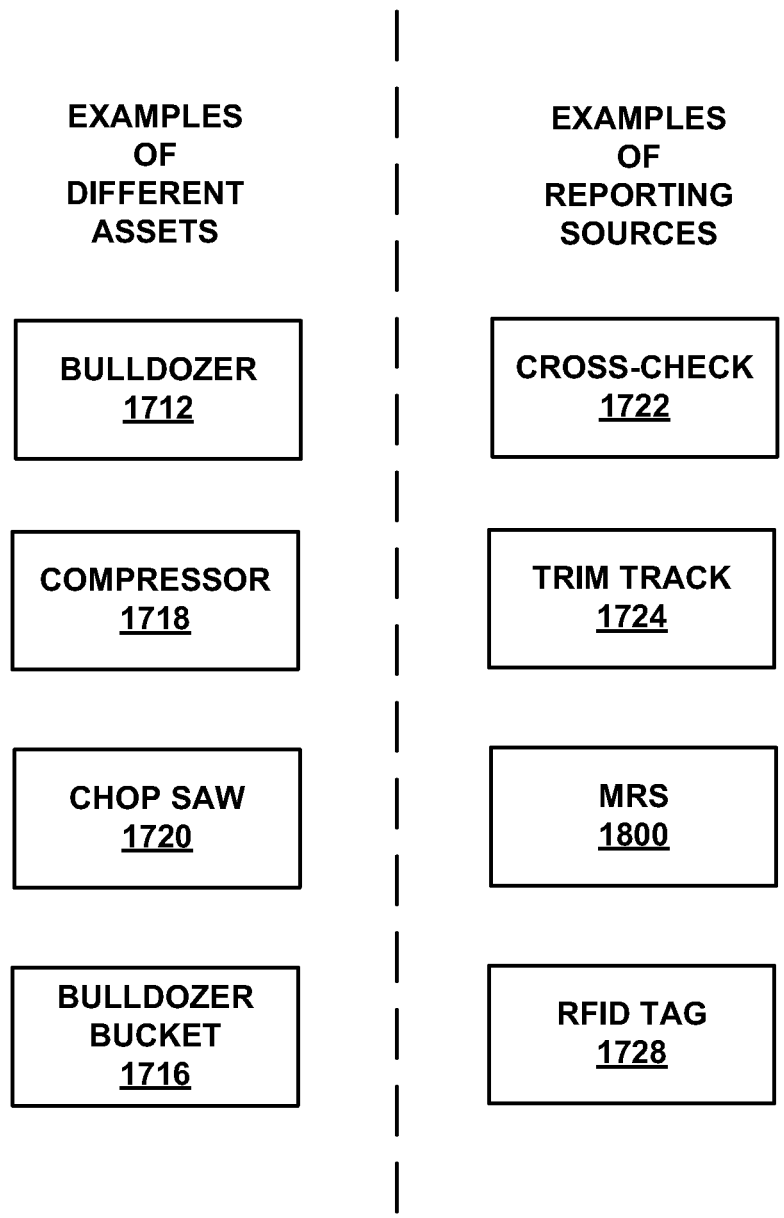
FIG. 17 depicts a block diagram of associating different types of reporting sources with different assets based on characteristics of the assets and objectives of the construction project, according to one embodiment.

FIG. 17 depicts a block diagram of associating different types of reporting sources with different assets based on characteristics of the assets and objectives of the construction project, according to one embodiment. FIG. 17 depicts a bulldozer 1712, a large compressor 1718, a chop saw 1720, and a bulldozer bucket 1716. The assets are ranked according to their cost, their likelihood of moving around, and the amount of information about the assets that will typically be collected. For example, bulldozers 1712 are more expensive, move around more, and engage in more activities for which information may be gathered than compressors 1718. More specifically, a bulldozer 1712 will typically be moving around constantly on a construction site whereas a compressor 1718 will tend to be relatively stationary. A bulldozer bucket 1716 does not provide power and is subjected to a fair amount of jostling.

Cost, mobility, and the amount of information about an asset are a few examples of characteristics about an asset. How the asset will be used as a part of the construction project and the amount of information that an asset management system would want to collect in order to manage an asset are examples of construction project objectives.

Therefore, according to one embodiment, different types of reporting sources—a CrossCheck® 1722, a TrimTrac™ 1724, a MRS 1800, and an RFID tag 1728 are associated with assets. FIG. 17 depicts several reporting sources that are associated with different assets, according to one embodiment. Typically bulldozers 1712 are constantly moving and are used for relatively complex activities. Therefore, there can be a relative large amount of information pertaining to a bulldozer 1712. Further, the asset management system may want to keep a close watch on the bulldozer 1712. Therefore, a reporting source, such as a CrossCheck® 1722, that has a constant supply of power and that is capable of frequently transmitting information about the bulldozer to an asset management system may be associated with the bulldozer 1712.

A large compressor 1718 moves around considerably less. Therefore a device that is capable of using power sparingly, such as a TrimTrac™ 1724, may be used. The TrimTrac™ 1724 can detect when the asset 1718 it is associated with is being moved. When the asset is stationary, the TrimTrac™ 1724 goes into an idle mode and saves power. When it detects that the asset is being moved the TrimTrac™ 1724 goes into an operating mode and starts to transmit information about the asset, which requires more power.

The mountable reporting source (MRS) 1800, according to one embodiment, does not require power from the asset it is associated with. According to one embodiment, the mountable reporting source 1800 is capable of communicating information about an asset, such as a chop saw 1720, to an asset management system. The RFID tag reporting source 1728 does not require power and is rugged and therefore would be suitable for assets, such as a bull dozer bucket 1716, which does not have power and is subjected to a fair amount of jarring.

The more expensive that an asset is the more justification there is to associate a relatively expensive reporting source with that asset. The more power and the more capabilities that a reporting source has the more expensive that reporting source will be. The CrossCheck® is relatively more expensive than the RFID tag type reporting source. The cost of the TrimTrac™ and the MRS 1800 are in between.

The CrossCheck®, the TrimTrac™, and the MRS 1800 are capable, according to one embodiment, of communicating information about the asset they are associated with to an asset management system, which is an example of "active" reporting. The RFID tag reporting source, according to one embodiment, is used as a part of "passive" reporting. For example, a rental company or a construction company typically has an area of land where assets such as compressors are kept waiting to be rented or used. An employee can walk around the area with a data collector that is capable of detecting the identifier transmitted by the RFID tags that are associated with assets. The data collector can be a device that a person is capable of holding in their hand. The data collector can communicate the identifier from the asset's RFID tag to an asset management system and the general location that it detected the presence of the asset's identifier, among other things.

Data Collectors

A data collector can be a device that a person is capable of holding in their hand. As already stated, an employee can walk around the area with a data collector that is capable of receiving the identifier transmitted by the RFID tags that are associated with assets. The data collector can communicate the identifier to the asset management system along with other information about the asset. The employee can input information into a data collector that is communicated, for example, to an asset management system. The employee may display information about an asset on the data collector in whatever way is beneficial to the employee. For example, the data collector may beep and display "Backhoe 123 just arrived."

A data collector, according to one embodiment, uses wireless technology. A Trimble® Recon® and a GIS type data collectors are examples of data collectors. Mobil Tech International™ also manufacturers data collectors. According to one embodiment, a data collector may be a data collector as described in U.S. patent application Ser. No. 10/651,586 by York, filed on Aug. 29, 2003 and entitled "Portable Electronic Instrument with Field-Replaceable Battery/Input/Output Module", assigned to the assignee of the present invention.

A Mountable Reporting Source

Figure 18:
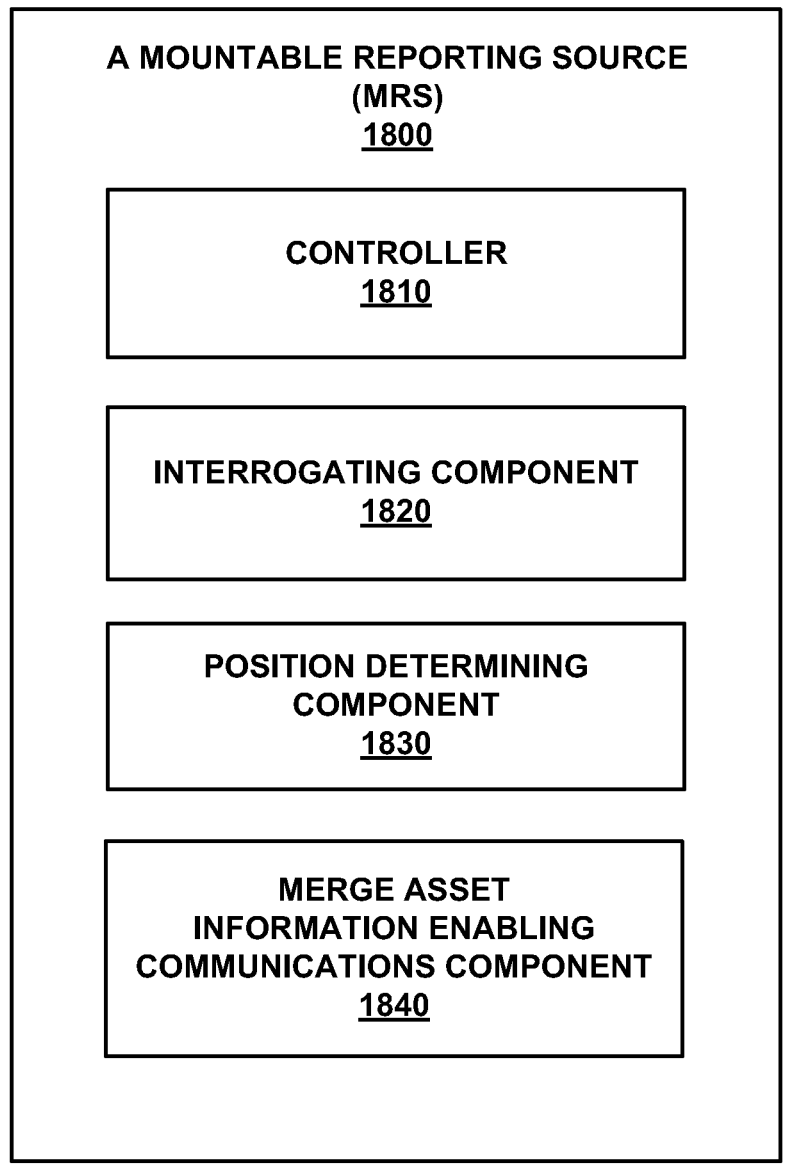
FIG. 18 depicts a block diagram of a mountable reporting source, according to one embodiment.

FIG. 18 depicts a block diagram of a mountable reporting source, according to one embodiment. The blocks that represent features in FIG. 18 can be arranged differently than as illustrated, and can implement additional or fewer features than what are described herein. Further, the features represented by the blocks in FIG. 18 can be combined in various ways. The mountable reporting source 1800 can be implemented using software, hardware, firmware, or a combination thereof.

The mountable reporting source 1800, according to one embodiment, includes a controller 1810, an interrogating component 1820, a position determining component 1830, and a merge asset information enabling communications component 1840. The mountable reporting source 1800 can be associated with an asset, for example, by mounting the reporting source 1800 on the asset. The asset that the mountable reporting source 1800 is mounted on shall be referred to as the "associated asset." According to one embodiment, the mountable reporting source 1800 is associated with an asset based on the characteristics of the asset and the objectives of the construction project. For more information on associating mountable reporting sources with assets refer to, among other places, Section V subheading "Associating Reporting Sources with Assets."

The controller 1810 is coupled to and controls the interrogating component 1820, the position determining component 1830, and the merge asset information enabling communications component 1840. The controller 1810, according to one embodiment, controls receiving and executing commands for determining a geographic location and for communicating the position of the associated asset to, for example, an asset management system. The controller 1810 according to another embodiment controls communicating information about the associated asset to the asset management system.

The interrogating component 1820, according to one embodiment, can store a received identifier on the mountable reporting source. The interrogating component 1820, according to another embodiment, can access the stored identifier and can communicate the identifier to the asset management system along with other pertinent information about the associated asset. According to one embodiment, the interrogating component 1820 stores the identifier into a radio frequency identifier (RFID) tag and receives the identifier from the RFID tag. The identifier can be communicated along with other information about the asset, for example, to an asset management system.

The position determining component 1830, according to one embodiment, determines the location of the associated asset. The position determining component 1830, according to one embodiment, includes a global positioning system (GPS) antenna and a GPS receiver. However, various embodiments of the present invention are well suited to utilize a variety of terrestrial based and satellite-based position determining systems as well.

The merge asset information enabling communications component 1840, according to one embodiment, communicates information about the asset, for example, to an asset management system. According to one embodiment, wireless communications are used for communicating information about the asset to the asset management system, among other things. The merge asset information enabling communications component 1840 can communicate a portion of information about an asset to an asset management system. For example, the mountable reporting source 1800 may communicate the location of the asset and whether the asset needs maintenance to an asset management system.

The asset management system can also receive a second portion of information about the same asset from another reporting source. For example, an employee may use a hand held reporting source that is implemented with a personal digital assistant (PDA) to communicate that the asset is in a dangerous location. Thus, the asset management system is enabled to merge the two portions of information about the asset.

According to one embodiment, the merge asset information enabling communications component 1840 is capable of frequently communicating information about an asset. According to another embodiment, the merge asset information enabling communications component 1840 is capable of communicating information about an asset less frequently. For example, the reporting source 1800 (FIG. 18), according to one embodiment, includes memory that it can store information about an asset on. The merge asset information enabling communications component 1840 can periodically communicate the stored information, for example, to an asset management system.

The merge asset information enabling communications component 1800 can use a number of various technologies to communicate for example with an asset management system. For example, the merge asset information enabling communications component 1800 may use Wireless Fidelity (Wi-Fi), satellite, or Internet Protocol (IP) Radio to communicate. Refer to the subheading "Communications" of Section V for more information.

According to one embodiment, a mountable reporting source 1800 can use a motion detector, which detects changes in motion of the associated asset, to save power. For example, the mountable reporting source 1800 can be in an idle mode, saving power, when it is stationary. The motion detector may detect that the mountable reporting source 1800 is being moved by detecting vibration and communicate this movement to the controller. When movement is detected, the mountable reporting source 1800 can switch to operating mode, which uses more power. The motion detector may be an acceleration sensor, a tilt sensor, a rotation sensor, a gyroscope, etc. A variety of devices for detecting movement are suitable for use as a motion detector.

A mountable reporting source 1800 can be added on to assets after they have been manufactured, purchased, and/or rented, for example. A mountable reporting source 1800, according to one embodiment, can be added onto assets manufactured by various manufacturers. Therefore, a mountable reporting source 1800 can be used as a part of providing a universal view of a construction project regardless of what the manufacturers of the assets are. According to another embodiment, a mountable reporting source 1800 is battery operated.

According to yet another embodiment, Hewlett Packard's™ (HP™) memory spot can be used as a part of implementing a mountable reporting source 1800. HP™'s memory spot is a small wireless data chip that can store between 256 kilobits and 4 megabits of information on flash memory. HP™'s memory spot provides an RFID tag and also provides data rates that are orders of magnitude higher than a conventional RFID tag. The memory spot can store more than 250 times as much data as an RFID and can transmit data more than 20 times faster. The memory spot can also encrypt the data.

Asset Management System

Figure 19:
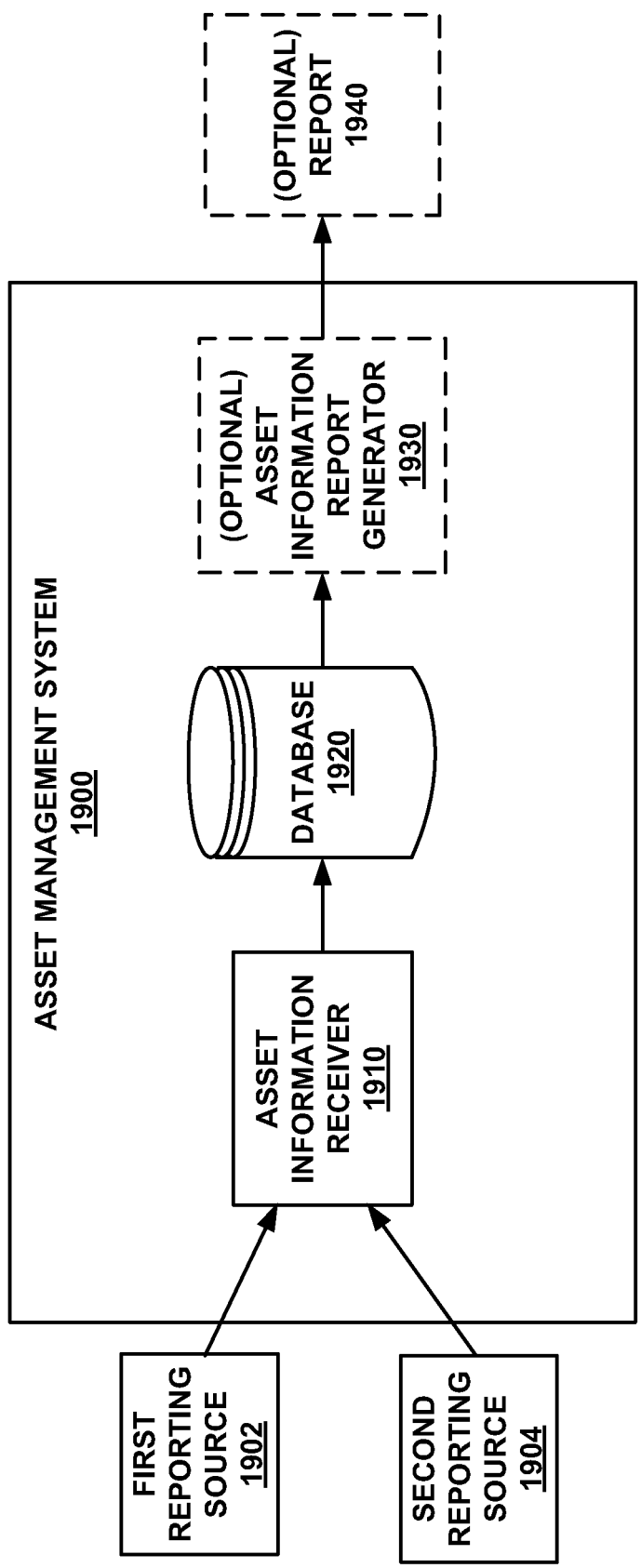
FIG. 19 depicts an asset management system for receiving information pertaining to a construction project, according to one embodiment.

FIG. 19 depicts an asset management system for receiving information pertaining to a construction project, according to one embodiment. The blocks that represent features in FIG. 19 can be arranged differently than as illustrated, and can implement additional or fewer features than what are described herein. Further, the features represented by the blocks in FIG. 19 can be combined in various ways. The system 1900 can be implemented using software, hardware, firmware, or a combination thereof.

FIG. 19 depicts an asset management system 1900 that includes an asset information receiver 1910 and a database 1920. The asset management system 1900 may include an asset information report generator 1930 which can generate an optional report 1940. The asset management system 1900 can receive information about an asset from more than one reporting source 1902 and 1904. For example, the first reporting source 1902 may report a first portion of information about an asset and the second reporting source 1904 may report a second portion of information about the asset. One of the reporting sources 1902 and 1904 may be a mountable reporting source 1800 (FIG. 18). The asset management system 1900 can merge the two portions of the information about the asset and populate the database 1920 with the information about the asset. Similarly, the asset management system 1900 can receive portions of information about other assets and populate the database 1920. The asset information generator 1930 can access the information about assets that are stored on the database 1920 and generate a report 1940.

Communications

According to one embodiment, short message service (SMS) is used for communicating, for example, between devices and/or systems such as a reporting source, a data collector, and an asset management system. According to one embodiment, unused portions of communications channels are used to communicate small packets of information between the devices and/or systems. According to one embodiment, various channels for various technologies, such as digital, analog, 800 MHz, 1900 MHz, radio-packet technologies, are scanned and a channel that provides the best or at least an acceptable level of service is selected. Examples of packet-radio technologies include but are not limited to GPRS over GSM and 1XRTT over CDMA. Robustness and overall coverage are provided since there are many channels to choose from.

According to another embodiment, the small packets of information are transmitted to a central hub over existing Signaling System 7 (SS#7) networks. Remote Access Application Messaging™ (RAAM™) can be used as a part of communicating the small packets of information over the selected channel. The hub can identify a service provider, which is the intended recipient of the small packets of information, and communicate the small packets of information to the service provider for example over a back-end link. The back-end link can include the Internet, dial-up and dedicated connectivity.

Figure 20:
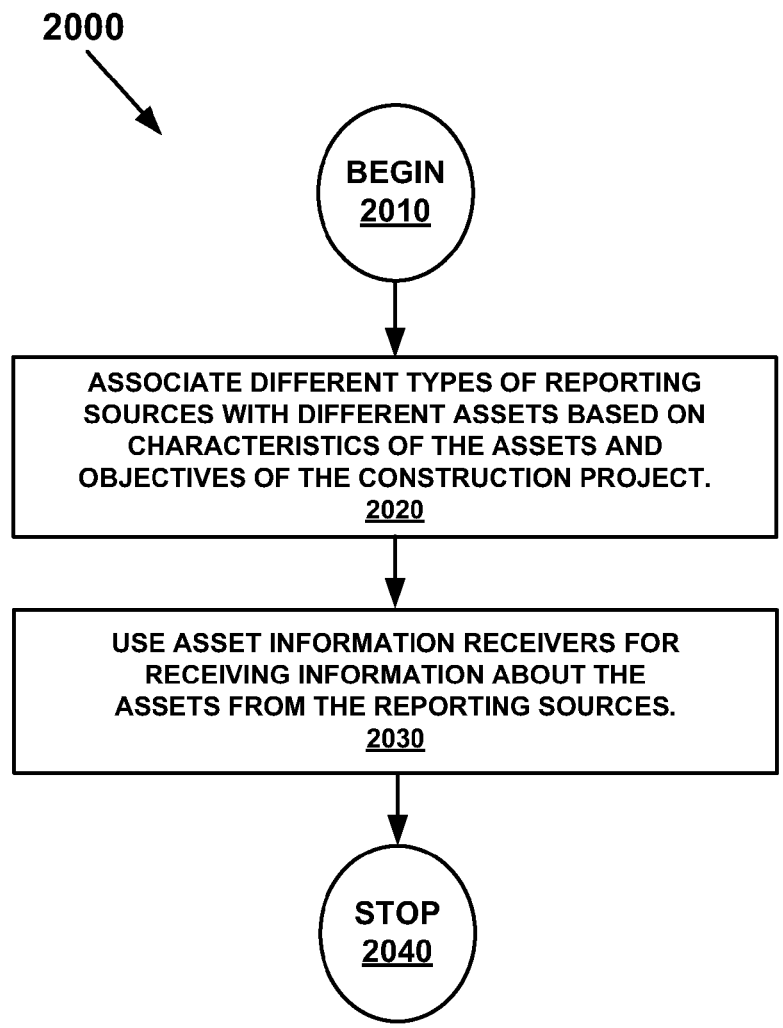
FIG. 20 is a flowchart of a method for receiving information pertaining to a construction project, according to one embodiment.

Operational Example of a Method for Receiving Information Pertaining to a Construction Project FIG. 20 is a flowchart of a method for receiving information pertaining to a construction project, according to one embodiment. Although specific steps are disclosed in flowchart 2000, such steps are exemplary. That is, embodiments of the present invention are well suited to performing various other steps or variations of the steps recited in flowchart 2000. It is appreciated that the steps in flowchart 2000 may be performed in an order different than presented, and that not all of the steps in flowchart 1600 may be performed.

All of, or a portion of, the embodiments described by flowchart 2000 can be implemented using computer-readable and computer-executable instructions which reside, for example, in computer-usable media of a computer system or like device. As described above, certain processes and steps of the present invention are realized, in one embodiment, as a series of instructions (e.g., software program) that reside within computer readable memory of a computer system and are executed by the of the computer system. When executed, the instructions cause the computer system to implement the functionality of the present invention as described below.

In step 2010, the method begins.

In step 2020, different types of reporting sources are associated with different assets based on characteristics of the assets and objectives of the construction project. For example, referring to the discussion of FIG. 17 in the subheading "Associating Reporting Sources with Assets" different reporting sources 1722-1728 were associated with different assets 1712-1720 based on the characteristics of the assets and the construction project's objectives. More specifically, a CrossCheck® 1722 was associated with the bulldozer 1712. The bulldozer 1712 is a very expensive asset that generates a lot of information. Further, it may be a construction objective to keep close watch over the bulldozer 1712. Therefore, a relatively expensive reporting source, such as a CrossCheck® 1722, which has a continuous supply of power and is capable of frequently communicating information about the bulldozer 1712, is justified. In contrast, a bulldozer bucket 1716 is less expensive, does not provide power, and is more stationary, therefore an RFID tag 1728 would be appropriate for it.

In step 2030, asset information receivers are used for receiving information about the assets from the reporting sources. Examples of asset information receivers are data collectors and an asset information receiver 1910 (FIG. 19). According to one embodiment, a data collector forwards information it has received to the asset information receiver 1910. Some reporting sources, such as the CrossCheck® 1722, are capable of providing relative large amounts of information about assets at a relatively frequent basis over long distances. Other reporting sources, such as the RFID tag 1728, are capable of only providing small amounts of information about assets over short distances. The asset information receivers that are used correspond to the capabilities of the reporting sources, according to one embodiment. For example, a data collector corresponds to the capabilities of the RFID tag type reporting source 1728 because a person can carry it with in relatively close proximity of the RFID tag type reporting source 1728. In contrast, the asset information receiver 1910 (FIG. 19) corresponds to the capabilities of the CrossCheck® 1722, the TrimTrac™ 1724 and the MRS 1800.

Two or more reporting sources are enabled to provide information about a particular asset. For example, the merge asset information enabling communications component 1840 can communicate a portion of information about an asset to an asset management system 1900. For example, the mountable reporting source 1800 may communicate the location of the asset and whether the asset needs maintenance to an asset management system 1900. The asset management system 1900 can also receive a second portion of information about the same asset from another reporting source. For example, an employee may use a hand held data collector to communicate that the asset is in a dangerous location. Thus, the asset management system 1900 is enabled to merge the two portions of information about the asset.

In step 2040, the method ends.

Section VI

Limiting Access to Asset Management Information

Overview

According to one embodiment, information about assets can be selectively provided to various entities, such as rental companies and construction companies. According to one embodiment, the information is stored in a database and includes information about assets that a rental company owns and about assets that are being rented to various construction companies. According to one embodiment, information about assets is selectively provided to various entities based on security issues. For example, a construction company C1 may have permission to only access information for the assets they rent and a construction company C2 may have permission to only access information for the assets they rent. The dealer, according to one embodiment, can access information for any or all of the assets that they own. According to yet another embodiment, access to asset management information is limited based on user preferences, as will become more evident. Although many embodiments are illustrated with respect to a dealer, various embodiments described herein would also work for a rental company that is not a dealer.

Business Model

FIG. 21 is a block diagram that depicts a relationship between manufacturers of construction assets, rental companies 2120 that rent construction assets, and construction companies 2130, according to one embodiment. In the past, construction companies 2130 typically bought all of their construction assets. However, since profit margins are narrowing, construction companies 2130 are moving more toward buying a core set of assets and then renting additional assets when they do not own enough assets to do a large construction project. Construction companies 2130 can rent these additional assets from either dealers 2122 or from rental companies 2124 that are not dealers. Dealers 2122 are typically the middle man between a particular manufacturer 2110 of construction assets, such as John Deere™ and Caterpillar™, and the construction company 2130. Examples of rental companies 2124 that are not dealers are United™, Hertz™ and Volvo™. Examples of construction companies 2130 include but are not limited to Kuwaiti™, Turner & Jacobs™, and Rudolph and Sletten™.

Since construction companies 2130 are moving toward renting a certain portion of the assets they need, dealers are selling less construction equipment. Therefore, dealers 2122 are entering the rental business to make up for profits they no longer make from sales.

Figure 22:
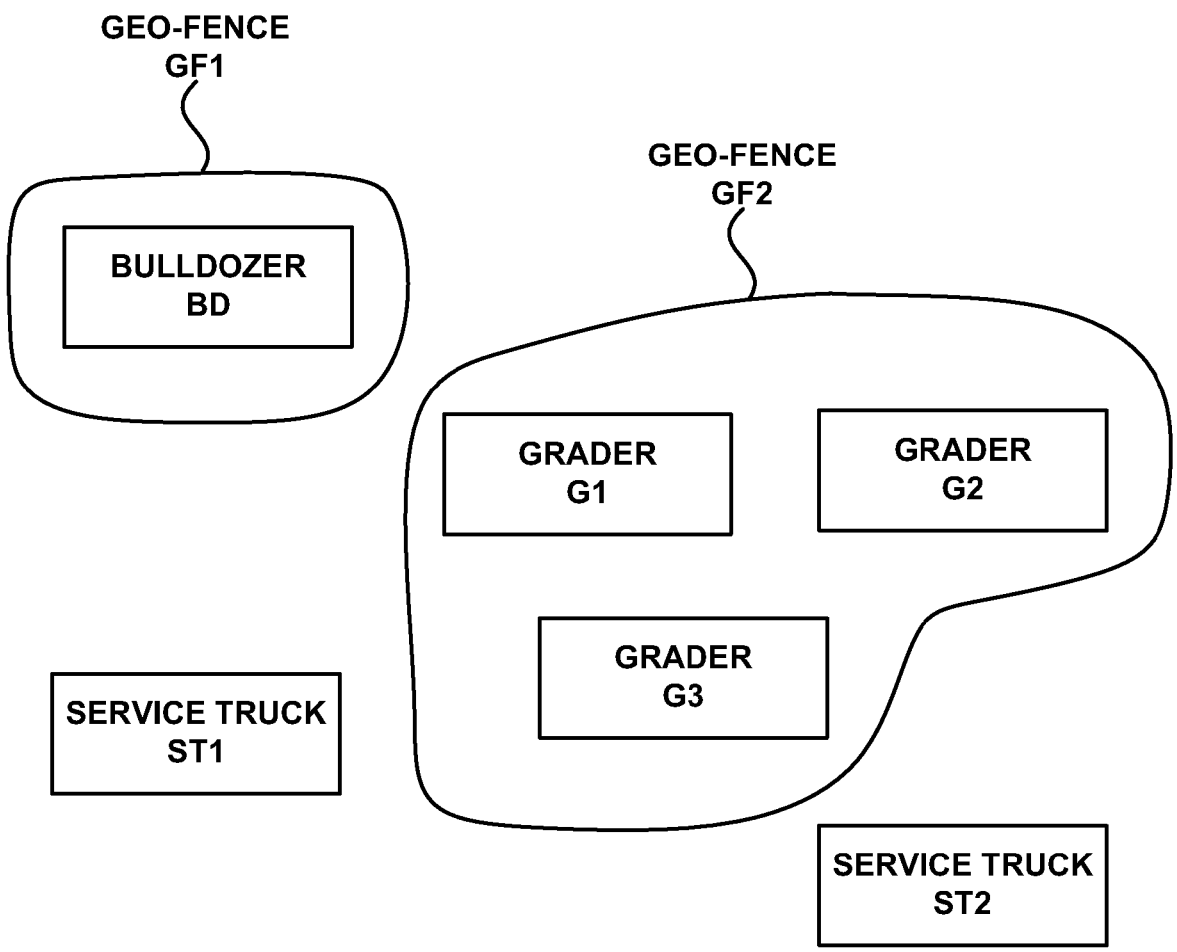
FIG. 22 depicts various assets that two construction companies have rented from a dealer and service trucks that a dealer owns, according to one embodiment.

FIG. 22 depicts various assets that two construction companies have rented from a dealer and service trucks that a dealer owns, according to one embodiment. The assets as depicted in FIG. 22 are three graders, G1, G2, and G3, a bulldozer, BD, two geo-fences, GF1 and GF2, and two service trucks, ST1 and ST2. Assume for the sake of illustration that construction companies C1 and C2 are two construction companies 2130. Assume for the sake of illustration that one construction company C1 has rented the bulldozer BD and the geo-fence GF1 and a second construction company C2 has rented three graders G1, G2, and G3 and a geo-fence GF2.

According to one embodiment, information pertaining to the assets depicted in FIG. 22 is stored in a database. According to one embodiment, access to asset management information is limited based on security issues. For example, the construction companies C1 and C2 would like to be able to obtain information pertaining to their own assets. However, a construction company 2130 probably does not want another construction company 2130 to have access to their information. Therefore, according to one embodiment, company C1 only sees their own assets BD and GF1. Similar construction company C2 only sees their own assets G1, G2, G3, and GF2.

Further, the dealer 2122 would also like to obtain information pertaining to the assets that they own, rent out, and/or maintain. For example, the dealer 2122 would like to obtain information pertaining to ST1, ST2, BD, GF1, G1, G2, G3, and GF2. More specifically, it is beneficial if the dealer 2122 can determine when and how much an asset has been used. For example, the dealer 2122 can use various embodiments to determine if a construction company 2130 used an asset for more time than they paid for. In another example, the dealer 2122 can use various embodiments to determine if any of the assets need maintenance, as will become more evident.

There are many different ways that a dealer 2122 can increase their profits using various embodiments described herein. In one example, a dealer 2122 can sell reporting sources 208 (FIG. 2A) to the construction company 2130. The construction company 2130 can use the reporting sources 208 to collect information that is transmitted to an asset management system that the dealer 2122 owns. The construction company 2130 can use the asset management system to access information about assets that they own or rent. The dealer 2122 can charge the construction company 2130 for the use of the asset management system, for example, on a monthly basis. The dealer 2122 could also charge the construction company 2130 a service fee when the dealer 2122 performs maintenance on assets that the construction company 2130 rents or owns.

Asset Management System

Figure 23:
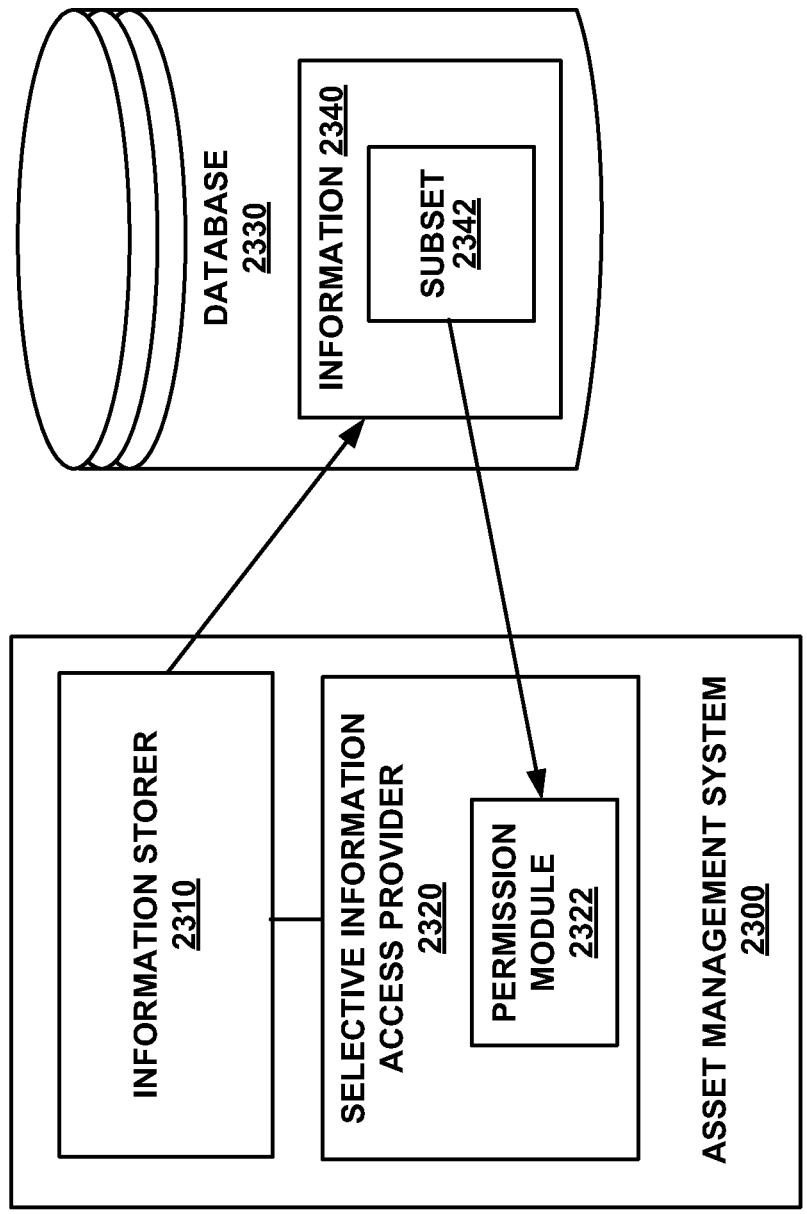
FIG. 23 depicts a block diagram of an asset management system, according to one embodiment.

FIG. 23 depicts a block diagram of an asset management system 2300, according to one embodiment. The blocks that represent features in FIG. 23 can be arranged differently than as illustrated, and can implement additional or fewer features than what are described herein. Further, the features represented by the blocks in FIG. 23 can be combined in various ways. The system 2300 can be implemented using software, hardware, firmware, or a combination thereof.

The asset management system 2300 includes an information storer 2310 and a selective information access provider 2320. The selective information access provider 2320 includes a permission module 2322. The information storer 2310 can store information about assets in a database 2330 resulting in stored information 2340. The selective information access provider 2320 uses the permission module 2322 to enable a first entity to access a first subset 2342 of the information 2340 stored in the database 2330 while not allowing a second entity to access the first subset 2342 of the information 2340, as will become more evident. According to one embodiment, the database 2330 is a relational database. According to one embodiment, database 205 (FIG. 2A) is an example of the database 2330 depicted in FIG. 23. According to one embodiment, SQL is used as a part of retrieving information 2340 from the database 2330.

Assets

Examples of assets include but are not limited to graters, levelers, dozers, saws, debris transportation vehicles, diggers, pavers, concrete trucks, supply trucks, cranes, tools, service trucks geo-fences, compressors and so on. Although many of the descriptions of embodiments provided herein refer to construction assets, various embodiments are well suited to other types of assets.

According to one embodiment, the assets are owned by a rental company 2120. The rental company 2120 can rent the assets to a construction company 2130. According to another embodiment, the assets are owned by the construction company 2130. A rental company 2120 may use various embodiments to maintain assets that the construction company 2130 either rents or owns. Refer to Section I for more information on assets.

Reporting Sources

Referring to FIG. 2A, examples of reporting sources 208 include, but are not limited to, permanently mounted devices 210, asset mountable/detachable device 215, portable computing device 220, personal digital assistant (PDA) 225, smart phone 230, mobile phone 235 and human intelligence 240. Refer to the discussion of reporting sources 208 in Section I for more information on reporting sources.

Information

According to one embodiment, information from a first reporting source about an asset is received and information from a second reporting source about the asset is also received. The information received from the two sources can be stored in a database 2330 resulting in stored information 2340. Refer to the description of step 406 (FIG. 4) for more information on populating a database.

According to one embodiment, the information 2340 is asset location data. Examples of asset location data include, but are not limited to, whether a vehicle is at a site, on a road, or in the correct area of a site. According to another embodiment, the information 2340 is asset operation data. Examples of asset operation data include, but are not limited to, speed an asset is traveling, time since the last oil change or other scheduled maintenance was performed on the asset, any indications of potential malfunction of the asset, and the activity the vehicle is currently engaging in or has previously engaged in. Squeaks may be an indication of potential malfunction of the asset.

The information 2340 can be used to determine how much an asset has been used, where the asset is located, whether it is being used appropriately, whether it has left a designated area as demarcated, for example, by a geo-fence, when the asset needs maintenance, which service truck would be best for performing the maintenance, and so on. Refer to the description of steps 402 and 404 (FIG. 4) of Section I for more information on "information about an asset."

Permissions and Security Issues

Figure 24:
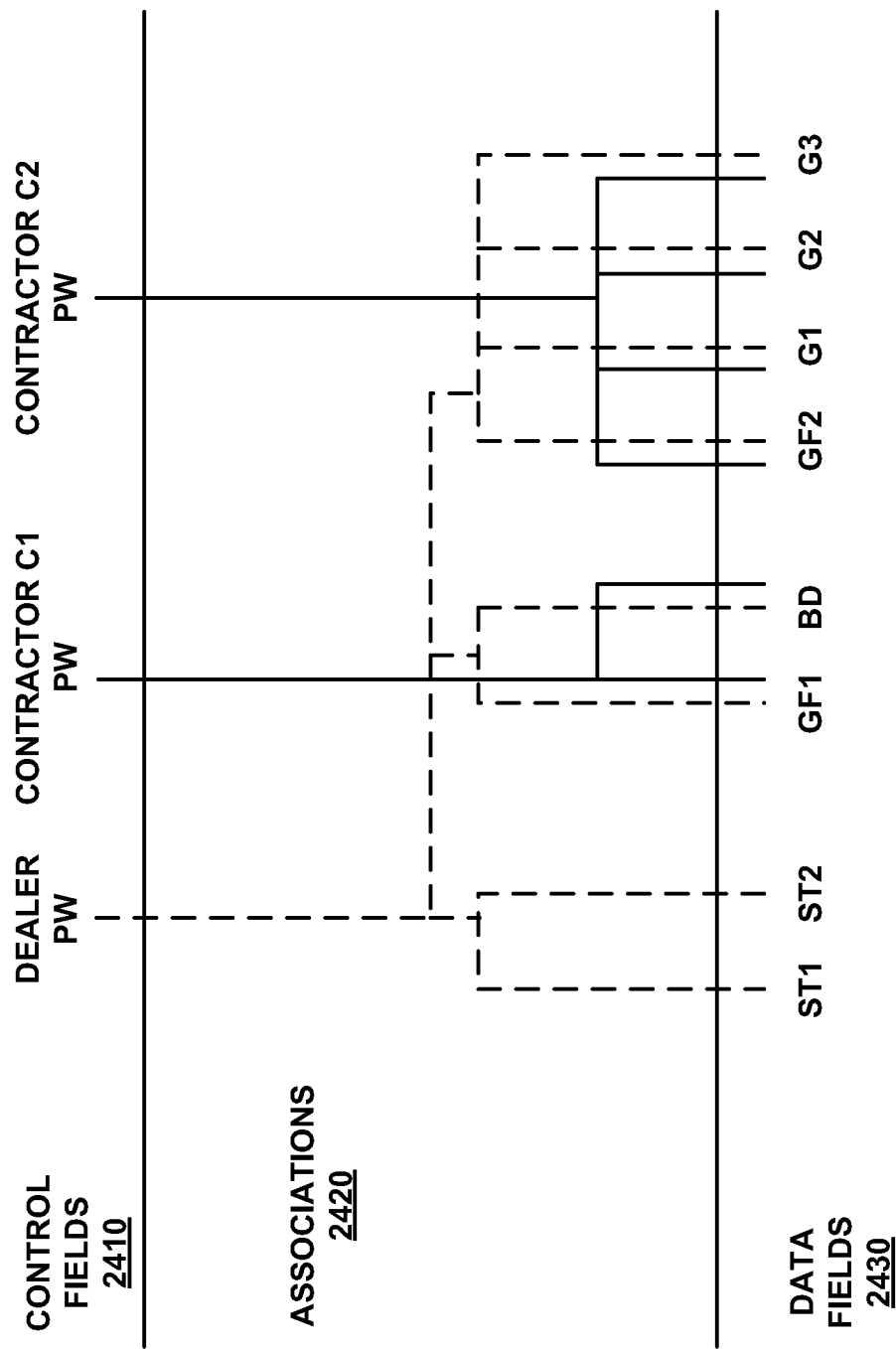
FIG. 24 is a diagram that illustrates using permissions to limit access to asset management information, according to one embodiment.

FIG. 24 is a diagram that illustrates using permissions to limit access to asset management information, according to one embodiment. FIG. 24 depicts control fields 2410, data fields 2430 and associations 2420 between the control fields 2410 and the data fields 2430. According to one embodiment, a database 2330 includes the control fields 2410, the data fields 2430 and the associations 2420. Data fields 2430, according to one embodiment, include information about assets, such as ST1, ST2, GF1, BD, GF2, G1, G2, and G3. A control field 2410 can include a password that is associated with an entity, such as a dealer 2122 or a construction company C1, C2. According to one embodiment, the dealer's password is associated with all of the assets ST1, ST2, GF1, BD, GF2, G1, G2, and G3 while the respective passwords for the construction companies 2130 is associated with the assets that they rent. The solid lines indicate the associations between the respective construction companies C1 and C2 and the respective assets that they are renting. The dashed lines indicate the associations between the dealer 2122 and the assets the dealer 2122 owns.

As depicted in FIG. 24, all of the assets are owned by the dealer 2122. However, according to another embodiment, assets may be owned by a construction company 2130. Assume for the sake of illustration that the construction company C1 owns graders G4 and G5. In this case, data fields 2430 may include information about the graders G4 and G5. The associations 2420 may indicate that the construction company C1's password can be used to access information about the graders G4 and G5. However, construction company C2's password would not enable construction company C2 to access information about the graders G4 and G5. According to another embodiment, the associations 2420 may also indicate that the dealer's password can be used to access information about the graders G4 and G5, thus, enabling the dealer 2122 to provide maintenance to graders G4 and G5 that the construction company C1 owns.

User Preferences

According to yet another embodiment, access to asset management information is limited based on user preferences. For example, a project manager that works for a construction company 2130 may be responsible for several projects. According to one embodiment, the project manager can access information that pertains to any or all of the projects they are responsible for. Similarly, a regional office, a district office or nation wide company can access information that pertains to any or all of the assets associated with them, for example, based on user preferences.

Other examples of user preferences include requesting to see how many of a particular type of asset are located at a particular store. For example, a customer, such as a construction company 2130's employee, may come in asking for a backhoe. Using various embodiments, an employee of the rental company 2120 could request to see how many backhoes are available for rental from the store at that location. Further, using various embodiments provide for determining not only if an asset is available but whether it is in good enough shape to be rented. For example, assume that a customer 2130 wants to rent a bulldozer. The rental company 2120's employee could use an asset management system 2300, according to one embodiment, to locate the bulldozers that are available at the rental store 2120's location. Assume that 3 bulldozers are available. However, two of the bulldozers are due for maintenance. Since the asset management system 2300 has access to information concerning maintenance, according to one embodiment, the asset management system 2300 could enable the rental store 2120's employee to determine to rent the bulldozer that does not need maintenance.

In another example, a user may specify that they want to see information about assets that will need maintenance within a certain period of time. The assets may be owned by either the dealer 2122 or the construction company 2130. The assets may be maintained at the rental company 2120's location or on the construction site. Further, the dealer 2122 can use the information 2340 stored in the database 2330 to determine which service truck ST1 or ST2 is closest to an asset that needs maintenance.

According to one embodiment, construction companies C1, C2 pay the dealer 2122 to maintain the assets. The dealer 2122 can maintain assets that are rented from the dealer 2122 or that are owned by the construction company C1, C2.

Project managers, rental company employees, district managers, regional managers, rental company owners, employees of a construction company, among other things, are examples of potential users of an asset management system 2300. According to various embodiments, a user of the asset management system 2300 can change the user preferences they are using and the assets that they access will be changed accordingly. For example, a project manager may request to access project A then later request to access project C. The selective information access provider 2320 can provide information about the appropriate assets based on whatever user preferences are requested. According to one embodiment, SQL is used to retrieve information 2340 from the database 2330 based on user preferences.

Dynamic Changes to the Information

The information 2340 stored in the database 2330 may be changed even as it is being viewed by various users. According to one embodiment, the asset management system 2300 handles these types of dynamic changes to the information 2340. For example, two rental store employees A and B may be looking to see what backhoes are available at the same time. Assume that employee A rents a backhoe out while employee B is still looking at the display of what backhoes are available.

According to one embodiment, the asset management system 2300 may prevent the same backhoe from being rented to two customers. For example, the asset management system 2300 may immediately update the information displayed to employee B as soon as the backhoe is rented. In another example, the asset management system 2300 does not immediately update the displayed backhoes that employee B sees. In this case, employee B may attempt to rent the same backhoe out. Then the asset management system 2300 can inform employee B that the backhoe has already been rented.

Figure 25:
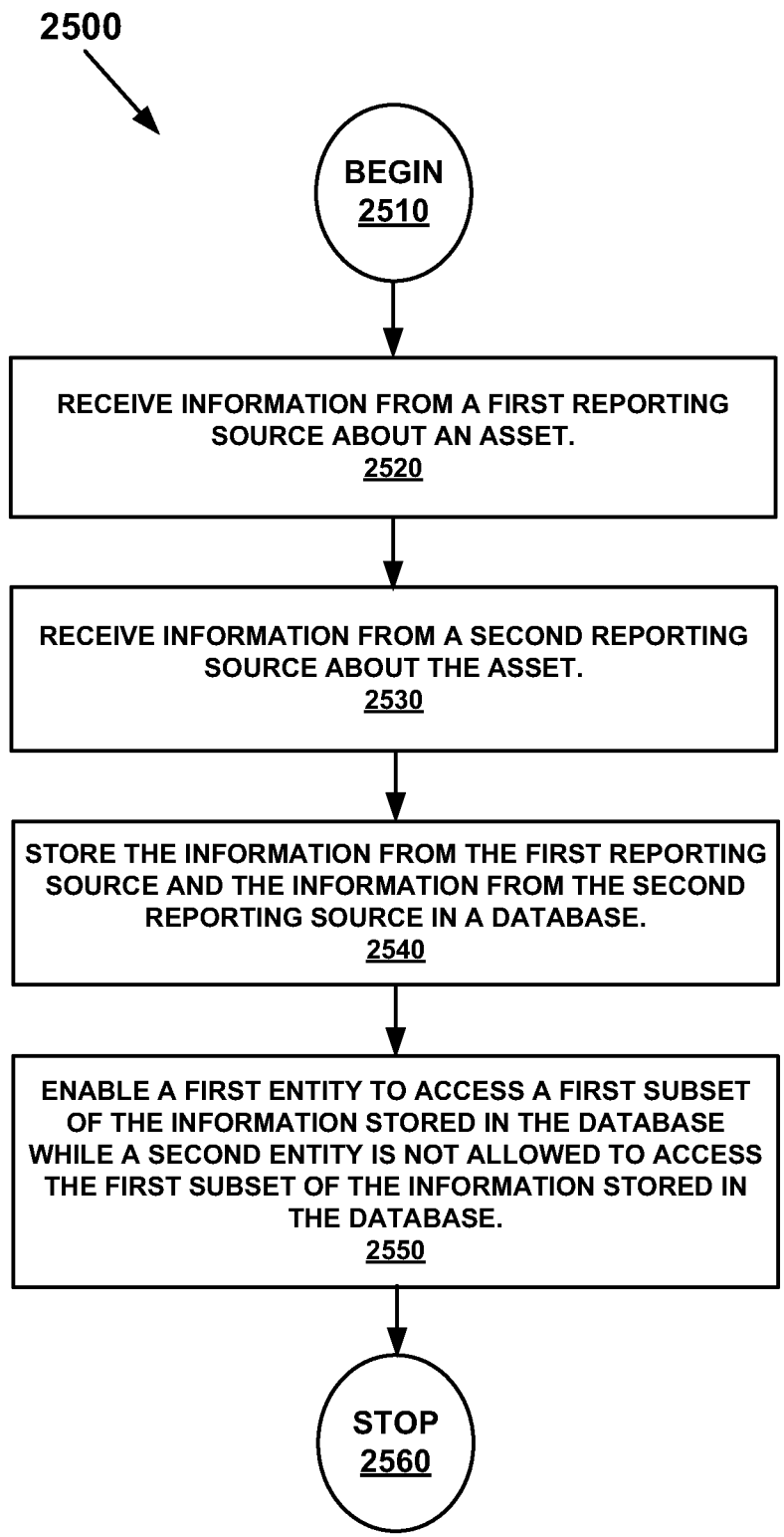
FIG. 25 is a flowchart of a method for limiting access to asset management information, according to one embodiment.

Operational Example of a Method for Limiting Access to Asset Management Information FIG. 25 is a flowchart of a method for limiting access to asset management information, according to one embodiment. Although specific steps are disclosed in flowchart 2500, such steps are exemplary. That is, embodiments of the present invention are well suited to performing various other steps or variations of the steps recited in flowchart 2500. It is appreciated that the steps in flowchart 2500 may be performed in an order different than presented, and that not all of the steps in flowchart 2500 may be performed.

All of, or a portion of, the embodiments described by flowchart 2500 can be implemented using computer-readable and computer-executable instructions which reside, for example, in computer-usable media of a computer system or like device. As described above, certain processes and steps of the present invention are realized, in one embodiment, as a series of instructions (e.g., software program) that reside within computer readable memory of a computer system and are executed by the of the computer system. When executed, the instructions cause the computer system to implement the functionality of the present invention as described below.

In step 2510, the method begins.

In step 2520, information from a first reporting source about an asset is received. For example, information from a first reporting source 208 can be received for assets as depicted in FIGS. 22 and 24. Assume for the sake of illustration that the first reporting source is an asset mountable/detachable device 215. The device 215 may be mounted on the assets ST1, ST2, BD, G1-G3, and so on.

A reporting source, such as the asset mountable/detachable device 215 used in step 2520, could automatically detect when an asset has been returned to a dealer and cause an asset management system to automatically update the database 2330 indicating that the asset had been returned. Further, a reporting source could communicate any kind of information already described herein to the database 2330.

Other types of information about an asset can also be received. Refer to the discussion of step 402 for more information on receiving information about an asset from a first reporting source. Refer to the "Asset" subheading of Section VI for more information on the types of assets that information may be received about. Refer to the "Information" subheading of Section VI for more information on the types of information that may be received.

In step 2530, information from a second reporting source about the asset is received. For example, information from a second reporting source 208 can be received for assets as depicted in FIGS. 22 and 24. Assume for the sake of illustration that the second reporting source is a personal digital assistant 225 (PDA). An employee of a construction company C1, C2 or a dealer 2122 may walk around and enter information pertaining to the assets ST1, ST2, BD, G1-G3 into the PDA 225. Therefore, according to one embodiment, information about an asset can be received from more than one reporting source 208 as already described in Section I.

As already stated, the device 215 could be used to automatically determine that an asset has been returned to a rental company and to cause an asset management system 2300 to update a database 2330. Similarly, a second reporting source, such as a PDA 225, used in step 2530 could be used to cause an asset management system 2300 to update a database 2330 when an asset is returned. Other types of information about an asset can also be received. Refer to the subheading "information" of Section I and the discussion of step 404 for more information on "receiving information about the asset from a second reporting source."

In step 2540, the information from the first and second reporting source is stored in the database. For example, an information storer 2310 can store the information received in steps 2520 and 2530 resulting in stored information 2340

(FIG. 23). Refer to the description of step 406 (FIG. 4) of Section I for more information on storing information in a database (also known as populating a database.)

In step 2550, a first entity is enabled to access a first subset of the information stored in the database while a second entity is not allowed access to the first subset of the information stored in the database. Assume for the sake of illustration that the first entity is a construction company C1 and the second entity is a construction company C2 as discussed in the context of FIG. 22. Further assume for the sake of illustration that the information storer 2310 stores information for the assets (ST1, ST2, GF1, GF2, BD, G1, G2, and G3) that the dealer 2122 owns and potentially rents in the database 2330. Further assume for the sake of illustration that the subset 2342 of information 2340 is about assets BD and GF1 that construction company C1 is renting. According to one embodiment, the permission module 2322 grants construction company C1 access to the subset 2342 of information 2340 while not granting construction company C2 access to the subset 2342 of information 2340.

Further, according to another embodiment, the permission module 2322 grants the dealer 2122 access to the subset 2342 of information 2340 while not granting the construction company C2 access to the subset 2342 of information 2340. Assuming for the sake of illustration that the information 2340 stored in the database 2330 pertains to one particular dealer 2122, according to one embodiment, the subset 2122 includes all of the information 2340 about assets that is stored in the database 2330.

According to one embodiment, when an entity wants to access information 2340, they can type their password into a user interface, for example, that communicates with an asset management system 2300 (FIG. 23). The permissions module 2322 can use the password to determine whether the subset 2342 of the information 2340 can be accessed. The selective information access provider 2320 can provide the subset 2342 of information 2340 if the permissions module 2322 grants access to the subset 2342. Refer to the subheading for "Permissions" of Section VI for more information.

According to another embodiment, access to information about assets can also be limited based on user preferences. For example, a project manager, a district manager, a nation wide company, and so on can use user preferences to limit access to information they are truly interested in. For example, a project manager may be interested in looking at information about project C. Then they may be interested in looking at information about project B. In another example, a rental company owner may be interested in how many assets of a particular type are available to be rented immediately.

In another example of user preferences, a user may specify that they want to see information about assets that will need maintenance within a certain period of time. The assets may be owned by either the dealer 2122 or the construction company 2330. The assets may be maintained at the rental company 2120's location or on the construction site. Refer to the subheading "User Preferences" of Section VI for more information about user preferences.

In step 2560, the method ends.

Conclusion

Various embodiments of the present invention can be used to limit access to asset management information. Access may be limited based on security issues or based on user preferences. By enabling customers, such as construction companies, to access the appropriate level of information, rental companies, that are dealers or non-dealers, can improve their relationships with their customers, which may lead to increased profits.

By enabling rental companies to view the appropriate level of information, rental companies are less likely to miss opportunities to rent assets. For example, conventional rental companies use a manual process of updating their asset tracking systems and therefore it takes a long time for an asset that has been returned to be entered into the system. Therefore, rental companies using conventional methods may think they do not have assets in stock when they do resulting in missed rental opportunities. However, using various embodiments of the present invention, the asset management system is immediately updated when an asset is returned therefore rental companies will miss fewer opportunities. Further, various embodiments enable a rental company to determine how long an asset has been used. If the asset was used longer than a construction company paid for, the rental company is in a position to charge the construction company more money. Various embodiments also enable a rental company to determine if an asset has been used appropriately and so on.

Although many embodiments are illustrated with respect to a dealer, various embodiments described herein would also work for a rental company that is not a dealer. Although many of the embodiments described herein referred to dealers, rental companies, and construction companies, various embodiments can be used for other types of businesses that involve asset management. Although many of the embodiments described herein referred to construction assets, various embodiments can be used for limiting access to information about other types of assets.

Section VII

Externally Augmented Asset Management

Overview

Embodiments described herein provide a method and system for externally augmented asset management. In general, embodiments described herein utilize a plurality of disparate sources for monitoring an asset and its environment. The disparate sources provide asset operational and environmental information which is populated in a database. The database is organized to combine the plurality of asset and environment information resulting in an organized single source of asset information. The resulting database will provide a vast plethora of asset management data with a depth significantly greater than a single information source can provide.

Moreover, by utilizing a plurality of disparate sources to provide asset and environment information, the asset manager's asset awareness is significantly increased while the opportunity for asset failure is significantly decreased. In other words, single asset or environment source reporter failure will not result in complete loss of asset management capabilities for the asset manager.

Furthermore, due to the asset management capabilities described herein a significant business management tool is realized. That is, because the asset management system is useful at all levels of asset management, the asset management system provides significant value added features at the manufacture level, the rental/lease level, and the owner level. Moreover, the value added features may very likely be "sell themselves" features.

Figure 26:
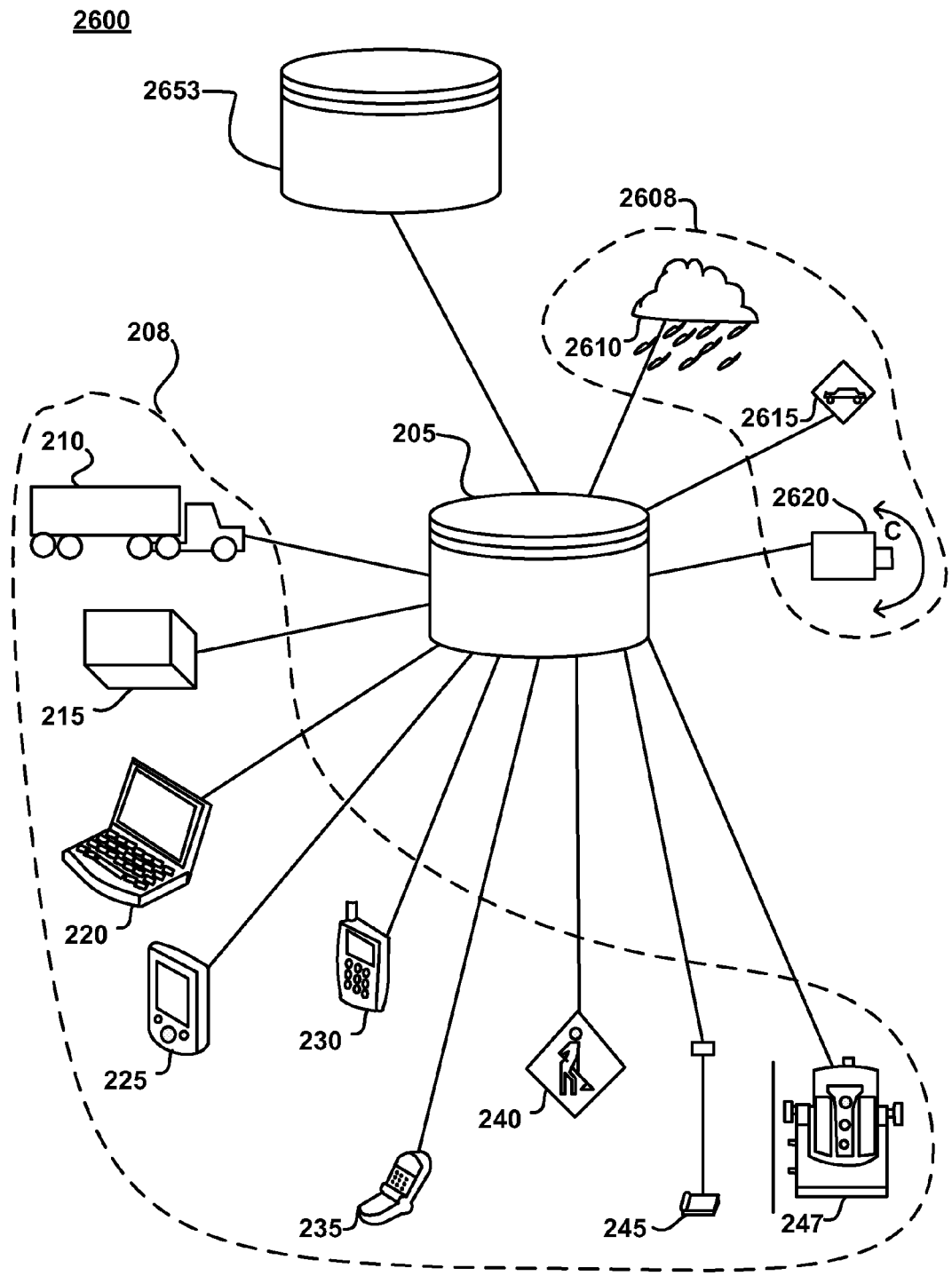
FIG. 26 is a network diagram of an exemplary method for externally augmented asset management in accordance with one embodiment of the present invention.

With reference now to FIG. 26, a network diagram of an exemplary method for externally augmented asset management is shown in accordance with one embodiment of the present invention. Asset management network 200 includes a database 205, a plurality of reporting sources 208, at least one environmental condition reporting source 2608 and a local business intelligence database 2653.

In general, database 205 receives information from at least two reporting sources 208 and the data within database 205 is organized such that information regarding an asset can be ascertained. For example, the data within database 205 may be organized such that information regarding a particular asset, or a plurality of assets, can be ascertained. This capability is described with respect to FIG. 2A and is not repeated herein for purposes of brevity and clarity.

In one embodiment, database 205 is a single database on a single computing system such as computing system 100. In another embodiment, database 205 may actually consist of a plurality of databases on a single computing system or on a plurality of computing systems. Moreover, the plurality of databases may be in the same location or spread throughout a plurality of locations. Additionally, the plurality of databases may be wired or wirelessly coupled together to form a network of databases upon which the asset information may be stored. In one embodiment, the asset may be machinery, a vehicle, an electrical or mechanical device, an inanimate object or any other traceable item.

Environmental reporting source(s) 2608 include devices such as, but not limited to, a weather reporting station 2610, a traffic reporting station 2615 and an imagery provider 2620. Moreover, reporting sources 2608 can include resources such as electronic devices, human sources, the asset being monitored, other assets, and the like. The local business intelligence database 2653 may be a local data source about the environment such as a local library, or a database maintaining environmental data. In one embodiment, the environmental data may include soils maps, geological maps, geographical maps, design files, imagery (e.g., satellite, video, still, etc), historical features, environmental protection regulations, protected flora and fauna, points of interest, and the like. In one embodiment, any or all of the environmental condition reporting sources 2608 are capable of providing environmental condition information including, but not limited to, traffic information, weather information, environment information, video or still imagery, and the like.

In general, weather reporting station 2610 may be an Internet weather resource, a weather satellite, a weather band radio broadcast, a weather station, a human report on the weather or the like which provides local, general or other weather related information. For example, weather reporting station 2610 may provide daily/weekly temperature ranges, precipitation, storm information, sky descriptions (e.g., cloudy, clear, foggy, etc.), forecasts, and the like. That is, weather reporting station 2610 will provide supplemental environmental information to the database 205 to provide actual weather conditions for an area in which the asset may be operating, an area in which the asset was supposed to operate, an area in which the asset had previously operated or any combinations thereof.

In general, the reported weather information may be used in both short term and long term planning. For example, in the short term, if an asset is needed at more than one location, the weather information may be reviewed per project location. If the weather is not suitable for the asset at the first location but is suitable at the second location, then the asset can be assigned to the second location. In so doing, in stead of the asset being sent to the first project location with weather conditions that are incompatible resulting in limited or non-use of the asset, the asset will be in an operational environment. In the long term, the weather history may be reviewed to extrapolate expected days of work, probable ground conditions, initial construction requirements, and the like. In one embodiment, the long term planning may provide a means of allocating assets, providing an initial manpower plan, etc.

Traffic reporting station 2615 may be an Internet traffic resource, a traffic camera, a traffic radio broadcast, a traffic metering device, a human report on the traffic or the like which provides local, general or other traffic related information. For example, traffic reporting station 2615 may provide daily/weekly traffic updates, accident reports, delays and the like. That is, traffic reporting station 2615 will provide supplemental environmental information to the database 205 to provide actual traffic conditions for an area in which the asset may be operating, an area in which the asset was supposed to operate, an area in which the asset had previously operated or any combinations thereof. For example, if an asset is traveling to a location, the traffic reporting may be used to generate the best route, provide a real time reroute based on present traffic conditions, and the like. Moreover, the traffic information may provide a forecasted route based on time of day, traffic accidents, road construction, etc.

Imagery provider 2620 may be an Internet camera, a traffic camera, a satellite, an image taken by a human or the like which provides local, general or other environmental condition related imagery. For example, imagery provider 2620 may provide daily/weekly/monthly/yearly imagery of any selected environment such as working location, selected location and the like. That is, imagery provider 2620 will provide supplemental environmental information to the database 205 to provide actual imagery for an area in which the asset may be operating, an area in which the asset was supposed to operate, an area in which the asset had previously operated or any combinations thereof.

In one embodiment, each reporting source 2608 may include capabilities such as position fixing, photography, text messaging, voice messaging, data messaging, radio frequency identification tag reading and the like. Furthermore, in one embodiment, any or all of the reporting sources 2608 may be capable of environmental condition monitoring for one or for a plurality of locations. For example, any or all of the reporting sources 2608 may be capable of providing precise location information, general area information and the like.

Figure 27:
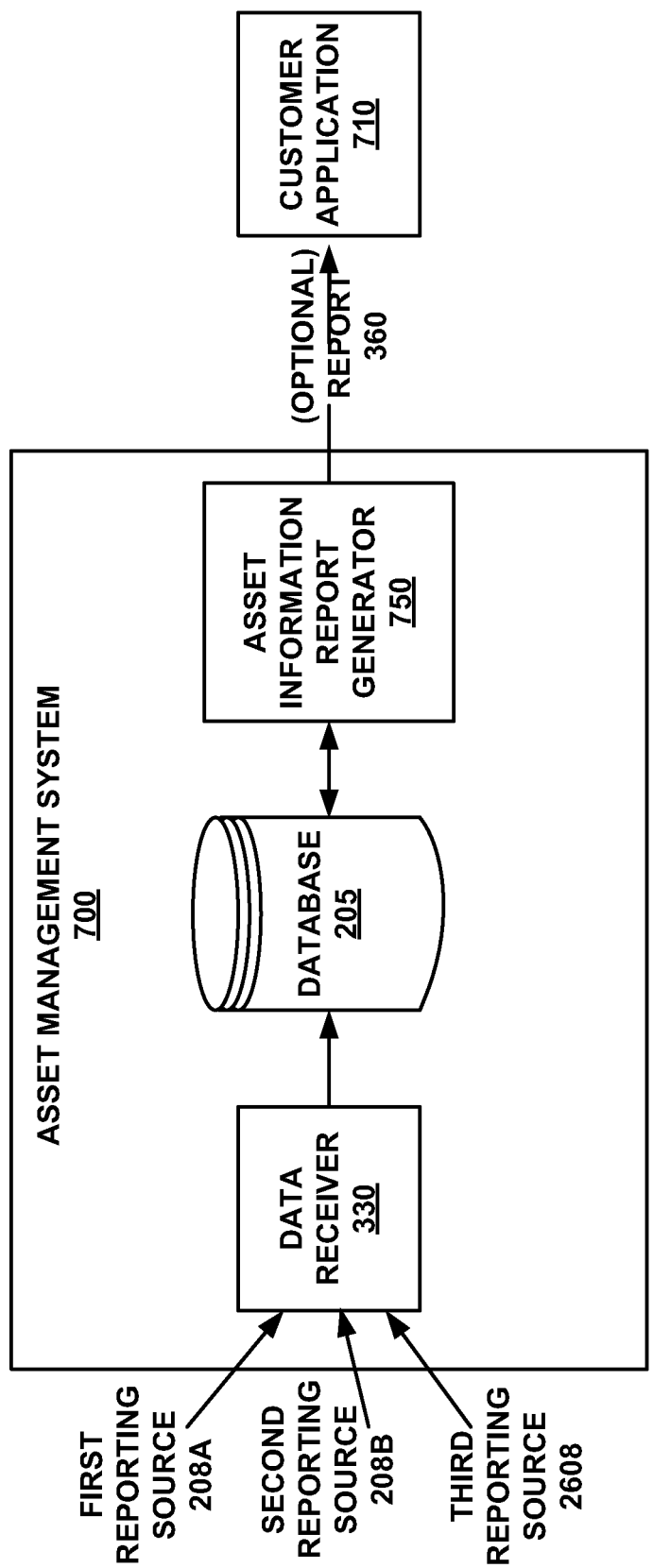
FIG. 27 is a block diagram of an exemplary externally augmented asset management system communicatively coupled with an optional customer application in accordance with one embodiment of the present invention.

With reference now to FIG. 27, an exemplary externally augmented asset management system 700 is shown communicatively coupled with an optional customer application 710 in accordance with one embodiment of the present invention. Asset management system 700 is comprised of data receiver 330, database 205, and an optional asset information report generator 750.

In general, data receiver 330 is configured for receiving information about an asset from multiple reporting sources (such as sources 208A and 208B). Moreover, data receiver 330 is configured for receiving information about the environment from at least one environmental reporting source 2608. Data receiver 330 reports this asset information to database 205, which is then populated with a first portion of information about an asset from a first reporting source 208A, a second portion of information about an asset from a second reporting source 208B, and so on for other reporting sources which report information about an asset. Moreover, database 205 may similarly receive and maintain information for a plurality of assets. The specific functions and operation of data receiver 330 and database 205 regarding the asset information reporting sources (e.g., 208A and 208B) have been previously described, and for purposes of brevity and clarity will not be re-described herein except as necessary to identify any differences or previously undescribed features.

At least one environmental reporting source 2608 provides environmental condition information in any or all of a plurality of methods to database 205. In general, the environmental information received to database 205 may be directed toward an asset location, to an area within which the asset is operating, or to an area in which the asset may plan to operate within. For example, if the asset were being moved on a freeway, the environmental information received to database 205 may include traffic information, accident information, weather information, imagery from the freeway, and the like. Moreover, in one embodiment, the environmental information received to database 205 may be time stamped and include location information or otherwise notated to ensure both time and location are verifiable. However, in another embodiment, the environmental information received to database 205 may only be time stamped or include location information. In yet another embodiment, the environmental information received to database 205 may not be time stamped and may not include location information or other notation.

The specific functions and operation of optional asset information report generator 750, optional report 360 and optional customer application 710 have been previously described herein, and for purposes of brevity and clarity the discussion will not be repeated.

Figure 28:
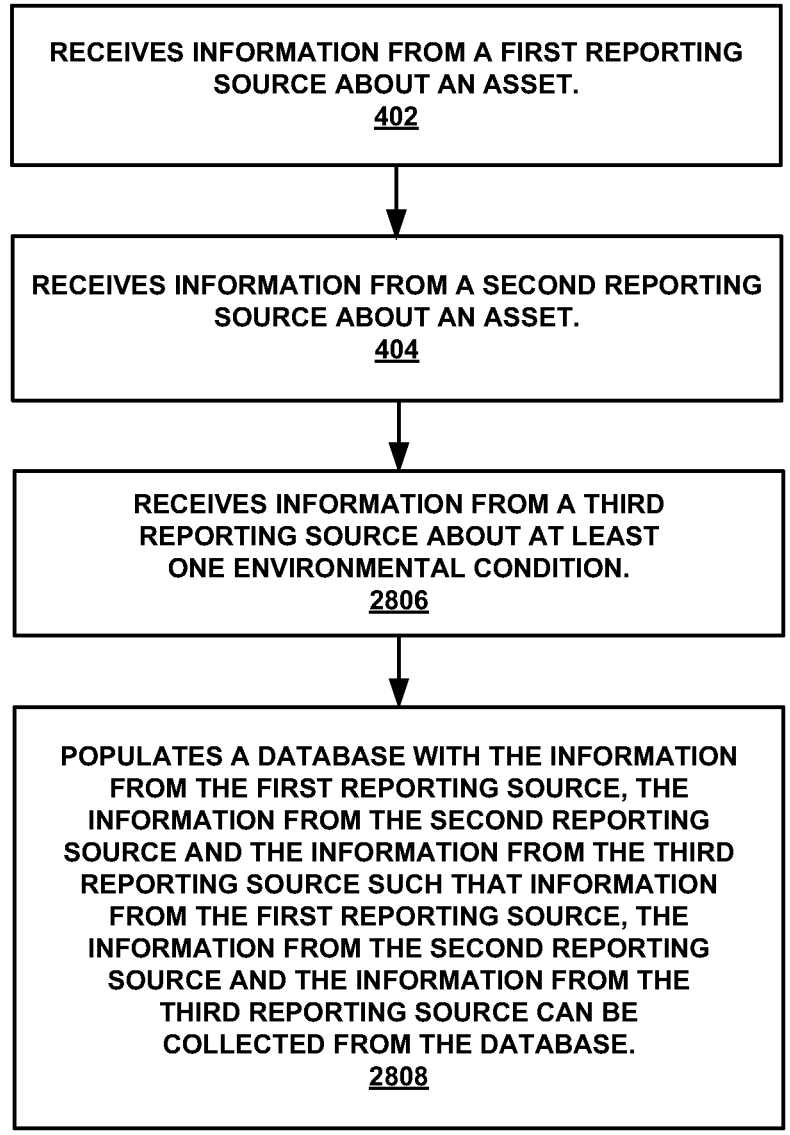
FIG. 28 is a flowchart of an exemplary method for providing externally augmented asset management in accordance with one embodiment of the present invention.

FIG. 28 is a flowchart 2800 of an exemplary method for providing externally augmented asset management in accordance with one embodiment of the present invention. In FIG. 28, elements 402 and 404 have been previously described, and in the interests of brevity and clarity will not be re-described. Instead reference is made to previous descriptions of these flowchart elements.

Referring now to 2806 of FIG. 28 and to FIG. 27, one embodiment receives environmental condition information from a third reporting source 2608 about an asset. As described in detail herein, in one embodiment, the environmental condition information is received to database 205 via data receiver 330. The information may be received wired or wirelessly as well as by direct connection of reporting source and data receiver 330 or over a network.

In one embodiment, the data receiver 330 receives environmental condition data from third reporting source 2608. As described herein, environmental condition data refers to environmental conditions pertaining to a geographic location. For example, if the asset is a vehicle, the environmental condition data may include, but is not limited to, the weather (e.g., sunny, foggy, rainy, etc.) within which the vehicle is traveling, the road conditions (e.g., delays, accidents, closures, etc.) and the like. In general, the environmental condition data may be received from sources such as, but not limited to, a weather station, the Internet, a radio station, a traffic camera, a satellite, human intelligence (HumInt) and the like.

Moreover, as described herein, although only one environmental condition reporting sources 2608 is shown, the present invention is well suited to receiving environmental condition information from more than one environmental condition reporting sources 2608 (as shown in FIG. 26). For example, in one embodiment, the data receiver 330 may receive environmental condition information from a multiplicity of sources such as any or all of sources 2610-2615.

With reference now to 2808 of FIG. 28 and to FIG. 27, one embodiment populates database 205 with information from first reporting source 208A, second reporting source 208B and third reporting source 2608 such that information regarding the asset and its operational environment can be ascertained from database 205. In one embodiment, the database 205 provides real-time location and/or operation monitoring capabilities for the asset and its environment. In another embodiment, the database 205 provides near real-time location and operation monitoring capabilities for asset and its environment.

That is, any or all of the reporting sources 208 providing information about the asset and environmental condition reporting sources 2608 providing environmental information may be configured to provide information constantly, provide regularly scheduled information updates, or provide information updates only when requested by a user.

For example, the environmental condition reporting source may be a traffic reporting device 2615 such as a highway traffic camera or the like. The traffic reporting device 2615 may provide constant highway information updates to the database. This may be important if the asset is regularly utilizing the highway. For example, the asset may be preparing to travel from point A to point B. However, by accessing the database, a user would be able to ascertain whether the regular route is available, if an alternate route is advisable, or other traffic conditions which may provide an insight to increase asset utilization efficiency.

In another example, the traffic reporting device 2615 may be used by a rental company to ensure the validity of a renter's excuse. For example, if a renter called and told the rental company on a Friday evening that the asset cannot be returned before closing due to traffic delays, the rental company would be able to check the database, e.g., view the optional report 360 or customer application 710 to ensure that the asset was indeed stuck in traffic. Thus, the rental company is not only capable of monitoring the asset to see if it was used on the weekend after the "stuck in traffic" call, but the rental company is also capable of checking to see if the asset was actually stuck.

In the same manner, any of the information about the environment can be constantly updated, the use of traffic information herein is merely provided as one example for purposes of brevity and clarity. However, if the environmental conditions do not require constant updates, then the information may not be constantly provided to the database 205. Using the traffic example again, if the asset is sitting in the same area, e.g., it is needed in the same location for the day, is broken, unused, awaiting maintenance, or the like, the environmental condition traffic information may only be provided on a scheduled update period. For example, in the morning the environmental conditions may be checked and then again in the evening, or only once a day, or only once a week, etc. Additionally, the environmental condition information may be modified based on the asset's status. That is, if the asset is unused, the environmental condition information may be updated only periodically or not at all. However, when the asset becomes operational, the environmental condition information may be updated on a more regular basis, or even constantly.

In addition, in one embodiment, the environmental condition and asset information is presented in the form of an asset information report 750 generated from the data in the database 205. In one embodiment, the data presented in environmental condition and asset information report 750 is a combination of all the information received about an asset and its environment. However, in another embodiment, the data presented in asset information report 750 is a combination of only portions of the information received about an asset and/or portions of the environmental condition information.

For example, database 205 may have redundant information regarding the asset and the environmental conditions from a plurality of reporting sources. That is, more than one reporting source may be providing environmental condition and asset location information. In one embodiment, all the information regarding the asset and the environmental conditions, including the redundant information, in the database may be used by report generator 750 when generating asset information report 360. However, in another embodiment, report generator 750 may remove the redundant information before generating asset information report 360 to reduce bandwidth, increase report clarity, or the like. In yet another embodiment, the redundant information may be removed at the database level to manage the size of database 205.

Moreover, in one embodiment asset information report 360 may be represented on a GUI, on paper, may be audibly provided, or may be provided in another user selected format. For example, the asset information report may be provided in an other than visual format for a user during times, such as, when the asset information report is being provided over a communications network, or for a visually impaired user, or for a user who cannot refer to a visual asset information report for operational/safety reasons, or the like.

Thus, embodiments of the present invention provide externally augmented asset management systems and methods. Embodiments further provide automated methods to customize asset information reports both visually and electronically. Embodiments also provide for automated methods to receive information reports from outside applications that run independently from the enhanced management system. Additionally, methods and systems are provided for combining outside information with asset management information in an electronic file formatted for use in a customer application or for manually or automatically providing such a formatted file to a customer application.

Section VIII

Impromptu Asset Tracking

Impromptu Asset Tracking System

An impromptu asset tracking system utilizes an asset management system, such as asset management system 700, and leverages the reporting capabilities of one or more reporting sources, such as reporting sources 208A and 208B (FIG. 3), to gather secondary reports of identification information associated with assets encountered on an impromptu basis, such as while driving past rental equipment assets in a rental yard or past construction equipment assets within a construction site. An example of the use of the use of reporting sources, such as 208A and 208B, to send such secondary reports is described in conjunction with FIG. 30 and illustrated by FIG. 31.

Figure 29:
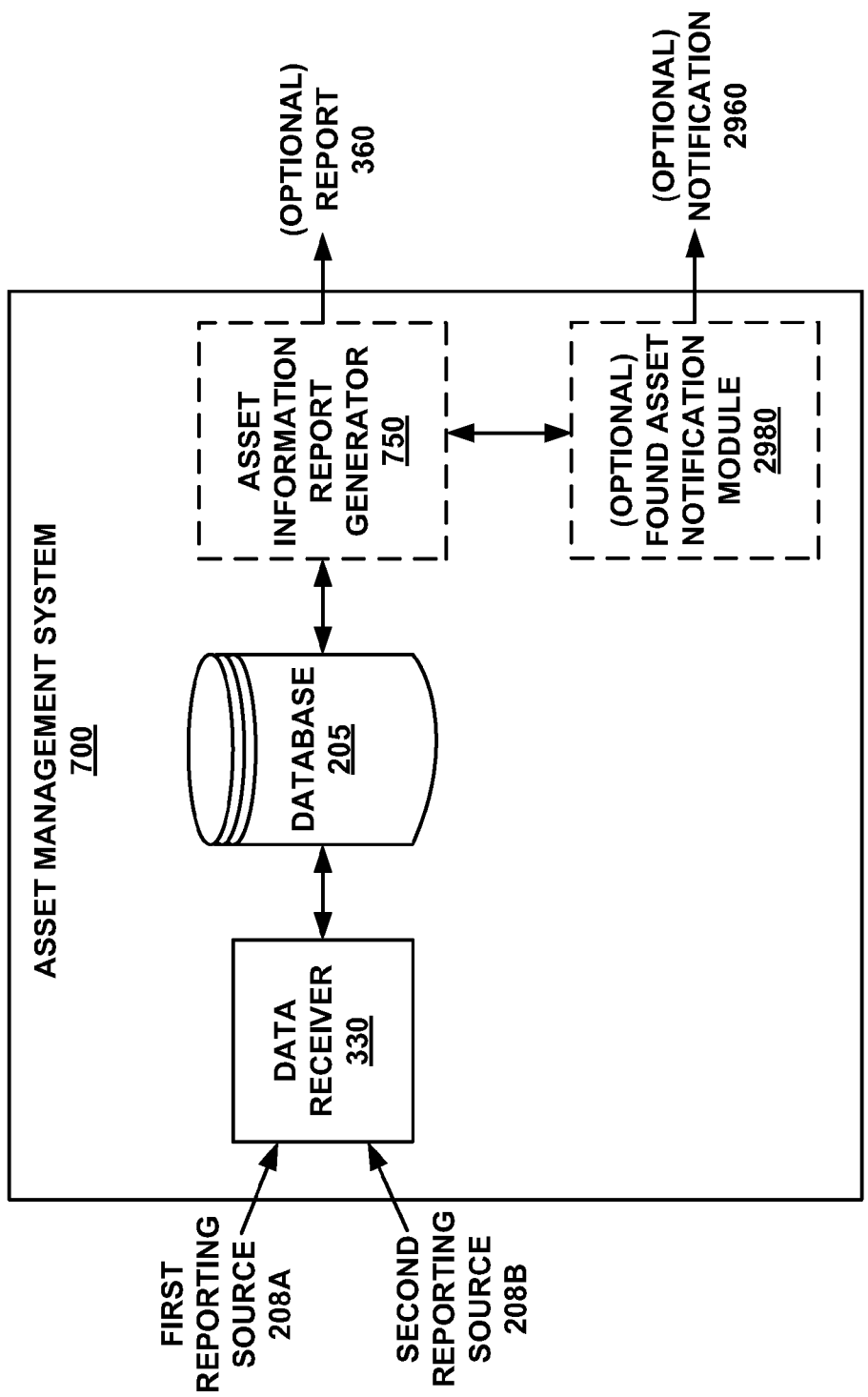
FIG. 29 is a block diagram of an exemplary asset management system utilized as an impromptu asset tracking system in accordance with one embodiment of the present invention.

With reference now to FIG. 29, a block diagram of an exemplary asset management system 700 utilized as an impromptu asset tracking system is shown in accordance with one embodiment of the present invention. Asset management system 700 is comprised of data receiver 330, database 205, optional asset information report generator 750, and optional found asset notification module 2980. The specific functions and operation of data receiver 330, database 205, and asset information report generator 750 have been previously described, and for purposes of brevity and clarity will not be re-described herein except as necessary to identify any differences or previously undescribed features.

In general, data receiver 330 is configured for receiving information about an asset from multiple reporting sources (such as sources 208A and 208B). As will be seen below, in one embodiment, this also includes receiving asset identification data and asset identification information that is gathered, for example on an impromptu basis, and then reported by reporting sources such as reporting sources 208A and 208B. In one embodiment, data receiver 330 reports this asset identification data and asset identification information to a database, such as database 205, which is then populated with the asset identification data and asset identification information. In some embodiments, this asset identification information and asset identification data is stored in the same database 205 along with previously described asset information that has been received from first reporting source 208A, from second reporting source 208B, and/or other reporting sources. In one embodiment, optional asset information report generator 750 is used to assign assets to groups and locations, assign reporting sources to groups, and to generate asset information reports 360 from asset information, asset identification data, and asset identification information held within database 205. As will be seen, in one embodiment, this includes generating asset information reports 360 which comprises asset identification information gathered on assets on an impromptu basis.

Optional found asset notification module 2980 is coupled asset information report generator and database 205, in one embodiment, and is used to register or "flag" assets of interest. Optional found asset notification module 2980 provides a user interface which allows information such as a serial number, type of asset, or inventory number of an asset to be flagged. A flagged asset may be a lost or misplaced asset, or simply an asset that a user has a particular interest in finding the location of. After such asset flagging information is entered, found asset notification module 2980 monitors database 205 for any identification information or identification data associated with a flagged asset or assets, which is subsequently populated into database 205.

In one embodiment, a user accesses any subsequently populated location information about a flagged asset at a later time, such as through asset information report 360 or via a graphical user interface provided by asset information report module 750. In one embodiment, optional found asset notification module 2980 allows a user to elect to receive from found asset notification module 2980 an optional notification 2960 such as, for example, a text message, a page, a cellular phone call, or an email in the event that the location of a flagged asset is subsequently populated into database 205. Although shown separately for purposes of clarity, it is appreciated that in one embodiment found asset notification module 2980 is integrated with another portion of asset management system 700, such as asset information report generator 750.

Method for Impromptu Tracking of an Asset

Figure 30:
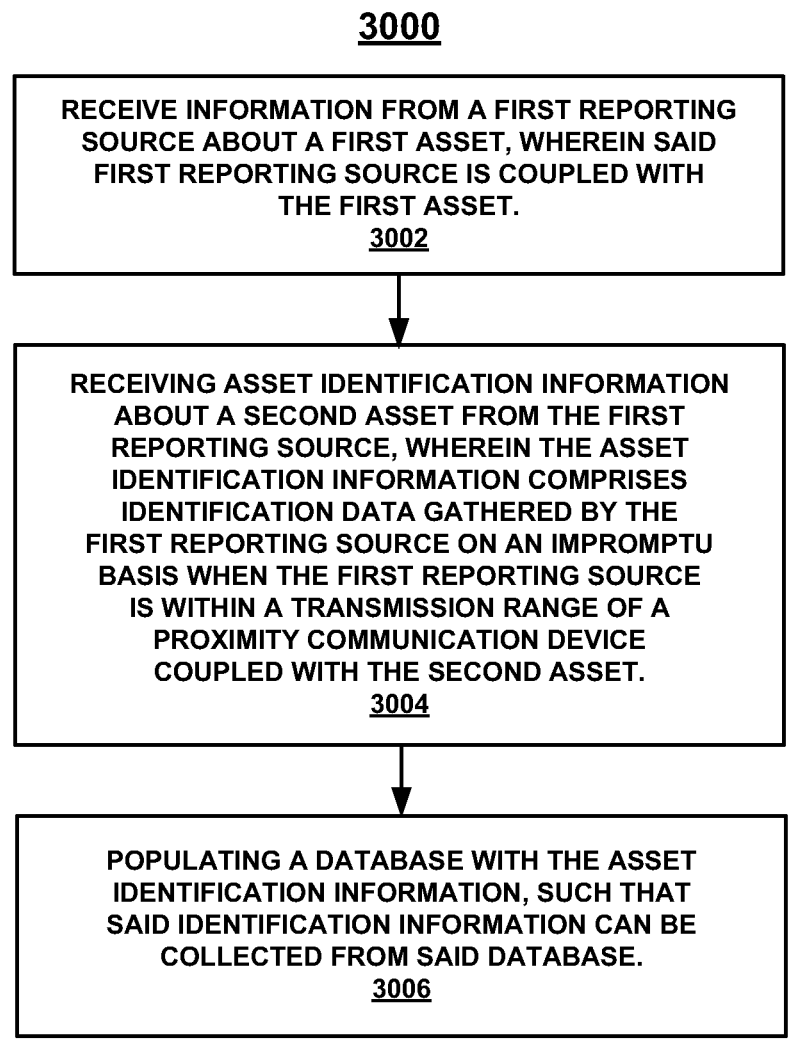
FIG. 30 is a flowchart of an exemplary method for impromptu tracking of asset locations in accordance with one embodiment of the present invention.

FIG. 30 is a flowchart of an exemplary method 3000 for impromptu tracking of asset locations in accordance with one embodiment of the present invention.

Figure 31:
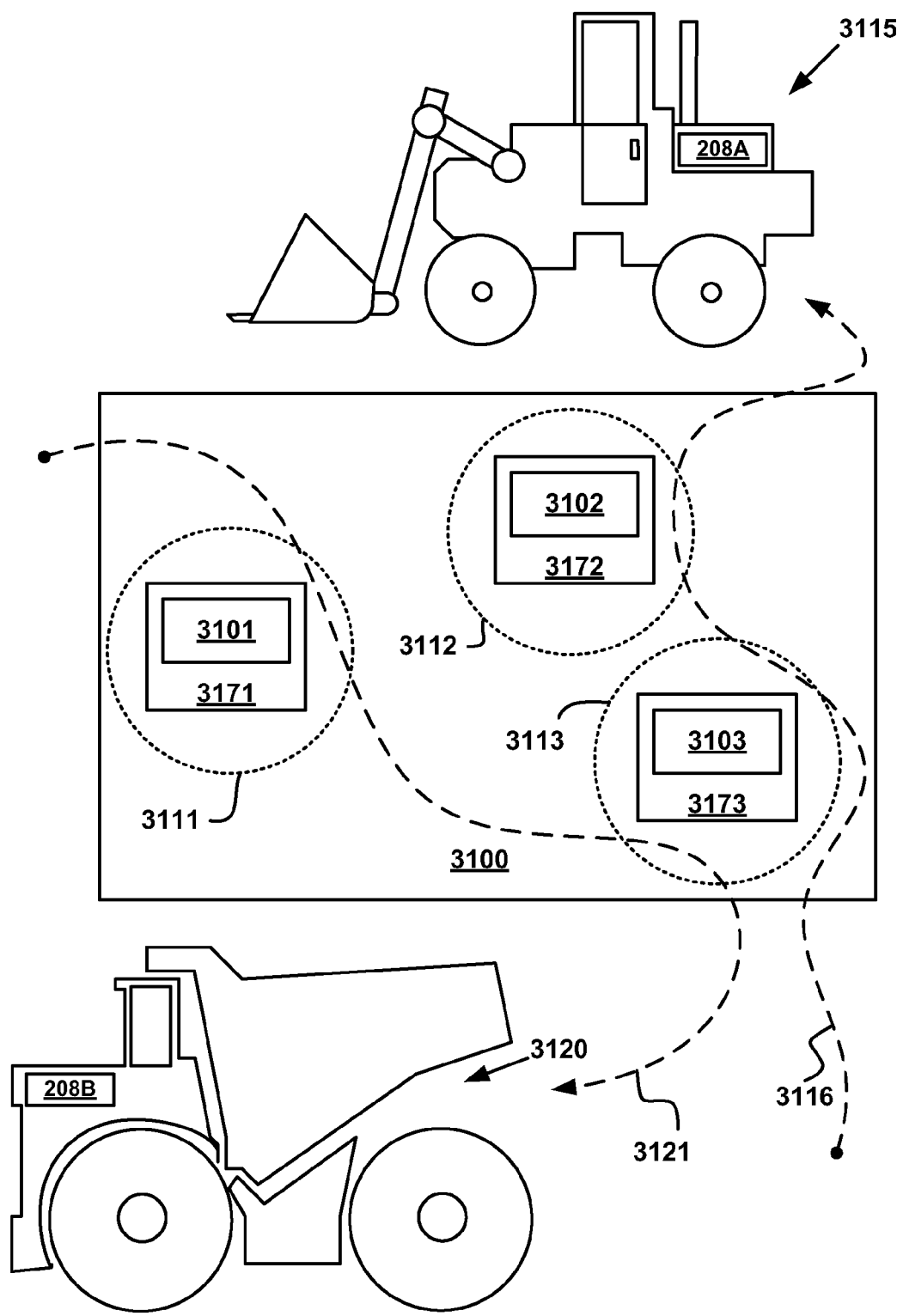
FIG. 31 is diagram of an exemplary embodiment of impromptu tracking of asset locations in accordance with one embodiment of the present invention.

With reference now to element 3002 of FIG. 30 and to FIG. 29, one embodiment receives information from a first reporting source 208A about a first asset. The first reporting source 208A is coupled with the first asset. This receipt of information is consistent with the receipt of information about an asset described in conjunction with 402 of method 400, except that in this case, the reporting source 208 is coupled with the asset that it is reporting information about. This contrasts with the reporting source 208 in element 402 which may or may not have been coupled with an asset that information was being reported about. As previously described, information received from reporting source 208A may be location information or operation information about the asset. FIG. 31 provides an example of two such reporting sources (208A and 208B) which are coupled with construction vehicles and report asset information about their respective vehicles.

With reference now to FIG. 31, a diagram of an exemplary embodiment of impromptu tracking of asset locations is shown in accordance with one embodiment of the present invention. In FIG. 31, a region such as a rental equipment yard, asset sales lot, or construction site is shown by region 3100. For purposes of this example, it may be assumed that region 3100 represents a construction site. Within construction site 3100, are located proximity communication devices 3101, 3102, and 3103. FIG. 31 also shows a loader 3115 which is equipped with a first reporting source 208A, and a dump truck 3120 which is equipped with a second reporting source 208B.

The primary purpose of the reporting sources 208A and 208B is to report location information and/or operation information about an asset, and as such each has an information module for gathering information associated with the asset to which it is coupled. For instance, in this example, the primary purpose of reporting source 208A is to report location information and/or operation information about loader 3115 with which it is coupled. Similarly, in this example, the primary purpose of reporting source 208B is to report location and/or operation information about dump truck 3120 with which it is coupled. As previously described, reporting sources 208A and 208B may comprise (or be configured with) global navigation satellite system (GNSS) receivers to facilitate reporting of location information. Likewise, reporting sources 208A and 208B may be coupled with one or more operation information providing source such as a J-bus, asset processor, diagnostic evaluator, engine microprocessor, mileage indicator, speedometer, tachometer, oil pressure indicator, wheel pressure indicator, hydraulic indicator, engine time, and ignition switched power source of the respective asset to which they each are coupled. As previously indicated, in various embodiments, a reporting source such as 208A and/or 208B, may comprise a TrimTrac™ device, a CrossCheck® device, a mobile phone (e.g., a cellular telephone), a personal digital assistant, a portable computing device, a radio frequency identifier, a smart phone, and the like.

With reference now to 3004 of FIG. 30, one embodiment receives asset identification information about a second asset from the first reporting source. In one embodiment, the asset identification information comprises identification data gathered by the first reporting source on an impromptu basis when the first reporting source is within a transmission range of a proximity communication device coupled with the second asset. In some embodiments, receiving asset identification information comprises receiving asset identification data alone, or else combined with other information such as location information and/or time information.

In one embodiment, for example, the identification data is combined with the location of reporting source 208A when the identification data was gathered. For example, a geographic location (latitude and longitude) or a particular site or area that reporting source 208A is operating in. In one embodiment, such location data is derived from a global navigation satellite system (GNSS) receiver of reporting source 208A. In another embodiment, the identification data is combined with the time when reporting source 208A gathered the identification data. The time may be taken from an internal clock of reporting source 208A, or may be from an outside source such as a satellite signal or cellular telephone signal that is received by reporting source 208A.

By "impromptu basis" what is meant is that gathering and reporting of information about additional assets is a secondary function of the first reporting source 208A that only occurs, for example, as a result of the first reporting source 208A coming within range of a transmission of asset identification data issued from a proximity communication device (3101, 3102, 3103) coupled with the second (or subsequent) asset. Though the gathering of identification data occurs on an impromptu basis, creation of this situation for gathering identification data may be purposeful or accidental. Thus, in a situation where reporting source 208A is coupled to a vehicle, the vehicle may be purposely driven through an area to encounter additional assets and gather identification data on these additional assets in the area. Likewise, even without this purposeful operator intent, reporting source 208A will still gather information from encountered additional assets as the vehicle is driven about at random, or in the performance of some other task.

Referring again to FIG. 31, reporting sources 208A and 208B are each configured to collect secondary information gathered about additional assets, such as from identification data transmitted by proximity communication devices coupled to these additional assets. To this end, each reporting source (208A, 208B) is configured with a proximity communication device, such as a radio frequency identification (RFID) reader, a Bluetooth device, and/or a wireless fidelity (WiFi) wireless local area network (WLAN) device for gathering identification data from additional assets equipped with complementary communication devices. Gathered identification data is then reported via a transmitter, such as by cellular telephone, to a data receiver, such as data receiver 330 (FIG. 29). This reporting is performed in the same fashion as has been previously described for the primary reporting of the asset operation information and/or asset location information reported by reporting sources 208A and 208B. For purposes of this example, it may be assumed that reporting sources 208A and 208B are each equipped with an RFID reader, a Bluetooth communication device, and a WiFi communication device.

Proximity communication devices 3101, 3102, and 3103 are communication devices with limited transmission ranges such as a few centimeters to several tens of meters. Proximity communication devices (3101, 3102, and 3103) comprise devices such as, but not limited to: radio frequency identification (RFID) tags, wireless fidelity (WiFi) device, or Bluetooth devices. For the purposes of this example, it may be assumed that that device 3101 is an RFID tag, that device 3102 is a WiFi device, and the device 3103 is a Bluetooth device. Though such proximity communication devices have limited transmission ranges, they have advantages such as low cost, low power requirements (in some cases no power requirements), small footprint, and ruggedization. The operation of such proximity communication devices is well known, and is for the purposes of brevity and clarity is not described in detail herein.

In FIG. 31, each proximity communication device (3101, 3102, 3103) is coupled with an asset, such as a construction equipment asset whose value does not justify an "active" asset management enabling device (such as a TrimTrac™ device or a CrossCheck® device), is too small for an active asset management enabling device, or has no power for an active asset management enabling device. Each proximity communication device (3101, 3102, 3103) is programmed to transmit identification data that is associated with the asset it is coupled with. Such identification data may comprise: a vehicle identification number; a serial number; an asset type (e.g., a generator, a portable light, a loader bucket, or some other asset type); a model number; an inventory number associated with the asset; or some other descriptive information about the asset to which the proximity communication device (3101, 3102, 3103) is coupled. For purposes of this example, it may be assumed that RFID tag 3101 is coupled with a loader bucket 3171 and is configured to transmit a signal comprising the serial number of loader bucket asset 3171 for a limited range 3111. Likewise, in this example, WiFi device 3102 is coupled with a portable light 3172 and is configured to transmit a signal comprising an inventory number associated with portable light asset 3172 for a limited range 3112. Finally, Bluetooth device 3103 is coupled with a generator 3173 and is configured to transmit a signal comprising the serial number associated with generator asset 3173 for a limited range 3113.

As loader 3115 drives on path 3116 through construction site 3100, it enters transmission range 3113 and reporting source 208A gathers identification data from Bluetooth device 3103. Reporting source 208A records a location of loader 3115 when the identification data was gathered and/or a time that the identification data was gathered from Bluetooth device 3103. As loader 3115 continues on through transmission range 3112, reporting source 208A gathers identification data from WiFi device 3102. Reporting source 208A records a location of loader 3115 when the identification data was gathered and/or a time that the identification data was gathered from WiFi device 3102. At some point, such as immediately after gathering identification data, after being queried, or at a scheduled time, reporting source 208A reports gathered identification information (identification data combined with location of gathering and/or time of gathering) to data receiver 330.

In a like manner, as dump truck 3120 drives on path 3121 through construction site 3100, it enters transmission range 3111 and reporting source 208B gathers identification data from RFID tag 3101. Reporting source 208B records a location of dump truck 3120 when the identification data was gathered and/or a time that the identification data was gathered from RFID device 3101. Similarly, as dump truck 3120 enters transmission range 3113, reporting source 208B gathers identification data from Bluetooth device 3103. Reporting source 208B records a location of dump truck 3120 when the identification data was gathered and/or a time that the identification data was gathered from Bluetooth device 3103. At some point, such as immediately after gathering information, after being queried, or at a scheduled time, reporting source 208B reports gathered identification information (identification data combined with location of gathering and/or time of gathering) to data receiver 330.

With reference now to 3006 of FIG. 30 and to FIG. 29 and FIG. 31, one embodiment populates a database 205 with the asset identification information. The information is populated is such that it can later be collected from database 205, for example, to be used in an asset information report. Thus in the embodiment illustrated by FIG. 31, the identification information received by data receiver 330 is populated into a database, such as database 205, where it is associated with an assigned asset. In one embodiment, this comprises populating identification information received from other reporting sources such as reporting source 208B. Thus, identification information, which is populated into database 205 for a particular asset, may be identification information that is received from a single reporting source or multiple reporting sources. It is appreciated that in one embodiment, such identification information is populated in a different database than database 205. It is also appreciated that such identification information may be populated in to a database that is shared with or separate from other asset information received from reporting sources such as reporting sources 208A and 208B.

Additionally, although method 3000 and FIG. 31 have described in conjunction with an exemplary embodiment where proximity communication devices 3101, 3102, and 3103 are coupled to construction equipment assets, it is appreciated that in other embodiments such proximity communication devices can also be coupled with other assets, such as rental equipment assets, material (e.g., I-beams, windows, furniture), or packaging material (e.g., pallets, boxes), for the purpose of tracking such assets on an impromptu basis when they are within transmission range of a reporting source, such as reporting source 208A. Furthermore, although only three proximity communication devices are shown in FIG. 31, it is appreciated that in other embodiments tens, hundreds, or more may be utilized, each coupled with an asset and configured to transmit identification data associated with that asset.

Similarly, in one embodiment, a reporting source such as reporting source 208A or 208B is capable of gathering and reporting (transmitting) the individual asset identification information that is gathered through impromptu interaction with such a plurality of proximity communication devices. Thus, in one embodiment, reporting source 208B receives a plurality of signals from a plurality of RFID tags that are coupled with a plurality of assets separate from, loaded in, or coupled with dump truck 3120, and which are encountered during the operation of dump truck 3120. Reporting source 3120 then reports (such as via a cellular telephone transmission) the identification information that is associated with this plurality of assets. The identification information is received by data receiver 330, and then populated into database 205.

Moreover, although reporting sources 208A and 208B have been described as being coupled with construction vehicles, it is appreciated that in other embodiments such reporting sources may have other configurations. For example, in one embodiment a reporting source 208A comprises a GNSS receiver and an RFID reader coupled to a cellular telephone. In this embodiment, reporting source 208A may be carried around by a person and would similarly report identification information gathered on an impromptu basis during the travels and movements of the person. In such an embodiment, the primary information being reported by a reporting source such as 208A is the location of the asset carrying the reporting source (which in this case is a person, such as a construction manager). The secondary information being reported is the asset identification information gathered on an impromptu basis as the reporting source 208A moves through a rental yard, sales lot, construction site, or the like, which contains assets equipped with proximity communication sources such as RFID tag 3101.

Reports and Notifications

In one embodiment, asset identification information is presented in the form of an asset information report 360 generated from the data in the database 205. In one embodiment, the data presented in asset information report 360 is a combination of all the information received about an asset from every reporting source 208. However, in another embodiment, the data presented in asset information report 360 is a combination of only portions of the information received about an asset from any or all of reporting sources 208.

Asset identification information in a database, such as database 205, may have redundant information regarding an asset from a plurality of reporting sources 208. That is, more than one reporting source 208 may be providing asset location information. For example, as illustrated in FIG. 31, reporting sources 208A and 208B each gathered identification data from proximity communication source 3103, which is coupled with generator 3173. Likewise, reporting sources 208A and 208B each reported identification information associated with generator 3173. In one embodiment, all the identification information in database 205 regarding the asset, including the redundant information, may be used by report generator 750 when generating asset information report 360. However, in another embodiment, report generator 750 may remove the redundant information before generating asset information report 360 to reduce bandwidth, increase report clarity, or the like. In yet another embodiment, the redundant information may be removed at the database level to manage the size of database 205. Asset information report generator 750 may combine asset information and asset identification information into a single asset information report 360 or generate separate asset information reports 360 with each type of information. Thus in one embodiment, asset information report generator 750 generates an asset information report 360 which comprises at least a portion of asset identification information.

Moreover, in one embodiment asset information report 360 may be represented on a GUI, on paper, may be audibly provided, or may be provided in another user selected format. For example, the asset information report may be provided in an other than visual format for a user during times, such as, when the asset information report is being provided over a communications network, or for a visually impaired user, or for a user who cannot refer to a visual asset information report for operational/safety reasons, or the like.

With reference now to FIG. 32, a block diagram of an exemplary printable format 3200 is shown of an asset information report 360 generated by asset management system 700 in accordance with one embodiment of the present invention. Exemplary printable format 3200 may also be viewed, such as on a video monitor coupled with a computer, or on a screen of a personal digital assistant. As seen in FIG. 32, asset information report generator 750 has extracted from database 205 identification information provided by proximity communication device 3103, which is coupled with generator asset 3173. In one embodiment, asset information report generator 750 provides a title 3205, such as "Asset Location Report." Such an asset location report can provide location information for one asset, a class of assets, or a group of assets. For example, in one embodiment, asset information report 360 comprises an asset location report for a group of assets which have been assigned, via asset information report generator 750, to a particular geo-fenced area, such as a construction site.

Printable format 3200 displays the identification information from database 205 as an asset location report for one asset. Report 3200 is formatted in columns which correspond to the asset 3202, the time 3203 that asset identification data was gathered by a reporting source, and the location 3204 of the reporting source when the identification data was gathered. Column 3202 shows that the asset is a generator. Column 3202 shows the various times, in this case including the dates, that identification information for the generator was received by a reporting source. Column 3204 shows the various locations of the reporting source which correspond to the different times that identification data was gathered by a reporting source. As can be seen, the location remains the same on four out of the five times that asset identification data was gathered. However, as shown in cell 3220, the generator was at a different location on 29 Aug. 2006 at 7:37 pm than it had been previously.

In one embodiment, found asset notification module 2980 is used to provide a notification when identification data for a flagged asset has been populated into a database. For example, assume a construction supervisor searched for generator 3173 on Aug. 22, 2006 and could not find it at or near latitude 38.1637/longitude 95.3221. He then flags generator asset 3173 using found asset notification module 2980. In one embodiment, when subsequent identification data for generator 3173 is populated into database 205, found asset notification module 2980 generates a notification, which is then issued, for example to the cellular phone of the construction supervisor. The notification indicates, for example, that on 29 Aug. 2006 identification data for the generator asset was gathered at the location of latitude 38.9886/Longitude −95.3029. The construction manager can then go to this location to look for generator 3173.

It is appreciated that the location information which is gathered and reported is actually location information associated with a reporting source, such as reporting source 208A. However, due to the short range of proximity communication devices (3101, 3102, and 3103 for example) the location information is accurate enough to help find the asset, or to pinpoint the location of an asset to a particular construction site, portion of a construction site, region of a rental yard, or a particular area that the asset is assigned to. This is useful when trying to locate a lost or misplaced asset, when determining what assets are located on a particular construction site, or in a particular rental yard. Thus, this location information is sufficient for a construction supervisor to realize that a generator asset 3173 has been left behind on an old job site, is misplaced behind a pile of junk, or is hidden by some tall vegetation which has grown up around it.

Figure 33:
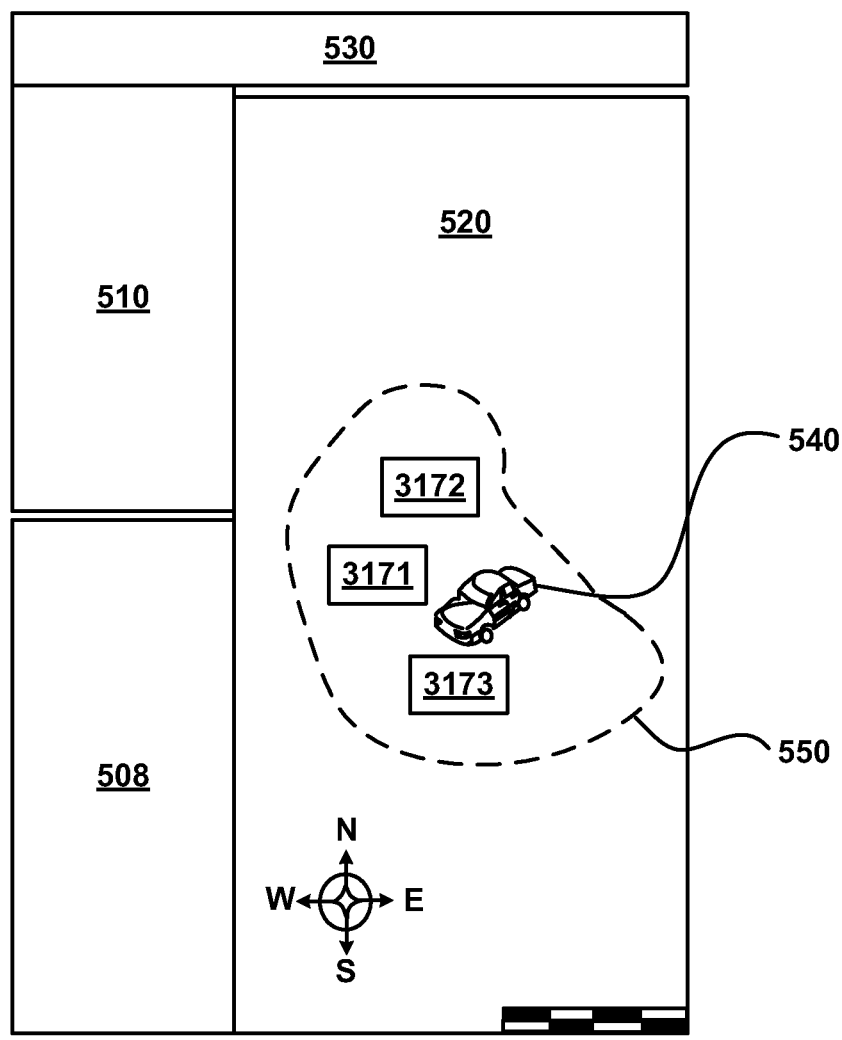
FIG. 33 is a block diagram of an exemplary GUI display of an asset information report generated by an asset management system in accordance with one embodiment of the present invention.

Referring now to FIG. 33, a block diagram of an exemplary GUI display 360B of an asset information report generated by an asset management system is shown in accordance with one embodiment of the present invention. GUI display 360B is similar to GUI display 360 of FIG. 5. In one embodiment, asset information report 360B includes an asset 540, an asset column 510, an information source column 508, a map section 520, and a user toolbar section 530. In general, the user toolbar section 530 provides a means for user interaction with asset information report 360. Map section 520 is automatically provided by asset information report generator 750 as a portion of asset information report 360B. Moreover, elements 508, 510, 520, 530, and 540 have been previously described, and are consistent with the previous descriptions of their like elements shown and descried in conjunction with FIG. 5.

Region 550 is a geo-fenced region, which may be considered, in this example, to correspond to construction site 3100 shown in FIG. 31. Geo-fenced region 550 is overlaid on map section 520 and shows, for example, all assets which have last been recorded as being located within geo-fenced area 550. Thus, asset 540, asset 3171, asset 3172, and asset 3173 are shown within geo-fenced region 550. In this example report, the location of asset 550 has been actively reported via a reporting source 208. While the locations reported for assets 3171, 3172, and 3173 have been tracked on an impromptu basis via the impromptu asset tracking method and system described above. The information displayed in a GUI allows for knowledge of and management of assets located in a region specified by a user, such as a construction supervisor, rental equipment manager, or the like.

Thus, embodiments of the present invention provide impromptu asset tracking systems and methods. Embodiments further provide automated methods to notify and report asset identification information that is gathered on an impromptu basis. This impromptu tracking resolves the problem of the high cost generally associated with tracking assets, by utilizing existing reporting sources in conjunction with proximity communication devices to provide a secondary (impromptu) reporting capability which can utilize an existing asset management system and infrastructure.

Section IX

Integrated Asset Management

Overview

Embodiments described herein provide systems and methods for integrated asset management. In general, embodiments described herein utilize a plurality of disparate sources for monitoring information about an asset, such as location and operation information about an asset. The information from these disparate sources is populated into a database. Inspection information is also received from one or more enabled devices, such as WiFi (wireless fidelity) wireless internet/network enabled devices or Bluetooth enabled devices, and populated into the database.

In some embodiments, such enabled devices are coupled with a client information system, such as a rental information system, inventory information system, maintenance information system, or the like, by the means of a coupling to the Internet, a blue tooth transceiver, or to a local or wide area network. Such enabled devices are often handheld, and can comprise a personal digital assistant, computer, or the like, which can be additionally coupled with a printer. In some embodiments, such enabled devices are primarily used to report "inspection information", which is information that is manually collected with the device (such as by reading a bar code on an asset or taking a picture of an asset) or manually input into the device following a visual inspection by a human. For example, after a visual inspection, a human operator may note visible asset damage, visible maintenance issues, overall asset cleanliness, or other similar visually observable characteristics and then enter the inspection information into the enabled device, which will in-turn upload the inspection information to a client information system. In some embodiments such enabled devices also receive asset data from the client information system. Many such enabled devices are known in the art.

The asset information and asset inspection information is populated into the database such that all or portions of it and any other information associated with an asset can be collected in an integrated manner from the database for use by a client information system or by an enabled device. In one embodiment, this comprises providing a customized extraction of data about an asset in a format usable by one or more enabled devices. In one embodiment, this comprises providing a customized extraction of data about an asset in a format usable by one or more client information systems. The data about an asset may be directed back to an enabled device or client information system that provided inspection information to the database, or to another client information system or enabled device. In one embodiment, a report can also be generated from the asset information, asset inspection information, and any other information associated with an asset and stored in the database.

Integrating Asset Management Information

Figure 34:
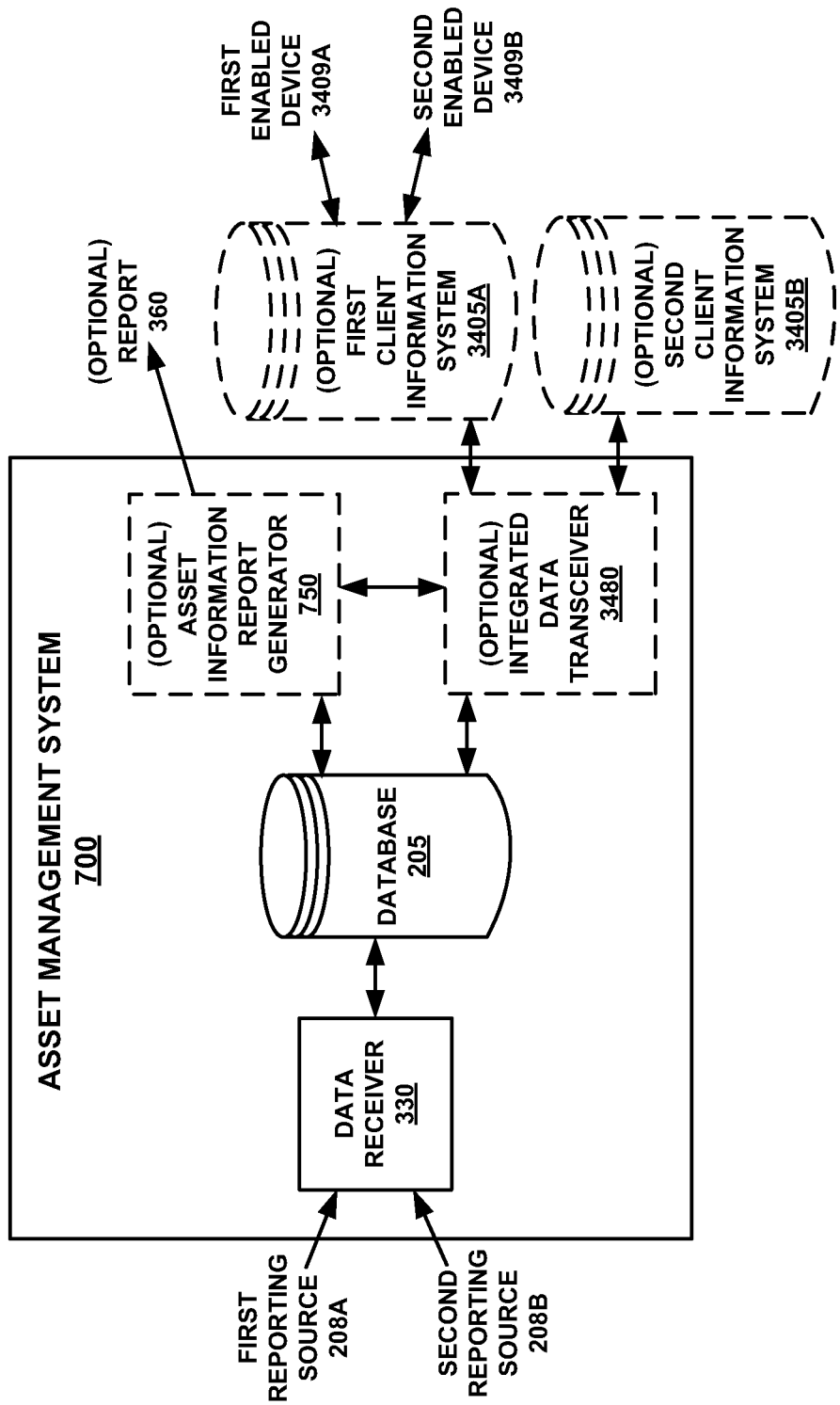
FIG. 34 is a block diagram of an exemplary asset management system in accordance with one embodiment of the present invention.

With reference now to FIG. 34, an exemplary asset management system 700 is shown communicatively coupled with a first reporting source 208A, a second reporting source 208B, an optional first client information system 3405A, and an optional second client information system 3405B, in accordance with one embodiment of the present invention. As shown in FIG. 34, asset management system 700 is also communicatively coupled with a first enabled device 3409A and with a second enabled device 3409B via first client information system 3405A. An enabled device is a device which is communicatively coupled with a client information system, such as by WiFi Internet or network link, Bluetooth link, or similar wireless coupling, for the purpose of reporting inspection information about an asset to the client information system. Likewise, in some embodiments, such an enabled device also receives information about the asset from the wireless coupling to the client information system.

Asset management system 700 is comprised of data receiver 330, database 205, and optional asset information report generator 750, and optional integrated data transceiver 3480. In general, data receiver 330 is configured for receiving information about an asset from multiple reporting sources (such as sources 208A and 208B). Data receiver 330 reports this asset information to database 205, which is populated with a first portion of information about an asset from a first reporting source 208A, a second portion of information about an asset from a second reporting source 208B, and so on for other reporting sources which report information about an asset. Moreover, database 205 may similarly receive and maintain information for a plurality of assets. The specific functions and operation of data receiver 330 and database 205 regarding the asset information reporting sources (e.g., 208A, and 208B) have been previously described, and for purposes of brevity and clarity will not be re-described herein except as necessary to identify any differences or previously undescribed features.

Optional integrated data transceiver 3480 is configured for coupling with client information systems, such as optional client information systems 3405A and 3405B for the purpose of providing integrated asset data extracted from database 205 and formatted by asset information report generator 3405A and also for the purpose of receiving asset investigation information. A client information system such as 3405A or 3405B is for example, an asset maintenance information system, an asset inventory information system, an asset rental information system, or the like. In general, a client information system is more than a simple customer application such as a spreadsheet, instead, it is a system that receives information inputs (such as from external enabled devices 3409A and 3409B) and issues reports, such as receipts, work orders, inventory lists or the like.

Figure 35:
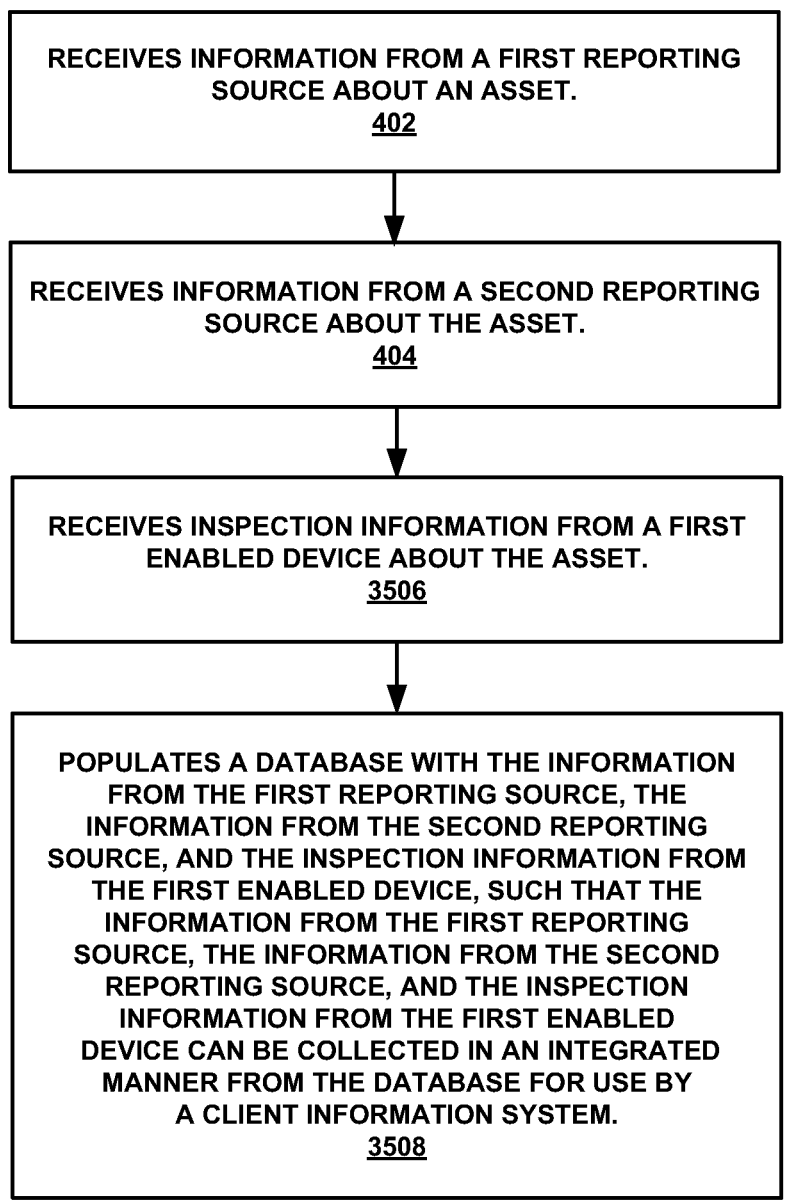
FIG. 35 is a flowchart of an exemplary method for integrating asset management information in accordance with one embodiment of the present invention.
Figure 36:
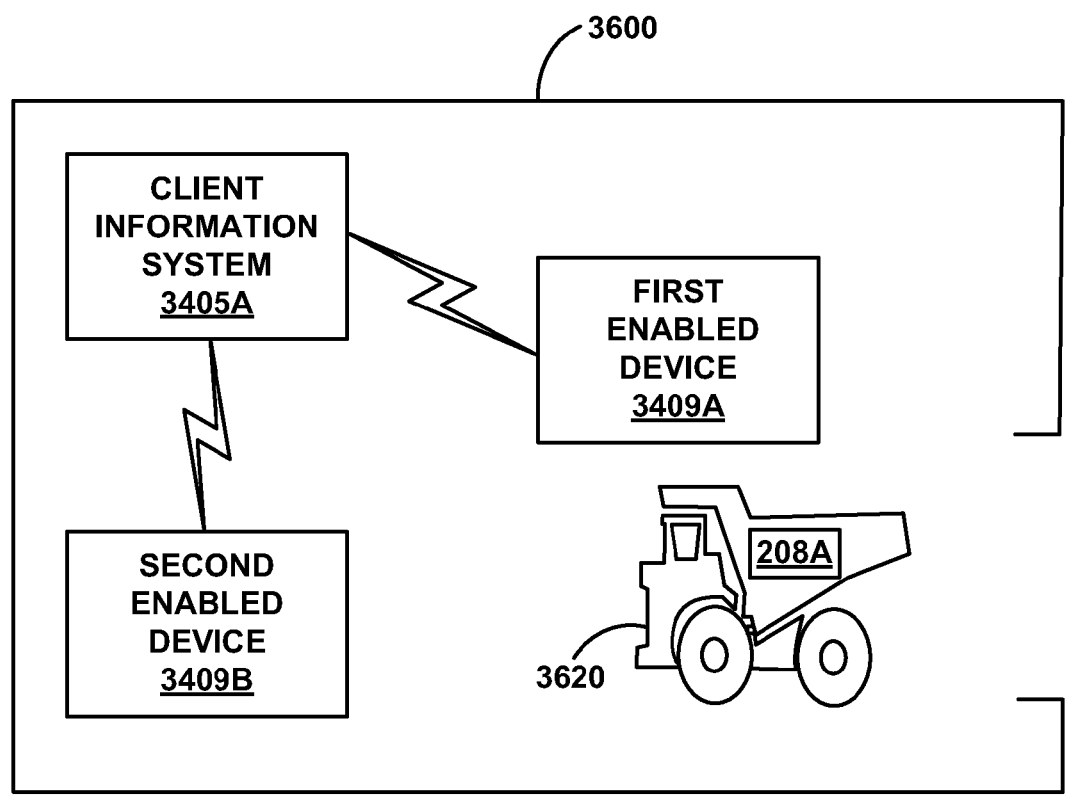
FIG. 36 is a block diagram of an exemplary asset being returned to an asset rental company in accordance with one embodiment of the present invention.

With reference now to FIG. 35, a flowchart of an exemplary method 3500 is shown for integrating asset management information in accordance with one embodiment of the present invention. Elements of method 3500 will be described with reference to FIG. 34 and to FIG. 36. FIG. 36 is a block diagram of an exemplary asset 3620 being returned to an asset rental company's rental yard 3600 in accordance with one embodiment of the present invention. Additionally, for purposes of example and not of limitation, client information system 3405A, of FIG. 36, will be described as a rental asset information system. It is appreciated, however, that the concepts demonstrated by this example implementation are equally applicable to other client information systems, such as inventory control information systems, maintenance information systems, payroll information systems, and the like.

With reference now to 402 of FIG. 35 and to FIG. 34 and FIG. 36, one embodiment receives information from a first reporting source about an asset. As previously described, a variety of reporting sources 208 can provide asset information about an asset. For purposes of example, and not of limitation, the asset can be considered to be a dump truck 3620 which was rented from rental yard 3600 and is equipped with first reporting source 208A. In general the received information from reporting source 208A comprises location and/or operation information about dump truck 3620. Element 402 and reporting source 208A have been previously described, and in the interests of brevity and clarity will not be re-described herein. Instead reference is made to these previous descriptions.

With reference now to 404 of FIG. 35 and to FIG. 34 and FIG. 36, one embodiment receives information from a second reporting source about the asset. As previously described, a variety of reporting sources 208 can provide asset information about an asset. For purposes of example, reporting source 208B can be considered to be a portable computer used to enter information about dump truck 3620 when in-field maintenance was performed on asset 3620 by rental company maintainers during the rental period. In general the received information comprises location and/or operation information about an asset, such as asset 3620. Element 404 and reporting source 208B have been previously described, and in the interests of brevity and clarity will not be re-described herein. Instead reference is made to these previous descriptions.

With reference now to 3506 of FIG. 35 and to FIG. 34 and FIG. 36, one embodiment receives inspection information from a first enabled device 3409A about the asset (dump truck 3620 in this example). For purposes of example and not of limitation, it may be assumed that first client information system 3405A, as shown in FIG. 36, is an asset rental information system. Client information system 3405A is populated with investigation information received from a WiFi enabled device, such as first enabled device 3409A when an asset, such as dump truck asset 3620, is checked back in to a rental yard after at the end of a rental period. In another embodiment, enabled device 3409A is a Bluetooth enabled device. In one embodiment, for example, a rental agent uses enabled device 3409A to gather investigation information about an asset, such as dump truck 3620, by a means such as taking a digital photograph of dump truck 3620 with enabled device 3409A, performing a walk-around condition inspection of dump truck 3620 (such as for cleanliness or the presence of damage) and entering inspection results into enabled device 3409A, inspecting dump truck 3620 for any maintenance issues (such as a visible maintenance problem like an oil leak) and entering the results into enabled device 3409A, and/or entering a work order for dump truck 3620 (such as for any cleaning or unscheduled maintenance needs noted during an asset inspection).

Thus inspection information may comprise information such as a digital photograph of an asset, an unscheduled work order request for an asset (for example, based on damage, cleanliness, or maintenance issues noted during an asset inspection), or some other visually observed information that is reported about an asset. In one embodiment, the reported investigation information is sent from enabled device 3409A to client information system 3405A, and from client information system 3405A to integrated data transceiver 3480, which populates the investigation information into a database, such as database 205. In another embodiment, investigation information is sent from enabled device 3409A to integrated data transceiver 3480, which populates the investigation information into a database, such as database 205.

Similarly, second enabled device 3409B is used in one embodiment to report investigation information about an asset, such as asset 3620. In one embodiment, the investigation information is the same or similar investigation information as reported by enabled device 3409A. In one embodiment, second enabled device 3409B reports additional investigation information, such as completion of a work order for an asset. For example, in one embodiment, enabled device 3409B is used to report completion of washing asset 3620 in response to a work order for washing asset 3620. In one embodiment, the reported investigation information is sent from enabled device 3409B to client information system 3405A, and from client information system 3405A to integrated data transceiver 3480, which populates the investigation information into a database, such as database 205. In another embodiment, investigation information is sent from enabled device 3409B to integrated data transceiver 3480, which populates the investigation information into a database, such as database 205. Although only two enabled devices, 3409A and 3409B, are shown in FIG. 34 and FIG. 36, it is appreciated that a plurality of such enabled devices (3409A . . . 3409n) may report investigation information about an asset in the manner described above.

With reference now to 3508 of FIG. 35 and to FIG. 34 and FIG. 36, one embodiment populates a database, such as database 205, with the information from the first reporting source 208A, the information from the second reporting source 208B, and the inspection information from the first enabled device 3409A, such that the information from the first reporting source 208A, the information from the second reporting source 208B, and the inspection information from the first enabled device 3409A can be collected in an integrated manner from the database 205 for use by a client information system, such as client information system 3405A. In one embodiment, this comprises storing the information from the first reporting source 208A, the information from the second reporting source 208B (along with any other asset information from other reporting sources), and the investigation information from enabled device 3409A (along with any other asset investigation information from other enabled devices) in such a manner that an asset information report 360 regarding the asset can be generated. As previously described, this can comprise storing the assorted information in a single database 205 or in a plurality of databases which can be jointly accessed.

In general, asset information report generator 750 is configured to communicatively couple with database 205 for generating an asset information report 360 from asset data provided from database 205. Asset information report 360 can include asset information reported from sources such as reporting sources 208A and 208B. Likewise, a asset information report 360 can also include inspection information, such as digital photographs of the asset, visible information recorded about the asset, or other inspection information reported from enabled devices such as 3409A and 3409B. In one embodiment, asset information report generator 750 generates an asset information report 360 comprising at least a portion of information from first reporting source 208A, at least a portion of information from second reporting source 208B, and at least of apportion of inspection information from the first enabled device 3409A.

An example of such an asset information report 360 is a comprehensive maintenance report which lists a scheduled maintenance due based on hours of use reported by reporting source 208A and miles driven reported by reporting source 208B, along with unscheduled maintenance needed based on visual inspection results reported by enabled device 3409A. The operation of asset information report generator 750 with regard to generating asset information report 360 has been previously described, and in the interests of brevity and clarity will not be re-described herein.

Figure 37:
FIG. 37 is a flowchart of an exemplary method for providing integrated asset management information in accordance with one embodiment of the present invention.

With reference now to FIG. 37, a flowchart of an exemplary method 3700 is shown for providing integrated asset management information in accordance with one embodiment of the present invention. Elements of method 3700 will be described in with reference to FIG. 34 and to FIG. 36.

With reference now to 3702 of FIG. 37 and to FIG. 34 and FIG. 36, one embodiment accesses a database 205 populated with information about an asset, such as dump truck 3620, received from a first reporting source 208A, information about the asset received from a second reporting source 208B, and inspection information about the asset received from a first enabled device 3409A. For example, in one embodiment, asset information report generator 750 is communicatively coupled with database 205 and queries and extracts integrated asset data about an asset, such as dump truck 3620, from a selection of the asset information, asset investigation information, and any other information associated with the asset and stored in database 205. In one embodiment, a custom report module (previously described) of asset information report generator 750 is used to conduct a customized asset data query and to format accessed integrated asset data for an intended client information system or enabled device. The integrated asset data that is extracted is for use by a client application such as client application 3405A or 3405B. In various embodiments, a portion of the integrated data that is accessed comprises: a digital photograph of the asset, results of a walk-around inspection of the asset, a work order request for the asset, a work order completion report for the asset, visual inspection information recorded for the asset, rental contract information for the asset (time out, time in, time used, day or days used, locations used, or other such information), location information (present or past) for the asset, and/or operation information for the asset.

With reference now to 3704 of FIG. 37 and to FIG. 34 and FIG. 36, one embodiment updates a client information system, such as client information system 3405A or client information system 3405B. For example, in one embodiment asset information report generator 750 supplies accessed data to integrated data transceiver 3480, which couples the accessed data to a customer information system such as 3405A or 3405B.

In one embodiment, for example, integrated data about an asset is used to supply additional rental contract information upon the return of an asset. Rather than simply enabling an operator or agent to print a receipt (as many systems currently are capable of doing), the provided integrated asset data comprises rental contract information which allows an operator or agent to determine whether terms of the rental contract were complied with. Consider, for example, a situation where dump truck 3620 is rented for use on a Saturday, to be used in a particular State where it is properly licensed and registered, such as Kansas. Consider additionally that the asset rental company is closed on Sunday, and that the asset is returned first thing the following Monday morning after being used in Missouri for ten hours on Sunday. Investigation information, such as the date and time of asset return, is reported via an enabled device such as first enabled device 3409A. This investigation information is added to database 205. Asset information report generator 750 then extracts and provides integrated asset data about the rental contract back to first enabled device 3409A via client information system 3405A to assist in accurate and expeditious rental contract completion.

For example, in one embodiment, the provided integrated asset data comprises rental contract information such as rental terms (check out date, return date, and the like) derived from information that was received from an enabled device such as 3409A or a client information system such as 3405A. In one embodiment, the integrated asset data also comprises rental contract information such as asset operation information and asset location information which are extracted from asset information provided by reporting sources such as reporting source 208A and/or 208B. In one embodiment, additional asset data, such as contract details are supplied by client information system 3405A. Based on this integrated asset data related to rental contract information, a rental agent will be able to ascertain that dump truck 3620 was used for eight hours on Saturday in Kansas and for ten hours on Sunday in Missouri. This will allow the rental agent to appropriately adjust the charges for an extra day of use and, if necessary, to add a penalty for operating the dump truck asset in Missouri in violation of the terms of the rental contract. This demonstrates one example of how asset data gathered from disparate sources and devices is integrated and leveraged by asset management system 700 to increase an asset manager's awareness of the days of use, hours of use, and locations of an asset.

In another example, in one embodiment, integrated data about an asset is used to supply a comprehensive work order which integrates both scheduled and unscheduled maintenance due for an asset. The comprehensive work order is used to update a maintenance information system, which for purposes of this example is system 3405B shown in FIG. 34. In one such embodiment, data for the unscheduled maintenance comes from inspection data reported by an enabled device such as enabled device 3409A, while data for the scheduled maintenance comes from operation information (hours of operation, engine time, oil level, and the like) reported by a reporting source such as reporting source 208A. Thus, in one embodiment, investigation information received via first client information system 3405A is integrated with other asset data can be extracted from database 205 to provide an update to second client information system 3405B. This allows for data sharing between client information systems which, in many cases do not normally share data. Such data sharing increases efficiency and streamlines operations of a company, such as an asset rental company, asset maintenance company, asset sales company, or asset operations company, or the like.

In one embodiment, asset information report generator 750 is communicatively coupled with integrated data transceiver 3480 and transmits the integrated data about an asset to a client information system, such as client information system 3405 or client information system 3405B. In one embodiment, asset information report generator 750 formats the integrated data about an asset for use by a client information system such as client information system 3405A or client information system 3405B. In one embodiment, this comprises an electronic format which is compatible with (readable and useable by) a client information system such as 3405A and/or its enabled devices, such as enabled devices 3409A and 3409B. In one embodiment, asset information report generator 750 formats the integrated data about an asset for use by an enabled device such as, for example, enabled device 3409A or enabled device 3409B. In such an embodiment, this comprises formatting any data and/or graphics such that they can be displayed and/or printed with or by enabled device 3409A and/or with or by enabled device 3409B. In one embodiment, for example, a custom report module (previously described) of asset information report generator 750 is utilized to extract integrated data about an asset from database 205 and to further customize the integrated data into a format that is useable, for example, by a client information system such as 3405A or 3405B or by an enabled device such as 3409A or 3409B.

Thus, embodiments of the present invention provide systems and methods to gather and integrate asset management information which can comprise a variety of asset information from a plurality of reporting sources and a variety of asset inspection information from a plurality of enabled devices. Embodiments further provide a means to populate this gathered information into a database, such as database 205. Embodiments also comprise systems and methods to provide integrated asset data updates to client information systems and to provide integrated asset data reports, both of which are derived from the asset information, asset inspection information, and any other asset data stored in and accessed from the database.

As can be seen, the methods and systems described above in conjunction with asset management system 700 reduce or eliminate inefficiencies due to overlapping processes, overlapping data collections, and disparate client information systems that are used by asset rental companies, asset sales companies, asset operating companies, and asset maintaining companies, and the like. This reduces information bottlenecks and enhances management awareness of the operation, location, and availability of an asset.

Section X

Detecting Construction Equipment Asset Process Failure

Overview

The asset location and operation information stored in database 205 can be analyzed and exploited for many purposes. One purpose is to detect and report a construction equipment asset process failure. The term "process failure" refers to the use of an asset to perform a process that another asset or combination of assets could perform more economically, efficiently, or expeditiously; or the improper use of the correct asset when performing a process. In embodiments described below, process failure is governed by compliance with one or more process norms that are assigned to a construction equipment asset or assets.

By detecting information in database 205 which indicates a violation of a process norm and by reporting the process failure in real-time or near-real-time, the process failure situation can be corrected. Similarly, delayed reporting of a process failure also allows a construction manager to determine improper use of a construction equipment asset, efficient and inefficient use patterns of a construction equipment asset, and efficient and inefficient use patterns of a worker who operates a particular construction equipment asset. Corrective action, such as operator retraining, asset reconfiguration, or alternate asset use can then be taken to reduce future process failures.

The overall result of detecting and reporting construction equipment asset process failure is a reduction in the occurrences of such process failure. This leads to a savings in money, time, or both for the asset operating company such as, for example, a material moving company. Although such process failure detection may be applied to many types of construction equipment assets, it is especially useful in the construction industry when applied to "material moving" type construction equipment assets, including: dozers, graders, excavators, scrapers, compactors, loaders, articulated dump trucks, haul trucks, dump trucks, pavers, stakers and the like which are used to move or work with dirt, gravel, ore, sand, or other similar types of material.

Asset Management System

Figure 38:
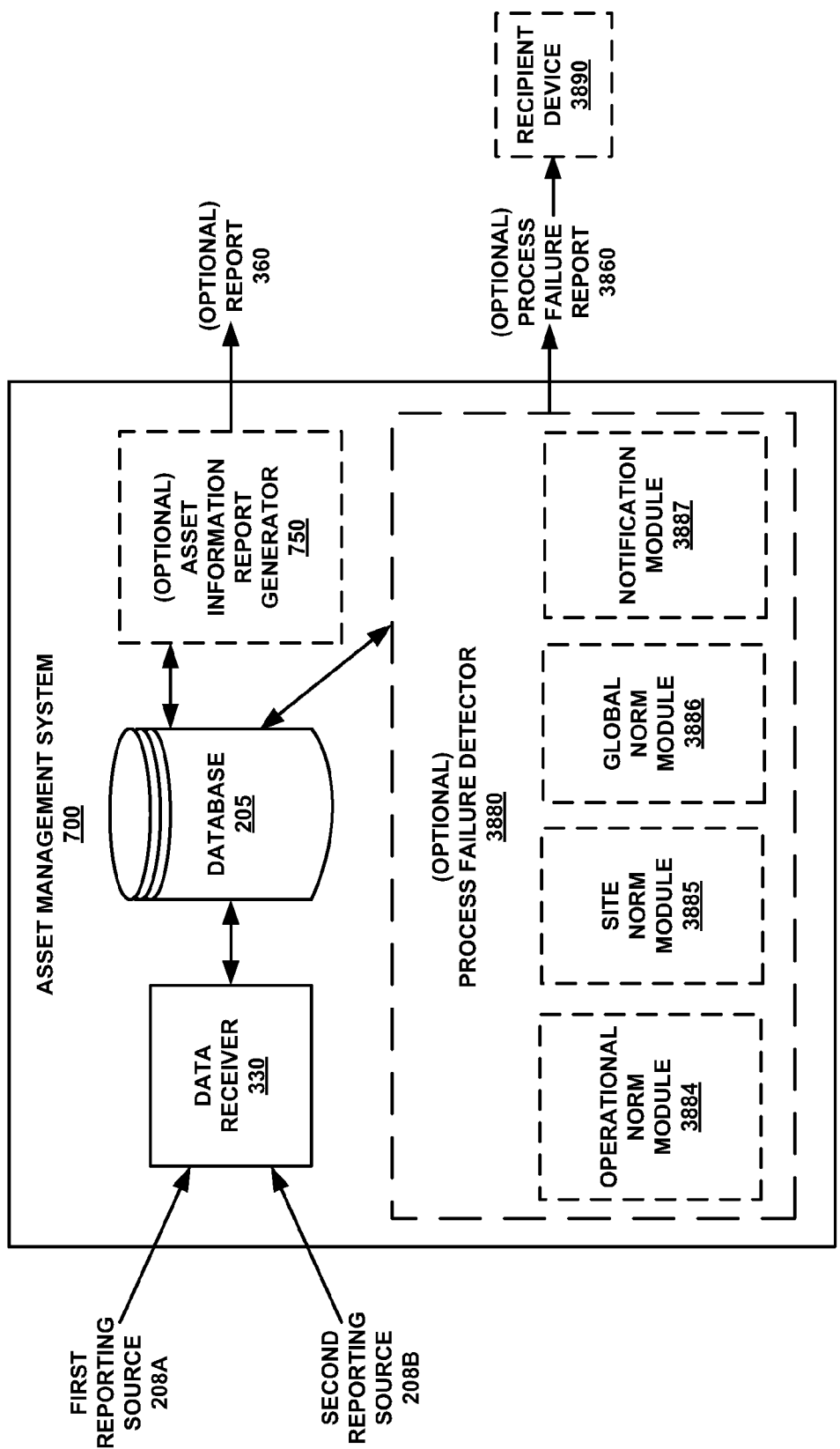
FIG. 38 is a block diagram of an exemplary asset management system configured with an optional process failure detector, in accordance with one embodiment of the present invention.

With reference now to FIG. 38, a block diagram of an exemplary asset management system 700 is shown configured with an optional process failure detector 3880 in accordance with one embodiment of the present invention. As shown in FIG. 38, asset management system 700 is comprised of data receiver 330, database 205, optional asset information report generator 750, and optional process failure detector 3880.

In general, data receiver 330 is configured for receiving information, such as location and/or operation information, about an asset from one or more reporting sources 208 (such as sources 208A and 208B). Data receiver 330 reports this asset information to database 205, which is then populated with a first portion of information about an asset from a first reporting source 208A, a second portion of information about an asset from a second reporting source 208B, and so on for other reporting sources which report information about an asset. Moreover, database 205 may similarly receive and maintain information for a plurality of assets. Optional asset information report generator 750 is configured to communicatively couple with database 205 for generating asset information report 360 from asset information data provided from database 205, and in some embodiments to couple asset information report 360 to a customer application.

Many of the components shown in asset management system 700 and FIG. 38 have been previously described in great detail. For instance, first reporting source 208A, second reporting source 208B, data receiver 330, database 205, optional asset information report generator 750, and optional report 360 have all been previously described. These previously described components operate in a manner consistent with their previous descriptions, and for the purposes of brevity and clarity will therefore not be re-described except as necessary to point out additional features, or previously undescribed methods of operation.

Optional process failure detector 3880, in one embodiment, monitors asset information stored in database 205 and compares the monitored asset information to one or more process norms assigned to a construction equipment asset. Through this comparison, process failure detector 3880 detects if a process failure for the construction equipment asset has occurred. Process failure detector 3880 automatically detects process failures for an asset such as: incorrect construction equipment asset selection for a task; incorrect construction equipment asset operation while performing a task; and incorrect process execution while performing a task. Process failure detector 3880 performs this automatic detection by detecting outliers from assigned process norms by combining and processing asset location information, asset operation information, and time information to determine if a construction equipment asset is being operated in a manner which violates a process norm assigned to the asset.

In various embodiments, the location information comprises two-dimensional or three-dimensional position information, which in some embodiments also comprises an orientation of the construction equipment asset. The location information is derived from one or more positioning sensors, such as Global Navigation Satellite System (GNSS) receivers (e.g., GPS, GLONASS, and/or Magellan), optical based position information, laser based position information, or some combination. The location information is received from one or more reporting sources 208 (previously described). Location information can be combined with operation information (described below) to determine, for example, the cycle distance of a push, haul, or other carrying of some load.

Operation information is gathered from sensor information received from one or more reporting sources 208, which in this embodiment, report data from sensors mounted on the construction equipment asset. Thus, from such sensors, asset operation information such as, for example: speed, heading, event data (e.g., loading, unloading, bucket angle, blade position, and other such operating event data), and/or engine health/machine health data (e.g. oil pressure, oil temperature, engine revolutions per minute, hydraulic fluid pressure, and the like).

In one embodiment, time information is gathered from database 205, such as, from time stamps sent along with operation and location information. In one embodiment, process failure detector 3880 derives time information by combining location and operation information in some fashion to determine to determine time information. Time information comprises data such as, cycle time, time to load, time to unload, time between loading an unloading, dead head time, time paused while waiting to load or unload, time elapsed to perform a task, overall operating time, and the like.

In one embodiment, process failure detector 3880 generates a process failure report 3860 when a process failure is detected. In one embodiment, process failure report 3860 or some other notification is sent to a recipient device 3890 in the event that a process failure is detected. This serves to notify a manager, supervisor, asset operator, or the like about the process failure (and optionally a recommended solution) so that the process failure can be corrected. In one embodiment, process failure detector 3880 comprises an operational norm module 3884, a site norm module 3885, a global norm module 3886, and a notification module 3887.

In one embodiment, operational norm module 3884 derives one or more operational norms for a construction equipment asset from observed asset information gathered about the construction equipment asset or similar construction equipment assets and stored in database 205. A derived operational norm is then either manually or automatically assigned to a construction equipment asset. One example of such an operational norm is the average cycle time for scraper to collect a load of material at a particular job site. Another example of an operational norm is the average pause time of a dump truck while waiting in a loading area at a job site.

Process failure detector 3880 compares asset information stored in database 205 to such operational norms to determine if a construction equipment asset is being operated in a manner which is inconsistent enough with an operational norm. If so, a process failure is detected by process failure detector 3880. In one embodiment, the variance from an operational norm which triggers detection of a process failure is automatically determined by operational norm module 3884 (for example based on a preset percentage of variation from the operational norm, a variation outside of a defined margin around the operational norm, or a pre-defined statistical variation from the operational norm). In one embodiment, the variance from an operation norm which triggers detection of a process failure is selected by a user of asset management system 700.

In one embodiment, site norm module 3885 comprises one or more job site specific norms assigned to a construction equipment asset. A site specific norm is typically entered by user of asset management system 700 and is based on tasks that will be performed at the job site and specific knowledge of materials, conditions, topology, special requirements or the like which are unique to the construction site. One example of such a site norm is the average cycle time between loading and unloading of a dump truck. For example, this time may be longer than would be typically expected due to extremely wet conditions at the job site. Another example of an operational norm is the optimal swing angle range for an excavator that is excavating material from a steep hillside on the job site.

Process failure detector 3880 compares asset information stored in database 205 to such site norms to determine if a construction equipment asset is being operated in a manner which is inconsistent enough with a site norm. If so, a process failure is detected by process failure detector 3880. In one embodiment, the variance from a site norm which triggers detection of a process failure is automatically determined by site norm module 3884 (for example based on a preset percentage of variation from the site norm, a variation outside of a defined margin around the site norm, or a pre-defined statistical variation from the site norm). In one embodiment, the variance from a site norm which triggers detection of a process failure is selected by a user of asset management system 700.

In one embodiment, global norm module 3886 comprises one or more global norms assigned to construction equipment asset. In general, a global norm is a norm or common standard which is defined or commonly understood by the construction industry or some subset of the construction industry as representing proper use and/or operation of a construction equipment asset. Typically, such global norms are outlined and published by industry associations and construction equipment asset manufactures, and depend upon factors such as: machine selection for a particular process, work tool selection, soil/material type that a process is being performed on, and surface conditions at a site. One example of such a global norm is the optimal push distance for a dozer. Another example of a global norm is the optimal engine revolutions per minute (RPMs) of a scraper when the scraper is loading or unloading a particular type of material.

Process failure detector 3880 compares asset information stored in database 205 to such global norms to determine if a construction equipment asset is being operated in a manner which is inconsistent enough with a global norm. If so, a process failure is detected by process failure detector 3880. In one embodiment, the variance from a global norm which triggers detection of a process failure is automatically determined by global norm module 3885 (for example based on a preset percentage of variation from the global norm, a variation outside of a defined margin around the global norm, or a pre-defined statistical variation from the global norm). In one embodiment, the variance from a global norm which triggers detection of a process failure is selected by a user of asset management system 700. In various embodiments, a global norm may be manually entered into global norm module 3886 by a user, selected from a list of global norms available within global norm module 3886 for a particular construction equipment asset or asset type, or sourced manually or automatically from some outside repository of global norms.

In one embodiment, notification module 3887 communicatively couples or issues optional process failure report 3860 to recipient device 3890 after a process failure is detected by process failure detector 3880. Recipient device 3890 can comprise a device such as, but not limited to: a telephone, a cellular phone, a personal digital assistant, a pager, a two-way radio, a computer, a computer network, a webpage, and an email account. Notification module 3887 issues process failure report 3860 in an appropriate format for the particular recipient device 3890 that that process failure report 3860 is being issued to. Thus, in various embodiments, notification module 3887 issues process failure report 3860 in formats which include: voice (such as a pre-recorded message), synthesized voice, text, email, hyper text mark-up language (or equivalent), and video (such as a digital photograph or video file).

Method for Detecting Process Failure

Figure 39:
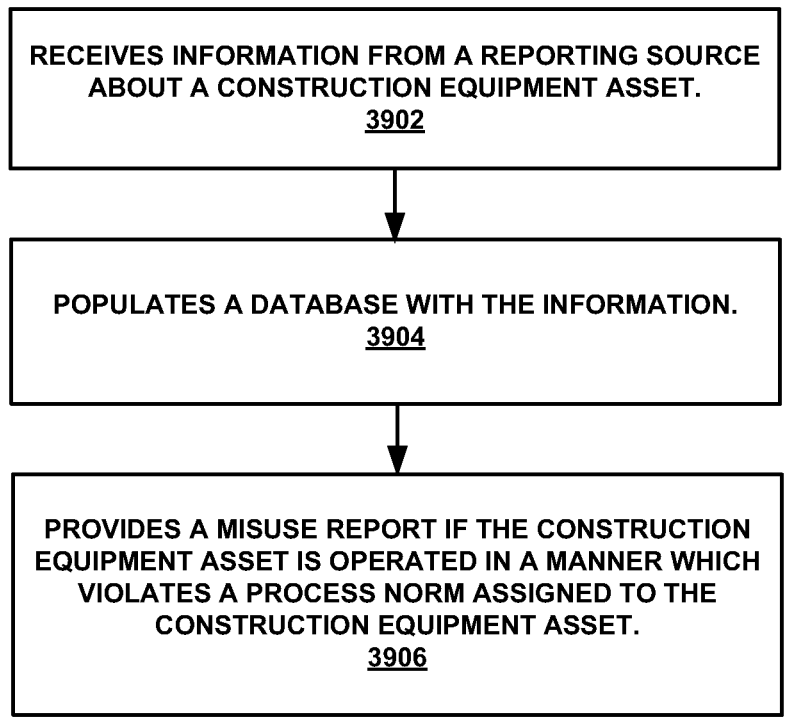
FIG. 39 is a flowchart of an exemplary method for detecting construction equipment process failure, in accordance with one embodiment of the present invention.

With reference now to FIG. 39, a flowchart of an exemplary method 3900 is shown for detecting construction equipment asset process failure in accordance with one embodiment of the present invention. Elements of method 3900 will be described in with reference to FIG. 38. Although specific steps are disclosed in method 3900, such steps are exemplary. That is, embodiments of the present invention are well suited to performing various other steps or variations of the steps recited method 3900. It is appreciated that the steps in method 3900 may be performed in an order different than presented, and that not all of the steps in method 3900 may be performed. All of, or a portion of, the steps described by method 3900 may be implemented using computer-readable and computer-executable instructions which reside, for example, in computer-usable media of a computer system such as, for example, computer system 100 (FIG. 1) or like device.

With reference now to 3902 of FIG. 39 and to FIG. 38, one embodiment receives information about a construction equipment asset from a reporting source. It is appreciated that in one embodiment, a reporting source such as reporting source 208A and/or 208B or other similar reporting source 208, may report some combination of asset location information, asset operation information, and asset time information for a construction equipment asset. For example, location information may be an asset's coordinate location on a map or an asset's position within a particular job site or geo-fenced area. Time information may be local time, GPS time, or some other time provided by a reporting source 208. Furthermore, in one embodiment a time is related to an event, such as a time that the asset was loaded with material. Operation information may indicate whether the asset has its engine running, is stopped, is moving, is moving at a particular speed, is loaded, is unloaded, is being operated in a particular mode, or like operation information. As previously described, in various embodiments, a reporting source such as reporting source 208A, comprises a source such as, but not limited to: a TrimTrac™ device, a CrossCheck® device, a mobile phone, a video device, a personal digital assistant, a portable computing device, a radio frequency identifier, a global navigation satellite system (GNSS) and human intelligence (HumInt). The function and operation of such reporting sources as 208A and 208B is consistent with the previous descriptions of these reporting sources.

With reference now to 3904 of FIG. 39 and to FIG. 38, one embodiment populates a database 205 with the received asset information. This is consistent with previous descriptions of receiving asset information and populating the information into database 205. For example, database 205 is populated with a first portion of information about an asset provided by a first reporting source 208A, and if available is also populated with a second portion of information about the asset from a second reporting source 208B, and so forth, depending on the number of reporting sources from which database 205 receives information about an asset.

Thus when such information is reported for an asset by one or more reporting sources (208A, 208B, . . . 208n), database 205 has stored within it a considerable amount of information about the location(s), operation, and general use of the asset. This is especially true when updates to asset information are received at short time intervals such as several times per second, every second, every several seconds, or every minute, or at some other short interval. As will be seen, this asset information is used by process failure detector 3880 to determine operational states of an asset, including: whether an asset is moving or stopped; whether an asset is loaded or unloaded; how far or fast an asset is traveling or has traveled; when and where the asset was loaded with material; what distance an asset has traveled in a particular operational mode (cycle distance); what angle a blade or bucket was positioned at while performing a process, when and where the asset loaded and offloaded material, and other such information.

With reference now to 3906 of FIG. 39 and to FIG. 38, one embodiment provides a misuse report 3860 if the construction equipment asset is operated in a manner which violates a process norm assigned to the construction equipment asset. Optional process failure detector 3880, as shown in FIG. 38, adds asset process failure detection and reporting functionality to asset management system 700. Process failure detector 3880 is communicatively coupled with database 205. Although shown and described as a separate entity in system 700, it is appreciated that in some embodiments, some or all of the functions of process failure detector 3880 may be distributed among or performed by or other entities, such as asset information report generator 750.

In one embodiment, process failure detector 3880 automatically receives selected information from database 205 about the location and/or operation of one or more particular construction assets, which it is monitoring for process failure. In another embodiment, process failure detector 3880 queries database 205 for selected information about location, operation, or time related to a particular asset or assets which it is monitoring for process failure. In general, the selected information that is received or queried for is related to one or more process norms which have been assigned to a particular asset that is being monitored for process failure. Process failure detector 3880 compares the selected information to one or more process norms assigned to an asset. Process failure detector 3880 generates a process failure report 3860 when, based on the comparison, the selected information indicates a violation of a process norm assigned to the asset.

In one embodiment, one or more process norm modules (3884, 3885, 3886) is used to assign one or more process norms to a construction equipment asset. The process norms assign boundaries that form an operational envelope for the construction asset. If selected information from database 205 indicates that the construction equipment asset is being operated inside of this envelope formed by the process norms(s), process failure detector 3880 considers the asset to be properly used and no process failure report 3860 is generated. If selected information from database 205 indicates that the construction equipment asset is being operated outside this envelope (by violating one or more process norms), process failure detector 3880 considers generates process failure report 3860.

Process Failure Detection Examples

In one embodiment, for example, process failure detector 3880 monitors a dozer asset for optimum push/haul distance. Process failure detector 3880 monitors asset location and operation information in database 205 about the push/haul distances of the dozer asset. This information is compared to a norm, such as a site norm or global norm, which indicates that the optimum push/haul distance for this dozer is in the range of 10 meters to 90 meters. Process failure detector 3880 generates a process failure report 3860 for the dozer if the dozer violates this process norm (for example if the average push/haul distance for ten consecutive push/hauls is 130 meters). In one embodiment, the process failure report 3860 includes a recommendation such as switching to a different asset (a scraper for instance). This particular embodiment is an example of generating a process failure report 3860 when process failure detector 3880 determines that a construction equipment asset, in this case a dozer, is an incorrect asset for performing a particular process according to an assigned process norm. In one embodiment, notification module 3887 issues the process failure report 3860 to a recipient device 3890.

In one embodiment, for example, process failure detector 3880 monitors an excavator asset for optimum swing angle during a mass excavation/loading operation. Process failure detector 3880 monitors asset location and operation information in database 205 about the swing angle of the excavator asset. This information is compared to a norm, such as an operational norm, site norm, or global norm, which indicates that the optimum swing angle of this excavator for this process is 60 degrees to 90 degrees. Process failure detector 3880 generates a process failure report 3860 for the excavator if the excavator violates this process norm (for example if the average swing angle for 15 consecutive iterations of the process is 50 degrees). In one embodiment, the process failure report 3860 includes a recommendation such as adjusting the excavator setup or the site setup. This particular embodiment is an example of providing a process failure report when process failure detector 3880 determines that a construction equipment asset, in this case an excavator, has performed a particular process improperly according to an assigned process norm. In one embodiment, notification module 3887 issues the process failure report 3860 to a recipient device 3890.

In one embodiment, for example, process failure detector 3880 monitors the operation of an excavator and truck (or trucks) for proper loading cycle time. Process failure detector 3880 monitors asset location and operation information in database 205 about the excavator and truck assets. Process failure detector 3880 also monitors and/or derives cycle time information and pause time information for the excavator and truck assets from information extracted from database 205. This cycle time information is compared to a norm, such as an operational norm, site norm, or global norm, which indicates that the optimum loading operation cycle time for this combination of assets is, for example, 90 seconds. Process failure detector 3880 generates a process failure report 3860 for the excavator and/or truck if the assets exceed this cycle time by more than, for example, 15%. In one embodiment, the process failure report 3860 includes a recommendation for altering the process. In one embodiment, process failure detector 3880 compares cycle times for a plurality of trucks used in the process to determine if a cause for the process failure can be ascertained. For example, if process failure detector 3880 notes that the excavator is pausing due to lack of trucks waiting to be loaded, then the recommendation is to add more trucks. Similarly, if process failure detector 3880 notes that the excavator is pausing but trucks are waiting to be loaded, a recommendation for adjusting the excavator or site set up is provided. In one embodiment, notification module 3887 issues the process failure report 3860 to a recipient device 3890.

In another embodiment, for example, process failure detector 3880 monitors the operation of an excavator and truck (or trucks) for proper loading cycle time. Process failure detector 3880 monitors asset location and operation information in database 205 about the excavator and truck assets. Process failure detector 3880 also monitors and/or derives cycle time information and pause time for the excavator and truck assets from information extracted from database 205. This pause time information is compared to a norm, such as an operational norm, site norm, or global norm, which indicates that the optimum pause time for either asset during a load cycle is zero (no wait of the truck or the excavator). Process failure detector 3880 generates a process failure report 3860 for the excavator and/or truck if either asset experiences a pause time, for example, of more than 10 seconds on three consecutive load cycles. In one embodiment, the process failure report 3860 includes a recommendation for altering the process. In one embodiment, process failure detector 3880 compares cycle times for the excavator to determine if a cause for the process failure can be ascertained. For example, if process failure detector 3880 notes that the excavator is requiring an average of more than 5 bucket cycles or more than 100 seconds to load, the recommendation is to use a larger excavator bucket. Similarly, if process failure detector 3880 notes that the excavator is using an optimal number of bucket cycles to fill a truck, but trucks are waiting, the recommendation is to use fewer trucks. In one embodiment, notification module 3887 issues the process failure report 3860 to a recipient device 3890.

In another embodiment, for example, process failure detector 3880 monitors the operation of a scraper for improper use or lack of operator training Process failure detector 3880 monitors asset location and operation information in database 205 about the scraper asset. For example, in one embodiment process failure detector monitors engine revolutions per minute (RPMs) of the scraper in a particular operational mode. In another embodiment, process failure detector 3880 also monitors and/or derives cycle time information and cycle distance information for the scraper asset from information extracted from database 205. This RPM information is compared to a norm, such as an operational norm, site norm, or global norm, which indicates that the optimum RPM range for a particular mode of scraper operation is 1700 to 2200 RPMs. Process failure detector 3880 generates a process failure report 3860 for the scraper, for example, if the scraper asset has average engine RPMs which deviates by more than 10% from this range for three operational cycles of performing a particular process. In one embodiment, the process failure report 3860 includes a recommendation for to check the configuration of the scraper or retrain the operator. In one embodiment, notification module 3887 issues the process failure report 3860 to a recipient device 3890.

Consider FIG. 40, which shows exemplary construction equipment assets of a loader 4015, a dump truck 4020 and a scraper 4030 in conjunction with an elevation view 4000 of mounds of material (4001, 4002, and 4003) on a job site. Site plan 4000 is not drawn to scale, but as shown, mound 4002 is more than 100 meters and less than 3000 meters away from mound 4001. Additionally, as shown, mound 4003 is more than 3000 meters away from mound 4001.

For efficiency purposes, global norm module 3886 has assigned to scraper 4030 a maximum average loaded cycle distance of 3000 meters as global norm. Thus, if the average loaded cycle distance of scraper 4030 exceeds 3000 meters for an arbitrary number of loads, such as three loads, process failure detector 3880 will generate a process failure report 3860. Similarly, for efficiency purposes, site norm module 3885 has assigned to dump truck 4020 a minimum average loaded cycle distance of 3000 meters as a site norm. Thus, if the minimum loaded cycle distance for dump truck 4020 falls below an average of 3000 meters for an arbitrary number of loads, such as five loads, process failure detector 3880 will generate a process failure report 3860. Additionally, based on collected data in database 205, operational norm module 3885 has assigned to loader 4015 a maximum loaded cycle distance of 100 meters as an operational norm. Thus, if the maximum loaded cycle distance for loader 4015 exceeds 100 meters when its scoop is loaded with material, process failure detector 3880 will generate a process failure report 3860.

In general, there are three ways in which construction assets 4015, 4020, and 4030 can be used to move material from mound 4001 to mound 4002 or to mound 4003. One way is to use scraper 4030 to load material at mound 4001, and then drive to mound 4002 or 4003 where scraper 4030 will offload the material. Another way is to use loader 4015 to scoop material from mound 4001 into dump truck 4020. Dump truck 4020 will then drive to mound 4002 or 4003 and dump the loaded material. Yet another way is to load material from mound 4001 into the scoop of loader 4015 and unload it at mound 4002 or 4003. In a case where a large amount of material needs to be moved from mound 4001, it may take tens, hundreds, or thousands of loads with loader 4015, dump truck 4020, scraper 4030, or some combination thereof, to move the material. With thin profit margins and tight deadlines for a construction company that performs this type of work, it becomes very important to use the right asset or combination of assets to perform the material moving task in the most efficient manner possible.

Thus in this example, process failure detector 3880 will generate a process failure report 3860 if loader 4015 is used to move material from mound 4001 to mound 4002 or to mound 4003, as this will require loader 4015 to travel more than 100 meters in a loaded operational mode. Similarly, process failure detector 3880 will generate a process failure report 3860 if dump truck 4020 is used to move five or more loads of material between mound 4001 and mound 4002, but no process failure report 3860 will be generated by using dump truck 4020 to move material from mound 4001 to mound 4003. Finally, process failure detector 3880 will generate a process failure report 3860 if scraper 4030 is used to move material from mound 4001 to mound 4003 (for more than three load cycles), but no process failure report 3860 will be generated when scraper 4030 is used to move material from mound 4001 to mound 4002.

Process Failure Reports

In one embodiment, a generated process failure report 3860 is saved by process failure detector 3880, such as to a computer memory or hard disk drive, where it can be accessed by a user immediately or at some later time. In one embodiment, notification module 3887 communicatively couples or issues process failure report 3860 to recipient device 3890.

Figure 41:
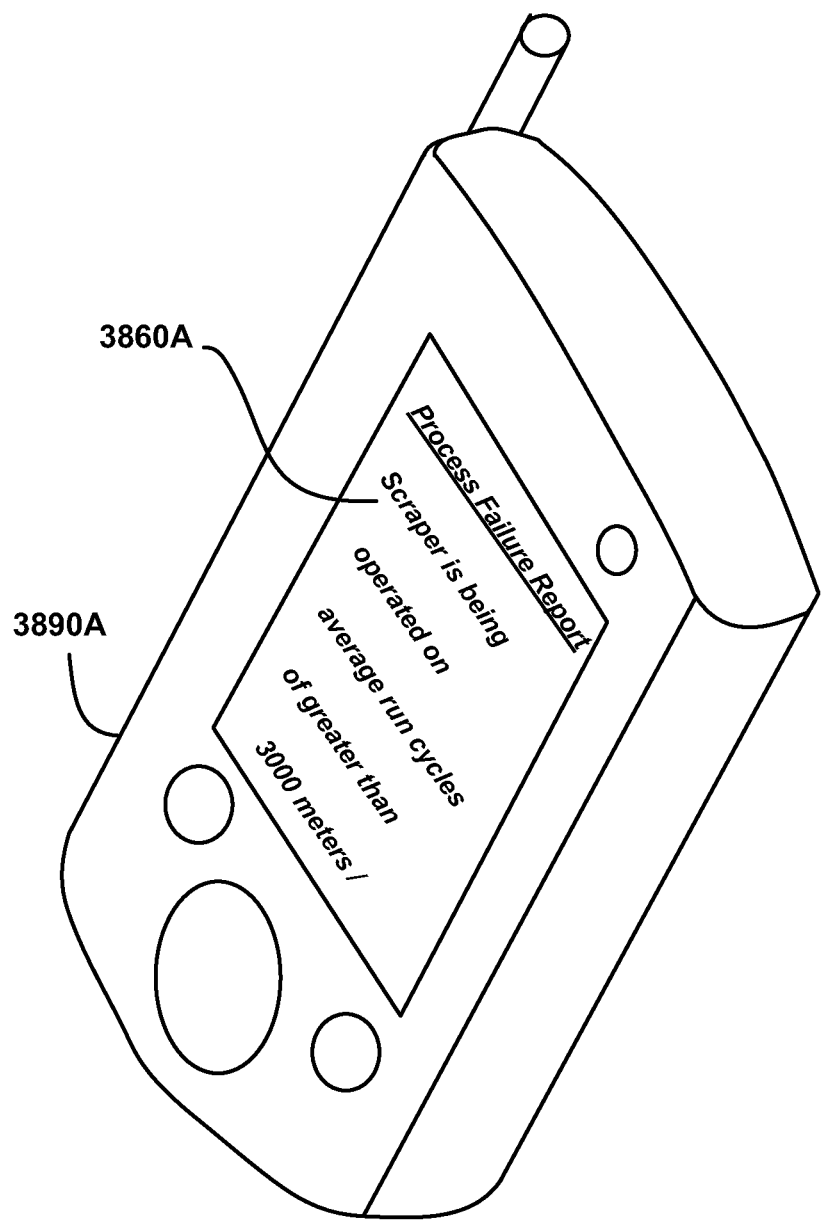
FIG. 41 shows an exemplary process failure report displayed on an exemplary recipient device, in accordance with one embodiment of the present invention.

Referring now to FIG. 41, an exemplary process failure report 3860A is shown displayed on an exemplary recipient device 3890A, in accordance with one embodiment. In FIG. 40, exemplary process failure report 3860A comprises an email message that has been sent to personal digital assistant 3890A. Following the example from FIG. 40, process failure report 3860A indicates that scraper 4030 is being operated on cycles of greater than 3000 meters average. In another embodiment, process failure report 3860A also includes a recommendation, such as using a dump truck/excavator combination instead of a scraper. Process failure report 3860A is sent to recipient device 3890A via, for example, a wired or wireless means, such as a wired or wireless coupling between recipient device 3890A and a computer network or the Internet, or a wireless coupling between recipient device 3890A and a radio, pager, or cellular telephone network.

Issuing a process failure report, such as process failure report 3860A, to a recipient device, such as recipient device 3890A, provides a means for real-time, near-real-time, or after-the-fact notification of process failure to a person such as a construction foreman, supervisor, manager, or even an equipment operator. This provides information to a responsible party that a particular construction equipment asset, such as scraper 4030, is being used improperly in some way which violates an established norm for the construction equipment asset. In the case of real-time and near-real-time notification, notification module 3887's swift delivery of a process failure report, such as process failure report 3860A, provides the opportunity for the process failure situation to be quickly addressed so that potential economic loss or inefficient asset use may mitigated or otherwise addressed.

Thus, embodiments of the present invention provide methods and systems for detecting and reporting process failure in the use of a construction equipment asset. Embodiments further provide methods and systems to assign one or more process norms to a construction equipment asset. Embodiments also provide for methods and systems to deliver or "issue" asset process failure reports to a variety of recipient devices in a format suited for the particular recipient device that the process failure report is sent to.

The disclosed methods and systems also allow a company or person to ensure that the proper construction equipment asset is being used a perform a task, and that while performing the task the construction equipment asset is being used properly or efficiently with respect to assigned process norms.

Section XI

Utilizing Historical Data in an Asset Management Environment

Overview

The asset location and operation information stored in database 205, of FIG. 7, can be analyzed and exploited for many purposes. One purpose is to detect and report a construction equipment asset process failure. The term "process failure" refers to the use of an asset to perform a process that another asset or combination of assets could perform more economically or more expeditiously, or the improper use of he correct asset when performing a process. Process failure is governed by one or more process norms that are assigned to a construction equipment asset.

A second purpose is to provide and implement a scheduled maintenance capability. For example, when an asset is in the field, the asset location and information stored in database 205 can provide up-to-date asset status such as time since last maintenance, any problems with the asset and the like. By monitoring the asset location and operation information, a management system can schedule the particular asset for maintenance based on the actual utilization of the asset instead of a guesstimate based on time-at-site, etc.

In other words, instead of missing maintenance because an asset was used more often than expected or taking an underused asset out of commission for unnecessary maintenance, the asset location and operation information can be used to ensure maintenance is timely. Moreover, because the asset location is known, the maintenance can be taken to the asset. In addition, because the operation information will provide times when the asset is not in operation or is in a state of reduced operation, a convenient time for performing the maintenance can be determined In many cases, the asset location and operation information that is analyzed and exploited is real-time or near real-time information. For example, when the asset information is received to the database it is quickly output in a report format that can be monitored by the asset management system, such as asset management system 700 of FIG. 7. In so doing, the asset management system 700 is able to provide an up-to date overview of the asset including location, operation, process failure, expected and unexpected maintenance requirements and the like.

However, in some cases any or all of the flow of asset location and operation information may be obstructed. For example, an asset reporting source such as first reporting source 208A may have transmission issues. That is, the transmitter may be in a location with no reception, the battery may be dead, the first reporting source 208A may be damaged or broken, or the like. As such, the information about the asset received to the database would be reduced. In some cases, this reduction may result in a portion of the asset management system 700 report 360 missing at least a portion of information. For example, the asset management system 700 may be able to provide an up-to-date overview of the asset including location information. However, due to the loss of the first reporting source 208A, operation, process failure, expected and unexpected maintenance requirements and the like may no longer be updated at the asset management system 700.

Thus, instead of the asset management system 700 simply maintaining the previous numbers until new information is received. That is, instead of missing any scheduled maintenance or other events, because the counters have stopped counting, the asset management system 700 will recognize the lack of updated data. The asset management system 700 will then refer to a historical data extrapolator to provide the operational information based on previously stored data. For example, if the asset was operated 10 hours a day for the past 10 days then the historical data extrapolator would provide an operational update of 10 hours per day such that any scheduled maintenance or other events would not be missed. Moreover, if an event was missed due to the loss of data, by providing extrapolated operational or location data, the asset management system 700 would be able to more quickly queue a user that an event was probably missed.

Asset Management System

Embodiments described in this section are utilized, in one embodiment, in conjunction with the exemplary asset management system 700 communicatively coupled with a customer application 710 of FIG. 7. As described in detail herein, asset management system 700 is comprised of data receiver 330, database 205, and asset information report generator 750. Various embodiments of the function and operation of asset management system 700 and its components are described herein and are not repeated for purposes of brevity and clarity, except for a plurality of alternate embodiments regarding asset information report generator 750 described in FIG. 42.

Figure 42:
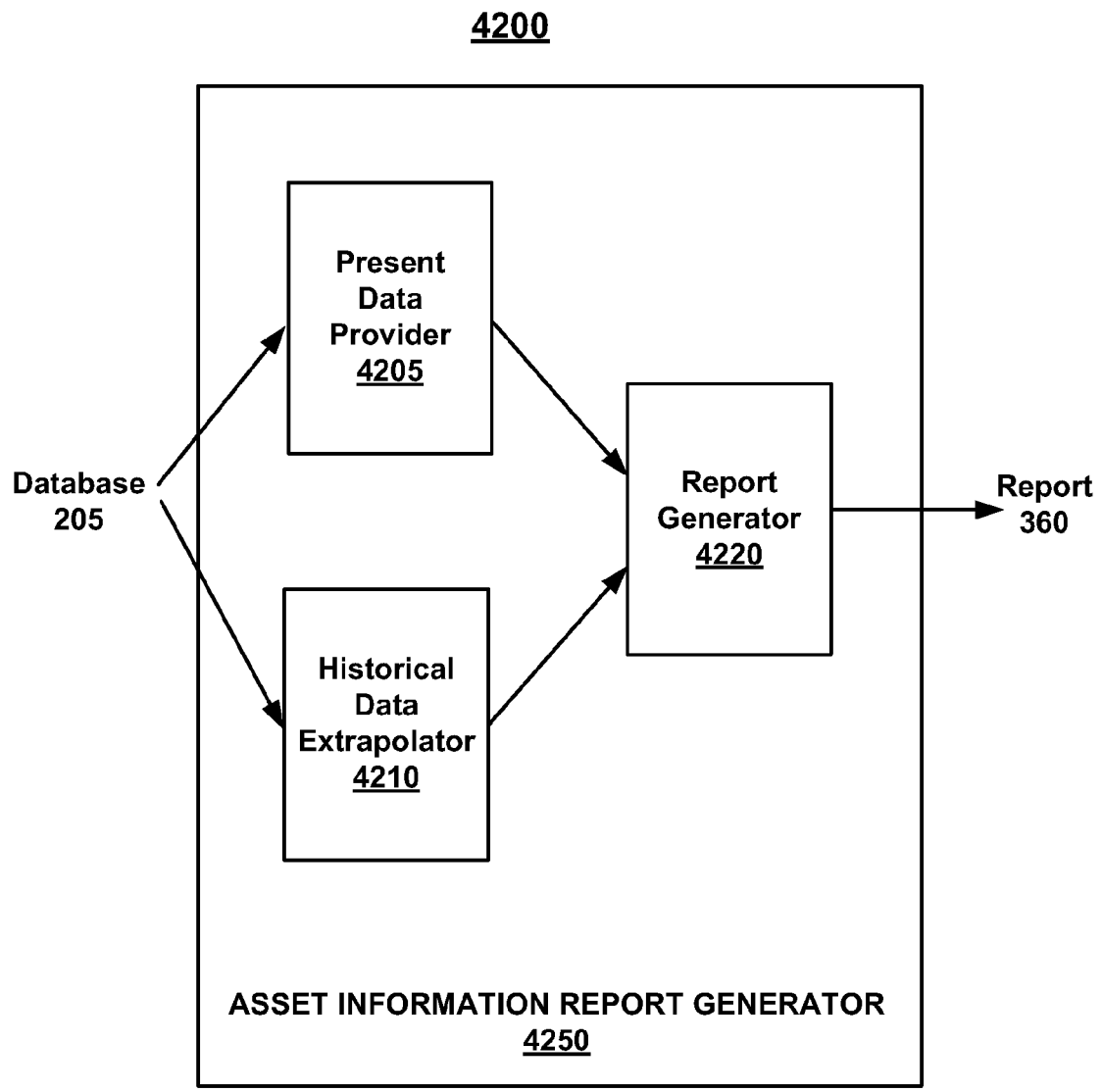
FIG. 42 is a block diagram of an exemplary asset information report generator in accordance with one embodiment of the present invention.

With reference now to FIG. 42, a block diagram of an exemplary asset information report generator 4250 is shown in accordance with one embodiment of the present invention. In one embodiment, asset information report generator 4250 includes a data provider 4205, a historical data extrapolator 4210, report generator 4220.

In one embodiment, data provider 4205 is configured to provide present data about an asset. In general, present data refers to real-time or near real-time data. In one embodiment, the present data about the asset is received from a database such as database 205 of FIG. 7. Historical data extrapolator 4210 is configured to provide extrapolated data about an asset based on historical asset data stored in database 205.

Report generator 4220 is configured to generate an asset information report 360 about at least one asset. For example, the asset report generator 4220 utilizes the extrapolated data about the asset in the asset information report 360 when at least one portion of the real-time data about the asset is absent. As described herein, in one embodiment the extrapolated data about the asset provided in the asset information report is used to trigger a missed event. For example, the extrapolated data about the asset provided in the asset information report may trigger a maintenance event.

With reference now to FIG. 43, a diagram of an exemplary printable format 4300 of a custom asset information report 360 generated by asset management system 700 incorporating asset information report generator 4250 is shown in accordance with one embodiment of the present invention. As shown in FIG. 43, an asset information report with a customized title 4310 "WEEKLY TRUCK USAGE REPORT" has been generated by a custom report module such as custom report module 959A of FIG. 9.

Report 4310 has been formatted with information from a customized query of asset information regarding asset 540B, a truck. Information is arranged in a customized configuration of rows and columns, where each row represents asset 540B and each column represents particular asset information pertaining to asset 540B. Column 601 represents asset type. Column 4304 represents a day of a work week. Column 4306 represents a calendar date associated with the particular day of the work week. Finally, column 4308 represents the total hours that asset 540B was utilized during a particular day and date.

This customized printable format 4300 is used, for instance, by a maintenance department to schedule maintenance. For example, the maintenance department can determine if the hours an asset has been operated correspond to a maintenance interval. In this example, during the week the asset has moved 37.7 hours along a maintenance interval. Furthermore, in one embodiment, if the asset is closing in on a scheduled maintenance call, then the maintenance department can monitor the asset to ensure that the maintenance is not missed. Although maintenance is described herein, embodiments are well suited to any type of asset monitoring. The use of a scheduled maintenance is merely one of a plurality of possible asset monitoring possibilities and is provided herein merely for purposes of brevity and clarity.

In one embodiment, customized printable format 4300 also includes an hours operated 4308 block 4335. In general, 4335 refers to a block that has been filled in with data extrapolated from historical information stored in database 205. For example, all other data, e.g., the hours operated on Monday-Wednesday and Friday are based on actual real-time data received by the asset management system 700. However, the hours operated on Thursday were either not recorded, lost, corrupt, or otherwise unusable.

Instead of leaving block 4335 blank, the historical data in database 205 was accessed by the historical data extrapolator 4210. The historical data extrapolator 4210 then arrived at the extrapolated 8.1 hours of operation for Thursday August 17th and that information was provided to report generator 4220 that resulted in the extrapolated information ending up in the report 4300. By providing the extrapolated results, the number of hours of asset operation remains fairly accurate. In other words, the maintenance schedule (or any other asset tracking information) is not on hold due to the missing asset operational data.

In general, the historical data extrapolator 4210 may utilize a plurality of methods for generating the extrapolated data. For example, the extrapolated data may be based on the average of a previous number of operational days (e.g., the average of the last 5 days of operation). In another embodiment, the extrapolated data may be based on the average of a previous number of same operational days (e.g., the average of the last 5 Thursdays of operation). In yet another embodiment, the extrapolated data may be based on the user utilizing the asset (e.g., bob utilizes the asset for an average 8.1 hours a day)—this may further be extrapolated based on the same operational days. In a further embodiment, the extrapolated data may be based on the weather (e.g., the database says Thursday was sunny, the average asset utilization on a sunny day is 8.1). Moreover, the extrapolated data may be based on the location of the asset (e.g., the database says the asset was in San Jose, the average asset utilization in San Jose is 8.1).

Thus, it is clear that the extrapolation of the historical data is limited only by ones imagination. In other words, the extrapolation may be based on any characteristic in the database, a combination of two or more characteristics in the database, a combination of at least one characteristic in the database and any other outside information, or the like. Moreover, as the database grows, there may be a comparison between the extrapolation and the actual result which could then be added to the database to further refine the accuracy of the historical data extrapolator 4210.

FIG. 44 is a flowchart of an exemplary method for utilizing historical data in an asset management environment in accordance with one embodiment of the present invention.

With reference now to 4402, one embodiment generates an asset information report 360 from a database 205, wherein the asset information report 360 comprises at least a portion of real-time information 4205 about the asset when the real-time information about the asset is available. As described herein, in one embodiment, the real-time information is location and/or operation information about the asset. In another embodiment, the real-time information is environmental condition information.

Referring now to 4404, one embodiment augments the asset information report 360 by extrapolating at least a portion of historical asset information 4210 stored at the database 205 when at least a portion of the real-time information 4205 is not available. As described herein, in one embodiment, the extrapolated information is location and/or operation information about the asset. In another embodiment, the extrapolated information is environmental condition information. Furthermore, as described herein, in one embodiment, the extrapolated asset information is used to trigger a missed event. That is, when the extrapolated data is input into the report 360, the addition of the previously missing data may provoke a missed event flag which would be provided by the asset management system 700. For example, if a maintenance call was due at the 800 hour mark and the addition of the extrapolated data to the report 360 resulted in the asset passing the 800 hour mark, then the 800 hour mark would be assumed as surpassed and a missed event notice, e.g., a maintenance event, may be triggered.

Thus, embodiments of the present invention provide methods and systems for utilizing historical data in an asset management environment. Embodiments further provide methods and systems for utilizing historical data in an asset management environment during real-time or near real-time operation. These methods and systems provide further tools for a company or person to manage efficient and economical use of assets that are being operated, and further to ensure that scheduled events are not missed indefinitely or rescheduled unnecessarily.

Section XII

Automatic Asset Classification

Embodiments of the present invention include a system and method for automatically classifying an asset. In general, a reporting device accesses at least one asset characteristic (e.g., asset VIN), reports the asset characteristic to an asset management system (e.g., asset management system 300 of FIG. 3) and the asset manager automatically classifies the asset based on the asset characteristic.

Asset characteristics to be used to classify an asset include but are not limited to asset make, model, serial number, year of manufacture, and other asset configuration specifics. The asset characteristics are used to automatically configure asset properties such as icon (graphical representation), description, name, maintenance intervals, etc maintained by an asset manager. Automatic classification and/or identification of assets is valuable in feature development and marketing for an asset management system because it is easy to use and implement.

In one embodiment of the invention, an interface (e.g., communication interface or bus) of an asset is accessed to gather information (e.g., asset characteristics) about the asset. Location-based assets could query the asset and report the asset characteristics to the asset manager. The asset manager would then interpret the asset characteristics (e.g., decode a VIN, etc.).

When new configuration information for an asset is received by the asset manager, the asset properties are configured based on the asset characteristics. For example, the make and/or model could be used to select from a list a graphical representation (e.g., icon) to associate the asset with. In one embodiment, a default name can be assigned to the asset. For example, if the asset is a bulldozer, and there are already ten bulldozers registered in the asset management system, a new bulldozer may be assigned a default name of Cat D8R #11. Other useful information (e.g., maintenance schedules) could be added to a description field associated with the asset. In one embodiment of the invention, asset information is stored in a database associated with the asset manager.

One advantage of the present invention for automatic asset classification is that many assets can be automatically configured (e.g., on the fly) saving time and effort for managing the assets. Additionally, the asset characteristics gathered provide useful information to improve feature development and/or marketing of the asset manager. Furthermore, since the reporting source can be easily moved from one asset to another, it is important for the reporting device to uniquely identify the asset it is coupled to as to reduce the possibility of using data (e.g., collected by the reporting device about the asset) that is labeled as being on a different asset. For example, if a reporting device is moved from a dozer to a tractor, the reporting device should recognize that the asset has changed from a dozer to a tractor. This feature is especially useful in the asset rental business because it reduces the chance of misidentifying assets on hand.

In one embodiment of the invention, automatic asset classification is performed when a reporting source is installed in an asset. For example, when a new asset is acquired, a reporting source can be installed to facilitate management of the asset. In one embodiment of the invention, the asset manager associates a particular reporting device (e.g., device serial number) with a particular asset.

During initial installation of the reporting device onto the asset, it is important to establish an association between the reporting device and the asset type. For example, it is important to determine whether the reporting device is coupled to a truck, a car, a tractor, a bulldozer, etc. If the asset is incorrectly classified, management of the asset becomes increasingly difficult.

Embodiments of the present invention automatically classify an asset based on at least one asset characteristic to improve asset classification and asset management. In one embodiment of the invention, the reporting device accesses asset characteristics (e.g., vehicle identification number, etc.) directly from a communication system associated with the asset. The asset characteristic is then reported to the asset manager and the asset manager automatically determines an asset classification and/or configuration based on the asset characteristic.

For example, if the vehicle identification number (VIN) is reported to the asset manager, the asset manager could either decode the VIN or use the VIN (e.g., connect to a manufacturer's database and look-up the VIN) to retrieve additional information about the asset (e.g., type, age, color, options, etc.) which can aid in classifying the asset. In one embodiment of the invention, a graphical icon is automatically assigned to the asset based on the asset characteristic. The graphical icon may also include an asset name and/or an asset description field.

Figure 45A:
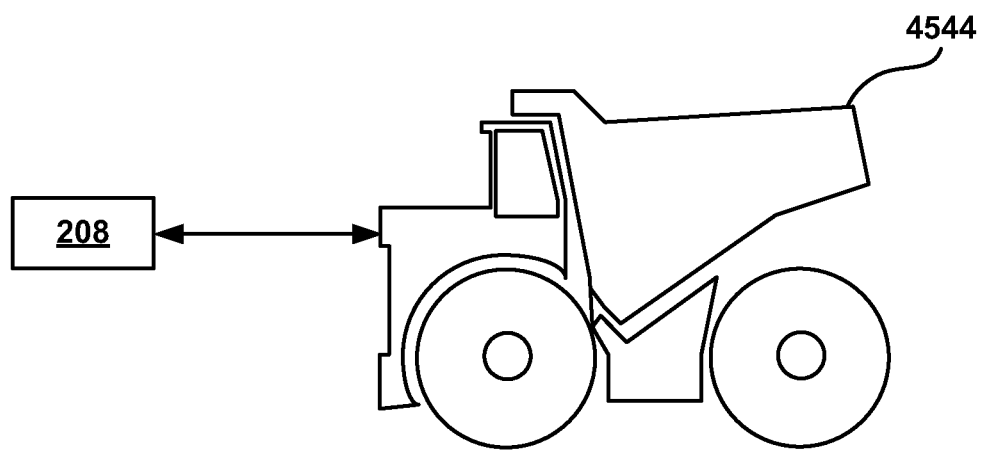
FIG. 45A is a block diagram of an exemplary reporting source coupled to an asset in accordance with one embodiment of the present invention.

FIG. 45A is an illustration of an exemplary reporting device 208 coupled to an asset 4544. In one embodiment of the invention, reporting device 208 is communicatively coupled to the asset 4544 and may interface with a communication system (e.g., BUS) associated with the asset 4544. In one embodiment of the invention, an asset characteristic is either automatically retrieved from the asset 4544 or is manually entered into the reporting device 208 (e.g., at the time of installation).

Figure 45B:
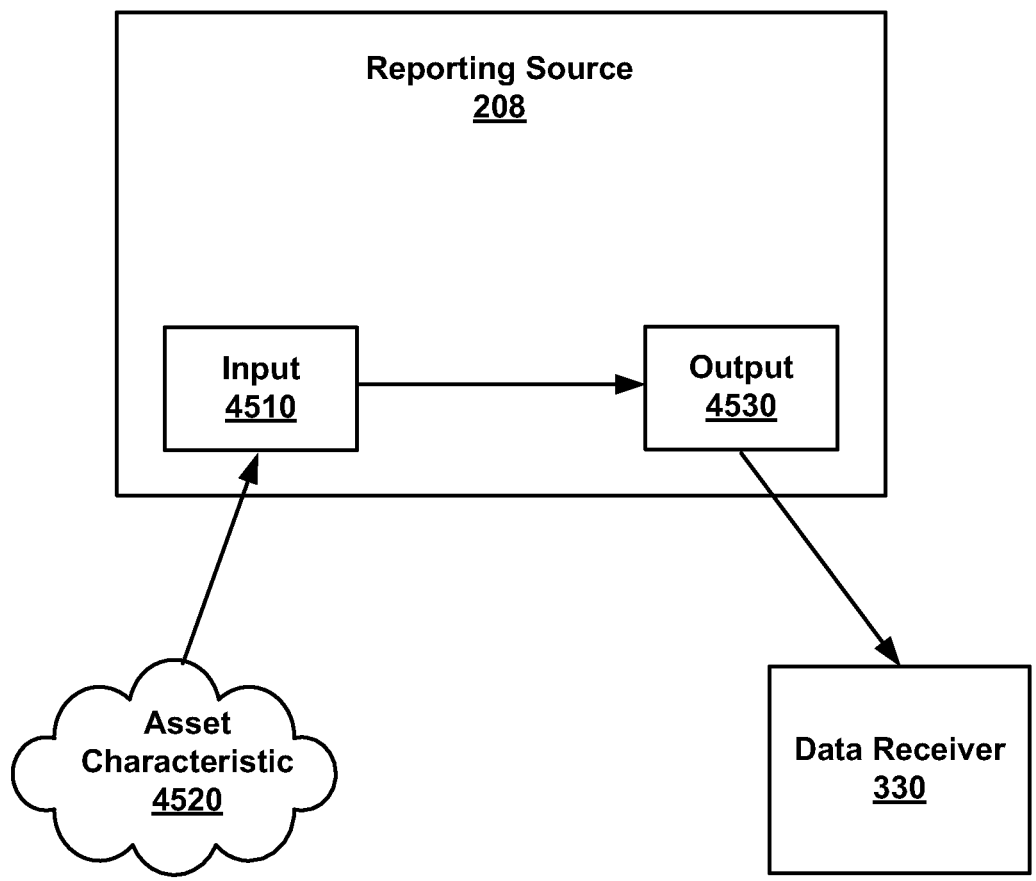
FIG. 45B is an illustration of an exemplary reporting device in accordance with one embodiment of the present invention.

FIG. 45B is a block diagram of an exemplary reporting device 208 in accordance with embodiments of the present invention. As stated above with reference to FIG. 2A, reporting device 208 could be a permanently mounted device 210, an asset mountable/detachable device 215, a portable computing device 220, a personal digital assistant 225, a smart phone 230, a mobile phone 235, human intelligence (HumInt) 240 or any other device capable of accessing information and reporting the information to an asset manager in accordance with embodiments off the present invention. For example, reporting sources 208 can include electronic devices, human sources, the asset being monitored, other assets, and the like. In one embodiment, the reporting source 208 is capable of providing asset information including, but not limited to, location information, operation information and status information and asset characteristics assessed from the asset itself or accessed from any other source.

In one embodiment, reporting device 208 may be a TrimTrac™ device, a CrossCheck® device, a radio frequency identifier, a global navigation satellite system (GNSS) and the like. Moreover, the reporting source 208 may include capabilities such as position fixing, photography, video/photograph recording, text messaging, voice messaging, data messaging, and the like. Furthermore, in one embodiment, the reporting source 208 may be capable of asset operation monitoring. For example, the reporting source 208 may be capable of being coupled to the asset by input 4510 to monitor asset characteristics 4520 including, but not limited to, a J-BUS, a controller area network bus (CAN-BUS), a processor coupled with the asset, a diagnostic evaluator, an engine microprocessor, a mileage indicator, a speedometer, a tachometer, an oil pressure indicator, a wheel pressure indicator, a hydraulic indicator, an engine time monitor, and the like. It is also appreciated that input 4510 may include means for manual input of asset characteristics (e.g., a key pad, touch screen, scanning device, etc.) by a reporting source installer for example. The reporting source also includes an output 4530 for providing the asset characteristic 4520 to the asset manager data receiver 330 (from FIG. 3).

Figure 46:
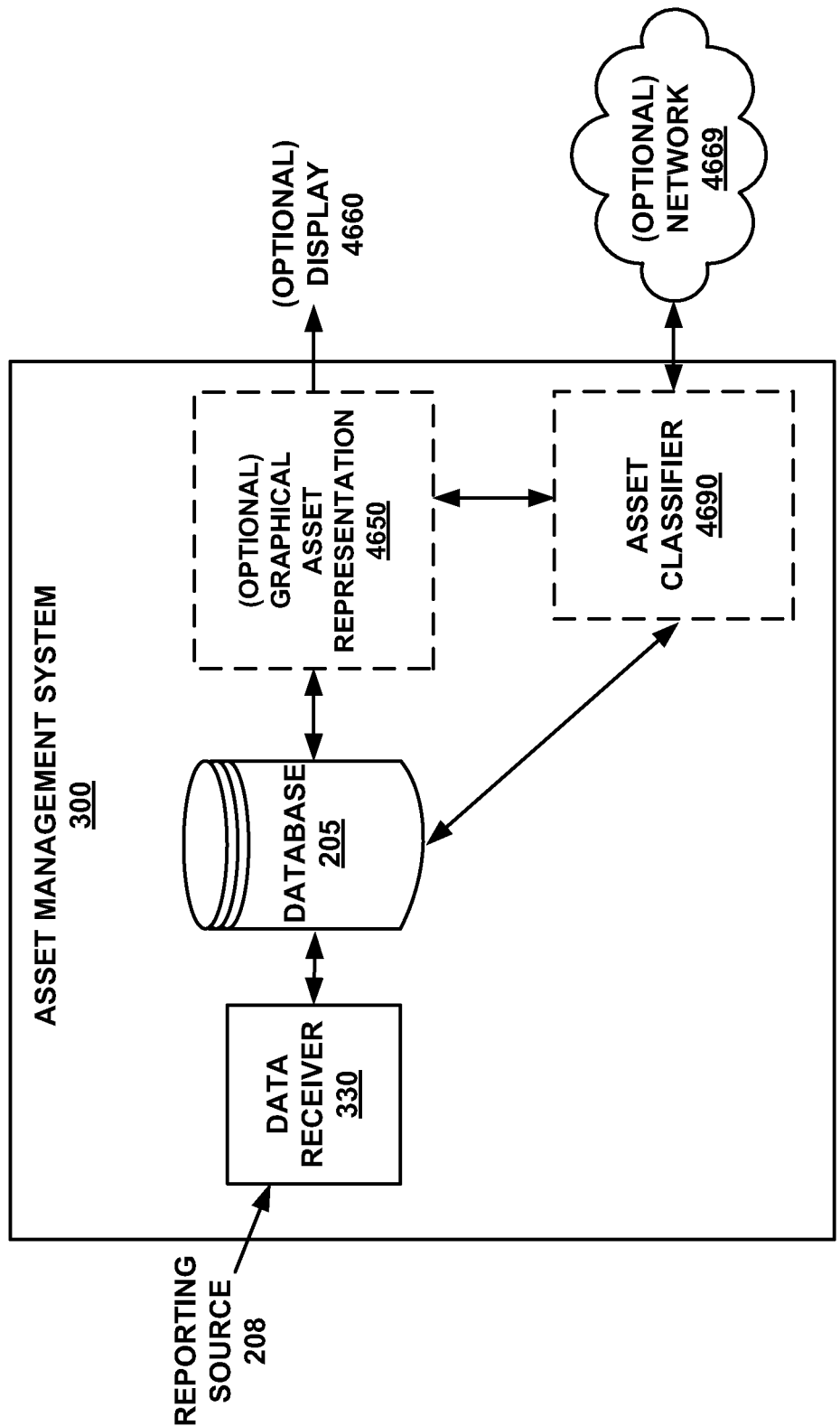
FIG. 46 is a block diagram of an exemplary system for automatically classifying an asset in accordance with one embodiment of the present invention.

FIG. 46 is a block diagram of an exemplary system for automatically classifying an asset in accordance with embodiments of the present invention. As stated above, the reporting device 208 reports an asset characteristic to the asset management system 300. In one embodiment of the invention, the reporting source 208 automatically reports the asset characteristic to the asset management system 300. In another embodiment of the invention, the asset manager 300 prompts the reporting device 208 to provide the asset characteristic and in yet another embodiment of the invention, the reporting source 208 periodically provides asset characteristics to the asset manager 300. It is appreciated that the asset manager 300 and the reporting source 208 can communicate in any number of ways such as wireless communication.

The asset characteristic is received by the data receiver 330. In one embodiment of the invention, database 205 is populated with the asset characteristic. In one embodiment of the invention, a reporting device identifier (e.g., a reporting device serial number) is also stored in the database 205. In one embodiment of the invention, the reporting device 208 is associated with the asset characteristic.

An asset classifier 4690 uses the asset characteristic to assign a particular asset classification to the asset. It is appreciated that any number of asset classifications could be assigned, for example, an asset classification could include an asset type, age, manufacturer, asset owner, service information, etc. It is appreciated that the asset classifier 4690 may retrieve additional asset information from sources outside the asset management system 300 such as from network 4669. It is appreciated that network 4690 may include the Internet.

In one embodiment of the invention, the asset classifier 4690 assigns a graphical representation (e.g., icon) of the asset based on the asset classification. A graphical asset presentation 4650 can be generated based on the classification of the asset determined by the asset classifier 4690. The graphical asset representation can be then provided to and displayed on display 4660. It is appreciated that display 4660 could be remote to the asset management system 300.

FIG. 47 is a flow diagram of an exemplary method 4700 for automatically associating an asset with a graphical representation based on an asset characteristic in accordance with embodiments of the present invention. In one embodiment of the invention, method 4700 is performed at the asset management system 300.

At step 4720, method 4700 includes receiving at least one asset characteristic from a reporting source. In one embodiment of the invention, the asset characteristic is accessed directly from a control or communication system associated with the asset. For example, the VIN associated with the asset could be retrieved from the asset CAN-BUS or J-BUS, however, it is appreciated that the asset characteristic can be retrieved in any number of ways. For example, the reporting device may include a scanner that can be used to scan information (e.g., a barcode) associated with the asset.

At step 4730, method 4700 includes automatically associating the asset characteristic with a graphical representation of the asset based on the asset characteristic. For example, if it is determined that the asset is a tractor, step 4730 would assign a tractor icon to the asset. In one embodiment of the invention, the reporting device may be associated with the asset and/or the graphical representation of the asset.

At step 4740, method 4700 includes providing the graphical representation of the asset on a graphical user interface. In one embodiment, asset management is observed on a graphical user interface. Automatically assigning an appropriate graphical representation of an asset facilitates asset management in accordance with embodiments of the present invention.

In one embodiment of the invention, method 4700 further includes automatically configuring the reporting device and/or the asset manager based on the graphical representation associated with the asset in step 4730.

In another embodiment of the invention, the reporting source is provided feedback (e.g., visual and/or audio) in response to the asset manager associating the asset with a graphical representation. For example, if the association is successful, a green light, can be illuminated and if the classification fails (and additional asset characteristics are needed), a red light can be illuminate.

In one embodiment of the invention, method 4700 includes populating a database with the asset characteristic. For example, the database could be populated with a reporting device identifier and an associated graphical representation.

FIG. 48 is a flow diagram of an exemplary method 4800 for automatically classifying an asset in accordance with embodiments of the present invention. At step 4820, method 4800 includes utilizing a reporting device associated with an asset to acquire at least one asset characteristic. It is appreciated that the asset characteristic can be acquired directly from the asset or can be manually entered into the reporting device.

At step 4830, method 4800 includes providing the asset characteristic to an asset manager. It is appreciated that the asset characteristic can be provided to the asset manager in any number of ways, including wireless communication.

At step 4840, method 4800 includes automatically determining an asset classification of the asset based on the asset characteristic. In one embodiment of the invention, the asset characteristic is used to determine additional asset characteristics. For example, from a VIN the make, year, etc of the asset could be determined.

In one embodiment of the invention, method 4800 further includes automatically configuring the reporting device and/or the asset manager based on the asset classification determined in step 4840.

In one embodiment of the invention, the reporting source is provided feedback (e.g., visual and/or audio) in response to the asset manager classifying the asset. For example, if the classification was successful, a green light could be illuminated and if the classification failed (and additional asset characteristics are needed), a red light could illuminate.

In one embodiment of the invention, method 4800 includes populating a database with the asset characteristic. For example, the database could be populated with a reporting device identifier and an associated asset characteristic.

Section XIII

Controlling Power Usage of a Reporting Device

Embodiments of the present invention include a system and method for managing power consumption of a reporting device associated with an asset. In particular, embodiments of the present invention are directed toward minimizing power consumption of the reporting device while still reporting necessary information back to an asset manager.

Many times, a reporting device is coupled to an asset that does not have a power source or the asset is unable to provide power to the asset. In this case, the reporting device must supply its own power (e.g., battery, solar, etc.). Often, the available power is limited and conservation of power is desired. To help reduce power consumption, in one embodiment of the invention, the reporting device has an active mode and a sleep mode. In the sleep mode, power consumption is greatly reduced compared to the active mode.

While conserving power is beneficial, it is still desired that the reporting device function as intended and report various information back to the asset manager as designed. In order to balance power consumption and functionality, embodiments of the present invention provide a system and method for controlling power usage of the reporting device.

In one embodiment of the invention, the reporting device remains in the sleep mode until a position change of the asset is determined. In response to the position change, the reporting device is powered up from the sleep mode to the active mode. In one embodiment of the invention, after powering up to the active mode, the reporting device transmits information back to the asset manager, including for example, the previous position and the new position.

In another embodiment of the invention, the reporting device periodically powers up from the sleep mode to the active mode to transmit information to the asset manager. In this case, the periodic powering can be overridden by a change in state, for example, unexpected movement of the asset. In this embodiment, in addition to the periodic reports to the asset manager, the reporting device also reports state changes to the asset manager.

Figure 49A:
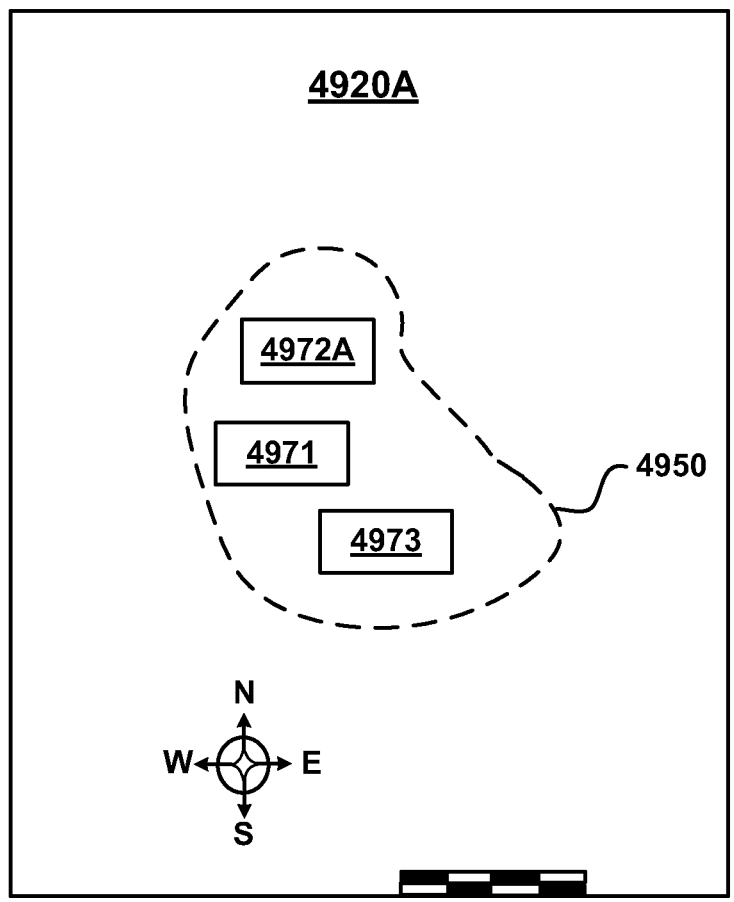
FIG. 49A is an illustration of an exemplary system for controlling power usage of a stationary reporting device in accordance with one embodiment of the present invention.

FIG. 49A is an illustration of an exemplary worksite 4920A comprising a plurality of reporting devices with reduced power consumption in accordance with embodiments of the present invention. It is appreciated that worksite 4920A is for illustrative purposes only and can be any area comprising traceable assets.

In one embodiment of the invention, worksite 4920A comprises a geo-fence 4950. In FIG. 49A, geo-fence 4950 includes reporting devices 4971, 4972A and 4973. It is appreciated that each of the reporting devices are coupled to an asset (not shown for clarity). Embodiments of the present invention notify an asset manager when an asset changes state, for example, leaves geo-fence 4950.

Figure 49B:
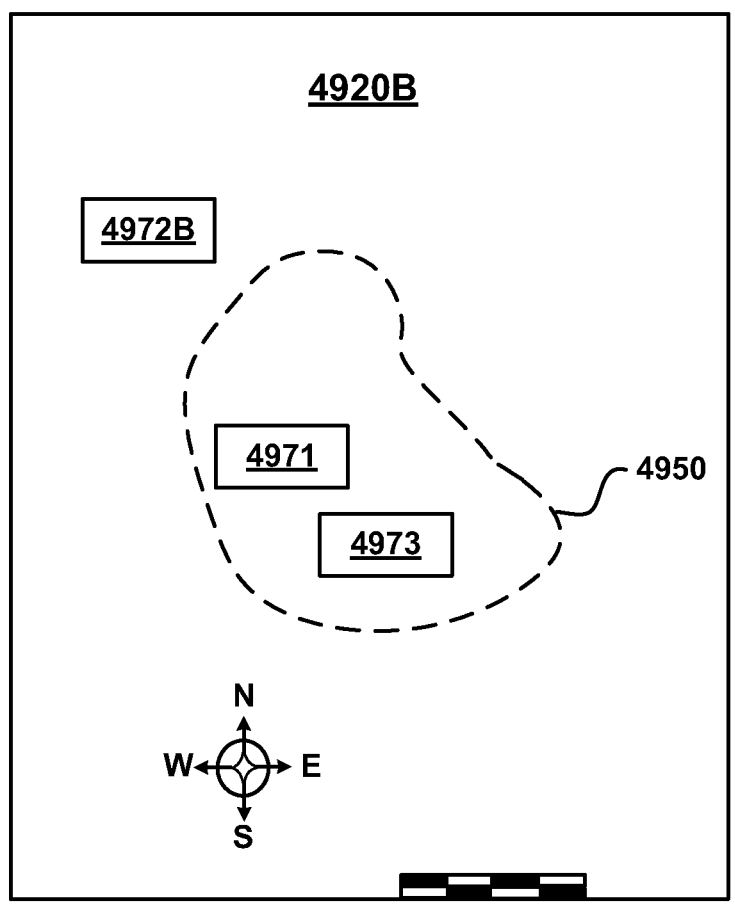
FIG. 49B is an illustration of an exemplary system for controlling power usage of a moved reporting device in accordance with one embodiment of the present invention.

Referring to FIG. 49B, reporting device 4972B is outside the geo-fence 4950. Embodiments of the present invention determine a state change (e.g., movement) of reporting device 4972B and report the state change to an asset manager (not shown). In one embodiment of the invention, threshold values can be assigned to states wherein an asset is permitted to operate within a predetermined range of a state before powering-up and reporting the state change to the asset manager. For example, an asset could be permitted to move within a geo-fence without triggering a state change power-up. It is appreciated that a state change is not limited to physical movement of an asset. For example, a state change could be any measurable parameter such as maintenance intervals, location, temperature, position, etc.

FIG. 50 is a block diagram of an exemplary method 5000 for managing power in a reporting device in accordance with embodiments of the present invention. At step 5002, method 5000 includes determining whether a reporting device is in a sleep mode or an active mode. In one embodiment of the invention, when the reporting device is in the sleep mode, less power is consumed than when the reporting device is in the active mode.

At step 5004, method 5000 includes in response to determining the device is in the sleep mode, step 5004 includes maintaining the sleep mode. In one embodiment of the invention, the default power state is the sleep mode to reduce overall power consumption of the reporting device.

At step 5006, method 5000 includes in response to determining a state change associated with the reporting device, step 5006 includes powering up the reporting device to the active mode At step 5008, method 5000 includes reporting the state change to an asset manager. It is appreciated that during step 5008, reporting device may report information in addition to or other than the state change to the asset manager. It is also appreciated that in response to the report to the asset manager, the asset manager may transmit information back to the reporting device. In one embodiment of the invention, communication between the reporting device and the asset manager is performed wirelessly.

In one embodiment of the invention, the reporting device powers down to the sleep mode after reporting the state change in step 5008. In one embodiment of the invention, the reporting device remains in the active mode for a predetermined period of time after reporting to the asset manager in step 5008.

In one embodiment of the invention, the reporting device periodically powers up to the active power state even if a state change is not determined. Periodically powering up provides a level of assurance that an asset is being monitored even if the asset did not change state. If reporting device fails to complete the periodic power-up, it can be assumed that there is a problem with the reporting device or the asset.

In one embodiment of the invention, the asset manager generates an alert in response to receiving a state change of one or more assets. In another embodiment of the invention, threshold values for states are implemented at the asset manager level wherein all state changes of assets are reported to the asset manager and the asset manager determines whether or not an alert should be generated.

FIG. 51 is a flow diagram of an exemplary method 5100 for powering up a reporting device in response to detecting movement of an asset in accordance with embodiments of the present invention.

At step 5102, method 5102 includes detecting an asset moving from a first position to a second position. In one embodiment of the invention, position movement is determined by a GPS. However, it is appreciated that any means for determining position can be used. For example, a mercury switch could be used to determine movement. In one embodiment of the invention, step 5102 includes determining a distance of movement. In this embodiment of the invention, a threshold value can be used to determine whether the distance triggers a powering up and report to the asset manager.

Provided the reporting device associated with an asset is in a sleep mode, step 5104 includes powering up the reporting device to an active mode and reporting the movement to an asset manager.

Provided the reporting device is in the active mode, step 5106 includes reporting the movement to the asset manager.

Step 5108 includes powering down the reporting device to the sleep mode in response to the reporting performed in step 5106.

Table 1 includes an exemplary pseudo code for a method of reducing power consumption of a reporting device in accordance with embodiments of the present invention.

TABLE 1

If (it is a Started Moving or a Stopped Moving event) and
    ((it's event_gmt is > = the most recent non-position event_gmt) or
    (this is the first event for this asset)) Then
    If the event is:
    Started moving:
    If MovingStatus is Stopped Then
    A started moving item will be added to the
    alert trigger service input queue
    Stopped moving:
    alert trigger service input queue
    Set MovingStatus to Stopped
Else
If (it is a Position event) and
(it's event_gmt > the most recent position event_gmt) and
(there is a previous position event)
Then
Calculate the Position Separation (PS) and the Time (Event_GMT)
Difference (TD) between this position and the most recent
previous position
If MovingStatus is:
    Moving or Stopping:
      if (PS is < 300 meters) and (TD is > 2 minutes) Then
Set MovingStatus to Stopped
Else
If (PS< 50 meters) and (TD is > 2 minutes) Then
If MovingStatus is:
Moving: Set MovingStatus to Stopping
Stopping: Set MovingStatus to Stopped
Else
Set MovingStatus to Moving
Stopped:
If (PS is > 300 meters) Then
A started moving item will be added to the
alert trigger service input queue
Set MovingStatus to Moving
Continue to process the new event.

Figure 52:
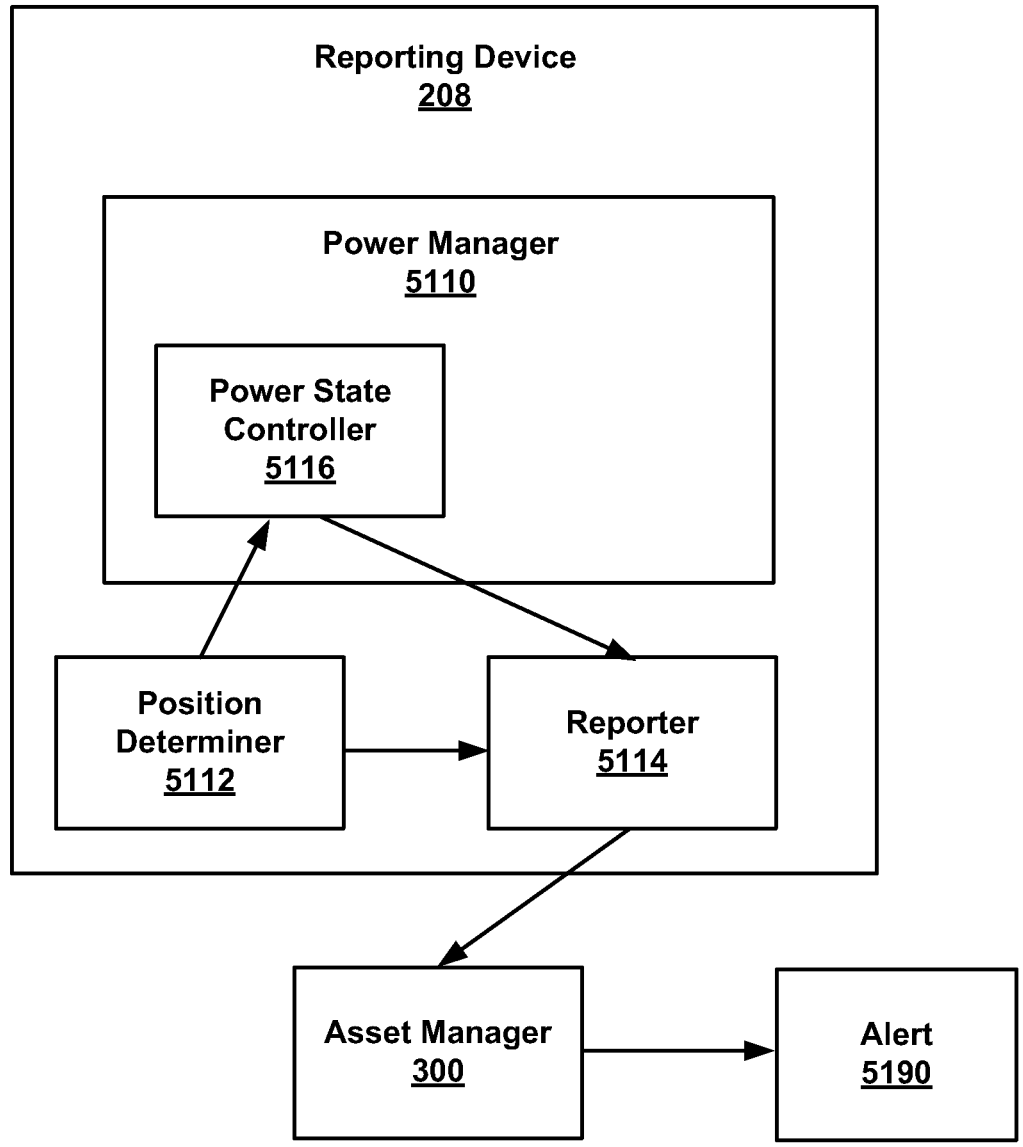
FIG. 52 is a block diagram of an exemplary system for controlling power usage of a reporting device in accordance with embodiments of the present invention.

FIG. 52 is a block diagram of an exemplary system for reducing power consumption of a reporting device 208 in accordance with embodiments of the present invention. In one embodiment of the invention, the reporting device 208 comprises a power manager 5110. In one embodiment of the invention, the power manager 5110 includes a power state controller 5116. The power state controller 5116 determines the power state of the reporting device and can power-up the reporting device to an active mode from a sleep mode and can power down the reporting device to the sleep mode from the active mode.

A position determiner 5112 provides position information to the power state controller 5116. It is appreciated that the position determiner 5112 can be any device capable of determining a position or location of the reporting device 208. It is also appreciated that position determiner 5112 may be part of the power manager 5110, part of the reporting device 208, or even external to the reporting device 208.

The reporting device 208 further includes a reporter 5114. The reporter communicates with the asset manager 300. In one embodiment of the invention, in response to receiving a report from the reporting device 208, the asset manager generates an alert 5190.

Section XIV

Delivering Tailored Asset Information to a Device

Overview

In general, the present technology provides a system and method for delivering asset information to a device in a user defined dashboard format tailored to a specific device. The term dashboard refers to a viewable display that provides information in a format similar to that of a vehicle. For example, in a vehicle a driver may monitor speed, RPM, oil temperature, and the like. In the same manner, a project manager may wish to monitor project metrics such as costs, asset utilization, manpower, safety, diversity, environmental concerns, and the like.

The dashboard provides one exemplary method for displaying any or all of the desired project metrics in a quick-to-comprehend overview type format. Moreover, in one embodiment, when interacting with the dashboard, the user may select one of the metrics, e.g., costs, which will then invoke a more in-detail dashboard view of the information behind the costs metric. For example, costs metric may include, labor, materials, fines, delays, savings, etc. In one embodiment, the layers of depth of the dashboard are limited only by the availability of asset data.

Basically, the present technology provides a data delivery system for presentation on a display of a computing device, e.g., mobile phone, personal digital assistant, laptop, desktop, and the like. In one embodiment, the data is mined from a database such as database 205 of FIG. 3 by an asset management system 300 and includes a status report for aspects of a project or job. In one embodiment, the data delivery is accessed via a direct link to the data mining server (e.g., a direct line of contact), via a network connection, via an Internet-based virtual circuit or the like.

In one embodiment, the display results are pre-determined or selected based on user-chosen fields in a setup menu and are easily adjustable per job, per level, per time period and the like. Moreover, the setup may be assessable from any Internet access device and may be adjusted via dropdown menus or may be custom tailored. In one embodiment, the dashboard may be a hardwired view e.g., providing access to the data via the device and allowing the device to format the incoming data to establish the dashboard view. However, the present technology is also well suited to allowing the device to have the option of utilizing a web view instead of a hardwired view. Basically, web view means that there is no need for the device's internal software to do any formatting. The formatting comes with the downloaded data from the web access. Thus, by allowing the web view to also be user formatted in a pre-defined manner there is no more extraneous 'stuff' on the web view than there is on the user defined display.

Figure 53A:
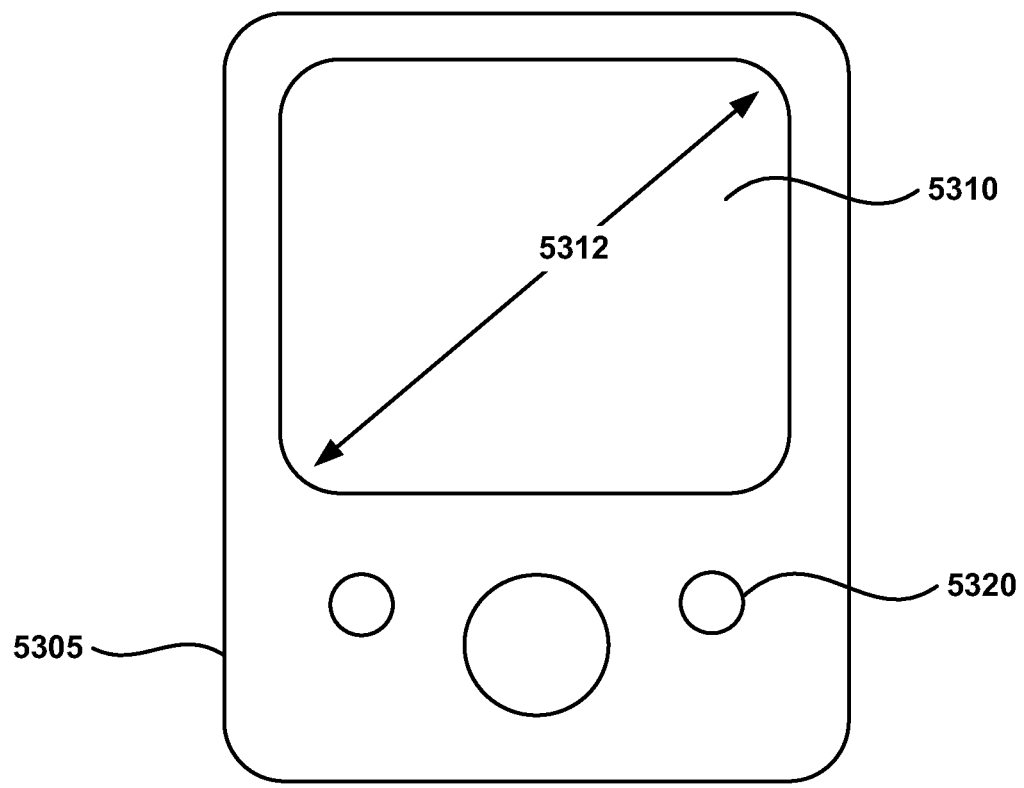
FIG. 53A is a block diagram of an exemplary handheld computing device in accordance with one embodiment of the present invention.

With reference now to FIG. 53A, a block diagram of an exemplary handheld computing device 5305 is shown in accordance with one embodiment of the present invention. In one embodiment, handheld computing device 5305 includes a GUI 5310 and interactive buttons 5320. In general, handheld computing device 5305 is a device such as, but not limited to, a personal digital assistant (PDA), a mobile telephone, a pager, hand portable computing device, and the like.

In one embodiment, the size of GUI 5310 of handheld computing device 5305 is also known. In one embodiment, the size is provided in a diagonal measurement 5312. However, the present technology is well suited to providing the size of GUI 5310 in other measurements such as length, width, pixilation, dots per inch (DPI) and the like.

Figure 53B:
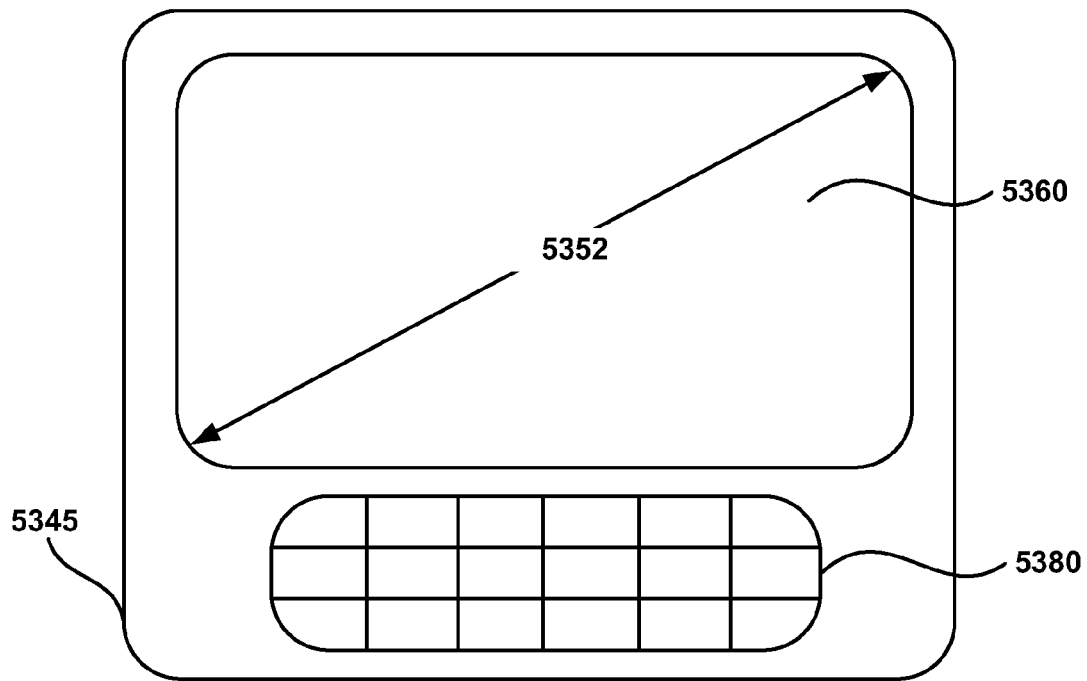
FIG. 53B is a block diagram of an exemplary computer system in accordance with one embodiment of the present invention.

Referring now to FIG. 53B, a block diagram of an exemplary computer system 5345 is shown in accordance with one embodiment of the present invention. In one embodiment, computer system 5345 includes a GUI 5360 and a key/thumb board 5380. In one embodiment, computer system 5345 is a device such as a laptop computer that is capable of being hand carried by a user. In another embodiment, computer system 5345 is a fixed computing device such as a desktop system, a vehicle mounted system, an in-dash computing system, a web television system, a server-terminal system, or any other type of computing device that includes a GUI 5360.

In one embodiment, the size of GUI 5360 of computer system 5345 is also known. In one embodiment, the size is provided in a diagonal measurement 5352. However, the present technology is well suited to providing the size of GUI 5360 in other measurements such as length, width, pixilation, DPI and the like.

With reference now to FIG. 54A, a block diagram of an exemplary listing 5400 of top level project related user selectable items 5410 for defining a GUI dashboard is shown in accordance with one embodiment of the present invention. In one embodiment, the project related user selectable options 5410 include schedule 5422, cost 5424, workforce 5426 and equipment 5428. In one embodiment, schedule 5422 refers to whether the project is on schedule or the time that the project is ahead or delayed. Cost 5424 refers to whether the project is at cost, under cost, or over cost. Workforce 5426 refers to the percent of manpower assigned and gainfully employed on the project. Equipment 5428 refers to the percent of machinery assigned and gainfully employed on the project.

Although a plurality of project related user selectable options 5410 are provided herein, they are exemplary. That is, the present technology is well suited to more of fewer project related user selectable options 5410. Moreover, the present technology is well suited to different project related user selectable options 5410 than those provided herein. The use of the provided project related user selectable options 5410 herein is merely for purposes of brevity and clarity.

Furthermore, project related user selectable options 5410 may be provided or limited based on the size of the GUI that will be displaying the information. For example, a user may initially be defining a dashboard for a handheld device such as device 5305 of FIG. 53A. As such, the user would input the device to receive the information. For example, the user may select a mobile phone with a standard display, a PDA with a 4 inch GUI, or the like. In so doing, project related user selectable options 5410 may be modified depending on the display screen.

In another embodiment, the list of project related user selectable options 5410 may not be modified based on GUI size, but the number of allowed selections may be limited. For example, a user establishing a dashboard for a mobile phone may only be able to select two of the four project related user selectable options 5410.

Generally, project related user selectable options 5410 may refer to any project that a user would want to receive information about. In other words, as described in more detail herein, there may be a plurality of projects and any or all may have project related user selectable options 5410 available. Thus, the user may select to receive information about one project, all projects, or any combination thereof. Moreover, for each selected project, the user may choose to receive similar information or different information.

Referring now to FIG. 54B, a block diagram of an exemplary listing of sub-level user selectable items 5460 for defining a GUI dashboard is shown in accordance with one embodiment of the present invention. In one embodiment, the selectable options level II 5460 is based on the initial selection of equipment 5428. Although the selectable options level II 5460 are focused on equipment 5428 this is exemplary. That is, the present technology is well suited to providing a second level of information based on any or all of the project related user selectable options 5410.

In one embodiment, equipment 5428 has a plurality of sub-levels including asset 5465, location 5470 and status 5475. In one embodiment, asset 5465 refers to the type of asset, the exact asset, a general overview of similar assets or the like, location 5470 refers to the location of the asset and status 5475 refers to the assets status, e.g., operational, broken, due for maintenance, and the like.

Although a plurality of sub-levels is provided herein, they are exemplary. That is, the present technology is well suited to more of fewer sub-levels. Moreover, the present technology is well suited to different sub-levels than those provided herein. The use of the provided sub-levels herein is merely for purposes of brevity and clarity.

Furthermore, the number of sub-level options may be provided or limited based on the size of the GUI that will be displaying the information. For example, a user may initially be defining a dashboard for a handheld device such as device 5305 of FIG. 53A. As such, the user would input the device as part of the user input. For example, the user may submit that the dashboard profile will be based on a mobile phone with a standard display, a PDA with a 4 inch GUI, or the like. In so doing, the second level options related to equipment 5460 may be modified depending on the display screen.

In another embodiment, the list of second level options related to equipment 5460 may not be modified, but the number of allowed selections may be limited. For example, a user establishing a dashboard for a mobile phone may only be able to select two of the four second level options related to equipment 5460.

With reference now to FIG. 55A, a block diagram of an exemplary top level user-defined GUI dashboard 5500 is shown in accordance with one embodiment of the present invention. In one embodiment, GUI dashboard 5500 includes a first project 5420A and a second project 5420B. Moreover, at GUI dashboard 5500 the user has selected to monitor schedule 5422, cost 5424, workforce 5426 and equipment 5428 for each project. Although, in one embodiment, the selections for each project are the same, the present technology is well suited to monitoring different aspects of each project. That is, the illustration of the same selections for each project are provided herein merely for purposes of brevity and clarity.

In one embodiment, the number of projects that are shown on GUI dashboard 5500 is both user selectable and limited to the present GUI size. Moreover, if more than two projects were selected, the present technology may allow a user to select the order of the projects to be displayed and may then rotate the projects based on the user selected order. For example, if five projects were selected to be monitored and the GUI was able to only show two at a time, then the projects may be rotated across the screen, either automatically or when prompted, in the user defined order. In another embodiment, the additional projects may be available via scroll bars, hot keys, or the like.

Referring now to FIG. 55B, a block diagram of an exemplary second level user-defined GUI dashboard 5550 is shown in accordance with one embodiment of the present invention. In one embodiment, second level user-defined GUI dashboard 5550 provides information regarding equipment 5428A from project 5420A. Moreover, at second level user-defined GUI dashboard 5550 the user has selected to monitor asset 5465, location 5470 and status 5475 for equipment 5428.

In one embodiment, the number of equipment sub-options that are shown on second level user-defined GUI dashboard 5550 is both user selectable and limited to the present GUI size. Moreover, if more than three columns of sub-options were selected, the present technology may allow a user to select the order of the sub-options to be displayed and may then rotate the sub-options based on the user selected order. For example, if five sub-options were selected to be monitored and the GUI was able to only show three at a time, then the sub-options may be rotated across the screen, either automatically or when prompted, in the user defined order. In another embodiment, the additional sub-options may be available via scroll bars, hot keys or the like.

With reference now to FIG. 56, a flowchart 5600 of an exemplary method for delivering tailored asset information to a device is shown in accordance with one embodiment of the present invention. As described herein, the present technology allows a user to tailor the asset information received to a device based on the GUI characteristics or other features of the device. For example, a user receiving asset information at a 17" display may tailor the asset information in a first layout, and when the user was going to receive the asset information at a 3" display, the user would tailor the asset information in a second layout. In one embodiment, the first and second layouts may differ in the amount of information provided within the asset information. In another embodiment, the first and second layouts may differ in the method of presentation. In yet another embodiment, the first and second layouts may differ in both the amount of asset information provided and the methods of presenting the asset information.

With reference now to 5602 of FIG. 56 and FIG. 3, one embodiment accesses a database 205 comprising information from a first reporting source about an asset and information from a second reporting source about the asset. Further detail of the database 205 is found in the description of FIG. 3 and is not repeated herein for purposes of brevity and clarity.

Referring now to 5604 of FIG. 56 and to FIG. 54A, one embodiment utilizes pre-defined user selectable criteria 5400 to select portions of the asset information from the first reporting source and the information from the second reporting source. For example, once the user selectable criteria 5400 has been defined, when the asset management system 300 of FIG. 3 is accessed, only the information selected by the user will be provided. Further detail of the asset management system 300 operation is previously provided herein and is not repeated herein for purposes of brevity and clarity.

With reference now to 5606 of FIG. 56 and to FIGS. 55A and 55B, one embodiment comprises tailoring the asset information report 5500, wherein the pre-defined portions of the information about the asset are utilized for tailoring the asset information report 5500. For example, in one embodiment, the tailored asset information report 5500 may include a first level of detail in the formatting of the tailored asset information report 5500. Furthermore, a user can also pre-define a second level of detail in the formatting of the tailored asset information report 5500. In other words, the first level of detail may be an overview such as the overview shown in GUI 5500 of FIG. 55A, while the second level of detail may be a drill down of a specific portion of the first level of detail as shown in GUI 5550 of FIG. 55B.

Moreover, the second level of detail may be defined and available for any or all of the information within the first level of detail overview. For example, a user may monitor the first level of detail, e.g., GUI 5500, and then may select one of the overview sections, e.g., equipment 5428A of FIG. 55B, to view in more detail.

Referring now to 5608 of FIG. 56 and to FIGS. 55A and 55B, one embodiment configures a layout of the tailored asset information report 5500 based on a GUI such as GUI 5310 of FIG. 53A. In one embodiment, the layout of the tailored asset information report 5500 is configured based on a display size of the GUI 5310. Moreover, a job identifier is assigned to the configuring of the layout of the tailored asset information report 5500.

For example, a company president may wish to view a pre-defined version of any or all projects in which the company is involved. In one embodiment, the company president will select the format of the pre-defined version utilizing a method such as user-selectable fields in a setup menu, collaborating with a technician, or the like. For example, the pre-defined version may be a high level overview of any or all of the projects and may include the project name, the project status, the project actual cost versus budget, or the like.

In addition, the company president may establish a plurality of pre-defined versions based on a disparity of GUI's that will be viewed. For example, when accessing the information on a portable computing system, such as a laptop computer 53B, the first pre-defined version may include a large number or even all of the projects related to the company. However, when accessing the information from a handheld device 53A, such as a mobile phone, personal digital assistant, or other reduced screen size device, the second pre-defined version may provide the projects in a rotating order, utilize scroll type functionality, monitor a lesser number of projects, reduce the variables shown per project and the like. In so doing, the user will receive the desired pre-defined information in an easily readable and navigable format based on the user defined preferences and the GUI characteristics of the device receiving the information.

In a different embodiment, a project manager may wish to view, e.g., on a GUI 5310 or the like, a pre-defined version of any or all of the projects in which the manager is involved. In one embodiment, the project manager will establish the pre-defined version by a method such as user-chosen fields in a setup menu, collaborating with a technician, or the like. For example, the pre-defined version may be a high level overview of any or all of the projects in which the manager is involved. The predefined version may include the project name, the project status, the project actual cost versus budget, or the like. In one embodiment, the project manager may establish a plurality of pre-defined versions based on a disparity of GUI's or devices that will be viewed in a manner similar to that described herein.

In addition, the project manager may establish a plurality of pre-defined drill down versions of the asset report. For example, the project manager may have an initial pre-defined version that provides the project name, status and manpower. The project manager may then establish a pre-defined version of each of the initial fields, such that a selection of one of the fields, e.g., manpower, provides a pre-defined version of any or all of the data related to manpower. For example, number of injuries, safety record, personnel at work, personnel not at work or the like.

In one embodiment, the number of user pre-defined levels is limited only by the data in the database and the desire of the user. For example, the company president may pre-define the drill down features to range from an overview of projects to the maintenance schedule of a particular truck. In so doing, the pre-defined asset management version may initially provide an entire company-project overview when accessed but also allow the user to delve into any pre-defined details.

Moreover, because the asset management information is pre-defined, if a particular aspect of a particular project becomes a point of focus, the company president, may re-define the initial top level GUI asset monitoring information to include details about the particular aspect of the particular project without requiring the user to delve at all. That is, the user is capable of defining what information is displayed at what level and what detail is provided within the information, per display being utilized. Conveniently, this is available without requiring a user to navigate through superfluous data, search a crowded report, navigate with an undersized display, and the like.

In one embodiment, when the layout of the tailored asset information report 5500 is larger than the display size of the GUI 5310, a user selectable order of rotation may be defined for the layout of the asset information within the report. For example, a first portion of the layout of the tailored asset information report 5500 will be initially shown on the GUI 5310. Then, either after a period of time, based on a user input, or any other criteria, the first portion of the layout of the tailored asset information report 5500 will be removed and a second portion of the layout of the tailored asset information report 5500 will then be shown on the GUI 5310. This rotation of pages can continue for any number of layout pages. Moreover, the rotation could be reversed, shuffled, hot keyed, or the like to allow a user to define the order in which the pages are viewed, modify the order in which the pages are viewed, or skip from one page to a specific other page regardless of any pre-designated page order.

In another embodiment, when the layout of the tailored asset information report 5500 is larger than the display size of the GUI 5310, a layout navigator is provided as a portion of the layout of the tailored asset information report 5500. For example, the layout navigator may be a scroll bar, a set of scroll bars, arrows, or any other type of receivable input that will allow a user to navigate a larger document layout with a window that is smaller than the size of the document layout being presented. In other words, if the layout is a virtual size of 10"×10" and the screen size is 5", then at any given time only a portion of the layout would be produced on the GUI 5310. However, the utilization of the layout navigator allows a user to modify which portion of the layout of the tailored asset information report 5500 is viewable on the GUI 5310. That is, the user is able to use the layout navigator to navigate within the virtual size of 10"×10" when the screen size is 5".

In addition to allowing a user to configure a first layout of the tailored asset information report 5500 based on a first display size of a GUI, the present technology also allows a user to configure a second layout of the tailored asset information report 5550, having at least one level of detail, based on a display size of a second GUI. For example, the user may configure a first tailored asset information report 5500 based on a first device, such as a laptop computer 5345 of FIG. 53B, having a screen size 5352 of 17". In addition, the user may configure a second tailored asset information report 5550 based on second device, such as a PDA 5305 of FIG. 53A, having a screen size 5312 of 5". Moreover, the user may assign a first job identifier to the first layout configuration and a second job identifier to the second layout configuration of the tailored asset information report 5550. Therefore, when the user prepares to access the information, the user may input the job identifier to receive the report configured to the device being utilized.

For example, if the user is utilizing the notebook, the user would access the Internet or another network to establish a connection with the asset management system providing the asset report. If required, the user may then login and provide a password to establish his identity with the asset management system. The user would then input the first job identifier. The asset management system would then provide the pre-defined layout which was configured to a 17" GUI. In one embodiment, the first layout may include many details because of the amount of room available for displaying information. However, if the user was utilizing the mobile device, the user would input the second job identifier and the received layout would be configured to a 5" display. Thus, in one embodiment, the second layout may not include as many details as the first layout, may monitor a fewer number of aspects than the first layout, may require a user to navigate through the layout, may require a number of pages to be scrolled through or the like. In other words, the user could specify that the second layout be reduced in information, or could specify that the information remain the same and design the method for navigating around within the layout.

Embodiments of the present invention, a system and method for asset management, are thus described. While the present invention has been described in particular embodiments, it should be appreciated that the present invention should not be construed as limited by such embodiments, but rather construed according to the following claims.

Section XV

Telematic Asset Microfluidic Analysis

Notation and Nomenclature

Unless specifically stated otherwise as apparent from the following discussions, it is appreciated that throughout the present Description of Embodiments, discussions utilizing terms such as "acquiring," "analyzing," "displaying," "providing," "initiating," "transmitting," "comparing," or the like, refer to the actions and processes of a computer system or similar electronic computing device (or portion thereof) such as, but not limited to: an electronic control module, telematics device, and/or a management system (or portion thereof). The electronic computing device manipulates and transforms data represented as physical (electronic) quantities within the electronic computing device's processors, registers, and/or memories into other data similarly represented as physical quantities within the electronic computing device's memories, registers and/or other such information storage, processing, transmission, or/or display components of the electronic computing device or other electronic computing device(s).

Overview of Discussion

Example techniques, devices, systems, and methods for analyzing fluids on-location and providing analysis results to a remote management system are described herein. Discussion begins with a high level description of a fluid analyzer and a high level description of a telematics device. An example fluid analysis system coupled with an asset and telematics device is then described. Discussion continues with description of an example fluid analysis system. Components of a fluid analysis system are then described. Discussion continues with description of a telematics device and an asset management system. Components of an asset management system are then described. Operation of the fluid analysis system is then further described in conjunction with description of an example method of analyzing fluids and providing results to an asset management system via a telematics device.

Fluid Analyzers

A fluid analyzer provides results related to a fluid's properties based on a set of parameters. Fluid analysis can be performed during routine maintenance to provide information on fluid condition. By tracking sample results over the life of a machine, a fluid analyzer assists tribologists by establishing trends which can help eliminate costly repairs. Fluid analyzers can analyze fluid properties, including fluid additives. They can determine whether fluid contaminants and particulates exist, and to what extent. Fluid analyzers can also determine the type of particulates found in a fluid sample. In addition, fluid analyzers can determine the existence of wear debris from machinery.

Fluid sampling is a procedure for collecting a volume of fluid from an asset for the purpose of analysis. It is important that the procedures used to collect and test the sample minimize disturbance of the sample during and after the sampling process. Conventionally, samples are sent to a laboratory for analysis.

Lab-on-a-chip ("LOC") devices were created to eliminate the time spent delivering fluid samples to labs. LOCs can analyze extremely small fluid volumes down to less than Pico liters. Microfluidic analyzers provide many advantages, specific to their application. These include, but are not limited to: low fluid volumes required for consumption; faster analysis and response times due to short diffusion distances, fast heating, high surface to volume ratios, and small heat capacities; better process control due to faster system response time; compactness of the system; parallelization due to compactness, which allows high-throughput analysis; low fabrication costs, allowing for cost-effective disposable chips, fabricated in mass production; and a safer platform for testing due to smaller fluid volumes.

Telematics Devices

Telematics refers to the integrated use of telecommunications and informatics. Telematics devices transmit data from the location of origin to a computing location, and may effect some control on a remote object. Telematics may refer to, for example: the technology of sending, receiving, and storing information via telecommunication devices in conjunction with effecting control on remote objects; integrating telecommunications and informatics for application in vehicles; or global positioning systems technology.

Figure 57:
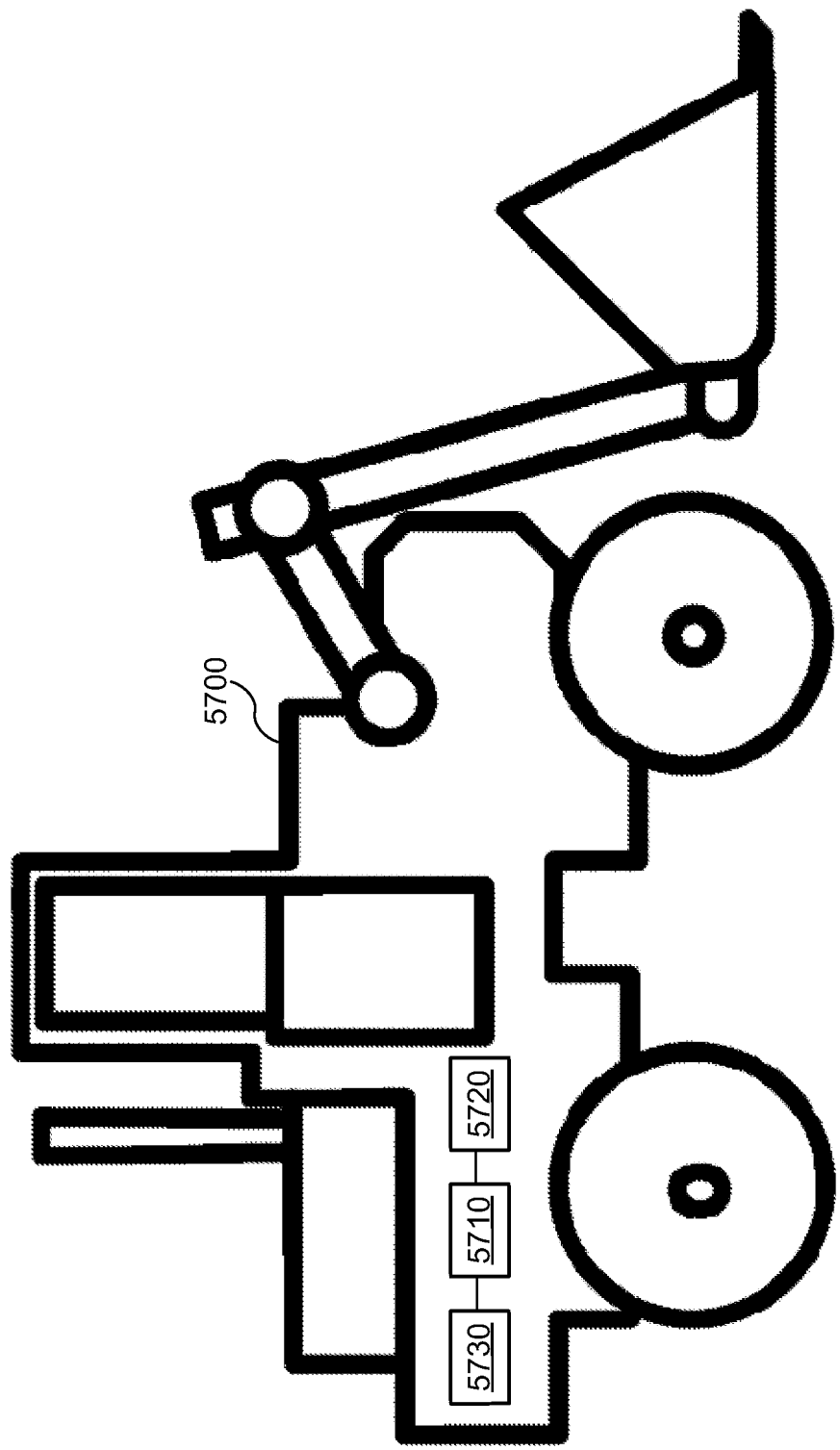
FIG. 57 is a diagram of an example of an asset coupled with an electronic control module, a fluid analysis control module, and a telematics device, according to various embodiments.

Example Asset Coupled with an Electronic Control Module, a Fluid Analysis Control Module, and a Telematics Device FIG. 57 is a diagram of an example of an asset 5700 coupled with an electronic control module 5730, a fluid analysis control module 5710, and a telematics device 5720. Fluid analysis control module 5710 receives a fluid sample from asset 5700. Microfluidic analysis may take place within fluid analysis control module 5710, for example via one or more LOCs included in or coupled with fluid analysis control module 5710. After analysis, fluid analysis control module 5710 sends results of the analysis to telematics device 5720.

In one embodiment, electronic control module 5730, fluid analysis control module 5710, and telematics device 5720 are physically connected to asset 5700. In this embodiment, a fleet manager can monitor the fluids in fleet assets during deployment without sending a technician to the location of asset 5700 to sample fluids and without sending sampled fluids to a lab and waiting for results to be returned. In an embodiment, electronic control module 5730 is comprised of a J1939 Vehicle Bus or other similar vehicle bus architecture, also known as a "J-Bus."

In another embodiment, electronic control module 5730, fluid analysis control module 5710, and telematics device 5720 are not attached to asset 5700. For example, one or more of electronic control module 5730, fluid analysis control module 5710, and telematics device 5720 may be housed in a hand-held device which a technician may plug into a fluid sample source of asset 5700. In various embodiments, electronic control module 5730, fluid analysis control module 5710, and telematics device 5720 may be housed together in one unit, or electronic control module 5730, fluid analysis control module 5710, and telematics device 5720 may be separate from each other.

In some embodiments, asset 5700 is a type of heavy machinery which would typically be used for construction. Heavy machinery includes, but is not limited to: backhoes, cherry pickers, cold planers, compactors, conveyors, cranes, cure rigs, dozers, dredgers, dumps, excavators, feller bunchers, forklifts, forwarders, graders, harvesters, handlers, haulers, loaders, pavers, pile drivers, pipe layers, reclaimers, rollers, shovels, skidders, soil stabilizers, street sweepers, tillers, tractors, trenchers, trucks, tunnel boring machines, and yarders. In other embodiments, asset 5700 may be, for example, a consumer automobile, a watercraft, an appliance, or a heavy duty tool which utilizes fluid analysis.

In other embodiments, asset 5700 is a type of vehicle including, but not limited to: aircraft, consumer trucks and automobiles, spacecraft, and watercraft. In other embodiments, asset 5700 is a non-vehicle, including, but not limited to: exoskeletons, habitats, stations, wind turbines, or greenhouses.

Example Telematic Asset Microfluidic Analysis System

Figure 58:
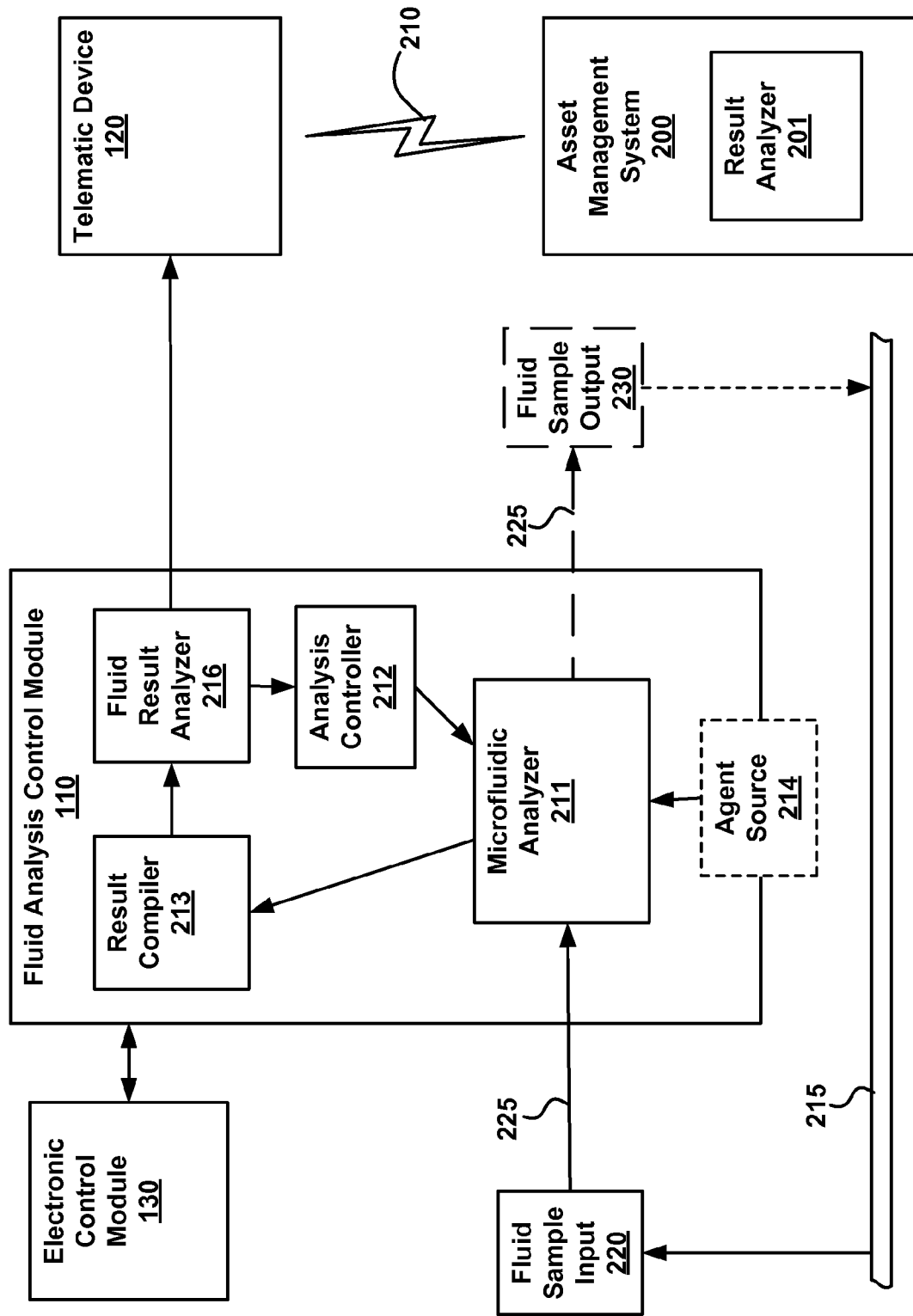
FIG. 58 is a block diagram of an example of a telematic asset microfluidic analysis system in accordance with various embodiments.
Figure 59:
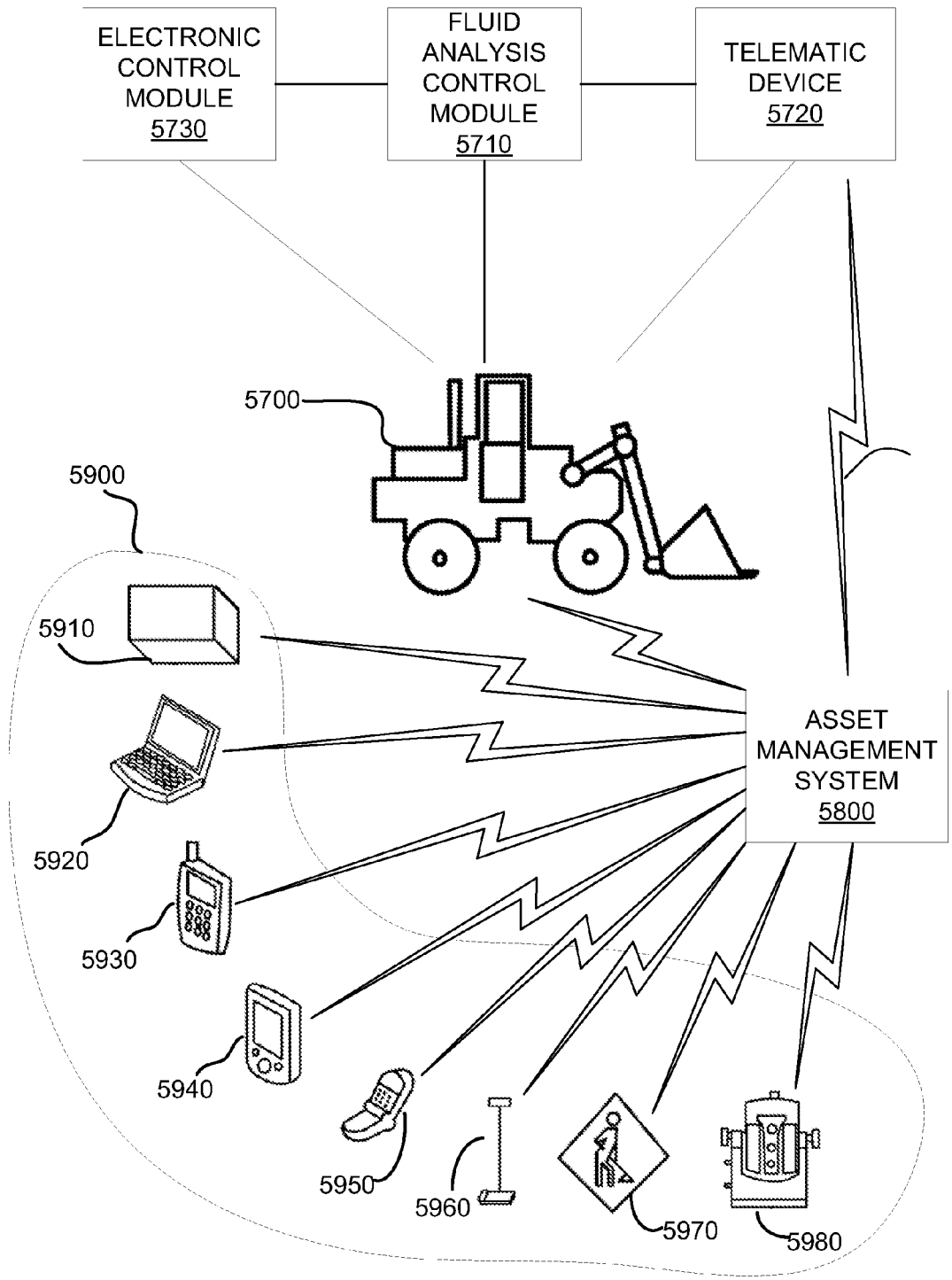
FIG. 59 illustrates an example of a system that provides fluidic analysis results according to embodiments.
Figure 60B:
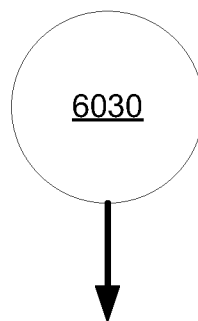
Figure 60C:
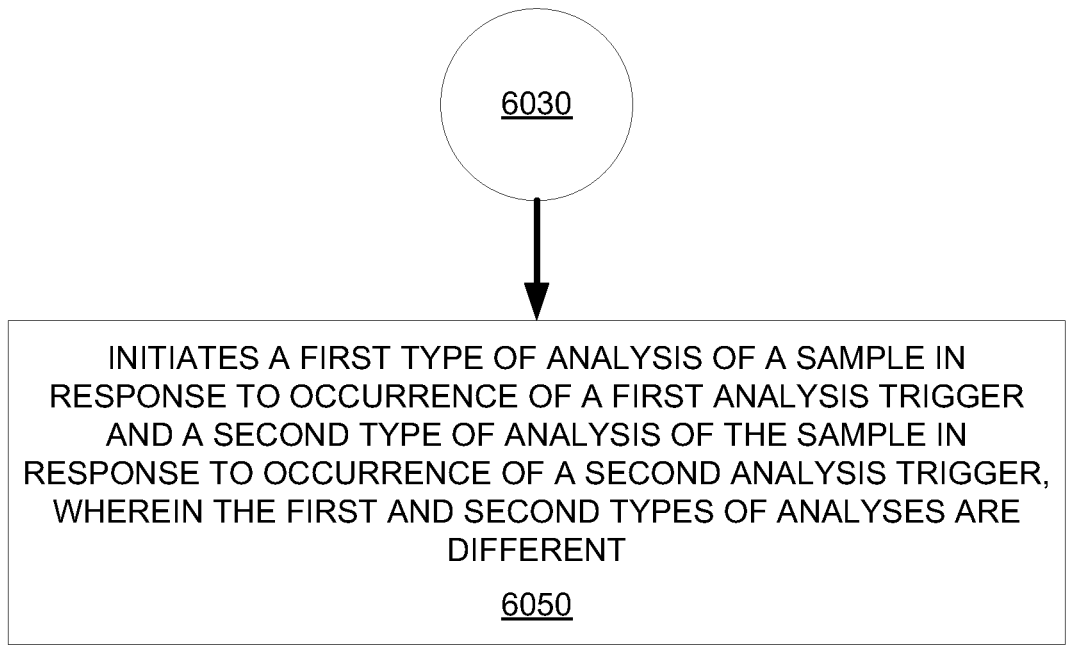
Figure 60D:
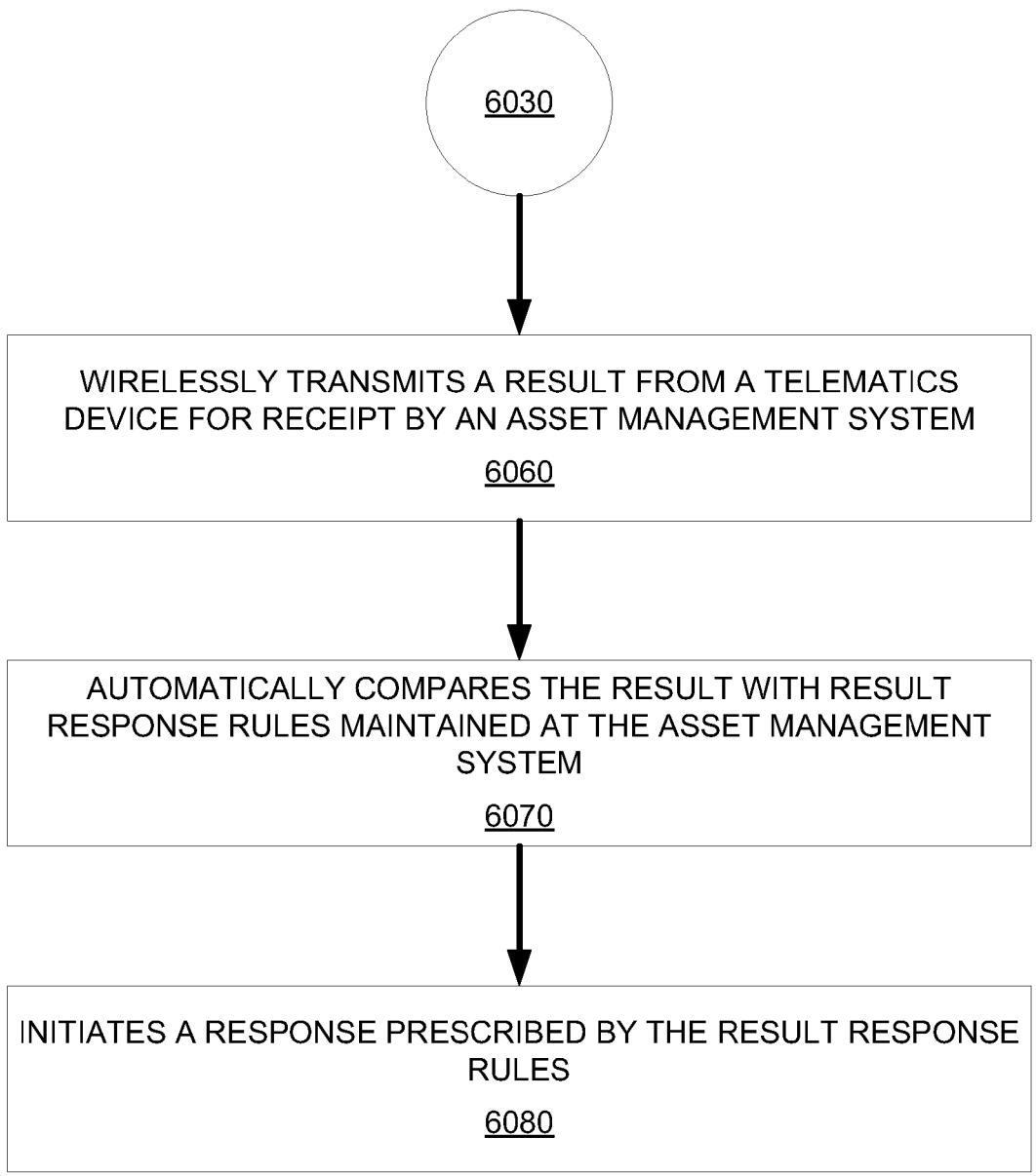

FIG. 58 is a block diagram of an example of a Telematic Asset Microfluidic Analysis system. Fluid analysis control module 5710 is coupled with telematics device 5720 which provides analysis results to an asset management system 5800, in accordance with an embodiment. FIG. 58 also illustrates the components which may comprise fluid analysis control module 5710. In one embodiment, fluid analysis control module 5710 includes a microfluidic analyzer 5811, an analysis controller 5812, a result compiler 5813, and a fluid result analyzer 5816.

In an embodiment, microfluidic analyzer 5811 receives fluid sample 5825 from a fluid sample input 5820. Fluid sample input 5820 may be fluidly coupled with a fluid source 5815 of asset 5700, and operates to acquire fluid sample 5825 as required. Fluid source 5815 may include, but is not limited to: an oil filter, oil reservoir, oil fluid line, hydraulic fluid reservoir, hydraulic fluid line, drilling fluid line, brake fluid reservoir, brake fluid line, transmission fluid reservoir, torque converter reservoir, clutch fluid reservoir, coolant reservoir, coolant fluid line, antifreeze reservoir, antifreeze fluid line, transfer case fluid reservoir, transaxle fluid reservoir, power steering fluid reservoir, power steering fluid line, battery, windshield wiper fluid reservoir, windshield wiper fluid line, and fluid filter. In some embodiments, microfluidic analyzer 5811 recycles sample 5825 back into fluid source 5815 via a fluid sample output 5830 which is fluidly coupled with fluid source 5815. In other embodiments, microfluidic analyzer 5811 disposes of fluid sample 5825 without returning it to fluid sample source 5815 via fluid sample output 5830. For example, an excess sample which is not entirely used up in analysis may be stored in an environmentally contained fashion by fluid sample output 5830 for later disposal.

Fluid analysis control module 5710 also includes analysis controller 5812 which initiates an acquisition of a fluid sample 5825 by fluid sample input 5820, and also initiates a microfluidic analysis of sample 5825. Analysis controller 5812 responds to the occurrence of an analysis trigger. An analysis trigger may be an internal trigger that is internal to either fluid analysis control module 5710 and/or asset 5700, or may be an externally received trigger. An analysis trigger, which is an internal trigger, may comprise an operating characteristic of asset 5700 which is coupled with fluid analysis control module 5710. Some examples of such internal analysis triggers include, but are not limited to: elapsed asset 5700 operating time, operating temperature of asset 5700, ambient temperature asset 5700 operates in, exceeding a predetermined revolution per minute (RPM) level in engine, exceeding a predetermined torque level in transmission, exceeding a predetermined period of time since last sample, time of day, asset 5700 power up, asset 5700 power down, oil temperature, oil pressure, hydraulic fluid pressure, hydraulic fluid temperature, power steering fluid pressure, and brake fluid pressure. Additionally, fluid analysis control module 5710 may include instructions which trigger an analysis when a certain combination of operating characteristics occurs. For example, according to one embodiment, such a combination may be engine RPMs exceeding a threshold (e.g., 4000 RPMs) within a specified period of time (e.g., two minutes) of asset startup when engine and/or ambient temperature is/are below a certain threshold level (e.g., −20 degrees Fahrenheit). An example of an external trigger is an instruction received via telematics device 5720, where the received instruction directs fluid analysis control module 5710 to sample and analyze a particular fluid of asset 5700.

Fluid analysis control module 5710 also includes fluid result analyzer 5816. Fluid result analyzer 5816 receives results from result compiler 5813. Once results are received, fluid result analyzer 5816 provides data to either analysis controller 5812, telematics device 5720, or both. In some embodiments, the outcome of a results analysis by fluid result analyzer 5816 can comprise a trigger for analysis controller 5812 to direct additional microfluidic analysis by microfluidic analyzer 5811. For example, in one embodiment, if a result of microfluidic analysis of engine oil was reviewed by fluid result analyzer 5816 and it was determined that viscosity of the oil was below an established threshold, this might be a trigger to perform a secondary microfluidic analysis for metallic particulates in the engine oil.

In some embodiments, analysis controller 5812 is configured for initiating a first type of analysis of a sample in response to a first analysis trigger, and a second, different type of analysis of the same sample in response to the occurrence of a second analysis trigger. In some embodiments, more than two analyses may be performed in response to various triggers. That is, in some embodiments, the number of analyses initiated by analysis controller 5812 is not limited to two, but instead may be three, four, or more, depending on the number and type of analysis triggers experienced and the microfluidic analysis capabilities resident in fluid analysis control module 5710. In some embodiments, analysis controller 5812 may be configured to initiate the acquisition of a second sample for a second type of analysis, rather than analyze the same sample with two different types of analyses. For example, if RPM level in asset 5700 exceeds a certain level; analysis controller 5812 may be triggered to initiate an oil analysis which analyzes oil for molecular breakdowns, and another analysis which analyzes oil particulates. In another example, if the oil temperature falls below a certain ambient temperature, analysis controller 5812 may analyze the viscosity of the oil. In another example, if the torque level in the transmission exceeds a certain level, analysis controller 5812 may be triggered and initiate a transmission fluid analysis.

After microfluidic analyzer 5811 has completed an analysis, it provides the results of the analysis to result compiler 5813. Result compiler 5813 is also included in fluid analysis control module 5710. In some embodiments, microfluidic analyzer 5811 may perform multiple analyses and result compiler 5813 will store and compile the results of the analyses before providing the results to fluid result analyzer 5816.

In some embodiments, an agent source 5814 adds an agent to microfluidic analyzer 5811 to facilitate certain types of tests. This agent may be some type of a fluid, or other type of matter, necessary to complete testing. The agent may be in a refillable container or may be recycled after each test is completed. In some embodiments, agent source 5814 is external to fluid analysis control module 5710.

In some embodiments, a fluid sample 5825 may include, but is not limited to, fluids such as: oil, hydraulic fluid, drilling fluid, antifreeze, coolant, transmission fluid, torque converter fluid, clutch fluid, differential fluid, transaxle fluid, transfer case fluid, brake fluid, power steering fluid, battery acid, and windshield washer fluid.

Telematics Device Providing Results to Asset Management System

FIG. 58 also illustrates telematics device 5720 coupled to fluid analysis control module 5710. In some embodiments, fluid result analyzer 5816 provides analysis results to telematics device 5720. After telematics device 5720 receives analysis results, telematics device 5720 wirelessly transmits the analysis results to asset management system 5800. It is appreciated that in some embodiments analysis results and/or other information received from telematics device 5720 may be stored in a storage system and/or database by asset management system 5800 which may receive other information about asset 5700 (and other assets) from telematics device 5720 or from other reporting sources (as have been described herein). As one non-limiting example another reporting source which is coupled with or independent from asset 5700 may provide a location of asset 5700 to asset management system independently of any information provided by telematics device 5720 to asset management system 5700.

In some embodiments, telematics device 5720 provides results to at least one asset management system 5800 via radio, microwave, or optical wireless communication devices. In some embodiments telematics device 5720 may provide results via a point-to-point link, broadcast links, or a multipoint link.

In some embodiments asset management system 5800 comprises a result analyzer 5801. Result analyzer 5801 converts the analysis results into various actions. For example, result analyzer 5801 may comprise a lookup table which correlates particular results with particular actions. Result analyzer 5801 may then command asset management system 5800 to send alerts to various employees, provide results to various receiving devices 5900, or remotely power down an asset 5700 that is in danger of becoming damaged.

In some embodiments, result analyzer 5801 may instruct an asset management system 5800 to provide results to various receiving devices 5900. For example, asset management system 5800 may: send alerts to cellular devices including smart phones and personal digital assistants; send alerts via email to a construction manager's laptop; or send commands to asset 5700 directly. In some embodiments, result analyzer 5801 may utilize information received from telematics device 5720 and from one or more additional reporting sources in determining an action such as an alert or notification. For example, if a fluid analysis result received from telematics device 5720 indicates that asset 5700 requires maintenance, a location of asset 5700 received from a secondary reporting source may be utilized by result analyzer 5801 to select a closest mechanic to asset 5700 (e.g., from a list of approved mechanics) to send a maintenance dispatch order to.

In some embodiments, asset management system 5800 may provide results to a graphical user interface. In other embodiments, the results may cause a receiving device to modify a behavior or operating characteristic of asset 5700. For example, via a coupling to a J-Bus or other system level bus of asset 5700, electronic control module 5730 may limit engine RPMs, shut down asset 5700, or lock-out asset 5700 (e.g., prevent start or use) of one or more operating modes of asset 5700. For example, asset management system may telematically direct that electronic control module 5730 (or other telematically coupled device located on/associated with asset 5700) to limit engine RPMs of asset 5700 in response to an analysis result which indicates a breakdown in motor oil viscosity.

Example Computer System Environment

With reference now to FIG. 1, all or portions of some embodiments described herein are composed of computer-readable and computer-executable instructions that reside, for example, in computer-usable/computer-readable storage media of a computer system. That is, FIG. 1 illustrates one example of a type of computer (computer system 100) that can be used in accordance with or to implement various embodiments which are discussed herein. It is appreciated that computer system 100 of FIG. 1 is only an example and that embodiments as described herein can operate on or within a number of different computer systems including, but not limited to, general purpose computer systems, networked computer systems, embedded computer systems, routers, switches, server devices, client devices, various intermediate devices/nodes, stand alone computer systems, media centers, handheld computer systems, multi-media devices, and the like. Computer system 100 of FIG. 1 is well adapted to utilize native or peripheral tangible computer-readable storage media such as, for example, RAM 104, ROM 106, and/or storage device 118 (which may be or utilize a direct access storage device, a floppy disc, an optical storage disc, universal serial bus "thumb" drive, removable memory card, among others).

Example Methods of Operation

With reference to FIGS. 60A-60D, flow diagram 6000 illustrates example procedures used by various embodiments. Flow diagram 6000 includes process and operations that, in various embodiments, are carried out by one or more of the devices illustrated in FIG. 58 or via computer system 100 or components thereof.

Although specific procedures are disclosed in flow diagram 6000, such procedures are examples. That is, embodiments are well suited to performing various other operations or variations of the operations recited in the processes of flow diagram 6000. Likewise, in some embodiments, the operations in flow diagram 6000 may be performed in an order different than presented, not all of the operations described in one or more of these flow diagrams may be performed, and/or one or more additional operation may be added.

The following discussion sets forth in detail the operation of some example methods of operation of embodiments. With reference to FIGS. 60A-60D, flow diagram 6000 illustrates example procedures used by various embodiments. Flow diagram 6000 includes some procedures that, in various embodiments, are carried out by a processor under the control of computer-readable and computer-executable instructions. In this fashion, procedures described herein and in conjunction with flow diagram 6000 are or may be implemented using a computer, in various embodiments. The computer-readable and computer-executable instructions can reside in any tangible computer readable storage media, such as, for example, in data storage features such as RAM 104, ROM 106, and/or storage device 118 (all of FIG. 1). The computer-readable and computer-executable instructions, which reside on tangible computer readable storage media, are used to control or operate in conjunction with, for example, one or some combination of processor 102, or other similar processor(s). Although specific procedures are disclosed in flow diagrams 6000, such procedures are examples. That is, embodiments are well suited to performing various other procedures or variations of the procedures recited in flow diagram 6000. Likewise, in some embodiments, the procedures in flow diagrams 400 may be performed in an order different than presented and/or not all of the procedures described in one or more FIGS. 60A-60D may be performed. It is further appreciated that one or more procedures described in flow diagram 6000 may be implemented in hardware, or a combination of hardware and firmware, or a combination of hardware and software running thereon.

FIG. 60A is a flow diagram 6000 of an example method of analyzing fluids, in accordance with an embodiment. Reference will be made to elements of FIGS. 57 and 58 to facilitate the explanation of the operations of the method of flow diagram 6000. In one embodiment, the method of flow diagram 6000 describes the use of microfluidic analyzer 5811 in analyzing fluids sampled from sample fluid input 5820.

At operation 6010, in one embodiment, fluid analysis control module 5710 samples an asset fluid in response to the occurrence of an analysis trigger. Analysis controller 5812 detects an analysis trigger, and initiates sample acquisition and microfluidic analysis. For example, the analysis trigger could be an event including, but not limited to: elapsed operating time, operating temperature of asset, ambient temperature asset operates in, exceeding a predetermined RPM level in the engine, exceeding a predetermined torque level in transmission, exceeding a predetermined period of time since last sample, time of day, asset power up, asset power down, oil temperature, oil pressure, hydraulic fluid pressure, hydraulic fluid temperature, power steering fluid pressure, and brake fluid pressure.

At operation 6020, in one embodiment, microfluidic analyzer 5811 analyzes a sample in response to an analysis trigger detected by analysis controller 5812.

At operation 6030, in one embodiment, microfluidic analyzer 5811 provides results from an analysis to telematics device 5720.

At 6040, in one embodiment, flow diagram 6000 further includes agent source 5814 which may provide microfluidic analyzer 5811 with a testing agent. For example, a microfluidic analyzer 5811 will gather a sample of oil via fluid sample input 5820. Next, agent source 5814 will provide microfluidic analyzer 5811 with a specially formulated chemical to facilitate certain types of testing within microfluidic analyzer 5811.

At 6050, in one embodiment, flow diagram 6000 further includes performing a first type of analysis of a sample in response to the occurrence of a first analysis trigger. The trigger is detected by analysis controller 5812 which initiates microfluidic analyzer 5811. Next, a second type of analysis of the sample occurs in response to a second, different analysis trigger. The second trigger is also detected by analysis controller 5812.

In one embodiment, the method of flow diagram 6000 further includes wirelessly transmitting results from telematics device 5720 that are received from fluid analysis control module 5710. The results are transmitted to asset management system 5800, in one embodiment.

At operation 6060, in one embodiment, telematics device 5720 transmits fluidic analysis results to asset management system 5800. Transmission of the results may occur via radio, microwave, or optical transmissions, for example.

At operation 6070, in one embodiment, result analyzer 5801 automatically compares the received result with result response rules maintained by asset management system 5800. For example, a result analyzer may look-up the result response rules, and cause asset management system 5800 to initiate a response.

At operation 6080, in one embodiment, asset management system 5800 initiates a response prescribed by response rules. For example, a response may include, but is not limited to: displaying analysis information on a graphical user interface to the asset's owner at a remote location; displaying analysis information on a graphical user interface to an asset's operator; powering down an asset, powering on an asset; and displaying analysis information on a PDA, cellular device, or other receiver.

Example embodiments of the subject matter are thus described. Although various embodiments of the subject matter have been described in a language specific to structural features and/or methodological acts, it is to be understood that the appended claims are not necessarily limited to the specific features or acts described above. Rather, the specific features and acts described above are disclosed as example forms of implementing the claims and their equivalents.

What is claimed is:

1. A fluid analyzing system comprising:
    a telematics device coupled with an asset;
    an electronic control module coupled with said asset and said telematics device, said electronic control module configured for initiating acquisition of a sample of a fluid of said asset and accomplishing a microfluidic analysis of said sample in response to occurrence of an analysis trigger, said analysis trigger comprising an operating characteristic of said asset; and
    an asset management system located remotely from said asset and said telematics device, said asset management system configured for wirelessly receiving results of said microfluidic analysis transmitted from said telematics device.

2. The fluid analyzing system of claim 1, wherein said electronic control module comprises:
    an analysis controller configured for initiating a first type of analysis of said sample in response to occurrence of a first analysis trigger and a second type of analysis of said sample in response to occurrence of a second analysis trigger, wherein said first and second types of analysis are different.

3. The fluid analyzing system of claim 1, wherein said fluid of said asset is selected from the group consisting of: oil, hydraulic fluid, drilling fluid, antifreeze, coolant, transmission fluid, torque converter fluid, clutch fluid, differential fluid, transaxle fluid, transfer case fluid, brake fluid, power steering fluid, battery acid, and windshield washer fluid.

4. The fluid analyzing system of claim 1, wherein said electronic control module is coupled with a part of said asset selected from the group consisting of: an oil filter, oil reservoir, oil fluid line, hydraulic fluid reservoir, hydraulic fluid line, drilling fluid line, brake fluid reservoir, brake fluid line, transmission fluid reservoir, torque converter reservoir, clutch fluid reservoir, coolant reservoir, coolant fluid line, antifreeze reservoir, antifreeze fluid line, transfer case fluid reservoir, transaxle fluid reservoir, power steering fluid reservoir, power steering fluid line, battery, windshield wiper fluid reservoir, and windshield wiper fluid line.

5. The fluid analyzing system of claim 1, wherein said analysis trigger is selected from the group consisting of: elapsed operating time, operating temperature of asset, ambient temperature asset operates in, exceeding a predetermined RPM level in engine, exceeding a predetermined torque level in transmission, exceeding a predetermined period of time since last sample, time of day, asset power up, asset power down, oil temperature, oil pressure, hydraulic fluid pressure, hydraulic fluid temperature, power steering fluid pressure, and brake fluid pressure.

6. The fluid analyzing system of claim 1, wherein said asset is selected from the group consisting of: an automobile, backhoe, cherry picker, cold planer, compactor, conveyor, crane, cure rig, dozer, dredger, dump, excavator, feller buncher, forklift, forwarder, grader, harvester, handler, hauler, loader, paver, pile driver, pipe layer, reclaimer, roller, shovel, skidder, soil stabilizer, street sweeper, tiller, tractor, trencher, truck, tunnel boring machine, and yarder.

7. A method for analyzing fluids comprising:
    acquiring a sample of an asset fluid in response to occurrence of an analysis trigger, said analysis trigger comprising an operating characteristic of asset;
    analyzing said sample in response to said analysis trigger, wherein said analysis is performed by a microfluidic analyzer coupled with said asset; and
    providing results of said analysis to a telematics device, wherein said acquiring, and said providing are performed by one or more computer processors and said analyzing performed under the direction of the one or more computer processors.

8. The method of claim 7, further comprising:
    adding a test agent to said microfluidic analyzer for use in said analysis of said sample, wherein said adding is performed under direction of said one or more computer processors.

9. The method of claim 7, further comprising:
initiating a first type of analysis of said sample in response to occurrence of a first analysis trigger and a second type of analysis of said sample in response to occurrence of a second analysis trigger, wherein said first and second types of analyses are different, wherein said initiating is performed by said one or more computer processors.

10. The method of claim 7, further comprising:
wirelessly transmitting said result from said telematics device for receipt by an asset management system, said asset management system located remotely from said asset and said telematics device;
automatically comparing said result with result response rules maintained at said asset management system; and
initiating a response prescribed by said result response rules, said response initiated by said asset management system, wherein said wirelessly transmitting, said automatically comparing and said initiating are performed by said one or more computer processors.

11. An electronic control module comprising:
a processor for executing instructions; and
a tangible computer-readable storage medium for storing the instructions, wherein,
an analysis controller configured for initiating analysis of a sample of an asset fluid in response to occurrence of an analysis trigger, said analysis trigger comprising an operating characteristic of said asset;
a microfluidic analyzer configured for analyzing said sample; and
a result compiler configured for accessing an analysis result from said microfluidic analyzer and providing said analysis result to a telematics device;
wherein the instructions implement said analysis controller and said result compiler and direct actions of said microfluidic analyzer.

12. The electronic control module of claim 11, wherein said instructions further direct actions of:
an agent source coupled with said microfluidic analyzer and configured for providing a testing agent for use in said analysis of said sample.

13. The electronic control module of claim 11, wherein said analysis controller is configured for initiating a first type of analysis of said sample in response to occurrence of a first analysis trigger and a second type of analysis of said sample in response to occurrence of a second analysis trigger, wherein said first and second types of analyses are different.

14. The electronic control module of claim 11, wherein said asset fluid is selected from the group consisting of: oil, hydraulic fluid, drilling fluid, antifreeze, coolant, transmission fluid, torque converter fluid, clutch fluid, differential fluid, transaxle fluid, transfer case fluid, brake fluid, power steering fluid, battery acid, and windshield washer fluid.

15. The electronic control module of claim 11, wherein said electronic control module is coupled with a part of said asset selected from the group consisting of: an oil filter, oil reservoir, oil fluid line, hydraulic fluid reservoir, hydraulic fluid line, drilling fluid line, brake fluid reservoir, brake fluid line, transmission fluid reservoir, torque converter reservoir, clutch fluid reservoir, coolant reservoir, coolant fluid line, antifreeze reservoir, antifreeze fluid line, transfer case fluid reservoir, transaxle fluid reservoir, power steering fluid reservoir, power steering fluid line, battery, windshield wiper fluid reservoir, windshield wiper fluid line, and fluid filter.

16. The electronic control module of claim 11, wherein said analysis trigger is selected from the group consisting of: elapsed operating time, operating temperature of asset, ambient temperature asset operates in, exceeding a predetermined RPM level in engine, exceeding a predetermined torque level in transmission, exceeding a predetermined period of time since last sample, time of day, asset power up, asset power down, oil temperature, oil pressure, hydraulic fluid pressure, hydraulic fluid temperature, power steering fluid pressure, and brake fluid pressure.

17. The electronic control module of claim 11, wherein said asset is selected from the group consisting of: an automobile, backhoe, cherry picker, cold planer, compactor, conveyor, crane, cure rig, dozer, dredger, dump, excavator, feller buncher, forklift, forwarder, grader, harvester, handler, hauler, loader, paver, pile driver, pipe layer, reclaimer, roller, shovel, skidder, soil stabilizer, street sweeper, tiller, tractor, trencher, truck, tunnel boring machine, and yarder.

18. A construction equipment asset comprising:
a telematics device physically coupled with said asset; and
an electronic control module fluidly coupled with said asset and electronically coupled with said telematics device, said electronic control module comprising:
an analysis controller configured for initiating analysis of a sample of an asset fluid in response to occurrence of an analysis trigger, said analysis trigger comprising an operating characteristic of said asset;
a microfluidic analyzer configured for analyzing said sample; and
a result compiler configured for accessing an analysis result from said microfluidic analyzer and providing said analysis result to a telematics device.

19. The construction equipment asset of claim 18, wherein said asset fluid is selected from the group consisting of: oil, hydraulic fluid, drilling fluid, antifreeze, coolant, transmission fluid, torque converter fluid, clutch fluid, differential fluid, transaxle fluid, transfer case fluid, brake fluid, power steering fluid, battery acid, and windshield washer fluid.

20. The construction equipment asset of claim 18, wherein said electronic control module is coupled with a part of said asset selected from the group consisting of: an oil filter, oil reservoir, oil fluid line, hydraulic fluid reservoir, hydraulic fluid line, drilling fluid line, brake fluid reservoir, brake fluid line, transmission fluid reservoir, torque converter reservoir, clutch fluid reservoir, coolant reservoir, coolant fluid line, antifreeze reservoir, antifreeze fluid line, transfer case fluid reservoir, transaxle fluid reservoir, power steering fluid reservoir, power steering fluid line, battery, windshield wiper fluid reservoir, and windshield wiper fluid line.

21. The construction equipment asset of claim 18, wherein said analysis trigger is selected from the group consisting of: elapsed operating time, operating temperature of asset, ambient temperature asset operates in, exceeding a predetermined RPM level in engine, exceeding a predetermined torque level in transmission, exceeding a predetermined period of time since last sample, time of day, asset power up, asset power down, oil temperature, oil pressure, hydraulic fluid pressure, hydraulic fluid temperature, power steering fluid pressure, and brake fluid pressure.

22. The construction equipment asset of claim 18, wherein said asset is selected from the group consisting of: an automobile, backhoe, cherry picker, cold planer, compactor, conveyor, crane, cure rig, dozer, dredger, dump, excavator, feller buncher, forklift, forwarder, grader, harvester, handler, hauler, loader, paver, pile driver, pipe layer, reclaimer, roller, shovel, skidder, soil stabilizer, street sweeper, tiller, tractor, trencher, truck, tunnel boring machine, and yarder.

* * * * *